(12) United States Patent
Chaki et al.

(10) Patent No.: US 6,288,041 B1
(45) Date of Patent: *Sep. 11, 2001

(54) SIALIC ACID DERIVATIVES

(75) Inventors: Haruyuki Chaki, Kanagawa; Naoko Ando; Tetsuo Jikihara, both of Tokyo; Ken-ichi Saito; Tomoko Yugami, both of Kanagawa, all of (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/981,240

(22) PCT Filed: Jun. 21, 1996

(86) PCT No.: PCT/JP96/01726

§ 371 Date: Dec. 19, 1997

§ 102(e) Date: Dec. 19, 1997

(87) PCT Pub. No.: WO97/00885

PCT Pub. Date: Jan. 9, 1997

(30) Foreign Application Priority Data

Jun. 23, 1995 (JP) .................................................. 7-157888
Jun. 23, 1995 (JP) .................................................. 7-157889

(51) Int. Cl.[7] .......................... A61K 31/70; A61K 31/58; C07H 5/06; C07J 41/00
(52) U.S. Cl. .......................... 514/42; 514/172; 536/29.1; 540/106
(58) Field of Search ..................... 514/42, 172; 536/29.1; 540/106

(56) References Cited

U.S. PATENT DOCUMENTS 5,712,254 * 1/1998 Chaki et al. ........................... 514/42
5,783,564 * 7/1998 Chaki et al. ........................... 514/42

FOREIGN PATENT DOCUMENTS 0267297  5/1988 (EP) .
0659762  6/1995 (EP) .
WO94/03469  2/1994 (WO) .

OTHER PUBLICATIONS

Database WPI, Section Ch, Week 9320, Derwent Publications Ltd., London, GB; Class B01, AN 93–162124, XP002082357 & 05 092991 A (Mitsubishi Kasei Corp), Apr. 16, 1993.
Veeneman et al., "Synthesis of sialic acid–lipid conjugates, and their neutritogenic effects on N1E. 115 neuroblastoma cells", Bioorganic and Medicinal Chemistry Letters, vol. 5, No. 1, 1995, pp. 9–14.
Merck Index, Ninth Edition, p. 282, 1976.*

* cited by examiner

Primary Examiner—Barbara P. Badio
(74) Attorney, Agent, or Firm—Wenderoth, Lind & Ponack, L.L.P.

(57) ABSTRACT

Sialic acid derivatives represented by the following general formula:

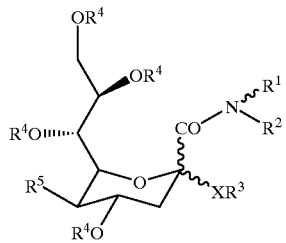

wherein $R^1$ represents a residue of a steroid compound excluding cholestane and cholestene residues, $R^2$ represents hydrogen or methyl group, $R^3$ represents a $C_1$–$C_6$ alkyl group and other, $R^4$ represents hydrogen or acyl group, $R^5$ represents a group of $R^{15}O-$ ($R^{15}$ represents a $C_2$–$C_7$ acyl group and other), and X represents oxygen or sulfur atom, and their derivatives. These derivatives have activating effect on choline acetyltransferase activity in the chlonergic neurons, and are useful for preventive and therapeutic treatment of dementia, memory disorder, peripheral nervous disorder and so forth.

34 Claims, No Drawings

SIALIC ACID DERIVATIVES

CROSS-REFERENCE TO RELATED APPLICATION

This application is a 371 application of International Application No. PCT/JP96/01726 filed Jun. 21, 1996.

TECHNICAL FIELD

The present invention relates to novel sialic acid derivatives which are useful for therapeutic and/or preventive treatment of various diseases caused by disorders of the cholinergic nerve cells.

BACKGROUND ART

Senile dementia including Alzheimer's disease is a disease with progressive memory disorder or cognition disorder. In the disease, remarkable disturbance is observed in the cholinergic nervous system which transmits signals from forebrain basal ganglia to cerebral cortex and hippocampus. This disturbance is caused by significant decrease of choline acetyltransferase (hereinafter abbreviated as "ChAT") activity, therefore, it is considered that agents that activate ChAT activity are effective medicament for therapeutic treatment of senile dementia including Alzheimer's disease. In addition, medicaments having such activity are also considered to be useful as therapeutic medicaments for peripheral nervous disorder.

Gangliosides, i.e., sphingoglycolipids containing sialic acid, are components for constituting biomembranes, and abundant in brains of higher animals. In recent years, various functions of gangliosides have been reported, and in particular, their roles in nervous systems have been focused because they almost specifically exist in membranes of nervous systems. Sialic acid is an important constituting element of gangliosides, and accordingly, various derivatives have been synthesized from viewpoints of relations with functions of gangliosides and medical applicability (Japanese Patent Unexamined Publication Nos. (Sho)55-89298/1980, (Sho)61-243096/1986, (Sho)61-282390/1986, (Sho)63-41492/1988, (Sho)63-41494/1988, (Sho)63-63697/1988, (Sho)63-68526/1988, (Sho)64-52794/1989, (Hei)1-190693/1989, and (Hei)3-151398/1991, and WO93/10134, WO94/03469 or other). Some articles report biological activities of the derivatives (Japanese Patent Unexamined Publication No. (Sho)62-265229/1987, (Hei)1-93529/1989, (Hei)3-77898/1992, and (Hei)3-81287/1992, and Brain Research, 438, pp.277–285, 1988). However, any derivatives that can sufficiently activate ChAT activity have not yet been known to date.

DISCLOSURE OF THE INVENTION

The present inventors conducted various researches to provide medicament for therapeutic treatment of disturbance of central nervous system such as senile dementia including Alzheimer's disease and disturbance of peripheral nervous system. As a result, they found that sialic acid derivatives having a specific type of amide bond can activate ChAT activity in the cholinergic nerve cells, and accordingly, the derivatives can be used as medicaments for improving disturbance of central nervous system such as memory disorder accompanied with senile dementia including Alzheimer's disease and peripheral nervous disorder such as diabetic neuropathy. The present invention was achieved on the basis of these findings.

The present invention provides sialic acid derivatives represented by the following general formula (1AA) or their salts, or hydrates or solvates thereof:

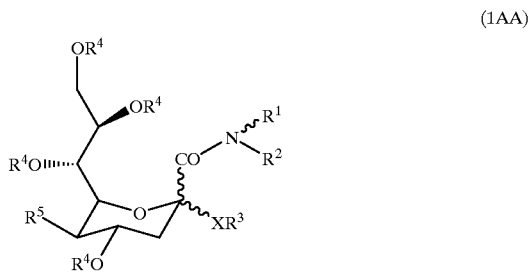

(1AA)

wherein $R^1$ represent a residue of a steroid compound excluding cholestane residue and cholestene residue, $R^2$ represents hydrogen atom or methyl group, $R^3$ represents a $C_1$–$C_6$ alkyl group, a group of formula:

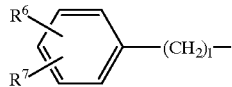

[wherein $R^6$ and $R^7$ independently represent hydrogen atom, a halogen atom, a $C_1$–$C_4$ alkyl group, hydroxyl group, a group of formula $R^8O$— (wherein $R^8$ represents a $C_1$–$C_4$ alkyl group, phenyl group, or a phenyl-($C_1$–$C_3$ alkyl) group), nitro group, amino group, a $C_1$–$C_4$ alkylamino group, a $C_2$–$C_8$ dialkylamino group, or a group of formula $R^9O$—CO— (wherein $R^9$ represents hydrogen atom, a $C_1$–$C_4$ alkyl group, phenyl group, or a phenyl-($C_1$—$C_3$ alkyl) group), and l represents an integer of 0–6]; a group of $R^{10}O(CH_2)_m$— (wherein $R^{10}$ represents hydrogen atom; a $C_1$–$C_4$ alkyl group; phenyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl) group which may optionally have one or more substituents selected from the group consisting of a $C_1$–$C_4$ alkyl group, a halogen atom, hydroxyl group, nitro group, amino group, and carboxyl group, and m represents an integer of 2–6); or a group of $(R^{11})(R^{12})N(CH_2)_n$— [wherein $R^{11}$ represents hydrogen atom or a $C_1$–$C_4$ alkyl group, and $R^{12}$ represents hydrogen atom; a $C_1$–$C_4$ alkyl group; a $C_2$–$C_7$ acyl group; a $C_1$–$C_4$ alkylsulfonyl group; phenylsulfonyl group which may optionally have one or more substituents selected from the group consisting of a $C_1$–$C_4$ alkyl group, a halogen atom, hydroxyl group, nitro group, amino group, and carboxyl group; or a group of $R^{13}O$—CO— (wherein $R^{13}$ represents a $C_1$–$C_4$ alkyl group, phenyl group, or a phenyl-($C_1$–$C_3$ alkyl) group), and n represents an integer of 2–6], $R^4$ represents hydrogen atom or a $C_2$–$C_7$ acyl group, $R^5$ represents a group of $R^{14}O$— (wherein $R^{14}$ represents hydrogen atom or a $C_2$–$C_7$ acyl group) or a group of $R^{15}NH$— [wherein $R^{15}$ represents a $C_2$–$C_7$ acyl group, a group of $R^{16}O(CH_2)_p$—CO— (wherein $R^{16}$ represents hydrogen atom, a $C_1$–$C_6$ alkyl group, phenyl group, or a phenyl-($C_1$–$C_3$ alkyl) group, and p represents an integer of 0–4); a $C_7$–$C_{11}$ aroyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl) carbonyl group which may optionally have one or more substituents selected from the group consisting of a $C_1$–$C_4$ alkyl group, a halogen atom, hydroxyl group, nitro group, amino group, and carboxyl group, and X represents oxygen atom or sulfur atom.

According to another aspect of the present invention, there are also provided sialic acid derivatives represented by the following general formula (1BB) or their salts, or hydrates or solvates thereof:

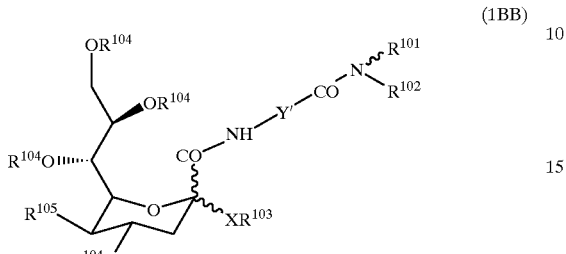

(1BB)

wherein $R^{101}$ represents a residue of a steroid compound, $R^{102}$ represents hydrogen atom or methyl group, $R^{103}$ represents a $C_1$–$C_6$ alkyl group, a group of:

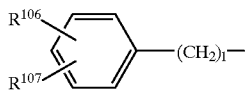

[wherein $R^{106}$ and $R^{107}$ independently represent hydrogen atom, a halogen atom, a $C_1$–$C_4$ alkyl group, hydroxyl group, a group of $R^{108}$O— (wherein $R^{108}$ represents a $C_1$–$C_4$ alkyl group, phenyl group, or a phenyl-($C_1$–$C_3$ alkyl) group), nitro group, amino group, a $C_1$–$C_4$ alkylamino group, a $C_2$–$C_8$ dialkylamino group, or a group of $R^{109}$O—CO— (wherein $R^{109}$ represents hydrogen atom, a $C_1$–$C_4$ alkyl group, phenyl group, or a phenyl-($C_1$–$C_3$ alkyl) group), and l represents an integer of 0–6]; a group of $R^{110}$O($CH_2$)$_m$— (wherein $R^{110}$ represents hydrogen atom; a $C_1$–$C_4$ alkyl group; phenyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl) group which may optionally have one or more substituents selected from the group consisting of a $C_1$–$C_4$ alkyl group, a halogen atom, hydroxyl group, nitro group, amino group, and carboxyl group, and m represents an integer of 2–6); or a group of ($R^{111}$)($R^{112}$)N($CH_2$)$_n$— [wherein $R^{111}$ represents hydrogen atom or a $C_1$–$C_4$ alkyl group, $R^{112}$ represents hydrogen atom; a $C_1$–$C_4$ alkyl group; a $C_2$–$C_7$ acyl group; a $C_1$–$C_4$ alkylsulfonyl group; phenylsulfonyl group which may optionally have one or more substituents selected from the group consisting of a $C_1$–$C_4$ alkyl group, a halogen atom, hydroxyl group, nitro group, amino group, and carboxyl group; or a group of $R^{113}$O—CO— (wherein $R^{113}$ represents a $C_1$–$C_4$ alkyl group, phenyl group, or a phenyl-($C_1$–$C_3$ alkyl) group), and n represents an integer of 2–6], $R^{104}$ represents hydrogen atom or a $C_2$–$C_7$ acyl group, $R^{105}$ represents a group of $R^{114}$O— (wherein $R^{114}$ represents hydrogen atom or a $C_2$–$C_7$ acyl group) or a group of $R^{115}$NH— [wherein $R^{115}$ represents a $C_2$–$C_7$ acyl group; a group of $R^{116}$O($CH_2$)$_p$—CO— (wherein $R^{116}$ represents hydrogen atom, a $C_1$–$C_6$ alkyl group, phenyl group, or a phenyl-($C_1$–$C_3$ alkyl) group, and p represents an integer of 0–4); a $C_7$–$C_{11}$ aroyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl)carbonyl group which may optionally have one or more substituents selected from the group consisting of a $C_1$–$C_4$ alkyl group, a halogen atom, hydroxyl group, nitro group, amino group, and carboxyl group, X represents oxygen atom or sulfur atom, and Y' represents a group of —($CH_2$)$_q$—CH($R^{120}$)—($CH_2$)$_r$— [wherein $R^{120}$ represents hydrogen atom; a $C_1$–$C_6$ alkyl group which may optionally have one or more substituents selected from the group consisting of a halogen atom, hydroxyl group, a $C_1$–$C_4$ alkoxy group, nitro group, amino group, a $C_2$–$C_7$ acylamino group, a group of $R^{121}$—O—CO—NH— (wherein $R^{121}$ represents a $C_1$–$C_6$ alkyl group or a phenyl-($C_1$–$C_3$ alkyl) group), and a group of $R^{122}$—O—CO— (wherein $R^{122}$ represents hydrogen atom, a $C_1$–$C_6$ alkyl group, or a phenyl-($C_1$–$C_3$ alkyl) group); a $C_7$–$C_{11}$ aroyl group which may optionally have one or more substituents selected from the group consisting of a $C_1$–$C_4$ alkyl group, a halogen atom, hydroxyl group, nitro group, amino group, and carboxyl group; phenyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl) group which may optionally have one or more substituents selected from the group consisting of a $C_1$–$C_4$ alkyl group, a $C_1$–$C_4$ alkoxy group, a phenyl-($C_1$–$C_3$ alkyloxy) group, a halogen atom, hydroxyl group, nitro group, amino group, and carboxyl group, and q and r independently represent an integer of 0–3]; or a group of:

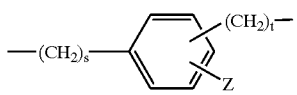

[wherein Z represents hydrogen atom, a $C_1$–$C_4$ alkyl group, a $C_1$–$C_4$ alkoxy group, a phenyl-($C_1$–$C_3$ alkyloxy) group, a halogen atom, hydroxyl group, nitro group, amino group, a $C_2$–$C_7$ acylamino group, or a group of $R^{123}$—O—CO— (wherein $R^{123}$ represents hydrogen atom, a $C_1$–$C_6$ alkyl group, or a phenyl-($C_1$–$C_3$ alkyl) group), and s and t independently represents an integer of 0–3].

According to further aspects of the present invention, there are provided medicaments comprising a substance selected from the group consisting of the above sialic acid derivatives and their salts, and hydrates and solvates thereof; and pharmaceutical compositions comprising as an active ingredient a substance selected from the group consisting of the above sialic acid derivatives and their salts, and hydrates and solvates thereof together with a pharmaceutically acceptable carrier. As preferred aspects of the invention, there are provided pharmaceutical compositions which are used for preventive and/or therapeutic treatment of dementia, memory disorder, or symptoms accompanied with the diseases; and pharmaceutical compositions which are used for preventive and/or therapeutic treatment of peripheral nervous disorder. In addition, according to further aspects of the present invention, there are provided a use of a substance as active ingredient which is selected from the group consisting of the above sialic acid derivative and its salt, and a hydrate and a solvate thereof for the manufacture of the aforementioned pharmaceutical composition; and a method for preventive and/or therapeutic treatment of dementia, memory disorder, or symptoms accompanied with said disease, or peripheral nervous disorder, which comprises the step of administering to a patient a preventively and/or therapeutically effective amount of a substance selected from the group consisting of the above sialic acid derivative and its salt, and a hydrate and a solvate thereof.

BEST MODE FOR CARRYING OUT THE INVENTION

The first aspect of the sialic acid derivatives of the present invention relates to the compounds represented by the above general formula (1AA). As to the aforementioned general formula (1AA), atoms and functional groups in $R^1$ to $R^{16}$ as defined above and those of $R^{17}$ to $R^{30}$, which will be included in the definition of $R^1$ as explained later, are specifically exemplified below.

Examples of $C_1$–$C_{10}$ alkyl group include, for example, methyl group, ethyl group, n-propyl group, i-propyl group, n-butyl group, t-butyl group, n-pentyl group, n-hexyl group, n-heptyl group, n-octyl group, n-nonyl group, n-decyl group, 1,5-dimethylhexyl group and the like. Examples of $C_1$–$C_6$ alkyl group include the exemplified $C_1$–$C_6$ alkyl groups among the aforementioned $C_1$–$C_{10}$ alkyl groups. Examples of $C_1$–$C_4$ alkyl group include the exemplified $C_1$–$C_4$ alkyl groups among the aforementioned $C_1$–$C_{10}$ alkyl groups. Examples of $C_1$–$C_3$ alkyl group include the exemplified $C_1$–$C_3$ alkyl groups among the aforementioned $C_1$–$C_{10}$ alkyl groups.

Examples $C_1$–$C_{10}$ alkoxy group include, for example, methoxy group, ethoxy group, n-propoxy group, i-propoxy group, n-butoxy group, n-hexyloxy group, n-octyloxy group, n-decyloxy group and the like. Examples of $C_1$–$C_4$ alkoxy group include the exemplified $C_1$–$C_4$ alkoxy groups among the aforementioned $C_1$–$C_{10}$ alkoxy groups. Examples of halogen atom include, for example, fluorine atom, chlorine atom, bromine atom and the like. Examples of phenyl-($C_1$–$C_3$ alkyl) group include, for example, benzyl group, phenethyl group and the like. Examples of $C_2$–$C_7$ acyl group include, for example, acetyl group, propionyl group, butyryl group, valeryl group, benzoyl group and the like. Examples of $C_2$–$C_4$ acyl group include the exemplified $C_2$–$C_4$ acyl groups among the aforementioned $C_2$–$C_7$ acyl groups.

Examples of $C_1$–$C_4$ alkylsulfonyl group include, for example, methylsulfonyl group, ethylsulfonyl group, n-propylsulfonyl group, n-butylsulfonyl group and the like. Examples of $C_1$–$C_4$ alkylamino group include, for example, methylamino group, ethylamino group, butylamino group and the like. Examples of $C_2$–$C_8$ dialkylamino group include, for example, dimethylamino group, diethylamino group, dibutylamino group and the like. Examples of $C_1$–$C_{10}$ aroyl group include, for example, benzoyl group, toluoyl group, naphthoyl group and the like. Examples of phenyl-($C_1$–$C_3$ alkyl)carbonyl group include, for example, benzylcarbonyl group, phenylethylcarbonyl group, phenylpropylcarbonyl group and the like. Examples of $C_2$–$C_{11}$ alkenyl group include, for example, vinyl group, allyl group, butenyl group, pentenyl group, hexenyl group and the like. Examples of 1,3-dioxolane residue include, for example, groups of:

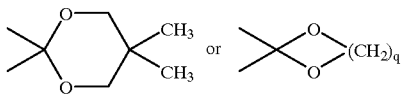

wherein q represents an integer of 1–4.

Groups not specifically mentioned in the above groups may be chosen by appropriate combination of the aforementioned atoms and functional groups or based on common knowledge of those skilled in the art.

As the residue of a steroid compound defined by $R^1$ in the above general formula (1AA), an example includes the residue of a steroid compound, excluding cholestane residue and cholestene residue, which is represented by the group of:

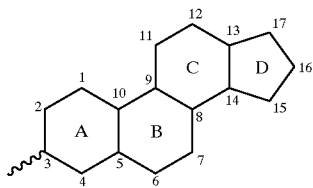

wherein the configuration at 3-position of the steroid skeleton is either α or β, rings A, B, C, and D independently represent a saturated ring, a partially saturated ring, or an unsaturated ring, and the rings A, B, C, and D may independently have one or more substituents selected from the group consisting of a $C_1$–$C_{10}$ alkoxy group; hydroxyl group; a $C_1$–$C_{10}$ alkyl group which may have one or more substituents selected from the group consisting of a $C_1$–$C_4$ alkyl group, a halogen atom, a $C_1$–$C_4$ alkoxy group, hydroxyl group, oxo group, 1,3-dioxolane residue, a group of —COOR$^{17}$ (wherein R$^{17}$ represents hydrogen atom, a $C_1$–$C_6$ alkyl group, or a phenyl-($C_1$–$C_3$ alkyl) group), and a group of —CONR$^{18}$R$^{19}$ (wherein R$^{18}$ and R$^{19}$ independently represent hydrogen atom, a $C_1$–$C_6$ alky group, or a phenyl-($C_1$–$C_3$ alkyl) group); a $C_2$–$C_{11}$ alkenyl group which may optionally have one or more substituents selected from the group consisting of a $C_1$–$C_4$ alkyl group, a halogen atom, a $C_1$–$C_4$ alkoxy group, hydroxyl group, oxo group, 1,3-dioxolane residue, a group of —COOR$^{17}$ (wherein R$^{17}$ has the same meaning as defined above), and a group of —CONR$^{18}$R$^{19}$ (wherein R$^{18}$ and R$^{19}$ have the same meanings as defined above); a halogen atom; oxo group; 1,3-dioxolane residue; a group of —COOR$^{20}$ (wherein R$^{20}$ represents hydrogen atom, a $C_1$–$C_6$ alkyl group, or a phenyl-($C_1$–$C_3$ alkyl) group); and a group of —CONR$^{21}$R$^{22}$ (wherein R$^{21}$ and R$^{22}$ independently represent hydrogen atom, a $C_1$–$C_6$ alkyl group or a phenyl-($C_1$–$C_3$ alkyl) group).

Among these residues of steroid compounds, those preferred include the residues of steroid compounds, excluding cholestane residue, represented by a group

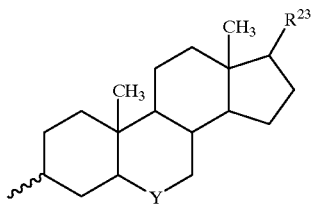

wherein the configuration at the 3-position of the steroid skeleton is either α or β, R$^{23}$ represents hydrogen atom; a $C_1$–$C_{10}$ alkyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{24}$ (wherein R$^{24}$ represents hydrogen atom, a $C_1$–$C_6$ alkyl group or a phenyl-($C_1$–$C_3$ alkyl) group), and a group of —CONR$^{25}$R$^{26}$ (wherein R$^{25}$ and R$^{26}$ independently represent hydrogen atom, a $C_1$–$C_6$ alkyl group or a phenyl-($C_1$–$C_3$ alkyl) group); a $C_2$–$C_{11}$ alkenyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{24}$ (wherein R$^{24}$ has the same meaning as defined above), and a group of —CONR$^{25}$R$^{26}$ (wherein R$^{25}$ and R$^{26}$ have the same meanings as defined above); a $C_1$–$C_4$ alkoxy group; hydroxyl group; oxo group; 1,3-dioxolane residue; a group of —COOR$^{27}$ (wherein R$^{27}$ represents hydrogen atom, a $C_1$–$C_6$ alkyl group, or a phenyl-($C_1$–$C_3$ alkyl) group); or a group of —CONR$^{28}$R$^{29}$ (wherein R$^{28}$ and R$^{29}$ independently represent hydrogen atom, a $C_1$–$C_6$ alkyl group or a phenyl-($C_1$–$C_3$ alkyl) group); and Y represents a group of:

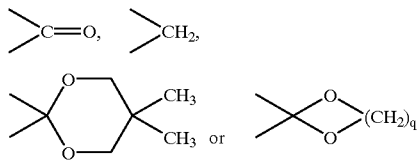

wherein q represents an integer of 1–4.

Furthermore, those most preferred include the residues of steroid compounds, excluding cholestane residue, represented by a group of:

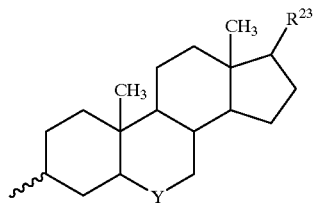

wherein the configuration at the 3-position of the steroid skeleton is either α or β, R$^{23}$ represents a $C_1$–$C_{10}$ alkyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{24}$ (wherein R$^{24}$ has the same meaning as defined above), and a group of —CONR$^{25}$R$^{26}$ (wherein R$^{25}$ and R$^{26}$ have the same meanings as defined above); or a $C_2$–$C_{11}$ alkenyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{24}$ (wherein R$^{24}$ has the same meaning as defined above), and a group of —CONR$^{25}$R$^{26}$ (wherein R$^{25}$ and R$^{26}$ have the same meanings as defined above); and Y has the same meaning as defined above.

Hydrogen atom is most preferable as R$^2$. As R$^3$, a $C_1$–$C_6$ alkyl group or a group of $C_6H_5$—(CH$_2$)$_l$— (wherein l represents an integer of 0–3) is preferred, and a $C_1$–$C_3$ alkyl group is most preferred. Hydrogen atom or acetyl group is preferred as R$^4$, and hydrogen atom is most preferred. As R$^5$, a group of R$^{14}$O— (wherein R$^{14}$ represents hydrogen atom or acetyl group), or a group of R$^{15}$NH— [wherein R$^{15}$ represents a $C_2$–$C_7$ acyl group, or a group of R$^{16}$O(CH$_2$)$_p$—CO— (wherein R$^{16}$ represents hydrogen atom, a $C_1$–$C_4$ alkyl group or a phenyl-($C_1$–$C_3$ alkyl) group, and p represents an integer of 0–4), or a $C_7$–$C_{11}$ aroyl group is preferred. A group of R$^{14}$O— (wherein R$^{14}$ represents hydrogen atom or acetyl group) or a group of R$^{15}$NH— (wherein R$^{15}$ represents a $C_2$–$C_4$ acyl group) is more preferred, and a group of R$^{15}$NH— (wherein R$^{15}$ represents acetyl group) is most preferred. Oxygen atom is most preferred as X.

Specific examples of preferred compounds represented by the above general formula (1AA) are listed in Tables 1AA, 2AA, 3AA, 4AA, 5AA, and 6AA set out below. Among them, most preferred compounds include, for example:

3β-[N-(5-acetamido-3,5-dideoxy-2O-methyl-α-D-glycero-D-galacto-2-nonulopyranosonyl)amino]-24-hydroxy-5β-cholane (β-isomer of Compound No. 4 in Table 1AA);

3α-[N-(5-acetamido-3,5-dideoxy-2O-methyl-α-D-glycero-D-galacto-2-nonulopyranosonyl)amino]-6-ketocholestane (α-isomer of Compound No. 61 in Table 1AA); and methyl 3α-[N-(5-acetamido-3,5-dideoxy-2O-methyl-α-D-glycero-D-galacto-2-nonulopyranosonyl)amino]-5β-cholanate (α-isomer of Compound No. 55 in Table 1AA).

The second aspect of the sialic acid derivatives of the present invention relates to the compounds represented by the general formula (1BB). The groups defined in the above general formula (1BB) will be explained.

Examples of $C_1$–$C_{10}$ alkyl group include, for example, methyl group, ethyl group, n-propyl group, i-propyl group, n-butyl group, t-butyl group, n-pentyl group, n-hexyl group, n-heptyl group, n-octyl group, n-nonyl group, n-decyl group, 1,5-dimethylhexyl group and the like. Examples of $C_1$–$C_6$ alkyl group include the exemplified $C_1$–$C_6$ alkyl groups among the aforementioned $C_1$–$C_{10}$ alkyl groups. Examples of $C_1$–$C_4$ alkyl group include the exemplified $C_1$–$C_4$ alkyl groups among the aforementioned $C_1$–$C_{10}$ alkyl groups. Examples of $C_1$–$C_3$ alkyl group include the exemplified $C_1$–$C_3$ alkyl groups among the aforementioned $C_1$–$C_{10}$ alkyl groups.

Examples $C_1$–$C_{10}$ alkoxy group include, for example, methoxy group, ethoxy group, n-propoxy group, i-propoxy group, n-butoxy group, n-hexyloxy group, n-octyloxy group, n-decyloxy group and the like. Examples of $C_1$–$C_4$ alkoxy group include the exemplified $C_1$–$C_4$ alkoxy groups among the aforementioned $C_1$–$C_{10}$ alkoxy groups. Examples of phenyl-($C_1$–$C_3$ alkyloxy) group include benzyloxy group, phenethyloxy group and the like. Examples of phenyl-($C_1$–$C_3$ alkyl) group include benzyl group, phenethyl group and the like. Examples of halogen atom include, for example, fluorine atom, chlorine atom, bromine atom, and the like.

Examples of $C_2$–$C_7$ acyl group include acetyl group, propionyl group, butyryl group, valeryl group, benzoyl group and the like. Examples of $C_2$–$C_4$ acyl group include the exemplified $C_2$–$C_4$ acyl groups among the aforementioned $C_2$–$C_7$ acyl groups. Examples of $C_1$–$C_4$ alkylsulfonyl group include, for example, methylsulfonyl group, ethylsulfonyl group, n-propylsulfonyl group, n-butylsulfonyl group and the like. Examples of $C_1$–$C_4$ alkylamino group include methylamino group, ethylamino group, butylamino group and the like. Examples of $C_2$–$C_8$ dialkylamino group include, for example, dimethylamino group, diethylamino group, dibutylamino group and the like.

Examples of $C_2$–$C_7$ acylamino group include acetylamino group, propionylamino group and the like. Examples of $C_7$–$C_{11}$ aroyl group include benzoyl group, toluoyl group, naphthoyl group and the like. Examples of phenyl-($C_1$–$C_3$ alkyl)carbonyl group include benzylcarbonyl group, phenylethylcarbonyl group, phenylpropylcarbonyl group and the like. Examples of $C_2$–$C_{11}$ alkenyl include vinyl group, allyl group, butenyl group, pentenyl group, hexenyl group and the like. Examples of 1,3-dioxolane residue groups of:

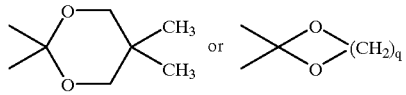

wherein q represents an integer of 1–4, and the like.

Groups not specifically mentioned in the above groups may be chosen by appropriate combination of the aforementioned atoms and functional groups or based on common knowledge of those skilled in the art.

As the residue of a steroid compound defined by $R^{101}$ in the above general formula (1BB), a preferred example includes the residue of a steroid compound represented by a group of:

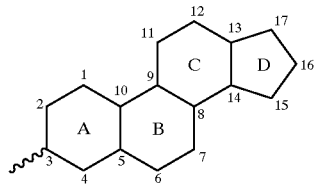

wherein the configuration at the 3-position of the steroid skeleton is either α or β, the rings A, B, C and D independently represent a saturated ring, a partially saturated ring, or an unsaturated ring, and the rings A, B, C and D may independently have one or more substituents selected from the group consisting of a $C_1$–$C_{10}$ alkoxy group; hydroxyl group; a $C_1$–$C_{10}$ alkyl group which may have one or more substituents selected from the group consisting of a $C_1$–$C_4$ alkyl group, a halogen atom, a $C_1$–$C_4$ alkoxy group, hydroxyl group, oxo group, 1,3-dioxolane residue, a group of —COOR$^{124}$ (wherein R$^{124}$ represents hydrogen atom, a $C_1$–$C_6$ alkyl group or a phenyl-($C_1$–$C_3$ alkyl) group), and a group of —CONR$^{125}$R$^{126}$ (wherein R$^{125}$ and R$^{126}$ independently represent hydrogen atom, a $C_1$–$C_6$ alkyl group or a phenyl-($C_1$–$C_3$ alkyl) group); a $C_2$–$C_{11}$ alkenyl group which may optionally have one or more substituents selected from the group consisting of a $C_1$–$C_4$ alkyl group, a halogen atom, a $C_1$–$C_4$ alkoxy group, hydroxyl group, oxo group, 1,3-dioxolane residue, a group of —COOR$^{124}$ (wherein R$^{124}$ represents hydrogen atom, a $C_1$–$C_6$ alkyl group, or a phenyl-($C_1$–$C_3$ alkyl) group), and a group of —CONR$^{125}$R$^{126}$ (wherein R$^{125}$ and R$^{126}$ independently represents hydrogen atom, a $C_1$–$C_6$ alkyl group, or a phenyl-($C_1$–$C_3$ alkyl) group); a halogen atom; oxo group; 1,3-dioxolane residue; a group of —COOR$^{127}$ (wherein R$^{127}$ represents hydrogen atom, a $C_1$–$C_6$ alkyl group or a phenyl-($C_1$–$C_3$ alkyl) group); and a group of —CONR$^{128}$R$^{129}$ (where R$^{128}$ and R$^{129}$ independently represent hydrogen atom, a $C_1$–$C_6$ alkyl group or a phenyl-($C_1$–$C_3$ alkyl) group).

A further preferred example includes the residue of a steroid compound represented by a group of:

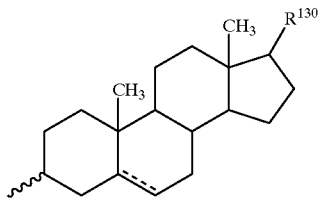

wherein the configuration at the 3-position of the steroid skeleton is either α or β, the broken line represents no bond or a single bond, and R$^{130}$ represents hydrogen atom; a $C_1$–$C_{10}$ alkyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{131}$ (wherein R$^{131}$ represents hydrogen atom, a $C_1$–$C_6$ alkyl group or a phenyl-($C_1$–$C_3$ alkyl) group), and a group of —CONR$^{132}$R$^{133}$ (wherein R$^{132}$ and R$^{133}$ independently represent hydrogen atom, a $C_1$–$C_6$ alkyl group or a phenyl-($C_1$–$C_3$ alkyl) group); a $C_2$–$C_{11}$ alkenyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{131}$ (wherein R$^{131}$ represents hydrogen atom, a $C_1$–$C_6$ alkyl group or a phenyl-($C_1$–$C_3$ alkyl) group), and a group of —CONR$^{132}$R$^{133}$ (where R$^{132}$ and R$^{133}$ independently represent hydrogen atom, a $C_1$–$C_6$ alkyl group or a phenyl-($C_1$–$C_3$ alkyl) group); a $C_1$–$C_4$ alkoxy group; hydroxyl group; oxo group; 1,3-dioxolane residue; a group of —COOR$^{134}$ (where R$^{134}$ represents hydrogen atom, a $C_1$–$C_6$ alkyl group or a phenyl-($C_1$–$C_3$ alkyl) group); or a group of —CONR$^{135}$R$^{136}$ (wherein R$^{135}$ and R$^{136}$ independently represent hydrogen atom, a $C_1$–$C_6$ alkyl group or a phenyl-($C_1$–$C_3$ alkyl) group).

A most preferred example includes the residue of a steroid compound represented by a group of:

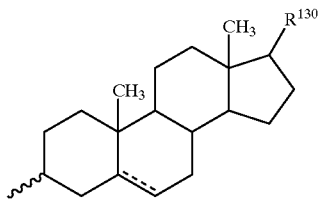

wherein the configuration at the 3-position of the steroid skeleton is either α or β, the broken line represents no bond or a single bond, and R$^{130}$ represents a $C_1$–$C_{10}$ alkyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{131}$ (wherein R$^{131}$ represents hydrogen atom, a $C_1$–$C_6$ alkyl group or a phenyl-($C_1$–$C_3$ alkyl) group), and a group of —CONR$^{132}$R$^{133}$ (wherein R$^{132}$ and R$^{133}$ independently represent hydrogen atom, a $C_1$–$C_6$ alkyl group, or a phenyl-($C_1$–$C_3$ alkyl) group); or a $C_2$–$C_{11}$ alkenyl group which may optionally have one or more substituents selected from the group consisting of a $C_1$–$C_4$ alkyl group, a $C_1$–$C_4$ alkoxy group, hydroxyl group, oxo group, 1,3-dioxolane residue, a group of —COOR$^{131}$ (wherein R$^{131}$ represents hydrogen atom, a $C_1$–$C_6$ alkyl group, or a phenyl-($C_1$–$C_3$ alkyl) group), and a group of —CONR$^{132}$R$^{133}$ (wherein R$^{132}$ and R$^{133}$ independently represent hydrogen atom, a $C_1$–$C_6$ alkyl group or a phenyl-($C_1$–$C_3$ alkyl) group).

Hydrogen atom is most preferred as $R^{102}$. As $R^{103}$, a $C_1$–$C_6$ alkyl group or a group of $C_6H_5$—$(CH_2)_l$— (wherein l represents an integer of 0–3) is preferred, and a $C_1$–$C_3$ alkyl group is most preferred. Hydrogen atom or a $C_2$–$C_4$ acyl group is preferred as $R^{104}$. Further preferred examples include hydrogen atom or acetyl group, and the most preferred example includes hydrogen atom. As $R^{105}$, a group of $R^{114}$O— (wherein $R^{114}$ represents hydrogen atom or acetyl group), or a group of $R^{115}$NH— [wherein $R^{115}$ represents a $C_2$–$C_4$ acyl group, or a group of $R^{116}$O$(CH_2)_p$—CO— (wherein $R^{116}$ represents hydrogen atom, a $C_1$–$C_4$ alkyl group, a phenyl-($C_1$–$C_3$ alkyl) group, or a $C_7$–$C_{11}$ aroyl group, and p represents an integer of 0–4)] is preferred, and further preferred examples include a group of $R^{114}$O— (wherein $R^{114}$ represents hydrogen atom or acetyl group) or a group of group $R^{115}$NH— (wherein $R^{115}$ represents a $C_2$–$C_4$ acyl group), and the most preferred example includes a group of $R^{115}$NH— (wherein $R^{115}$ represents acetyl group). Oxygen atom is most preferred as X.

Preferred examples as Y include a group represented by the following formula: —$(CH_2)_q$—CH($R^{120}$)—$(CH_2)_r$— [wherein $R^{120}$ represents hydrogen atom; a $C_1$–$C_6$ alkyl group which may optionally have one or more substituents selected from the group consisting of hydroxyl group, a $C_1$–$C_4$ alkoxy group, amino group, a $C_2$–$C_7$ acylamino group, a group of $R^{121}$—O—CO—NH— (wherein $R^{121}$ represents a $C_1$–$C_6$ alkyl group or a phenyl-($C_1$–$C_3$ alkyl) group), and a group of $R^{122}$—O—CO— (wherein $R^{122}$ represents hydrogen atom, a $C_1$–$C_6$ alkyl group or a phenyl-($C_1$–$C_3$ alkyl) group); a $C_7$–$C_{11}$ aroyl group which may optionally have one or more substituents selected from the group consisting of a $C_1$–$C_4$ alkyl group, hydroxyl group, amino group and carboxyl group; phenyl group which may optionally have one or more substituents selected from the group consisting of a $C_1$–$C_4$ alkyl group, hydroxyl group, amino group, and carboxyl group; or a phenyl-($C_1$–$C_3$ alkyl) group which may optionally have one or more substituents selected from the group consisting of a $C_1$–$C_4$ alkyl group, a $C_1$–$C_4$ alkoxy group, a phenyl-($C_1$–$C_3$ alkyloxy) group, hydroxyl group, amino group, and carboxyl group, and q and r independently represent an integer of 0–3]; or a group represented by the following formula:

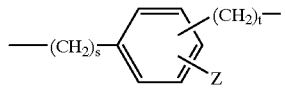

wherein Z represents hydrogen atom, a $C_1$–$C_4$ alkyl group, a $C_1$–$C_4$ alkoxy group, a phenyl-($C_1$–$C_3$ alkyloxy) group, hydroxyl group, amino group, a $C_2$–$C_7$ acylamino group or a group of $R^{123}$—O—CO— (wherein $R^{123}$ represents hydrogen atom, a $C_1$–$C_6$ alkyl group, or a phenyl-($C_1$–$C_3$ alkyl) group), and s and t independently represent an integer of 0–3. Most preferred examples include a group represented by the following formula: —$(CH_2)_q$—CH($R^{120}$)—$(CH_2)_r$— [wherein $R^{120}$ represents hydrogen atom; a $C_1$–$C_6$ alkyl group which may optionally have one or more substituents selected from the group consisting of hydroxyl group, a $C_1$–$C_4$ alkoxy group, amino group, a $C_2$–$C_7$ acylamino group, a group of $R^{121}$—O—CO—NH— (wherein $R^{121}$ represents a $C_1$–$C_6$ alkyl group or a phenyl-($C_1$–$C_3$ alkyl) group), and a group of $R^{122}$—O—CO— (wherein $R^{122}$ represents hydrogen atom, a $C_1$–$C_6$ alkyl group or a phenyl-($C_1$–$C_3$ alkyl) group); or a phenyl-($C_1$–$C_3$ alkyl) group which may optionally have one or more substituents selected from the group consisting of a $C_1$–$C_4$ alkoxy group, a phenyl-($C_1$–$C_3$ alkyloxy) group, and hydroxyl group, and q and r independently represent 0 or 1]; or a group represented by the following formula:

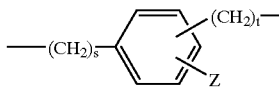

wherein Z represents hydrogen atom, a $C_1$–$C_4$ alkyl group, a $C_1$–$C_4$ alkoxy group, a phenyl-($C_1$–$C_3$ alkyloxy) group, hydroxyl group, amino group, a $C_2$–$C_7$ acylamino group or a group of $R^{123}$—O—CO— (wherein $R^{123}$ represents hydrogen atom, a $C_1$–$C_6$ alkyl group, or a phenyl-($C_1$–$C_3$ alkyl) group), and s and t independently represent 0 or 1.

Specific examples of preferred compounds represented by the above general formula (1BB) are listed in Tables 1BB, 2BB, 3BB, 4BB, 5BB, and 6BB set out below. Among them, most preferred compounds include:

3α-[N-[N-(5-acetamido-3,5-dideoxy-2-O-methyl-α-D-glycero-D-galacto-2-nonulopyranosonyl)]-D-serylamino]cholestane (Compound No. 4 in Table 1BB, wherein the configuration at the 3-position of cholestane is α and the configuration of the serine residue is D);

3α-[N-[N-(5-acetamido-3,5-dideoxy-2O-methyl-α-D-glycero-D-galacto-2-nonulopyranosonyl)]-O-benzyl-D-serylamino]cholestane (Compound No. 12 in Table 1BB, wherein the configuration at the 3-position of cholestane is α and the configuration of the serine residue is D);

3α-[N-[N-(5-acetamido-3,5-dideoxy-2-O-methyl-α-D-glycero-D-galacto-2-nonulopyranosonyl)]-L-serylamino]cholestane (Compound No. 4 in Table 1BB, wherein the configuration at the 3-position of cholestane is αand the configuration of the serine residue is L);

3α-[N-[N-(5-acetamido-3,5-dideoxy-2-O-methyl-α-D-glycero-D-galacto-2-nonulopyranosonyl)]-O-benzyl-L-serylamino]cholestane (Compound No. 12 in Table 1BB, wherein the configuration at the 3-position of cholestane is α and the configuration of the serine residue is L);

3α-[N-[N$^α$-(5acetamido-3,5-dideoxy-2-O-methyl-α-D-glycero-D-galacto-2-nonulopyranosonyl)]-L-lysylamino]cholestane (Compound No. 14 in Table 1BB, wherein the configuration at the 3-position of cholestane is α and the configuration of the lysin residue is L);

3α-[N-[N$^α$-(5-acetamido-3,5-dideoxy-2-O-methyl-α-D-glycero-D-galacto-2-nonulopyranosonyl)]-N$^ε$-benzyloxycarbonyl-L-lysylamino]cholestane (Compound No. 16 in Table 1BB, wherein the configuration at the 3-position of cholestane is α and the configuration of the lysin residue is L);

3α-[N-[N-(5-acetamido-3,5-dideoxy-2-O-methyl-α-D-glycero-D-galacto-2-nonulopyranosonyl)]-L-asparagylamino]cholestane (Compound No. 24 in Table 1BB, wherein the configuration at the 3-position of cholestane is α and the configuration of asparagine residue is L);

3α-[N-[4-[N-(5-acetamido-4,7,8,9-tetra-O-acetyl-3,5-dideoxy-2-O-methyl-α-D-glycero-D-galacto-2-nonulopyranosonyl)amino]benzoyl]amino]cholestane (Compound No. 59 in Table 1BB, wherein the configuration at the 3-position of cholestane is α);

3α-[N-[4-[N-(5-acetamido-3,5-dideoxy-2-O-methyl-α-D-glycero-D-galacto-2-nonulopyranosonyl)amino]benzoyl]amino]cholestane (Compound No. 60 in Table 1BB, wherein the configuration at the 3-position of cholestane is α);

3α-[N-[2-acetamido-4-[N-(5-acetamido-4,7,8,9-tetra-O-acetyl-3,5-dideoxy-2-O-methyl-α-D-glycero-D-galacto-2-nonulopyranosonyl)amino]benzoyl]amino]-cholestane (Compound No. 69 in Table 1BB, wherein the configuration at the 3-position of cholestane is α); and 3α-[N-[3-[N-(5-acetamido-3,5-dideoxy-2-O-methyl-α-D-glycero-D-galacto-2-nonulopyranosonyl)amino]propionyl]amino]cholestane (Compound No. 22 in Table 1BB, wherein the configuration at the 3-position of cholestane is α).

TABLE 1AA

| Compound No. | $R^1$ | $R^2$ | $R^3$ | $R^4$ |
|---|---|---|---|---|
| 1 | cholestanyl-butanol group | H | —$CH_3$ | —$COCH_3$ |
| 2 | " | H | —$CH_3$ | —$COCH_2CH_3$ |
| 3 | " | H | —$CH_3$ | —$COC_6H_5$ |
| 4 | " | H | —$CH_3$ | H |
| 5 | " | —$CH_3$ | —$CH_3$ | —$COCH_3$ |
| 6 | " | —$CH_3$ | —$CH_3$ | H |
| 7 | " | H | —$CH_2CH_3$ | —$COCH_3$ |
| 8 | " | H | —$CH_2CH_3$ | H |
| 9 | " | H | —$(CH_2)_2CH_3$ | H |
| 10 | " | H | —$(CH_2)_3CH_3$ | H |
| 11 | " | H | —$(CH_2)_5CH_3$ | —$COCH_3$ |
| 12 | " | H | —$(CH_2)_5CH_3$ | H |
| 13 | " | H | —$C_6H_5$ | —$COCH_3$ |
| 14 | " | H | —$C_6H_5$ | H |
| 15 | cholestanyl-butanol group | H | —$CH_2C_6H_5$ | —$COCH_3$ |
| 16 | " | H | —$CH_2C_6H_5$ | H |
| 17 | " | H | —$(CH_2)_2C_6H_5$ | H |
| 18 | " | H | —$(CH_2)_3C_6H_5$ | H |
| 19 | " | H | 4-Cl-$C_6H_4$— | —$COCH_3$ |
| 20 | " | H | 4-Cl-$C_6H_4$— | H |

TABLE 1AA-continued
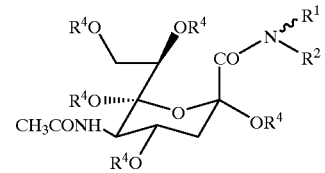
| Compound No. | R¹ | R² | R³ | R⁴ |
|---|---|---|---|---|
| 21 | " | H |  | H |
| 22 | " | H | 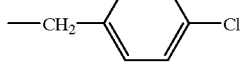 | H |
| 23 | 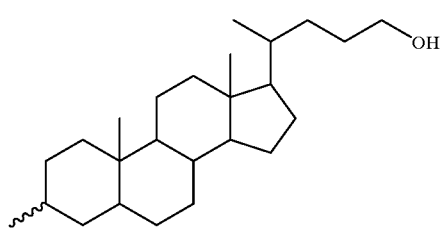 | H | 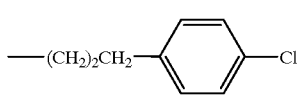 | H |
| 24 | " | H | 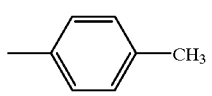 | H |
| 25 | " | H | 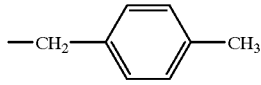 | H |
| 26 | " | H | 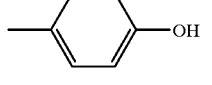 | H |
| 27 | " | H | 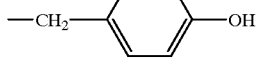 | H |
| 28 | " | H | 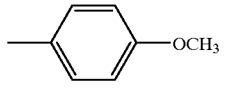 | H |
| 29 | 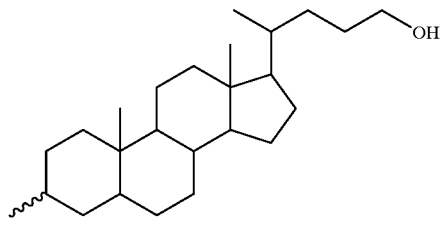 | H | 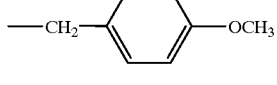 | H |
| 30 | " | H | 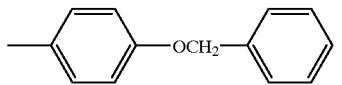 | H |

TABLE 1AA-continued
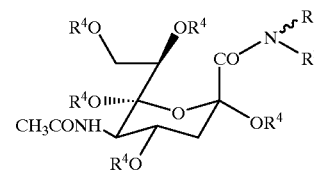
| Compound No. | R¹ | R² | R³ | R⁴ |
|---|---|---|---|---|
| 31 | " | H | 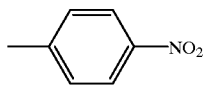 | H |
| 32 | " | H | 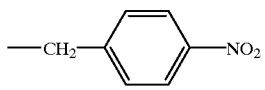 | H |
| 33 | " | H | 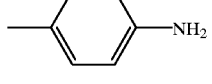 | H |
| 34 | " | H | 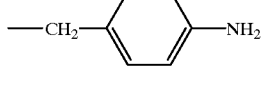 | H |
| 35 | 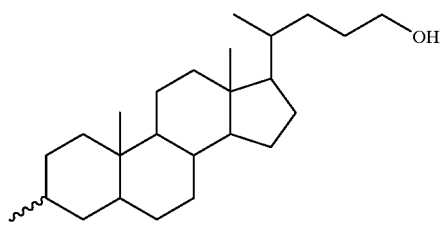 | H | 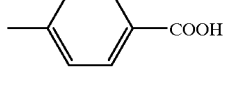 | H |
| 36 | " | H | 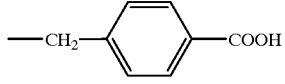 | H |
| 37 | " | H | 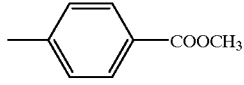 | H |
| 38 | " | H |  | H |
| 39 | " | H | —(CH$_2$)$_2$OH | —COCH$_3$ |
| 40 | " | H | —(CH$_2$)$_2$OH | H |
| 41 | " | H | —(CH$_2$)$_2$OCH$_3$ | H |
| 42 | " | H | —(CH$_2$)$_2$OCH$_2$C$_6$H$_5$ | H |
| 43 | " | H | —(CH$_2$)$_2$NH$_2$ | —COCH$_3$ |
| 44 | " | H | —(CH$_2$)$_2$NH$_2$ | H |
| 45 | " | H | —(CH$_2$)$_4$NH$_2$ | H |
| 46 | " | H | —(CH$_2$)$_2$NHCOCH$_3$ | —COCH$_3$ |

TABLE 1AA-continued

[Structure: pyranose ring with R⁴O, OR⁴, CH₃CONH, R⁴O substituents, CO-N(R¹)(R²), OR⁴, and R³ substituents]

| Compound No. | R¹ | R² | R³ | R⁴ |
|---|---|---|---|---|
| 47 | [cholestane-type steroid with side chain terminating in OH, attached via wavy bond at position 3] | H | —(CH₂)₂NHCOCH₃ | H |
| 48 | " | H | —(CH₂)₄NHCOCH₃ | H |
| 49 | " | H | —(CH₂)₂NHCOOCH₂C₆H₅ | —COCH₃ |
| 50 | " | H | —(CH₂)₂NHCOOCH₂C₆H₅ | H |
| 51 | " | H | —(CH₂)₂NHSO₂CH₃ | —COCH₃ |
| 52 | " | H | —(CH₂)₂NHSO₂CH₃ | H |
| 53 | " | H | —(CH₂)₂NHSO₂—C₆H₅ | H |
| 54 | [steroid with side chain terminating in COOCH₃, attached via wavy bond at position 3] | H | —CH₃ | —COCH₃ |
| 55 | " | H | —CH₃ | H |
| 56 | [steroid with side chain terminating in COOH, attached via wavy bond at position 3] | H | —CH₃ | —COCH₃ |
| 57 | " | H | —CH₃ | H |
| 58 | [cholestane with isooctyl side chain and 1,3-dioxolane at position 6, attached via wavy bond at position 3] | H | —CH₃ | —COCH₃ |
| 59 | " | H | —CH₃ | H |

TABLE 1AA-continued

| Compound No. | R¹ | R² | R³ | R⁴ |
|---|---|---|---|---|
| 60 | (cholestan-6-one steroid) | H | —CH₃ | —COCH₃ |
| 61 | " | H | —CH₃ | H |
| 62 | (7-hydroxy cholanic acid methyl ester steroid) | H | —CH₃ | —COCH₃ |
| 63 | " | H | —CH₃ | H |
| 64 | (7-hydroxy cholanic acid steroid) | H | —CH₃ | —COCH₃ |
| 65 | " | H | —CH₃ | H |
| 66 | (diol steroid) | H | —CH₃ | —COCH₃ |
| 67 | " | H | —CH₃ | H |

TABLE 1AA-continued
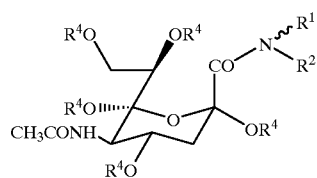
| Compound No. | R[1] | R[2] | R[3] | R[4] |
|---|---|---|---|---|
| 68 | (steroid with ketone) | H | —CH$_3$ | —COCH$_3$ |
| 69 | " | H | —CH$_3$ | H |
| 70 | (steroid with CONH$_2$) | H | —CH$_3$ | —COCH$_3$ |
| 71 | " | H | —CH$_3$ | H |
| 72 | (steroid with CONHCH$_3$) | H | —CH$_3$ | —COCH$_3$ |
| 73 | " | H | —CH$_3$ | H |
| 74 | (steroid with CON(CH$_3$)$_2$) | H | —CH$_3$ | —COCH$_3$ |
| 75 | " | H | —CH$_3$ | H |

TABLE 2AA

| Compound No. | R¹ | R² | R³ | R⁴ |
|---|---|---|---|---|
| 76 | steroid with OH | H | —CH₃ | —COCH₃ |
| 77 | " | H | —CH₃ | H |
| 78 | " | H | —CH₃ | —COCH₂CH₃ |
| 79 | steroid with OH | H | —CH₃ | —COC₆H₅ |
| 80 | " | —CH₃ | —CH₃ | H |
| 81 | " | H | —CH₂CH₃ | H |
| 82 | " | H | —C₆H₅ | H |
| 83 | " | H | —CH₂C₆H₅ | H |
| 84 | " | H | —(CH₂)₂OH | H |
| 85 | " | H | —(CH₂)₂NH | H |
| 86 | steroid with COOCH₃ | H | —CH₃ | —COCH₃ |
| 87 | " | H | —CH₃ | H |
| 88 | steroid with COOH | H | —CH₃ | —COCH₃ |
| 89 | " | H | —CH₃ | H |

TABLE 2AA-continued
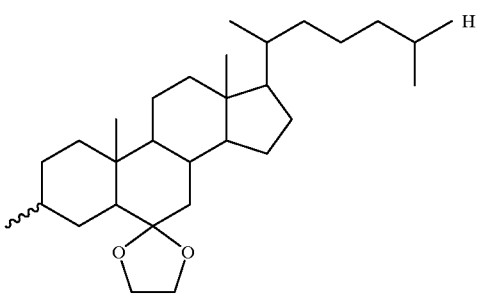
| Compound No. | R¹ | R² | R³ | R⁴ |
|---|---|---|---|---|
| 90 | 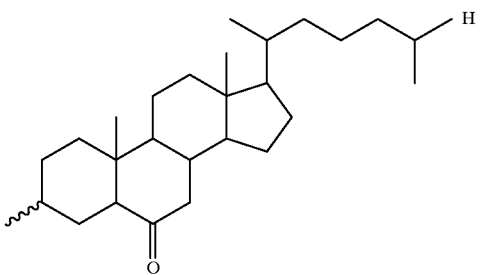 | H | —CH₃ | —COCH₃ |
| 91 | " | H | —CH₃ | H |
| 92 | 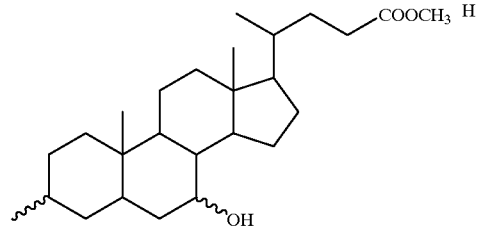 | H | —CH₃ | —COCH₃ |
| 93 | " | H | —CH₃ | H |
| 94 | 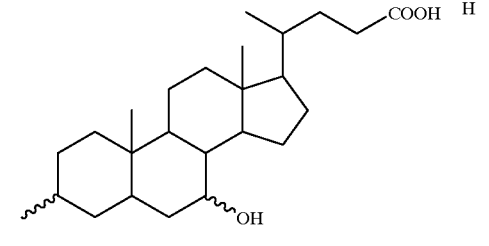 | H | —CH₃ | —COCH₃ |
| 95 | " | H | —CH₃ | H |
| 96 | 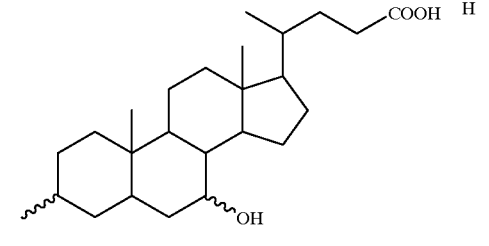 | H | —CH₃ | —COCH₃ |
| 97 | " | H | —CH₃ | H |

TABLE 2AA-continued

| Compound No. | R¹ | R² | R³ | R⁴ |
|---|---|---|---|---|
| 98 | (dihydroxy steroid structure) | H | —CH$_3$ | —COCH$_3$ |
| 99 | " | H | —CH$_3$ | H |
| 100 | (ketosteroid structure) | H | —CH$_3$ | —COCH$_3$ |
| 101 | " | H | —CH$_3$ | H |
| 102 | (CONH$_2$ steroid structure) | H | —CH$_3$ | —COCH$_3$ |
| 103 | " | H | —CH$_3$ | H |
| 104 | (CONHCH$_3$ steroid structure) | H | —CH$_3$ | —COCH$_3$ |
| 105 | " | H | —CH$_3$ | H |
| 106 | (CON(CH$_3$)$_2$ steroid structure) | H | —CH$_3$ | —COCH$_3$ |

TABLE 2AA-continued

| Compound No. | R¹ | R² | R³ | R⁴ |
|---|---|---|---|---|
| 107 | " | H | —CH₃ | H |

TABLE 3AA

| Compound No. | R¹ | R² | R³ | R⁴ |
|---|---|---|---|---|
| 108 | [cholesterol-like steroid with terminal OH] | H | —CH₃ | —COCH₃ |
| 109 | " | H | —CH₃ | H |
| 110 | [steroid with terminal OH] | H | —CH₃ | —COCH₂CH₃ |
| 111 | " | H | —CH₃ | —COC₆H₅ |
| 112 | " | —CH₃ | —CH₃ | H |
| 113 | " | H | —CH₂CH₃ | H |
| 114 | " | H | —C₆H₅ | H |
| 115 | " | H | —CH₂C₆H₅ | H |
| 116 | " | H | —(CH₂)₂OH | H |
| 117 | " | H | —(CH₂)₂NH | H |
| 118 | [steroid with terminal COOCH₃] | H | —CH₃ | —COCH₃ |
| 119 | " | H | —CH₃ | H |

TABLE 3AA-continued

| Compound No. | R¹ | R² | R³ | R⁴ |
|---|---|---|---|---|
| 120 | cholanic acid-COOH steroid | H | —CH₃ | —COCH₃ |
| 121 | " | H | —CH₃ | H |
| 122 | cholestane with spiro-dioxolane steroid | H | —CH₃ | —COCH₃ |
| 123 | " | H | —CH₃ | H |
| 124 | 6-oxo-cholestane steroid | H | —CH₃ | —COCH₃ |
| 125 | " | H | —CH₃ | H |
| 126 | 7-hydroxy cholanic acid methyl ester steroid | H | —CH₃ | —COCH₃ |
| 127 | " | H | —CH₃ | H |

TABLE 3AA-continued

| Compound No. | R¹ | R² | R³ | R⁴ |
|---|---|---|---|---|
| 128 | [steroid with COOH and OH substituents] | H | —CH₃ | —COCH₃ |
| 129 | " | H | —CH₃ | H |
| 130 | [steroid with HO and OH (diol) substituents] | H | —CH₃ | —COCH₃ |
| 131 | " | H | —CH₃ | H |
| 132 | [steroid with ketone] | H | —CH₂ | —COCH₃ |
| 133 | " | H | —CH₃ | H |
| 134 | [steroid with CONH₂ substituent] | H | —CH₃ | —COCH₃ |
| 135 | " | H | —CH₃ | H |
| 136 | [steroid with CONHCH₃ substituent] | H | —CH₃ | —COCH₃ |
| 137 | " | H | —CH₃ | H |

TABLE 3AA-continued
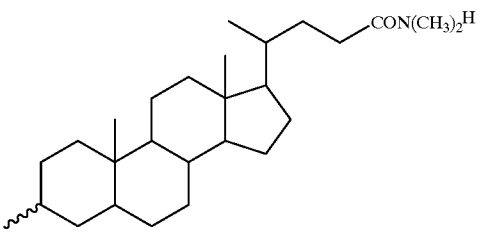
| Compound No. | R¹ | R² | R³ | R⁴ |
| --- | --- | --- | --- | --- |
| 138 | (cholestane with CON(CH₃)₂ side chain) | H | —CH₃ | —COCH₃ |
| 139 | " | H | —CH₃ | H |
TABLE 4AA
| Compound No. | R¹ | R² | R³ | R⁴ |
| --- | --- | --- | --- | --- |
| 140 | (cholestane with OH side chain) | H | —CH₃ | —COCH₃ |
| 141 | (cholestane with OH side chain) | H | —CH₃ | H |
| 142 | " | H | —CH₃ | —COCH₂CH₃ |
| 143 | " | H | —CH₃ | —COC₆H₅ |
| 144 | " | —CH₃ | —CH₃ | H |
| 145 | " | H | —CH₂CH₃ | H |
| 146 | " | H | —C₆H₅ | H |
| 147 | " | H | —CH₂C₆H₅ | H |
| 148 | " | H | —(CH₂)₂OH | H |
| 149 | " | H | —(CH₂)₂NH | H |

TABLE 4AA-continued

| Compound No. | R¹ | R² | R³ | R⁴ |
|---|---|---|---|---|
| 150 | [steroid with COOCH₃ side chain] | H | —CH₃ | —COCH₃ |
| 151 | " | H | —CH₃ | H |
| 152 | [steroid with COOH side chain] | H | —CH₃ | —COCH₃ |
| 153 | " | H | —CH₃ | H |
| 154 | [steroid with isoprenyl side chain and dioxolane] | H | —CH₃ | —COCH₃ |
| 155 | " | H | —CH₃ | H |
| 156 | [steroid with isoprenyl side chain and 6-keto] | H | —CH₃ | —COCH₃ |
| 157 | " | H | —CH₃ | H |

TABLE 4AA-continued

| Compound No. | R¹ | R² | R³ | R⁴ |
|---|---|---|---|---|
| 158 | (steroid with COOCH₃ side chain and OH) | H | —CH₃ | —COCH₃ |
| 159 | " | H | —CH₃ | H |
| 160 | (steroid with COOH side chain and OH) | H | —CH₃ | —COCH₃ |
| 161 | " | H | —CH₃ | H |
| 162 | (steroid with HO and OH diol side chain) | H | —CH₃ | —COCH₃ |
| 163 | " | H | —CH₃ | H |
| 164 | (steroid with ketone) | H | —CH₃ | —COCH₃ |
| 165 | " | H | —CH₃ | H |
| 166 | (steroid with CONH₂ side chain) | H | —CH₃ | —COCH₃ |
| 167 | " | H | —CH₃ | H |

TABLE 4AA-continued

| Compound No. | R¹ | R² | R³ | R⁴ |
|---|---|---|---|---|
| 168 | [cholestane-CONHCH₃] | H | —CH₃ | —COCH₃ |
| 169 | " | H | —CH₃ | H |
| 170 | [cholestane-CON(CH₃)₂] | H | —CH₃ | —COCH₃ |
| 171 | " | H | —CH₃ | H |

TABLE 5AA

| Compound No. | R¹ | R⁴ | R⁵ |
|---|---|---|---|
| 172 | [cholestane-OH] | H | CH₃CH₂CONH— |
| 173 | [cholestane-OH] | H | CH₃(CH₂)₂CONH— |

TABLE 5AA-continued

| Compound No. | R¹ | R⁴ | R⁵ |
|---|---|---|---|
| 174 | " | H | $(CH_3)_2CHCONH-$ |
| 175 | " | H | $CH_3(CH_2)_3CONH-$ |
| 176 | " | H | $CH_3(CH_2)_4CONH-$ |
| 177 | " | H | $CH_3(CH_2)_5CONH-$ |
| 178 | " | H | $HOCH_2CONH-$ |
| 179 | " | H | $CH_3OCH_2CONH-$ |
| 180 | " | H | $C_6H_5OCH_2CONH-$ |
| 181 | " | H | $C_6H_5CH_2OCH_2CONH-$ |
| 182 | " | H | $HO(CH_2)_2CONH-$ |
| 183 | " | H | $HO(CH_2)_3CONH-$ |
| 184 | " | H | $HO(CH_2)_4CONH-$ |
| 185 | " | H | $CH_3OCONH-$ |
| 186 | " | H | $CH_3CH_2OCONH-$ |
| 187 | " | H | $CH_3(CH_2)_2OCONH-$ |
| 188 | " | H | $CH_3(CH_2)_3OCONH-$ |
| 189 | " | H | $(CH_3)_3OCONH-$ |
| 190 | " | H | $C_6H_5CH_2OCONH-$ |
| 191 | " | H | $C_6H_5CONH-$ |
| 192 | (steroid with OH) | H | (2-naphthyl-C(O)NH–) |
| 193 | " | H | (1-naphthyl-C(O)NH–) |
| 194 | " | H | (4-methylphenyl-C(O)NH–) |
| 195 | " | H | (3-methylphenyl-C(O)NH–) |
| 196 | " | H | (2-methylphenyl-C(O)NH–) |

TABLE 5AA-continued

[Structure: pyranose ring with substituents R⁴O, OR⁴, R⁴O, R⁵, R⁴O, CO-NH-R¹, OCH₃]

| Compound No. | R¹ | R⁴ | R⁵ |
|---|---|---|---|
| 197 | [steroid structure with side chain ending in OH] | H | [4-chlorobenzoyl-NH-] |
| 198 | | H | [4-hydroxybenzoyl-NH-] |
| 199 | | H | [4-nitrobenzoyl-NH-] |
| 200 | | H | [4-aminobenzoyl-NH-] |
| 201 | | H | [4-carboxybenzoyl-NH-] |
| 202 | | H | [phenylacetyl-NH-] |
| 203 | | H | —OH |
| 204 | [steroid structure with side chain ending in OH] | CH₃CO— | CH₃CH₂CONH— |
| 205 | " | CH₃CO— | CH₃(CH₂)₂CONH— |
| 206 | " | CH₃CO— | (CH₃)₂CHCONH— |
| 207 | " | CH₃CO— | CH₃(CH₂)₃CONH— |
| 208 | " | CH₃CO— | CH₃(CH₂)₄CONH— |
| 209 | " | CH₃CO— | CH₃(CH₂)₅CONH— |
| 210 | " | CH₃CO— | HOCH₂CONH— |
| 211 | " | CH₃CO— | CH₃OCH₂CONH— |
| 212 | " | CH₃CO— | C₆H₅OCH₂CONH— |
| 213 | " | CH₃CO— | C₆H₅CH₂OCH₂CONH— |
| 214 | " | CH₃CO— | HO(CH₂)₂CONH— |
| 215 | " | CH₃CO— | HO(CH₂)₃CONH— |
| 216 | " | CH₃CO— | HO(CH₂)₄CONH— |

TABLE 5AA-continued

| Compound No. | R¹ | R⁴ | R⁵ |
|---|---|---|---|
| 217 | " | CH₃CO— | CH₃OCONH— |
| 218 | " | CH₃CO— | CH₃CH₂OCONH— |
| 219 | " | CH₃CO— | CH₃(CH₂)₂OCONH— |
| 220 | " | CH₃CO— | CH₃(CH₂)₃OCONH— |
| 221 | " | CH₃CO— | (CH₃)₃OCONH— |
| 222 | " | CH₃CO— | C₆H₅CH₂OCONH— |
| 223 | " | CH₃CO— | C₆C₅CONH— |
| 224 | [cholestane-type steroid with OH] | CH₃CO— | [2-naphthoyl-NH—] |
| 225 | " | CH₃CO— | [1-naphthoyl-NH—] |
| 226 | " | CH₃CO— | [4-methylbenzoyl-NH—] |
| 227 | " | CH₃CO— | [3-methylbenzoyl-NH—] |
| 228 | " | CH₃CO— | [2-methylbenzoyl-NH—] |
| 229 | [cholestane-type steroid with OH] | CH₃CO— | [4-chlorobenzoyl-NH—] |

TABLE 5AA-continued
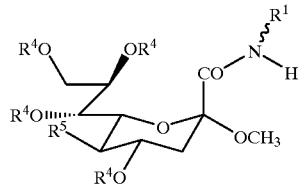
| Compound No. | R¹ | R⁴ | R⁵ |
|---|---|---|---|
| 230 | " | $CH_3CO-$ | 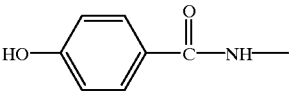 |
| 231 | " | $CH_3CO-$ | 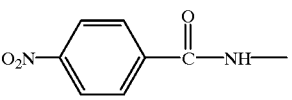 |
| 232 | " | $CH_3CO-$ | 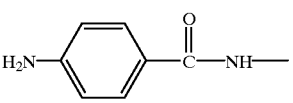 |
| 233 | " | $CH_3CO-$ | 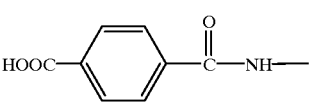 |
| 234 | " | $CH_3CO-$ | 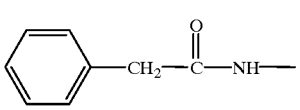 |
| 235 | " | $CH_3CO-$ | $CH_3COO-$ |
| 236 | 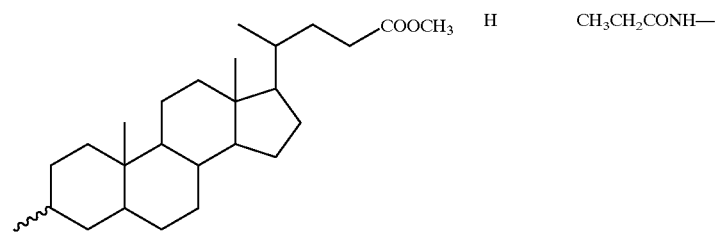 | H | $CH_3CH_2CONH-$ |
| 237 | " | H | $HOCH_2CONH-$ |
| 238 | " | H | $(CH_3)_3OCONH-$ |
| 239 | " | H | $C_6H_5CH_2OCONH-$ |
| 240 | " | H | 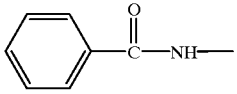 |
| 241 | " | H | $HO-$ |
| 242 | " | $CH_3CO-$ | $CH_3COO-$ |

TABLE 5AA-continued

| Compound No. | R¹ | R⁴ | R⁵ |
|---|---|---|---|
| 243 | (cholanic acid-type steroid with COOH) | H | HOCH$_2$CONH— |
| 244 | " | H | (CH$_3$)$_3$OCONH— |
| 245 | " | H | C$_6$H$_5$CH$_2$OCONH— |
| 246 | " | H | HO— |
| 247 | (cholanic acid-type steroid with COOH) | CH$_3$CO— | CH$_3$COO— |
| 248 | (cholestane-type steroid with dioxolane) | H | HOCH$_2$CONH— |
| 249 | " | H | HO— |
| 250 | " | CH$_3$CO— | CH$_3$COO— |
| 251 | (cholestane-type steroid with 6-oxo) | H | HOCH$_2$CONH— |
| 252 | " | H | HO— |
| 253 | " | CH$_3$CO— | CH$_3$COO— |

TABLE 5AA-continued
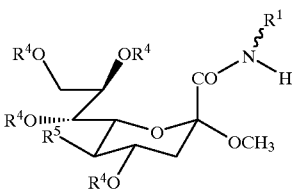
| Compound No. | R[1] | R[4] | R[5] |
|---|---|---|---|
| 254 | (steroid with COOCH₃ side chain and OH) | H | HOCH₂CONH— |
| 255 | " | H | HO— |
| 256 | " | CH₃CO— | CH₃COO— |
| 257 | (steroid with COOH side chain and OH) | H | HOCH₂CONH— |
| 258 | " | H | HO— |
| 259 | " | CH₃CO— | CH₃COO— |
| 260 | (steroid with HO and OH diol side chain) | H | HOCH₂CONH— |
| 261 | " | H | HO— |
| 262 | (steroid with HO and OH diol side chain) | CH₃CO— | CH₃COO— |
| 263 | (steroid with ketone) | H | HOCH₂CONH— |

TABLE 5AA-continued

| Compound No. | R¹ | R⁴ | R⁵ |
|---|---|---|---|
| 264 | " | H | HO— |
| 265 | " | CH₃CO— | CH₃COO— |
| 266 | [steroid-CONH₂] | H | HOCH₂CONH— |
| 267 | " | H | HO— |
| 268 | " | CH₃CO— | CH₃COO— |
| 269 | [steroid-CONHCH₃] | H | HOCH₂CONH— |
| 270 | " | H | HO— |
| 271 | " | CH₃CO— | CH₃COO— |
| 272 | [steroid-CONH(CH₃)₂] | H | HOCH₂CONH— |
| 273 | " | H | HO— |
| 274 | " | CH₃CO— | CH₃COO— |

TABLE 6AA

| Compound No. | R¹ | R⁴ | R⁵ |
|---|---|---|---|
| 275 | [steroid with side chain terminating in OH] | H | HOCH$_2$CONH— |
| 276 | " | H | HO— |
| 277 | " | CH$_3$CO— | CH$_3$COO— |
| 278 | [steroid with side chain terminating in COOCH$_3$] | H | HOCH$_2$CONH— |
| 279 | " | H | HO— |
| 280 | " | CH$_3$CO— | CH$_3$COO— |
| 281 | [steroid with side chain terminating in COOH] | H | HOCH$_2$CONH— |
| 282 | " | H | HO— |
| 283 | " | CH$_3$CO— | CH$_3$COO— |
| 284 | [steroid with isopropyl-terminated side chain and dioxolane] | H | HOCH$_2$CONH— |
| 285 | " | H | HO— |
| 286 | " | CH$_3$CO— | CH$_3$COO— |

TABLE 6AA-continued

| Compound No. | R¹ | R⁴ | R⁵ |
|---|---|---|---|
| 287 | (cholestanone-like steroid) | H | HOCH$_2$CONH— |
| 288 | " | H | HO— |
| 289 | " | CH$_3$CO— | CH$_3$COO— |
| 290 | (steroid with COOCH$_3$ and 7-OH) | H | HOCH$_2$CONH— |
| 291 | (steroid with COOCH$_3$ and 7-OH) | H | HO— |
| 292 | " | CH$_3$CO— | CH$_3$COO— |
| 293 | (steroid with COOH and 7-OH) | H | HOCH$_2$CONH— |
| 294 | " | H | HO— |
| 295 | " | CH$_3$CO— | CH$_3$COO— |

TABLE 6AA-continued

| Compound No. | R¹ | R⁴ | R⁵ |
|---|---|---|---|
| 296 | (steroid with HO, OH side chain) | H | HOCH$_2$CONH— |
| 297 | " | H | HO— |
| 298 | " | CH$_3$CO— | CH$_3$COO— |
| 299 | (steroid with ketone) | H | HOCH$_2$CONH— |
| 300 | " | H | HO— |
| 301 | " | CH$_3$CO— | CH$_3$COO— |
| 302 | (steroid with CONH$_2$ side chain) | H | HOCH$_2$CONH— |
| 303 | " | H | HO— |
| 304 | " | CH$_3$CO— | CH$_3$COO— |
| 305 | (steroid with CONHCH$_3$ side chain) | H | HOCH$_2$CONH— |
| 306 | " | H | HO— |
| 307 | " | CH$_3$CO— | CH$_3$COO— |

TABLE 6AA-continued
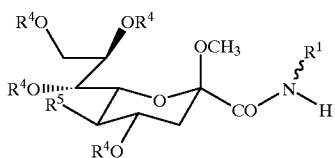
| Compound No. | R¹ | R⁴ | R⁵ |
|---|---|---|---|
| 308 | (cholestane-CON(CH₃)₂ group) | H | HOCH₂CONH— |
| 309 | " | H | HO— |
| 310 | " | CH₃CO— | CH₃COO— |
TABLE 1BB
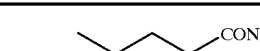
| Compound No. | $R^{101}$ | Y | $R^{102}$ | $R^{103}$ | $R^{104}$ |
|---|---|---|---|---|---|
| 1 | (cholestanyl) | (CH(CH₂OH)CH—) | H | —CH₃ | —COCH₃ |
| 2 | " | " | H | —CH₃ | —COCH₂CH₃ |
| 3 | " | " | H | —CH₃ | —COC₆H₅ |
| 4 | " | " | H | —CH₃ | H |
| 5 | " | " | —CH₃ | —CH₃ | —COCH₃ |
| 6 | " | " | —CH₃ | —CH₃ | H |
| 7 | " | " | H | —CH₂CH₃ | —COCH₃ |
| 8 | " | " | H | —CH₂CH₃ | H |
| 9 | " | " | H | —CH₂C₆H₅ | —COCH₃ |
| 10 | " | " | H | —CH₂C₆H₅ | H |
| 11 | (cholestanyl) | (CH(CH₂OCH₂C₆H₅)CH—) | H | —CH₃ | —COCH₃ |
| 12 | " | " | H | —CH₃ | H |

TABLE 1BB-continued
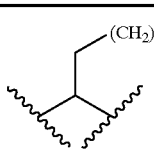
| Compound No. | R[101] | Y | R[102] | R[103] | R[104] |
|---|---|---|---|---|---|
| 13 | " | 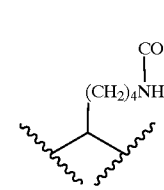 | H | —CH₃ | —COCH₃ |
| 14 | " | " | H | —CH₃ | H |
| 15 | " | 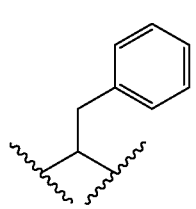 | H | —CH₃ | —COCH₃ |
| 16 | " | " | H | —CH₃ | H |
| 17 | " | 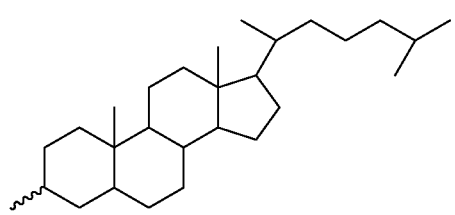 | H | —CH₃ | —COCH₃ |
| 18 | " | " | H | —CH₃ | H |
| 19 | 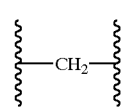 | 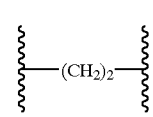 | H | —CH₃ | —COCH₃ |
| 20 | " | " | H | —CH₃ | H |
| 21 | " | 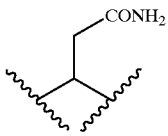 | H | —CH₃ | —COCH₃ |
| 22 | " | " | H | —CH₃ | H |
| 23 | " |  | H | —CH₃ | —COCH₃ |
| 24 | " | " | H | —CH₃ | H |

TABLE 1BB-continued

| Compound No. | R¹⁰¹ | Y | R¹⁰² | R¹⁰³ | R¹⁰⁴ |
|---|---|---|---|---|---|
| 25 | " | 4-(benzyloxy)benzyl-substituted | H | —CH₃ | —COCH₃ |
| 26 | " | " | H | —CH₃ | H |
| 27 | cholestanyl | 4-hydroxybenzyl-substituted | H | —CH₃ | —COCH₃ |
| 28 | " | " | H | —CH₃ | H |
| 29 | " | CONH₂-substituted | H | —CH₃ | —COCH₃ |
| 30 | " | " | H | —CH₃ | H |
| 31 | " | COOH-substituted | H | —CH₃ | —COCH₃ |
| 32 | " | " | H | —CH₃ | H |
| 33 | " | COOH-substituted | H | —CH₃ | —COCH₃ |
| 34 | " | " | H | —CH₃ | H |

TABLE 1BB-continued

| Compound No. | R¹⁰¹ | Y | R¹⁰² | R¹⁰³ | R¹⁰⁴ |
|---|---|---|---|---|---|
| 35 | cholestanyl | -CH(CH₂NHC(=NH)NH₂)- (CH₂)₃NH-C(=NH)NH₂ branch | H | —CH₃ | —COCH₃ |
| 36 | " | " | H | —CH₃ | H |
| 37 | " | imidazolylmethyl (histidine side chain) | H | —CH₃ | —COCH₃ |
| 38 | " | " | H | —CH₃ | H |
| 39 | " | CH(CH(OH)CH₃)- | H | —CH₃ | —COCH₃ |
| 40 | " | " | H | —CH₃ | H |
| 41 | " | CH(CH(CH₃)₂)- | H | —CH₃ | —COCH₃ |
| 42 | " | " | H | —CH₃ | H |
| 43 | " | CH(CH(CH₃)CH₂CH₃)- | H | —CH₃ | —COCH₃ |
| 44 | " | " | H | —CH₃ | H |

TABLE 1BB-continued
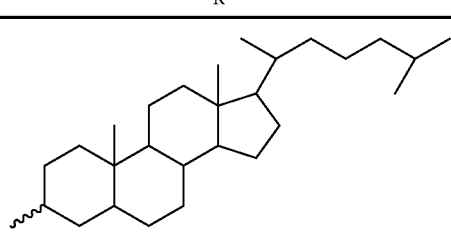
| Compound No. | R¹⁰¹ | Y | R¹⁰² | R¹⁰³ | R¹⁰⁴ |
|---|---|---|---|---|---|
| 45 | 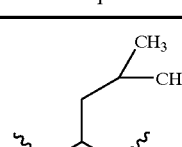 | 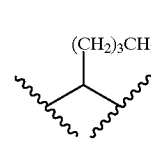 | H | —$CH_3$ | —$COCH_3$ |
| 46 | " | " | H | —$CH_3$ | H |
| 47 | " | 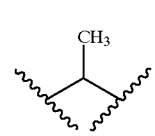 | H | —$CH_3$ | —$COCH_3$ |
| 48 | " | " | H | —$CH_3$ | H |
| 49 | " | 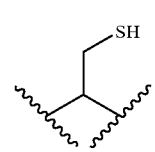 | H | —$CH_3$ | —$COCH_3$ |
| 50 | " | " | H | —$CH_3$ | H |
| 51 | " | 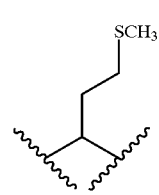 | H | —$CH_3$ | —$COCH_3$ |
| 52 | " | " | H | —$CH_3$ | H |
| 53 | " | 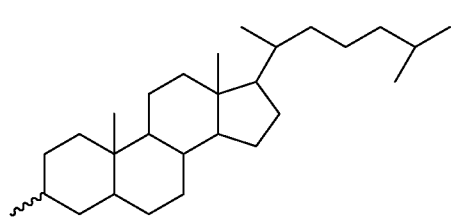 | H | —$CH_3$ | —$COCH_3$ |
| 54 | " | " | H | —$CH_3$ | H |
| 55 | 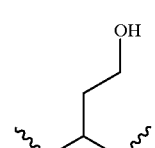 |  | H | —$CH_3$ | —$COCH_3$ |
| 56 | " | " | H | —$CH_3$ | H |

TABLE 1BB-continued

| Compound No. | R¹⁰¹ | Y | R¹⁰² | R¹⁰³ | R¹⁰⁴ |
|---|---|---|---|---|---|
| 57 | " | (indol-2-ylmethyl-CH branching) | H | —CH₃ | —COCH₃ |
| 58 | " | " | H | —CH₃ | H |
| 59 | " | (1,4-phenylene) | H | —CH₃ | —COCH₃ |
| 60 | " | " | H | —CH₃ | H |
| 61 | " | (1,4-C₆H₄—CH₂) | H | —CH₃ | —COCH₃ |
| 62 | " | " | H | —CH₃ | H |
| 63 | " | (CH₂—1,4-C₆H₄) | H | —CH₃ | —COCH₃ |
| 64 | " | " | H | —CH₃ | H |
| 65 | (cholestanyl) | (2-hydroxy-1,4-phenylene) | H | —CH₃ | —COCH₃ |
| 66 | " | " | H | —CH₃ | H |
| 67 | " | (2-hydroxy-1,3-phenylene) | H | —CH₃ | —COCH₃ |
| 68 | " | " | H | —CH₃ | H |

TABLE 1BB-continued

[Structure: Sugar with OR$^{104}$, OR$^{104}$, R$^{104}$O, CH$_3$CONH, R$^{104}$O substituents on pyranose ring, with OR$^{103}$, and CONH—Y—CON(R$^{101}$)(R$^{102}$)]

| Compound No. | R$^{101}$ | Y | R$^{102}$ | R$^{103}$ | R$^{104}$ |
|---|---|---|---|---|---|
| 69 | " | phenyl with NHAc | H | —CH$_3$ | —COCH$_3$ |
| 70 | " | " | H | —CH$_3$ | H |
| 71 | " | phenyl with AcHN | H | —CH$_3$ | —COCH$_3$ |
| 72 | " | " | H | —CH$_3$ | H |
| 73 | cholesteryl | CH(CH$_2$OH) | H | —CH$_3$ | —COCH$_3$ |
| 74 | " | " | H | —CH$_3$ | H |
| 75 | " | CH(CH$_2$)$_4$NH$_2$ | H | —CH$_3$ | —COCH$_3$ |
| 76 | " | " | H | —CH$_3$ | H |
| 77 | " | p-phenylene | H | —CH$_3$ | —COCH$_3$ |
| 78 | " | " | H | —CH$_3$ | H |
| 79 | " | phenyl with NHAc | H | —CH$_3$ | —COCH$_3$ |
| 80 | " | " | H | —CH$_3$ | H |
| 81 | " | CH(CH$_2$CONH$_2$) | H | —CH$_3$ | —COCH$_3$ |

TABLE 1BB-continued

| Compound No. | R¹⁰¹ | Y | R¹⁰² | R¹⁰³ | R¹⁰⁴ |
|---|---|---|---|---|---|
| 82 | " | " | H | —CH₃ | H |
| 83 | cholesterol structure | —(CH₂)₂— | H | —CH₃ | —COCH₃ |
| 84 | " | " | H | —CH₃ | H |
| 85 | cholesterol structure | CH(CH₂OH) | H | —CH₃ | —COCH₃ |
| 86 | " | " | H | —CH₃ | H |
| 87 | cholesterol derivative with OH | CH(CH₂OH) | H | —CH₃ | —COCH₃ |
| 88 | " | " | H | —CH₃ | H |
| 89 | cholesterol derivative with OH | CH(CH₂OCH₂C₆H₅) | H | —CH₃ | —COCH₃ |
| 90 | " | " | H | —CH₃ | H |

TABLE 1BB-continued
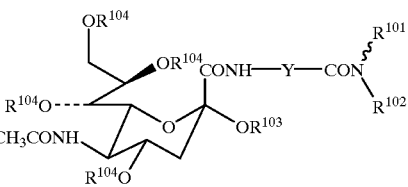
| Compound No. | R¹⁰¹ | Y | R¹⁰² | R¹⁰³ | R¹⁰⁴ |
|---|---|---|---|---|---|
| 91 | [steroid with OAc side chain] | [CH with OH] | H | —CH₃ | —COCH₃ |
| 92 | " | [CH with OCH₂C₆H₅] | H | —CH₃ | —COCH₃ |
| 93 | [steroid with COOCH₃ side chain] | [CH with OH] | H | —CH₃ | —COCH₃ |
| 94 | " | " | H | —CH₃ | H |
| 95 | [steroid with COOH side chain] | [CH with OH] | H | —CH₃ | —COCH₃ |
| 96 | " | " | H | —CH₃ | H |
| 97 | [cholestane with dioxolane] | " | H | —CH₃ | —COCH₃ |
| 98 | " | " | H | —CH₃ | H |

TABLE 1BB-continued
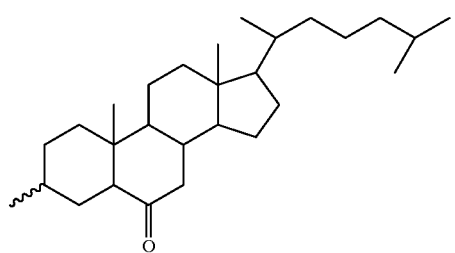
| Compound No. | R[101] | Y | R[102] | R[103] | R[104] |
|---|---|---|---|---|---|
| 99 | 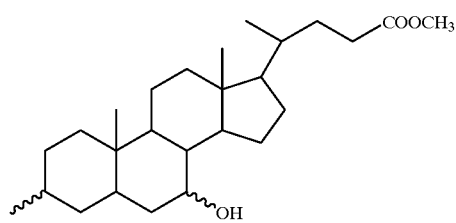 | " | H | —CH₃ | —COCH₃ |
| 100 | " | " | H | —CH₃ | H |
| 101 | 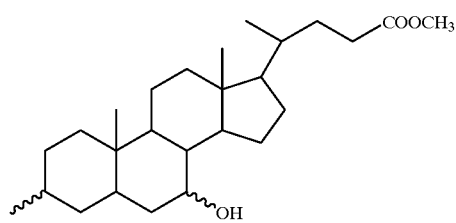 | 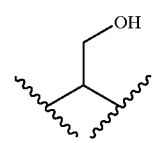 | H | —CH₃ | —COCH₃ |
| 102 | " | " | H | —CH₃ | H |
| 103 | 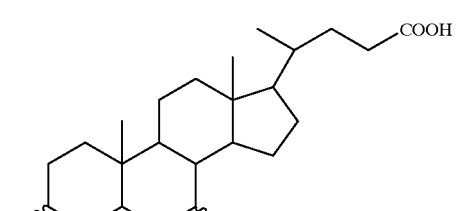 | " | H | —CH₃ | —COCH₃ |
| 104 | " | " | H | —CH₃ | H |
| 105 | 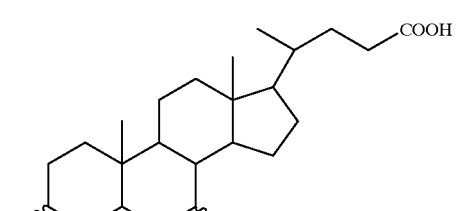 | " | H | —CH₃ | —COCH₃ |
| 106 | " | " | H | —CH₃ | H |
| 107 | 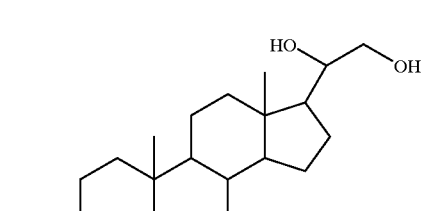 | 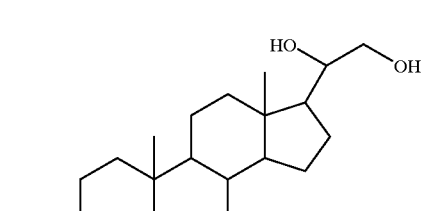 | H | —CH₃ | —COCH₃ |

TABLE 1BB-continued
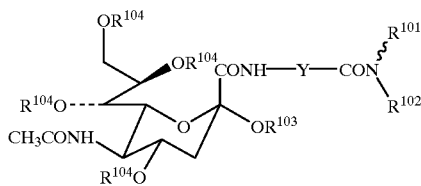
| Compound No. | R[101] | Y | R[102] | R[103] | R[104] |
|---|---|---|---|---|---|
| 108 | " | " | H | —CH₃ | H |
| 109 | (steroid with ketone) | " | H | —CH₃ | —COCH₃ |
| 110 | " | " | H | —CH₃ | H |
| 111 | (steroid-CONH₂) | " | H | —CH₃ | —COCH₃ |
| 112 | " | " | H | —CH₃ | H |
| 113 | (steroid-CONHCH₃) | (CH with OH branch) | H | —CH₃ | —COCH₃ |
| 114 | " | " | H | —CH₃ | H |
| 115 | (steroid-CON(CH₃)₂) | " | H | —CH₃ | —COCH₃ |
| 116 | " | " | H | —CH₃ | H |

TABLE-2BB

Structure: R¹⁰¹—[sugar ring with OR¹⁰⁴, R¹⁰⁴O, R¹⁰⁴O, CH₃CONH, SR¹⁰³, CONH—Y—CONR¹⁰¹R¹⁰²]

| Compound No. | $R^{101}$ | Y | $R^{102}$ | $R^{103}$ | $R^{104}$ |
|---|---|---|---|---|---|
| 117 | cholestanyl | —CH(CH₂OH)— | H | —CH₃ | —COCH₃ |
| 118 | " | " | H | —CH₃ | —COCH₂CH₃ |
| 119 | " | " | H | —CH₃ | —COC₆H₅ |
| 120 | " | " | H | —CH₃ | H |
| 121 | " | " | —CH₃ | —CH₃ | —COCH₃ |
| 122 | " | " | —CH₃ | —CH₂CH₃ | H |
| 123 | " | " | H | —CH₂CH₃ | —COCH₃ |
| 124 | " | " | H | —CH₂C₆H₅ | H |
| 125 | " | " | H | —CH₂C₆H₅ | —COCH₃ |
| 126 | " | " | H | —CH₃ | —COCH₃ |
| 127 | " | —CH(CH₂OCH₂C₆H₅)— | H | —CH₃ | —COCH₃ |
| 128 | cholestanyl | " | H | —CH₃ | H |

TABLE-2BB-continued
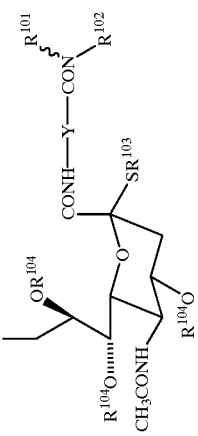
| Compound No. | $R^{101}$ | Y | $R^{102}$ | $R^{103}$ | $R^{104}$ |
|---|---|---|---|---|---|
| 129 | " |  | H | $-CH_3$ | $-COCH_3$ |
| 130 | " | " | H | $-CH_3$ | H |
| 131 | " | 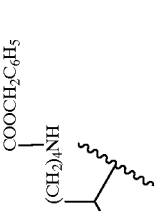 | H | $-CH_3$ | $-COCH_3$ |
| 132 | " | " | $-CH_3$ | $-CH_3$ | H |
| 133 | " | H | H | $-COCH_3$ | |
| 134 | " | " | H | $-CH_3$ | H |

TABLE-2BB-continued

| Compound No. | R¹⁰¹ | Y | R¹⁰² | R¹⁰³ | R¹⁰⁴ |
|---|---|---|---|---|---|
| 135 | (cholestane) | CH₂ | H | —CH₃ | —COCH₃ |
| 136 | " | " | H | —CH₃ | H |
| 137 | " | (CH₂)₂ | H | —CH₃ | —COCH₃ |
| 138 | " | " | H | —CH₃ | H |
| 139 | " | CH-CONH₂ branch | H | —CH₃ | —COCH₃ |
| 140 | " | " | H | —CH₃ | H |

TABLE-2BB-continued

| Compound No. | R[101] | Y | R[102] | R[103] | R[104] |
|---|---|---|---|---|---|
| 141 | " | (4-benzyloxybenzyl) | H | —CH₃ | —COCH₃ |
| 142 | " | " | H | —CH₃ | H |
| 143 | " | (4-hydroxybenzyl) | H | —CH₃ | —COCH₃ |
| 144 | " | (cholestanyl) | H | —CH₃ | H |

TABLE-2BB-continued
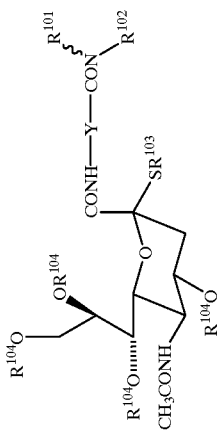
| Compound No. | $R^{101}$ | Y | $R^{102}$ | $R^{103}$ | $R^{104}$ |
|---|---|---|---|---|---|
| 145 | " | CONH$_2$ branch | H | —CH$_3$ | —COCH$_3$ |
| 146 | " | " | H | —CH$_3$ | H |
| 147 | " | COOH branch | H | —CH$_3$ | —COCH$_3$ |
| 148 | " | " | H | —CH$_3$ | H |
| 149 | " | COOH branch | H | —CH$_3$ | —COCH$_3$ |
| 150 | " | " | H | —CH$_3$ | H |

TABLE-2BB-continued

| Compound No. | R[101] | Y | R[102] | R[103] | R[104] |
|---|---|---|---|---|---|
| 151 | (steroid structure) | (CH₂)₃NH-C(=NH)NH₂ | H | —CH₃ | —COCH₃ |
| 152 | " | " | H | —CH₃ | H |
| 153 | " | (imidazole-CH₂-) | H | —CH₃ | —COCH₃ |
| 154 | " | " | H | —CH₃ | H |
| 155 | " | CH(OH)CH₃ | H | —CH₃ | —COCH₃ |
| 156 | " | " | H | —CH₃ | H |

TABLE-2BB-continued
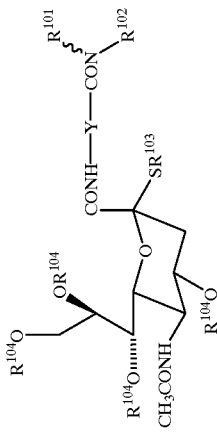
| Compound No. | R[101] | Y | R[102] | R[103] | R[104] |
|---|---|---|---|---|---|
| 157 | " | H3C-CH(CH3)-CH(-)-CH(-) | H | —CH3 | —COCH3 |
| 158 | " | " | H | —CH3 | H |
| 159 | " | H3C-CH2-CH(CH3)-CH(-)-CH(-) | H | —CH3 | —COCH3 |
| 160 | " | " | H | —CH3 | H |
| 161 | " | (CH3)2CH-CH(-)-CH(-) | H | —CH3 | —COCH3 |
| 162 | " | cholestanyl | H | —CH3 | H |

TABLE-2BB-continued
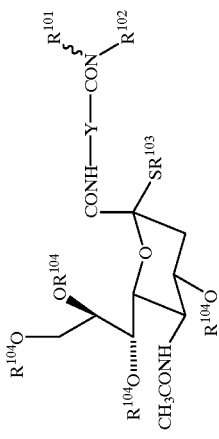
| Compound No. | R¹⁰¹ | Y | R¹⁰² | R¹⁰³ | R¹⁰⁴ |
|---|---|---|---|---|---|
| 163 | " | (CH₂)₃CH₃ | H | —CH₃ | —COCH₃ |
| 164 | " | " | H | —CH₃ | H |
| 165 | " | CH₃ | H | —CH₃ | —COCH₃ |
| 166 | " | " | H | —CH₃ | H |
| 167 | " | SH | H | —CH₃ | —COCH₃ |
| 168 | " | " | H | —CH₃ | H |
| 169 | " | SCH₃ | H | —CH₃ | —COCH₃ |
| 170 | " | " | H | —CH₃ | H |

TABLE-2BB-continued $$R^{104}O\text{-}CH_2\text{-}C(OR^{104})\text{-}C(R^{104}O)\text{-}C(CH_3CONH)\text{-}C(SR^{103})\text{-}O\text{-}CONH\text{-}Y\text{-}CON(R^{101})(R^{102})$$

| Compound No. | $R^{101}$ | Y | $R^{102}$ | $R^{103}$ | $R^{104}$ |
|---|---|---|---|---|---|
| 171 | cholestanyl | -CH(CH$_2$CH$_2$OH)- | H | -CH$_3$ | -COCH$_3$ |
| 172 | " | " | H | -CH$_3$ | H |
| 173 | " | -CH(CH$_2$-(2-indolyl))- | H | -CH$_3$ | -COCH$_3$ |
| 174 | " | " | H | -CH$_3$ | H |
| 175 | " | -CH$_2$-(1,4-phenylene)-CH$_2$- | H | -CH$_3$ | -COCH$_3$ |
| 176 | " | " | H | -CH$_3$ | H |

TABLE-2BB-continued
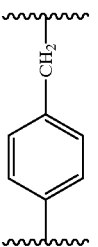
| Compound No. | $R^{101}$ | Y | $R^{102}$ | $R^{103}$ | $R^{104}$ |
|---|---|---|---|---|---|
| 177 | " | ![p-xylylene] | H | $-CH_3$ | $-COCH_3$ |
| 178 | " | ![p-xylylene] | H | $-CH_3$ | H |
| 179 | " | ![p-xylylene] | H | $-CH_3$ | $-COCH_3$ |
| 180 | " | ![p-xylylene] | H | $-CH_3$ | H |
| 181 | " | ![hydroxyphenyl] | H | $-CH_3$ | $-COCH_3$ |
| 182 | " | | H | $-CH_3$ | H |
| 183 | " | ![hydroxyphenyl] | H | $-CH_3$ | $-COCH_3$ |
| 184 | " | | H | $-CH_3$ | H |

TABLE-2BB-continued

| Compound No. | R[101] | Y | R[102] | R[103] | R[104] |
|---|---|---|---|---|---|
| 185 | | phenyl with NHAc | H | —CH₃ | —COCH₃ |
| 186 | " | " | H | —CH₃ | H |
| 187 | " | phenyl with AcHN | H | —CH₃ | —COCH₃ |
| 188 | " | " | H | —CH₃ | H |
| 189 | " | CH(CH₂OH) branched | H | —CH₃ | —COCH₃ |
| 190 | cholesteryl | " | H | —CH₃ | H |

TABLE-2BB-continued
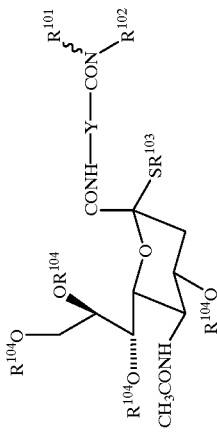
| Compound No. | $R^{101}$ | Y | $R^{102}$ | $R^{103}$ | $R^{104}$ |
|---|---|---|---|---|---|
| 191 | " | $(CH_2)_4NH_2$ | H | $—CH_3$ | $—COCH_3$ |
| 192 | " | " | H | $—CH_3$ | H |
| 193 | " | (para-phenylene) | H | $—CH_3$ | $—COCH_3$ |
| 194 | " | " | H | $—CH_3$ | H |
| 195 | " | (NHAc-phenylene) | H | $—CH_3$ | $—COCH_3$ |
| 196 | " | " | H | $—CH_3$ | H |
| 197 | " | ($CONH_2$ branch) | H | $—CH_3$ | $—COCH_3$ |
| 198 | " | " | H | $—CH_3$ | H |

TABLE-2BB-continued

| Compound No. | $R^{101}$ | Y | $R^{102}$ | $R^{103}$ | $R^{104}$ |
|---|---|---|---|---|---|
| 199 | (cholesteryl) | $(CH_2)_2$ | H | $-CH_3$ | $-COCH_3$ |
| 200 | " | " | H | $-CH_3$ | H |
| 201 | " | CH(CH₂OH) | H | $-CH_3$ | $-COCH_3$ |
| 202 | (cholesteryl) | " | H | $-CH_3$ | H |

TABLE-2BB-continued

| Compound No. | R[101] | Y | R[102] | R[103] | R[104] |
|---|---|---|---|---|---|
| 203 | [cholesterol-type steroid with side chain terminating in OH] | [CH2OH branch] | H | —CH3 | —COCH3 |
| 204 | " | " | H | —CH3 | H |
| 205 | [cholesterol-type steroid with side chain terminating in OH] | [CH2OCH2C6H5 branch] | H | —CH3 | —COCH3 |
| 206 | " | " | H | —CH3 | H |
| 207 | [cholesterol-type steroid with side chain terminating in OAc] | [CH2OH branch] | H | —CH3 | —COCH3 |

TABLE-2BB-continued

[Structure shown: sugar moiety with R¹⁰⁴O-CH₂ group, OR¹⁰⁴, R¹⁰⁴O, CH₃CONH, SR¹⁰³, and CONH—Y—CON(R¹⁰¹)(R¹⁰²) substituents]

| Compound No. | R¹⁰¹ | Y | R¹⁰² | R¹⁰³ | R¹⁰⁴ |
|---|---|---|---|---|---|
| 208 | [cholestanyl-COOCH₃] | -CH(CH₂OCH₂C₆H₅)- | H | —CH₃ | —COCH₃ |
| 209 | " | -CH(CH₂OH)- | H | —CH₃ | —COCH₃ |
| 210 | " | " | H | —CH₃ | H |
| 211 | [cholestanyl-COOH] | -CH(CH₂OH)- | H | —CH₃ | —COCH₃ |
| 212 | " | " | H | —CH₃ | H |

TABLE-2BB-continued

| Compound No. | R¹⁰¹ | Y | R¹⁰² | R¹⁰³ | R¹⁰⁴ |
|---|---|---|---|---|---|
| 213 | (cholestane with dioxolane) | " | H | —CH₃ | —COCH₃ |
| 214 | " | " | H | —CH₃ | H |
| 215 | " | " | H | —CH₃ | —COCH₃ |
| 216 | (cholestane with ketone) | " | H | —CH₃ | H |

TABLE-2BB-continued
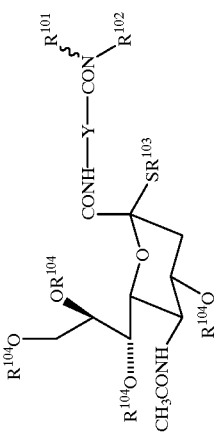
| Compound No. | R¹⁰¹ | Y | R¹⁰² | R¹⁰³ | R¹⁰⁴ |
|---|---|---|---|---|---|
| 217 | 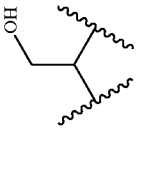 | 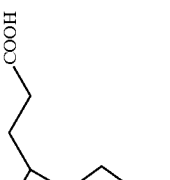 | H | —CH₃ | —COCH₃ |
| 218 | " | " | H | —CH₃ | H |
| 219 | 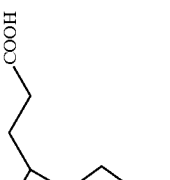 | " | H | —CH₃ | —COCH₃ |
| 220 | " | " | H | —CH₃ | H |
| 221 | 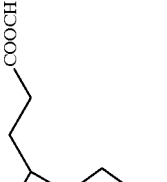 | " | H | —CH₃ | —COCH₃ |

TABLE-2BB-continued

| Compound No. | R¹⁰¹ | Y | R¹⁰² | R¹⁰³ | R¹⁰⁴ |
|---|---|---|---|---|---|
| 222 | " | | H | —CH₃ | H |
| 223 | | | H | —CH₃ | —COCH₃ |
| 224 | " | " | H | —CH₃ | H |
| 225 | | | H | —CH₃ | —COCH₃ |
| 226 | " | " | H | —CH₃ | H |

TABLE-2BB-continued

| Compound No. | R[101] | Y | R[102] | R[103] | R[104] |
|---|---|---|---|---|---|
| 227 | (cholestanyl-CONH₂ group) | (sugar linker structure) | H | —CH₃ | —COCH₃ |
| 228 | " | " | H | —CH₃ | H |
| 229 | (cholestanyl-CONHCH₃ group) | (CH₂OH branched linker) | H | —CH₃ | —COCH₃ |

TABLE-2BB-continued
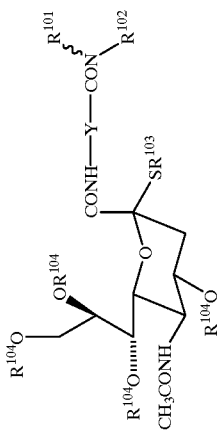
| Compound No. | R[101] | Y | R[102] | R[103] | R[104] |
|---|---|---|---|---|---|
| 230 | " | " | H | —CH$_3$ | H |
| 231 | " | " | H | —CH$_3$ | —COCH$_3$ |
| 232 | " | " | H | —CH$_3$ | H |

TABLE 3BB

| Compound No. | R¹⁰¹ | Y | R¹⁰² | R¹⁰³ | R¹⁰⁴ |
| --- | --- | --- | --- | --- | --- |
| 233 | cholestanyl | –CH₂OH branch | H | —CH₃ | —COCH₃ |
| 234 | " | " | H | —CH₃ | —COCH₂CH₃ |
| 235 | " | " | H | —CH₃ | —COC₆H₅ |
| 236 | " | " | H | —CH₃ | H |
| 237 | " | " | —CH₃ | —CH₃ | —COCH₃ |
| 238 | " | " | —CH₃ | —CH₃ | H |
| 239 | " | " | H | —CH₂CH₃ | —COCH₃ |
| 240 | " | " | H | —CH₂CH₃ | H |
| 241 | " | " | H | —CH₂C₆H₅ | —COCH₃ |
| 242 | " | " | H | —CH₂C₆H₅ | H |
| 243 | cholestanyl | –CH₂OCH₂C₆H₅ branch | H | —CH₃ | —COCH₃ |
| 244 | " | " | H | —CH₃ | H |
| 245 | " | –(CH₂)₄NH₂ branch | H | —CH₃ | —COCH₃ |
| 246 | " | " | H | —CH₃ | H |
| 247 | " | –(CH₂)₄NHCOOCH₂C₆H₅ branch | H | —CH₃ | —COCH₃ |
| 248 | " | " | H | —CH₃ | H |
| 249 | " | –CH₂C₆H₅ branch | H | —CH₃ | —COCH₃ |
| 250 | " | " | H | —CH₃ | H |

TABLE 3BB-continued

| Compound No. | R¹⁰¹ | Y | R¹⁰² | R¹⁰³ | R¹⁰⁴ |
|---|---|---|---|---|---|
| 251 | cholestanyl | —CH₂— | H | —CH₃ | —COCH₃ |
| 252 | " | " | H | —CH₃ | H |
| 253 | " | —(CH₂)₂— | H | —CH₃ | —COCH₃ |
| 254 | " | " | H | —CH₃ | H |
| 255 | " | -CH(CH₂CONH₂)- | H | —CH₃ | —COCH₃ |
| 256 | " | " | H | —CH₃ | H |
| 257 | " | -CH(CH₂-C₆H₄-O-CH₂-C₆H₅)- | H | —CH₃ | —COCH₃ |
| 258 | " | " | H | —CH₃ | H |
| 259 | cholestanyl | -CH(CH₂-C₆H₄-OH)- | H | —CH₃ | —COCH₃ |
| 260 | " | " | H | —CH₃ | H |

TABLE 3BB-continued
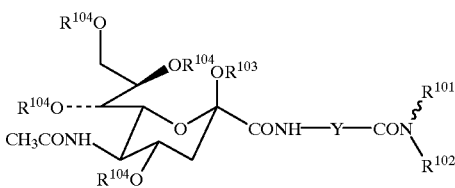
| Compound No. | R$^{101}$ | Y | R$^{102}$ | R$^{103}$ | R$^{104}$ |
|---|---|---|---|---|---|
| 261 | " | (CONH$_2$ branched) | H | —CH$_3$ | —COCH$_3$ |
| 262 | " | " | H | —CH$_3$ | H |
| 263 | " | (COOH branched) | H | —CH$_3$ | —COCH$_3$ |
| 264 | " | " | H | —CH$_3$ | H |
| 265 | " | (COOH branched) | H | —CH$_3$ | —COCH$_3$ |
| 266 | " | " | H | —CH$_3$ | H |
| 267 | (cholestanyl) | (CH$_2$)$_3$NH-C(=NH)NH$_2$ branched | H | —CH$_3$ | —COCH$_3$ |
| 268 | " | " | H | —CH$_3$ | H |
| 269 | " | (imidazole-CH$_2$ branched) | H | —CH$_3$ | —COCH$_3$ |
| 270 | " | " | H | —CH$_3$ | H |
| 271 | " | H$_3$C-CH(OH) branched | H | —CH$_3$ | —COCH$_3$ |

TABLE 3BB-continued
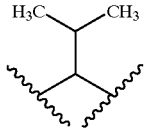
| Compound No. | R^{101} | Y | R^{102} | R^{103} | R^{104} |
|---|---|---|---|---|---|
| 272 | " | " | H | —CH$_3$ | H |
| 273 | " | 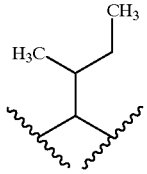 | H | —CH$_3$ | —COCH$_3$ |
| 274 | " | " | H | —CH$_3$ | H |
| 275 | " | 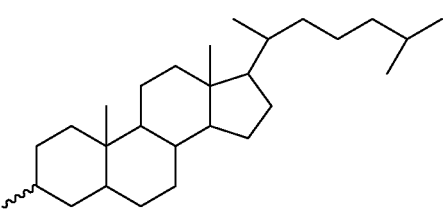 | H | —CH$_3$ | —COCH$_3$ |
| 276 | " | " | H | —CH$_3$ | H |
| 277 | 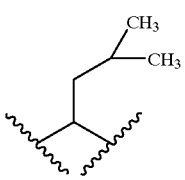 | 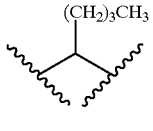 | H | —CH$_3$ | —COCH$_3$ |
| 278 | " | " | H | —CH$_3$ | H |
| 279 | " | 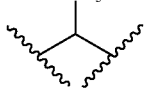 | H | —CH$_3$ | —COCH$_3$ |
| 280 | " | " | H | —CH$_3$ | H |
| 281 | " | 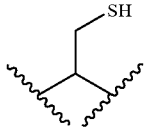 | H | —CH$_3$ | —COCH$_3$ |
| 282 | " | " | H | —CH$_3$ | H |
| 283 | " |  | H | —CH$_3$ | —COCH$_3$ |
| 284 | " | " | H | —CH$_3$ | H |

TABLE 3BB-continued
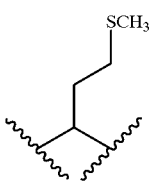
| Compound No. | R¹⁰¹ | Y | R¹⁰² | R¹⁰³ | R¹⁰⁴ |
|---|---|---|---|---|---|
| 285 | " | 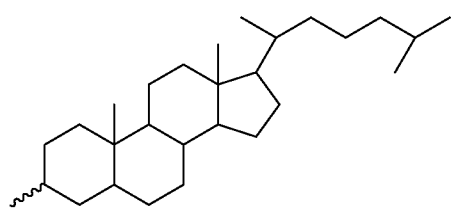 | H | —CH₃ | —COCH₃ |
| 286 | " | " | H | —CH₃ | H |
| 287 | 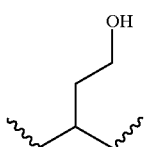 | 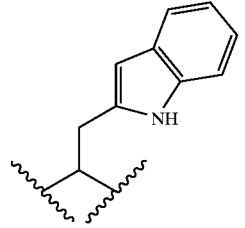 | H | —CH₃ | —COCH₃ |
| 288 | " | " | H | —CH₃ | H |
| 289 | " | 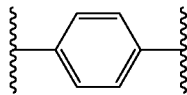 | H | —CH₃ | —COCH₃ |
| 290 | " | " | H | —CH₃ | H |
| 291 | " | 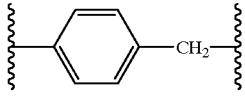 | H | —CH₃ | —COCH₃ |
| 292 | " | " | H | —CH₃ | H |
| 293 | " | 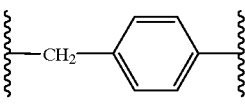 | H | —CH₃ | —COCH₃ |
| 294 | " | " | H | —CH₃ | H |
| 295 | " |  | H | —CH₃ | —COCH₃ |
| 296 | " | " | H | —CH₃ | H |

TABLE 3BB-continued
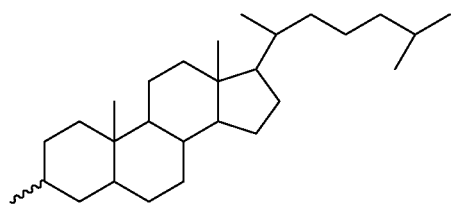
| Compound No. | R¹⁰¹ | Y | R¹⁰² | R¹⁰³ | R¹⁰⁴ |
|---|---|---|---|---|---|
| 297 | 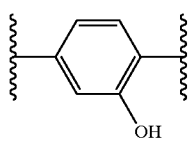 | 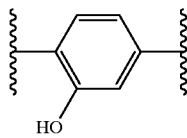 | H | —CH₃ | —COCH₃ |
| 298 | " | " | H | —CH₃ | H |
| 299 | " | 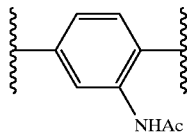 | H | —CH₃ | —COCH₃ |
| 300 | " | " | H | —CH₃ | H |
| 301 | " | 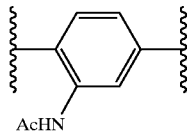 | H | —CH₃ | —COCH₃ |
| 302 | " | " | H | —CH₃ | H |
| 303 | " | 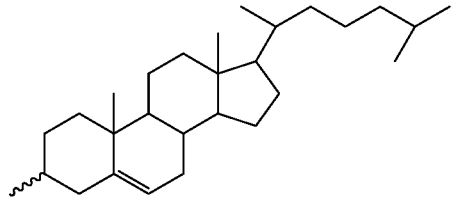 | H | —CH₃ | —COCH₃ |
| 304 | " | " | H | —CH₃ | H |
| 305 | 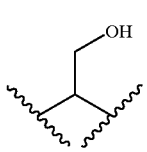 | 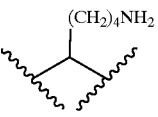 | H | —CH₃ | —COCH₃ |
| 306 | " | " | H | —CH₃ | H |
| 307 | " | (CH₂)₄NH₂ | H | —CH₃ | —COCH₃ |
| 308 | " | " | H | —CH₃ | H |

TABLE 3BB-continued

[Structure: Sugar ring with R¹⁰⁴O, OR¹⁰⁴, OR¹⁰³, CH₃CONH, R¹⁰⁴O substituents, CONH—Y—CON(R¹⁰¹)(R¹⁰²)]

| Compound No. | R¹⁰¹ | Y | R¹⁰² | R¹⁰³ | R¹⁰⁴ |
|---|---|---|---|---|---|
| 309 | " | *para*-phenylene | H | —CH₃ | —COCH₃ |
| 310 | " | " | H | —CH₃ | H |
| 311 | " | phenylene with NHAc | H | —CH₃ | —COCH₃ |
| 312 | " | " | H | —CH₃ | H |
| 313 | " | CH with CH₂CONH₂ branch | H | —CH₃ | —COCH₃ |
| 314 | " | " | H | —CH₃ | H |
| 315 | cholesteryl | —(CH₂)₂— | H | —CH₃ | —COCH₃ |
| 316 | " | " | H | —CH₃ | H |
| 317 | ergosteryl-type | CH with CH₂OH branch | H | —CH₃ | —COCH₃ |
| 318 | " | " | H | —CH₃ | H |
| 319 | steroid with (CH₂)₃OH side chain | CH with CH₂OH branch | H | —CH₃ | —COCH₃ |

TABLE 3BB-continued
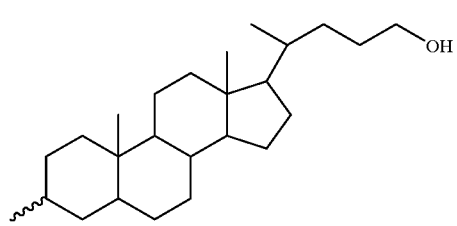
| Compound No. | R[101] | Y | R[102] | R[103] | R[104] |
|---|---|---|---|---|---|
| 320 | " | " | H | —CH₃ | H |
| 321 | 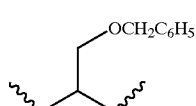 | 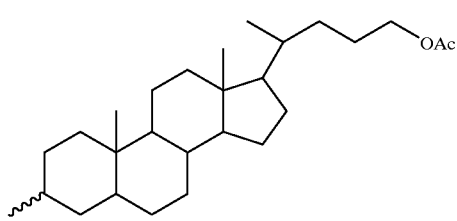 | H | —CH₃ | —COCH₃ |
| 322 | " | " | H | —CH₃ | H |
| 323 | 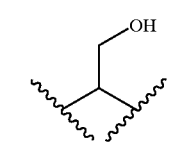 | 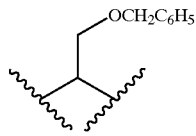 | H | —CH₃ | —COCH₃ |
| 324 | " | 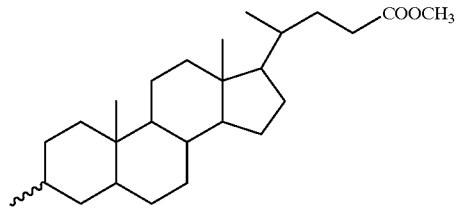 | H | —CH₃ | —COCH₃ |
| 325 | 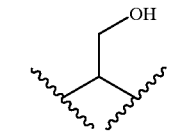 | 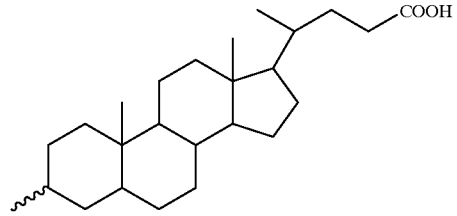 | H | —CH₃ | —COCH₃ |
| 326 | " | " | H | —CH₃ | H |
| 327 | 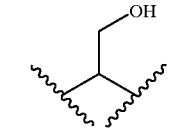 | 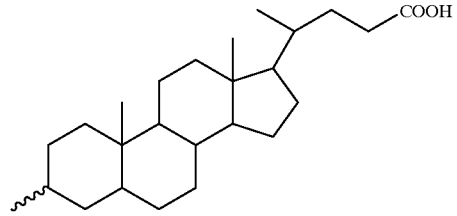 | H | —CH₃ | —COCH₃ |
| 328 | " | " | H | —CH₃ | H |

TABLE 3BB-continued

| Compound No. | R¹⁰¹ | Y | R¹⁰² | R¹⁰³ | R¹⁰⁴ |
|---|---|---|---|---|---|
| 329 | [cholestane with dioxolane spiro group] | " | H | —CH₃ | —COCH₃ |
| 330 | " | " | H | —CH₃ | H |
| 331 | [cholestane with 6-keto] | " | H | —CH₃ | —COCH₃ |
| 332 | " | " | H | —CH₃ | H |
| 333 | [cholestane with COOCH₃ side chain and 7-OH] | [CH(CH₂OH) branch] | H | —CH₃ | —COCH₃ |
| 334 | " | " | H | —CH₃ | H |
| 335 | [cholestane with COOH side chain and 7-OH] | " | H | —CH₃ | —COCH₃ |
| 336 | " | " | H | —CH₃ | H |

TABLE 3BB-continued
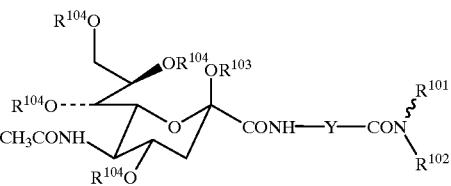
| Compound No. | R¹⁰¹ | Y | R¹⁰² | R¹⁰³ | R¹⁰⁴ |
|---|---|---|---|---|---|
| 337 | 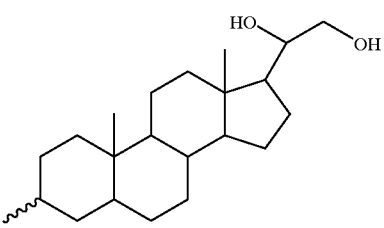 | " | H | —$CH_3$ | —$COCH_3$ |
| 338 | " | " | H | —$CH_3$ | H |
| 339 | 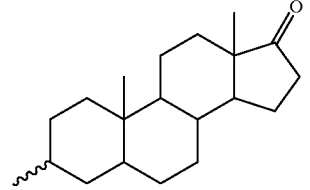 | 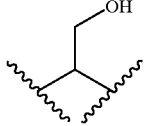 | H | —$CH_3$ | —$COCH_3$ |
| 340 | " | " | H | —$CH_3$ | H |
| 341 | 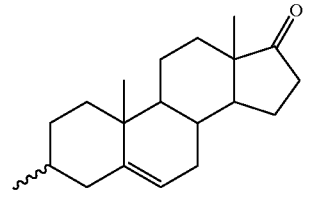 | " | H | —$CH_3$ | —$COCH_3$ |
| 342 | " | " | H | —$CH_3$ | H |
| 343 | 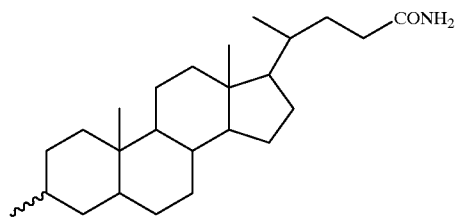 | " | H | —$CH_3$ | —$COCH_3$ |

TABLE 3BB-continued
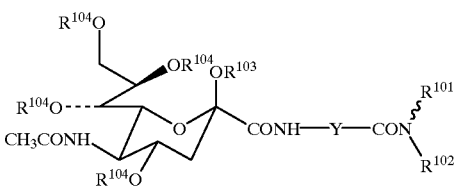
| Compound No. | R[101] | Y | R[102] | R[103] | R[104] |
|---|---|---|---|---|---|
| 344 | " | " | H | —CH$_3$ | H |
| 345 | (steroid-CONHCH$_3$) | (CH$_2$OH branch) | H | —CH$_3$ | —COCH$_3$ |
| 346 | " | " | H | —CH$_3$ | H |
| 347 | (steroid-CON(CH$_3$)$_2$) | " | H | —CH$_3$ | —COCH$_3$ |
| 348 | " | " | H | —CH$_3$ | H |

TABLE-4BB

| Compound No. | R101 | Y | R102 | R103 | R104 |
|---|---|---|---|---|---|
| 349 | cholestanyl | CH(CH2OH)- | H | —CH3 | —COCH3 |
| 350 | " | " | H | —CH3 | —COCH2CH3 |
| 351 | " | " | H | —CH3 | —COC6H5 |
| 352 | " | " | H | —CH3 | H |
| 353 | " | " | —CH3 | —CH3 | —COCH3 |
| 354 | " | " | —CH3 | —CH3 | H |
| 355 | " | " | H | —CH2CH3 | —COCH3 |
| 356 | " | " | H | —CH2CH3 | H |
| 357 | " | " | H | —CH2C6H5 | —COCH3 |
| 358 | " | " | H | —CH2C6H5 | H |
| 359 | " | CH(CH2OCH2C6H5)- | H | —CH3 | —COCH3 |
| 360 | cholestanyl | " | H | —CH3 | H |

TABLE-4BB-continued
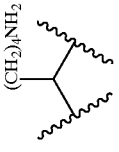
| Compound No. | R¹⁰¹ | Y | R¹⁰² | R¹⁰³ | R¹⁰⁴ |
|---|---|---|---|---|---|
| 361 | '' | | H | —CH$_3$ | —COCH$_3$ |
| 362 | '' | (CH$_2$)$_4$NH$_2$ structure | H | —CH$_3$ | H |
| 363 | '' | '' | H | —CH$_3$ | —COCH$_3$ |
| 364 | '' | COOCH$_2$C$_6$H$_5$ / (CH$_2$)$_4$NH structure | H | —CH$_3$ | H |
| 365 | '' | '' | H | —CH$_3$ | —COCH$_3$ |
| 366 | '' | benzyl structure | H | —CH$_3$ | H |

TABLE-4BB-continued

| Compound No. | R¹⁰¹ | Y | R¹⁰² | R¹⁰³ | R¹⁰⁴ |
|---|---|---|---|---|---|
| 367 | [cholestanyl] | CH₂ | H | —CH₃ | —COCH₃ |
| 368 | " | " | H | —CH₃ | H |
| 369 | " | " | H | —CH₃ | —COCH₃ |
| 370 | " | (CH₂)₂ | H | —CH₃ | H |
| 371 | " | " | H | —CH₃ | —COCH₃ |
| 372 | " | CH(CONH₂)CH₂ | H | —CH₃ | H |

TABLE-4BB-continued

| Compound No. | R¹⁰¹ | Y | R¹⁰² | R¹⁰³ | R¹⁰⁴ |
|---|---|---|---|---|---|
| 373 | | 4-benzyloxybenzyl branched | H | —CH₃ | —COCH₃ |
| 374 | " | " | H | —CH₃ | H |
| 375 | " | 4-hydroxybenzyl branched | H | —CH₃ | —COCH₃ |
| 376 | " | cholestanyl | H | —CH₃ | H |

TABLE-4BB-continued
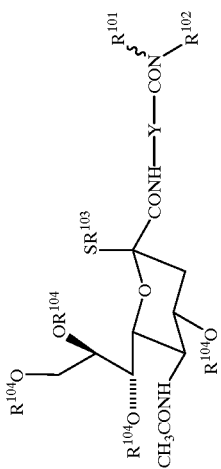
| Compound No. | R¹⁰¹ | Y | R¹⁰² | R¹⁰³ | R¹⁰⁴ |
|---|---|---|---|---|---|
| 377 | " | CONH₂ branched | H | —CH₃ | —COCH₃ |
| 378 | " | " | H | —CH₃ | H |
| 379 | " | COOH branched | H | —CH₃ | —COCH₃ |
| 380 | " | " | H | —CH₃ | H |
| 381 | " | COOH branched | H | —CH₃ | —COCH₃ |
| 382 | " | " | H | —CH₃ | H |

TABLE-4BB-continued

| Compound No. | R¹⁰¹ | Y | R¹⁰² | R¹⁰³ | R¹⁰⁴ |
|---|---|---|---|---|---|
| 383 | cholestanyl | -(CH₂)₃NHC(=NH)NH₂ | H | -CH₃ | -COCH₃ |
| 384 | " | " | H | -CH₃ | H |
| 385 | " | " | H | -CH₃ | -COCH₃ |
| 386 | " | imidazolylmethyl | H | -CH₃ | H |
| 387 | " | CH(OH)CH₃ | H | -CH₃ | -COCH₃ |
| 388 | " | " | H | -CH₃ | H |

TABLE-4BB-continued
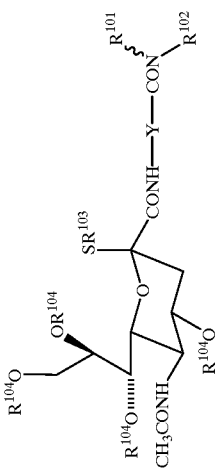
| Compound No. | R¹⁰¹ | Y | R¹⁰² | R¹⁰³ | R¹⁰⁴ |
|---|---|---|---|---|---|
| 389 | " | H₃C—CH(CH₃)—CH< | H | —CH₃ | —COCH₃ |
| 390 | " | " | H | —CH₃ | H |
| 391 | " | CH₃—CH(CH₃)—CH₂—CH< | H | —CH₃ | —COCH₃ |
| 392 | " | " | H | —CH₃ | H |
| 393 | " | (CH₃)₂CH—CH₂—CH< | H | —CH₃ | —COCH₃ |
| 394 | cholestanyl | " | H | —CH₃ | H |

TABLE-4BB-continued
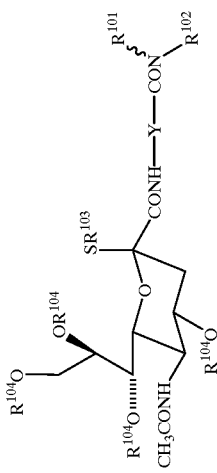
| Compound No. | R¹⁰¹ | Y | R¹⁰² | R¹⁰³ | R¹⁰⁴ |
|---|---|---|---|---|---|
| 395 | " | $-CH(CH_2)_3CH_3-$ | H | $-CH_3$ | $-COCH_3$ |
| 396 | " | " | H | $-CH_3$ | H |
| 397 | " | $-CH(CH_3)-$ | H | $-CH_3$ | $-COCH_3$ |
| 398 | " | " | H | $-CH_3$ | H |
| 399 | " | $-CH(CH_2SH)-$ | H | $-CH_3$ | $-COCH_3$ |
| 400 | " | " | H | $-CH_3$ | H |
| 401 | " | $-CH(CH_2SCH_3)-$ | H | $-CH_3$ | $-COCH_3$ |
| 402 | " | " | H | $-CH_3$ | H |

TABLE-4BB-continued

[Structure shown: sugar ring with substituents R¹⁰⁴O—, OR¹⁰⁴, R¹⁰⁴O(axial), CH₃CONH, SR¹⁰³, and CONH—Y—CON(R¹⁰¹)(R¹⁰²)]

| Compound No. | R¹⁰¹ | Y | R¹⁰² | R¹⁰³ | R¹⁰⁴ |
|---|---|---|---|---|---|
| 403 | [cholestanyl group] | [CH₂CH₂OH-bearing branch] | H | —CH₃ | —COCH₃ |
| 404 | " | " | H | —CH₃ | H |
| 405 | " | " | H | —CH₃ | —COCH₃ |
| 406 | " | [indol-2-ylmethyl branch] | H | —CH₃ | H |
| 407 | " | " | H | —CH₃ | —COCH₃ |
| 408 | " | [p-phenylene] | H | —CH₃ | H |

TABLE-4BB-continued

| Compound No. | R¹⁰¹ | Y | R¹⁰² | R¹⁰³ | R¹⁰⁴ |
|---|---|---|---|---|---|
| 409 | cholestanyl | -C₆H₄-CH₂- | H | —CH₃ | —COCH₃ |
| 410 | cholestanyl | -C₆H₄-CH₂- | H | —CH₃ | H |
| 411 | cholestanyl | -CH₂-C₆H₄-CH₂- | H | —CH₃ | —COCH₃ |
| 412 | cholestanyl | -CH₂-C₆H₄-CH₂- | H | —CH₃ | H |
| 413 | cholestanyl | hydroxyphenyl | H | —CH₃ | —COCH₃ |
| 414 | cholestanyl | hydroxyphenyl | H | —CH₃ | H |
| 415 | cholestanyl | hydroxyphenyl | H | —CH₃ | —COCH₃ |
| 416 | cholestanyl | hydroxyphenyl | H | —CH₃ | H |

TABLE-4BB-continued

[Structure: R¹⁰⁴O—CH₂ group on pyranose ring with R¹⁰⁴O, R¹⁰⁴O, CH₃CONH substituents, SR¹⁰³, and CONH—Y—CONH—R¹⁰¹/R¹⁰² at anomeric position]

| Compound No. | R¹⁰¹ | Y | R¹⁰² | R¹⁰³ | R¹⁰⁴ |
|---|---|---|---|---|---|
| 417 | [cholesteryl group] | [1,4-phenylene with NHAc substituent] | H | —CH₃ | —COCH₃ |
| 418 | " | " | H | —CH₃ | H |
| 419 | " | [1,4-phenylene with AcHN substituent] | H | —CH₃ | —COCH₃ |
| 420 | " | " | H | —CH₃ | H |
| 421 | " | [CH₂OH-bearing branched linker] | H | —CH₃ | —COCH₃ |
| 422 | " | " | H | —CH₃ | H |

TABLE-4BB-continued
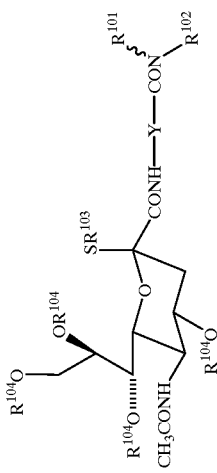
| Compound No. | $R^{101}$ | Y | $R^{102}$ | $R^{103}$ | $R^{104}$ |
|---|---|---|---|---|---|
| 423 | " | 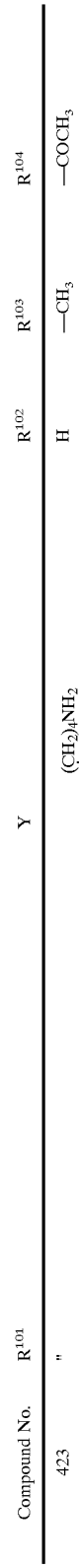 | H | $-CH_3$ | $-COCH_3$ |
| 424 | " | " | H | $-CH_3$ | H |
| 425 | " |  | H | $-CH_3$ | $-COCH_3$ |
| 426 | " | " | H | $-CH_3$ | H |
| 427 | " | 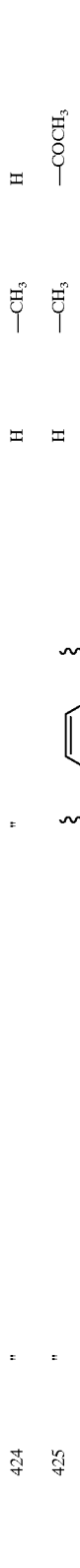 | H | $-CH_3$ | $-COCH_3$ |
| 428 | " | " | H | $-CH_3$ | H |
| 429 | " | 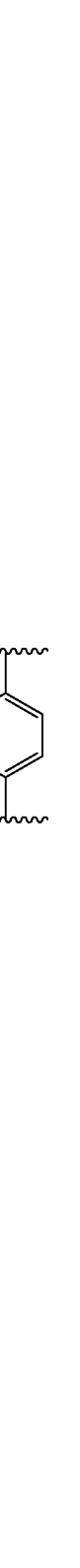 | H | $-CH_3$ | $-COCH_3$ |
| 430 | " | " | H | $-CH_3$ | H |

TABLE-4BB-continued

| Compound No. | R¹⁰¹ | Y | R¹⁰² | R¹⁰³ | R¹⁰⁴ |
|---|---|---|---|---|---|
| 431 | cholesteryl | —(CH₂)₂— | H | —CH₃ | —COCH₃ |
| 432 | " | " | H | —CH₃ | H |
| 433 | " | CH₂CH(OH)CH< | H | —CH₃ | —COCH₃ |
| 434 | cholesteryl | " | H | —CH₃ | H |

TABLE-4BB-continued

| Compound No. | $R^{101}$ | Y | $R^{102}$ | $R^{103}$ | $R^{104}$ |
|---|---|---|---|---|---|
| 435 | (cholestanol-OH) | (CH2OH branch) | H | —CH3 | —COCH3 |
| 436 | " | " | H | —CH3 | H |
| 437 | (cholestanol-OH) | (CH2OCH2C6H5 branch) | H | —CH3 | —COCH3 |
| 438 | " | " | H | —CH3 | H |
| 439 | (cholestanol-OAc) | (CH2OH branch) | H | —CH3 | —COCH3 |

TABLE-4BB-continued

| Compound No. | R¹⁰¹ | Y | R¹⁰² | R¹⁰³ | R¹⁰⁴ |
|---|---|---|---|---|---|
| 440 | " | OCH₂C₆H₅ branched | H | —CH₃ | H |
| 441 | [cholestane-COOCH₃ structure] | OH branched | H | —CH₃ | —COCH₃ |
| 442 | " | " | H | —CH₃ | H |
| 443 | [cholestane-COOH structure] | OH branched | H | —CH₃ | —COCH₃ |
| 444 | " | " | H | —CH₃ | H |

TABLE-4BB-continued

| Compound No. | R[101] | Y | R[102] | R[103] | R[104] |
|---|---|---|---|---|---|
| 445 | (cholestanyl dioxolane steroid) | " | H | —CH₃ | —COCH₃ |
| 446 | " | " | H | —CH₃ | H |
| 447 | (cholestanyl ketone steroid) | " | H | —CH₃ | —COCH₃ |
| 448 | " | " | H | —CH₃ | H |

TABLE-4BB-continued

| Compound No. | R[101] | Y | R[102] | R[103] | R[104] |
|---|---|---|---|---|---|
| 449 | (cholesterol-like steroid with COOCH3 side chain, OH) | (CH2OH branched) | H | —CH3 | —COCH3 |
| 450 | " | " | H | —CH3 | H |
| 451 | (steroid with COOH side chain, OH) | " | H | —CH3 | —COCH3 |
| 452 | " | " | H | —CH3 | H |
| 453 | (steroid with diol side chain, OH) | " | H | —CH3 | —COCH3 |

TABLE-4BB-continued
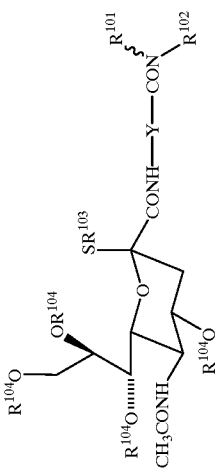
| Compound No. | R101 | Y | R102 | R103 | R104 |
|---|---|---|---|---|---|
| 454 | (steroid structure) | " | H | —CH₃ | H |
| 455 | | | H | —CH₃ | —COCH₃ |
| 456 | (steroid structure) | " | H | —CH₃ | H |
| 457 | | | H | —CH₃ | —COCH₃ |
| 458 | (steroid structure with double bond) | " | H | —CH₃ | H |

TABLE-4BB-continued

| Compound No. | R¹⁰¹ | Y | R¹⁰² | R¹⁰³ | R¹⁰⁴ |
|---|---|---|---|---|---|
| 459 | [cholestane-CONH₂ structure] | | H | —CH₃ | —COCH₃ |
| 460 | " | " | H | —CH₃ | H |
| 461 | [cholestane-CONHCH₃ structure] | [CH(CH₂OH) branch] | H | —CH₃ | —COCH₃ |

TABLE-4BB-continued
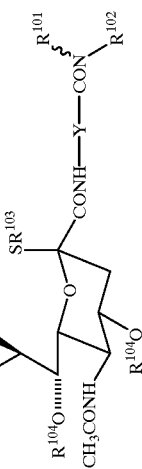
| Compound No. | $R^{101}$ | Y | $R^{102}$ | $R^{103}$ | $R^{104}$ |
|---|---|---|---|---|---|
| 462 | " | " | H | —$CH_3$ | H |
| 463 | " | " | H | —$CH_3$ | —$COCH_3$ |
| 464 | " | " | H | —$CH_3$ | H |

TABLE 5BB
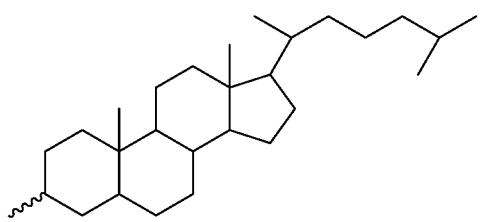
| Compound No. | R¹⁰¹ | Y | R¹⁰⁴ | R¹⁰⁵ |
|---|---|---|---|---|
| 465 | 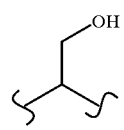 | 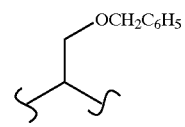 | —COCH$_3$ | HOCH$_2$CONH— |
| 466 | " | " | H | HOCH$_2$CONH— |
| 467 | " | " | —COCH$_3$ | CH$_3$COO— |
| 468 | " | " | H | HO— |
| 469 | " | " | H | C$_6$H$_5$CONH— |
| 470 | " | " | H | C$_6$H$_5$CH$_2$OCONH— |
| 471 | " | " | H | CH$_3$CH$_2$CONH— |
| 472 | " | 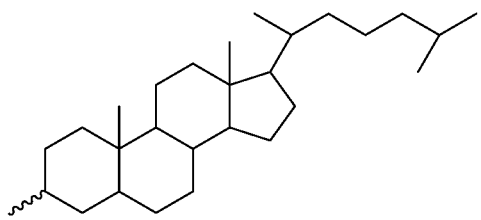 | —COCH$_3$ | HOCH$_2$CONH— |
| 473 | " | " | H | HOCH$_2$CONH— |
| 474 | " | " | —COCH$_3$ | CH$_3$COO— |
| 475 | 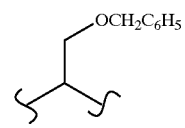 | " | H | HO— |
| 476 | " | 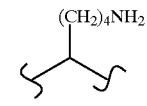 | —COCH$_3$ | HOCH$_2$CONH— |
| 477 | " | " | H | HOCH$_2$CONH— |
| 478 | " | " | —COCH$_3$ | CH$_3$COO— |
| 479 | " | " | H | HO— |
| 480 | " | 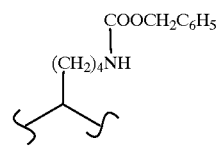 | —COCH$_3$ | CH$_3$COO— |
| 481 | " | " | H | HO— |

TABLE 5BB-continued

| Compound No. | R[101] | Y | R[104] | R[105] |
|---|---|---|---|---|
| 482 | " | (CH(CH₂Ph) group - benzyl-substituted methine) | —COCH₃ | CH₃COO— |
| 483 | " | " | H | HO— |
| 484 | (cholestanyl group) | —CH₂— | —COCH₃ | CH₃COO— |
| 485 | " | " | H | HO— |
| 486 | " | —(CH₂)₂— | —COCH₃ | CH₃COO— |
| 487 | " | " | H | HO— |
| 488 | " | (CH(CH₂CONH₂) group) | —COCH₃ | CH₃COO— |
| 489 | " | " | H | HO— |
| 490 | " | (CH(CH₂-C₆H₄-O-CH₂Ph) group) | —COCH₃ | CH₃COO— |
| 491 | " | " | H | HO— |

TABLE 5BB-continued

| Compound No. | R[101] | Y | R[104] | R[105] |
|---|---|---|---|---|
| 492 | cholestanyl | CH₂-C₆H₄-OH (para) branched | —COCH₃ | CH₃COO— |
| 493 | " | " | H | HO— |
| 494 | " | CH₂-CH₂-CONH₂ branched | —COCH₃ | CH₃COO— |
| 495 | " | " | H | HO— |
| 496 | " | CH₂-CH₂-COOH branched | —COCH₃ | CH₃COO— |
| 497 | " | " | H | HO— |
| 498 | " | CH₂-COOH branched | —COCH₃ | CH₃COO— |
| 499 | " | " | H | HO— |
| 500 | cholestanyl | (CH₂)₃NH-C(=NH)NH₂ branched | —COCH₃ | CH₃COO— |
| 501 | " | " | H | HO— |

TABLE 5BB-continued
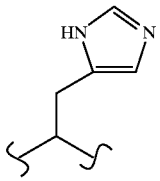
| Compound No. | R[101] | Y | R[104] | R[105] |
|---|---|---|---|---|
| 502 | " | 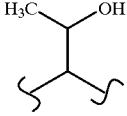 | —COCH₃ | CH₃COO— |
| 503 | " | " | H | HO— |
| 504 | " | 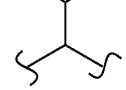 | —COCH₃ | CH₃COO— |
| 505 | " | " | H | HO— |
| 506 | " | 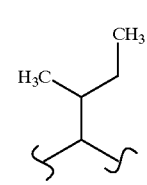 | —COCH₃ | CH₃COO— |
| 507 | " | " | H | HO— |
| 508 | " | 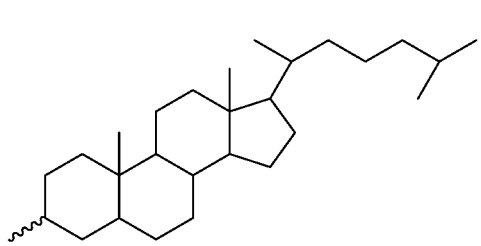 | —COCH₃ | CH₃COO— |
| 509 | " | " | H | HO— |
| 510 | 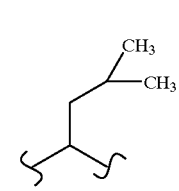 | 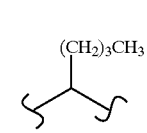 | —COCH₃ | CH₃COO— |
| 511 | " | " | H | HO— |
| 512 | " | (CH₂)₃CH₃ | —COCH₃ | CH₃COO— |
| 513 | " | " | H | HO— |

TABLE 5BB-continued

| Compound No. | R¹⁰¹ | Y | R¹⁰⁴ | R¹⁰⁵ |
|---|---|---|---|---|
| 514 | " | -CH(CH₃)- | —COCH₃ | CH₃COO— |
| 515 | " | " | H | HO— |
| 516 | " | -CH(CH₂SH)- | —COCH₃ | CH₃COO— |
| 517 | " | " | H | HO— |
| 518 | " | -CH(CH₂CH₂SCH₃)- | —COCH₃ | CH₃COO— |
| 519 | " | " | H | HO— |
| 520 | cholesteryl | -CH(CH₂CH₂OH)- | —COCH₃ | CH₃COO— |
| 521 | " | " | H | HO— |
| 522 | " | -CH(CH₂-indol-2-yl)- | —COCH₃ | CH₃COO— |
| 523 | " | " | H | HO— |
| 524 | " | -p-C₆H₄- | —COCH₃ | CH₃COO— |
| 525 | " | " | H | HO— |

TABLE 5BB-continued
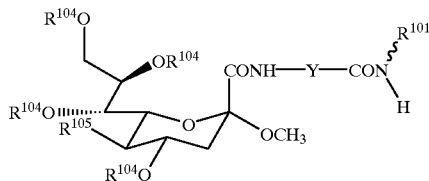
| Compound No. | R[101] | Y | R[104] | R[105] |
|---|---|---|---|---|
| 526 | " | 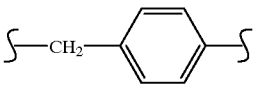 | —COCH₃ | CH₃COO— |
| 527 | " | " | H | HO— |
| 528 | " | 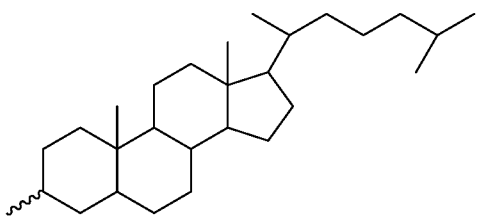 | —COCH₃ | CH₃COO— |
| 529 | " | " | H | HO— |
| 530 | 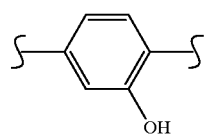 | 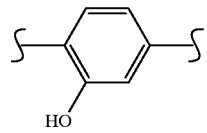 | —COCH₃ | CH₃COO— |
| 531 | " | " | H | HO— |
| 532 | " | 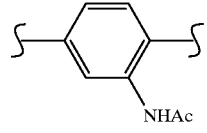 | —COCH₃ | CH₃COO— |
| 533 | " | " | H | HO— |
| 534 | " | 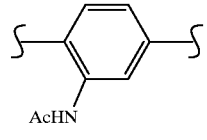 | —COCH₃ | CH₃COO— |
| 535 | " | " | H | HO— |
| 536 | " |  | —COCH₃ | CH₃COO— |
| 537 | " | " | H | HO— |

TABLE 5BB-continued

| Compound No. | R¹⁰¹ | Y | R¹⁰⁴ | R¹⁰⁵ |
|---|---|---|---|---|
| 538 | cholesteryl | CH(CH₂OH)- | —COCH₃ | CH₃COO— |
| 539 | " | " | H | HO— |
| 540 | " | CH((CH₂)₄NH₂)- | —COCH₃ | CH₃COO— |
| 541 | " | " | H | HO— |
| 542 | " | 1,4-phenylene | —COCH₃ | CH₃COO— |
| 543 | " | " | H | HO— |
| 544 | " | 2-NHAc-1,4-phenylene | —COCH₃ | CH₃COO— |
| 545 | " | " | H | HO— |
| 546 | " | CH(CH₂CONH₂)- | —COCH₃ | CH₃COO— |
| 547 | " | " | H | HO— |
| 548 | cholesteryl | (CH₂)₂ | —COCH₃ | CH₃COO— |
| 549 | " | " | H | HO— |

TABLE 5BB-continued

| Compound No. | R[101] | Y | R[104] | R[105] |
|---|---|---|---|---|
| 550 | cholesteryl (Δ5, with isopropyl sidechain) | CH(CH₂OH)— | —COCH₃ | CH₃COO— |
| 551 | " | " | H | HO— |
| 552 | cholestanyl with (CH₂)₃OH sidechain | CH(CH₂OH)— | —COCH₃ | CH₃COO— |
| 553 | " | " | H | HO— |
| 554 | cholestanyl with (CH₂)₃OH sidechain | CH(CH₂OCH₂C₆H₅)— | —COCH₃ | CH₃COO— |
| 555 | " | " | H | HO— |
| 556 | cholestanyl with (CH₂)₃OAc sidechain | CH(CH₂OH)— | —COCH₃ | CH₃COO— |
| 557 | " | CH(CH₂OCH₂C₆H₅)— | —COCH₃ | CH₃COO— |

TABLE 5BB-continued

| Compound No. | R¹⁰¹ | Y | R¹⁰⁴ | R¹⁰⁵ |
|---|---|---|---|---|
| 558 | [steroid with COOCH₃ side chain] | [CH(CH₂OH) linker] | —COCH₃ | CH₃COO— |
| 559 | " | " | H | HO— |
| 560 | [steroid with COOH side chain] | [CH(CH₂OH) linker] | —COCH₃ | CH₃COO— |
| 561 | " | " | H | HO— |
| 562 | [steroid with dioxolane] | " | —COCH₃ | CH₃COO— |
| 563 | " | " | H | HO— |
| 564 | [cholestane with 6-keto] | " | —COCH₃ | CH₃COO— |
| 565 | " | " | H | HO— |

TABLE 5BB-continued

| Compound No. | R¹⁰¹ | Y | R¹⁰⁴ | R¹⁰⁵ |
|---|---|---|---|---|
| 566 | [cholic acid methyl ester steroid with OH] | [CH₂OH branched linker] | —COCH₃ | CH₃COO— |
| 567 | " | " | H | HO— |
| 568 | [cholic acid steroid with COOH and OH] | " | —COCH₃ | CH₃COO— |
| 569 | " | " | H | HO— |
| 570 | [steroid with diol side chain] | " | —COCH₃ | CH₃COO— |
| 571 | " | " | H | HO— |
| 572 | [17-keto steroid] | [CH₂OH branched linker] | —COCH₃ | CH₃COO— |
| 573 | " | " | H | HO— |
| 574 | [17-keto-5-ene steroid] | " | —COCH₃ | CH₃COO— |

TABLE 5BB-continued
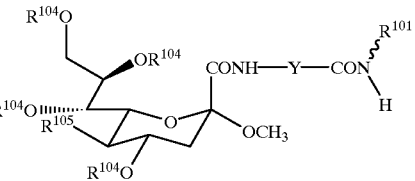
| Compound No. | $R^{101}$ | Y | $R^{104}$ | $R^{105}$ |
|---|---|---|---|---|
| 575 | " | " | H | HO— |
| 576 | (steroid with CONH$_2$) | " | —COCH$_3$ | CH$_3$COO— |
| 577 | " | " | H | HO— |
| 578 | (steroid with CONHCH$_3$) | (CH$_2$CH(CH$_2$OH)CH$_2$) | —COCH$_3$ | CH$_3$COO— |
| 579 | " | " | H | HO— |
| 580 | (steroid with CON(CH$_3$)$_2$) | " | —COCH$_3$ | CH$_3$COO— |
| 581 | " | " | H | HO— |

TABLE 6BB

| Compound No. | R¹⁰¹ | Y | R¹⁰⁴ | R¹⁰⁵ |
|---|---|---|---|---|
| 582 | cholestanyl | –CH(CH₂OH)– | —COCH₃ | HOCH₂CONH— |
| 583 | " | " | H | HOCH₂CONH— |
| 584 | " | " | —COCH₃ | CH₃COO— |
| 585 | " | " | H | HO— |
| 586 | " | " | H | C₆H₅CONH— |
| 587 | " | " | H | C₆H₅CH₂OCONH— |
| 588 | " | " | H | CH₃CH₂CONH— |
| 589 | " | –CH(CH₂OCH₂C₆H₅)– | —COCH₃ | HOCH₂CONH— |
| 590 | " | " | H | HOCH₂CONH— |
| 591 | " | " | —COCH₃ | CH₃COO— |
| 592 | cholestanyl | –CH(CH₂OCH₂C₆H₅)– | H | HO— |
| 593 | " | –CH((CH₂)₄NH₂)– | —COCH₃ | HOCH₂CONH— |
| 594 | " | " | H | HOCH₂CONH— |
| 595 | " | " | —COCH₃ | CH₃COO— |
| 596 | " | " | H | HO— |
| 597 | " | –CH((CH₂)₄NH-COOCH₂C₆H₅)– | —COCH₃ | CH₃COO— |
| 598 | " | " | H | HO— |

TABLE 6BB-continued
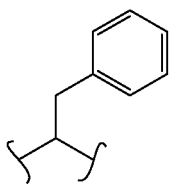
| Compound No. | R[101] | Y | R[104] | R[105] |
|---|---|---|---|---|
| 599 | " | 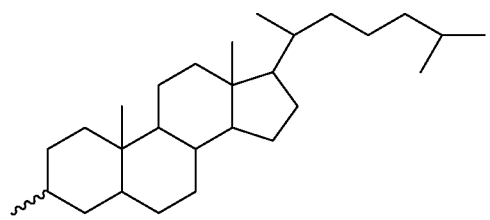 | —COCH$_3$ | CH$_3$COO— |
| 600 | " | " | H | HO— |
| 601 | 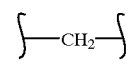 | 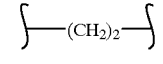 | —COCH$_3$ | CH$_3$COO— |
| 602 | " | " | H | HO— |
| 603 | " | 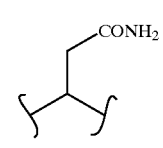 | —COCH$_3$ | CH$_3$COO— |
| 604 | " | " | H | HO— |
| 605 | " | 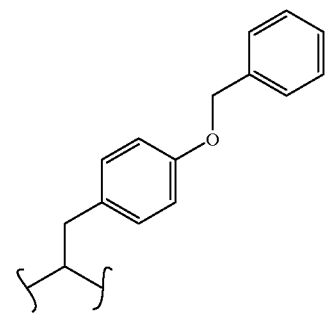 | —COCH$_3$ | CH$_3$COO— |
| 606 | " | " | H | HO— |
| 607 | " | " | —COCH$_3$ | CH$_3$COO— |
| 608 | " | " | H | HO— |

TABLE 6BB-continued
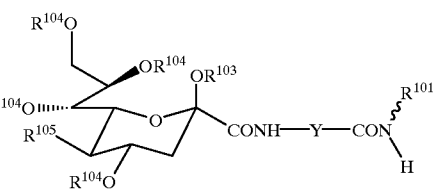
| Compound No. | R^101 | Y | R^104 | R^105 |
|---|---|---|---|---|
| 609 | (cholestanyl) | (4-hydroxybenzyl-CH) | —COCH$_3$ | CH$_3$COO— |
| 610 | " | " | H | HO— |
| 611 | " | (CH$_2$CH$_2$CONH$_2$) | —COCH$_3$ | CH$_3$COO— |
| 612 | " | " | H | HO— |
| 613 | " | (CH$_2$CH$_2$COOH) | —COCH$_3$ | CH$_3$COO— |
| 614 | " | " | H | HO— |
| 615 | " | (CH$_2$COOH) | —COCH$_3$ | CH$_3$COO— |
| 616 | " | " | H | HO— |
| 617 | (cholestanyl) | (CH$_2$)$_3$NH-C(=NH)NH$_2$ | —COCH$_3$ | CH$_3$COO— |
| 618 | " | " | H | HO— |

TABLE 6BB-continued

| Compound No. | R[101] | Y | R[104] | R[105] |
|---|---|---|---|---|
| 619 | " | imidazolyl-CH2-CH< | —COCH3 | CH3COO— |
| 620 | " | " | H | HO— |
| 621 | " | CH3-CH(OH)-CH< | —COCH3 | CH3COO— |
| 622 | " | " | H | HO— |
| 623 | " | (CH3)2CH-CH< | —COCH3 | CH3COO— |
| 624 | " | " | H | HO— |
| 625 | " | CH3-CH(CH2CH3)-CH< | —COCH3 | CH3COO— |
| 626 | " | " | H | HO— |
| 627 | cholestanyl | (CH3)2CH-CH2-CH< | —COCH3 | CH3COO— |
| 628 | " | " | H | HO— |
| 629 | " | CH3(CH2)3-CH< | —COCH3 | CH3COO— |
| 630 | " | " | H | HO— |

TABLE 6BB-continued

[Structure: pyranose ring with R¹⁰⁴O-CH₂, OR¹⁰⁴, OR¹⁰³, R¹⁰⁴O, R¹⁰⁵, R¹⁰⁴O substituents, connected via —CONH—Y—CON(H)—R¹⁰¹]

| Compound No. | R¹⁰¹ | Y | R¹⁰⁴ | R¹⁰⁵ |
|---|---|---|---|---|
| 631 | " | —CH(CH₃)— branched | —COCH₃ | CH₃COO— |
| 632 | " | " | H | HO— |
| 633 | " | —CH(CH₂SH)— | —COCH₃ | CH₃COO— |
| 634 | " | " | H | HO— |
| 635 | " | —CH(CH₂CH₂SCH₃)— | —COCH₃ | CH₃COO— |
| 636 | " | " | H | HO— |
| 637 | cholestanyl | —CH(CH₂CH₂OH)— | —COCH₃ | CH₃COO— |
| 638 | " | " | H | HO— |
| 639 | " | —CH(CH₂-indol-2-yl)— | —COCH₃ | CH₃COO— |
| 640 | " | " | H | HO— |
| 641 | " | —(p-C₆H₄)— | —COCH₃ | CH₃COO— |
| 642 | " | " | H | HO— |

TABLE 6BB-continued

[Structure: Pyranose ring with R¹⁰⁴O-CH₂, OR¹⁰⁴, OR¹⁰³, R¹⁰⁴O, R¹⁰⁵, R¹⁰⁴O substituents, and —CONH—Y—CON(H)—R¹⁰¹ side chain]

| Compound No. | R¹⁰¹ | Y | R¹⁰⁴ | R¹⁰⁵ |
|---|---|---|---|---|
| 643 | " | -[1,4-phenylene-CH₂]- | —COCH₃ | CH₃COO— |
| 644 | " | " | H | HO— |
| 645 | " | -[CH₂-1,4-phenylene]- | —COCH₃ | CH₃COO— |
| 646 | " | " | H | HO— |
| 647 | [cholestanyl group] | -[phenylene with OH]- | —COCH₃ | CH₃COO— |
| 648 | " | " | H | HO— |
| 649 | " | -[phenylene with HO]- | —COCH₃ | CH₃COO— |
| 650 | " | " | H | HO— |
| 651 | " | -[phenylene with NHAc]- | —COCH₃ | CH₃COO— |
| 652 | " | " | H | HO— |
| 653 | " | -[phenylene with AcHN]- | —COCH₃ | CH₃COO— |
| 654 | " | " | H | HO— |

TABLE 6BB-continued
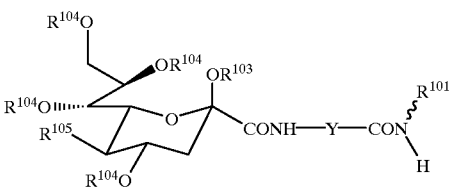
| Compound No. | $R^{101}$ | Y | $R^{104}$ | $R^{105}$ |
|---|---|---|---|---|
| 655 | (cholesteryl group) | CH(CH$_2$OH)– | —COCH$_3$ | CH$_3$COO— |
| 656 | " | " | H | HO— |
| 657 | " | CH((CH$_2$)$_4$NH$_2$)– | —COCH$_3$ | CH$_3$COO— |
| 658 | " | " | H | HO— |
| 659 | " | –C$_6$H$_4$– | —COCH$_3$ | CH$_3$COO— |
| 660 | " | " | H | HO— |
| 661 | " | –C$_6$H$_3$(NHAc)– | —COCH$_3$ | CH$_3$COO— |
| 662 | " | " | H | HO— |
| 663 | " | CH(CH$_2$CONH$_2$)– | —COCH$_3$ | CH$_3$COO— |
| 664 | " | " | H | HO— |
| 665 | CH((CH$_2$)$_4$NH$_2$)– | –(CH$_2$)$_2$– | —COCH$_3$ | CH$_3$COO— |
| 666 | " | " | H | HO— |

TABLE 6BB-continued

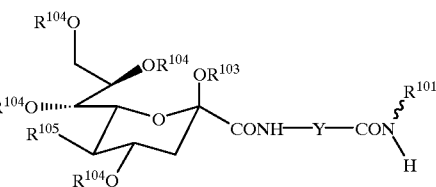

| Compound No. | R[101] | Y | R[104] | R[105] |
|---|---|---|---|---|
| 667 | cholesterol-like steroid (5-ene, iso-octyl side chain) | CH₂CH(CH₂OH)CH₂ | —COCH₃ | CH₃COO— |
| 668 | " | " | H | HO— |
| 669 | steroid with side chain terminating in OH | CH₂CH(CH₂OH)CH₂ | —COCH₃ | CH₃COO— |
| 670 | " | " | H | HO— |
| 671 | steroid with side chain terminating in OH | CH₂CH(CH₂OCH₂C₆H₅)CH₂ | —COCH₃ | CH₃COO— |
| 672 | " | " | H | HO— |
| 673 | steroid with side chain terminating in OAc | CH₂CH(CH₂OH)CH₂ | —COCH₃ | CH₃COO— |
| 674 | " | CH₂CH(CH₂OCH₂C₆H₅)CH₂ | —COCH₃ | CH₃COO— |

TABLE 6BB-continued
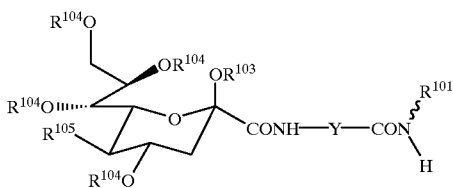
| Compound No. | R[101] | Y | R[104] | R[105] |
|---|---|---|---|---|
| 675 | (cholanic acid methyl ester steroid with COOCH₃) | (CH₂)₂CH(OH) branched | —COCH₃ | CH₃COO— |
| 676 | " | " | H | HO— |
| 677 | (steroid with COOH) | (CH₂)₂CH(OH) branched | —COCH₃ | CH₃COO— |
| 678 | " | " | H | HO— |
| 679 | (cholestane with dioxolane) | " | —COCH₃ | CH₃COO— |
| 680 | " | " | H | HO— |
| 681 | (6-oxocholestane) | " | —COCH₃ | CH₃COO— |
| 682 | " | " | H | HO— |

TABLE 6BB-continued

| Compound No. | R¹⁰¹ | Y | R¹⁰⁴ | R¹⁰⁵ |
|---|---|---|---|---|
| 683 | (cholic acid methyl ester steroid with 7-OH) | CH₂CH(OH)CH₂ | —COCH₃ | CH₃COO— |
| 684 | " | " | H | HO— |
| 685 | (cholic acid steroid with 7-OH, COOH) | " | —COCH₃ | CH₃COO— |
| 686 | " | " | H | HO— |
| 687 | (steroid with 20,21-diol) | " | —COCH₃ | CH₃COO— |
| 688 | " | " | H | HO— |
| 689 | (17-keto steroid) | CH₂CH(OH)CH₂ | —COCH₃ | CH₃COO— |
| 690 | " | " | H | HO— |
| 691 | (17-keto Δ⁵ steroid) | " | —COCH₃ | CH₃COO— |

TABLE 6BB-continued

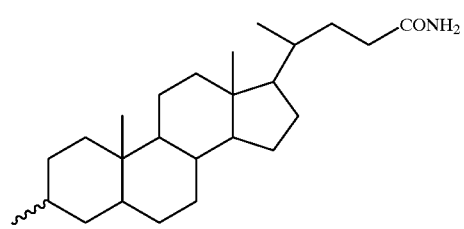

| Compound No. | R^101 | Y | R^104 | R^105 |
|---|---|---|---|---|
| 692 | " | " | H | HO— |
| 693 | 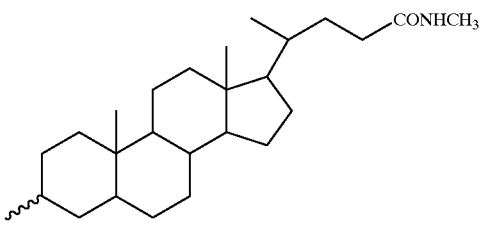 | " | —COCH$_3$ | CH$_3$COO— |
| 694 | " | " | H | HO— |
| 695 | 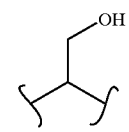 | ⎯OH | —COCH$_3$ | CH$_3$COO— |
| 696 | " | " | H | HO— |
| 697 | 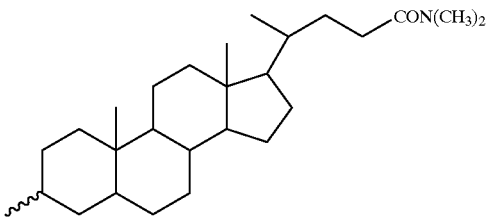 | " | —COCH$_3$ | CH$_3$COO— |
| 698 | " | " | H | HO— |

Salts formed with the carboxyl group of the compound represented by the general formulae (1AA) and (1BB) may preferably be pharmaceutically acceptable salts. Examples include salts with alkali metals such as sodium salt or potassium salt; a salt with ammonia; or salts with organic amine compounds such as tris(hydroxymethyl)aminomethane, N, N-bis(hydroxyethyl)piperazine, 2-amino-2-methyl-1-propanol, ethanolamine, N-methylglucamine, or L-glucamine.

Salts formed with the amino group of the compound represented by the general formulae (1AA) and (1BB) may preferably be pharmaceutically acceptable salts. Examples include inorganic salts such as hydrochloride, hydrobromide, hydroiodide, sulfate, phosphate; organic acid salts such as oxalate, maleate, fumarate, lactate, malate, citrates, tartrate, benzoate, methanesulfonate, or camphorsulfonate.

The compounds represented by the general formulae (1AA) and (1BB) and salts thereof may exist in the form of hydrates or solvates, and such hydrates and solvates fall within the scope of the present invention. Examples of a solvent that forms the solvate include methanol, ethanol, isopropanol, acetone, ethyl acetate, methylene chloride and the like.

The compounds represented by the general formulae (1AA) and (1BB) have asymmetric carbon atoms, and accordingly, a lot of optical isomers and diastereoisomers thereof may exist. It should be understood that such isomers also fall within the scope of the present invention.

The compounds of the present invention represented by the general formula (1AA) can be prepared according to methods explained below.

1. Compounds of the general formula (1AA) wherein R$^5$ is a group of CH$_3$—CO—NH—
    (a) Method for the preparation of α-isomers at the 2-position of sialic acid (i) Where X is oxygen atom:

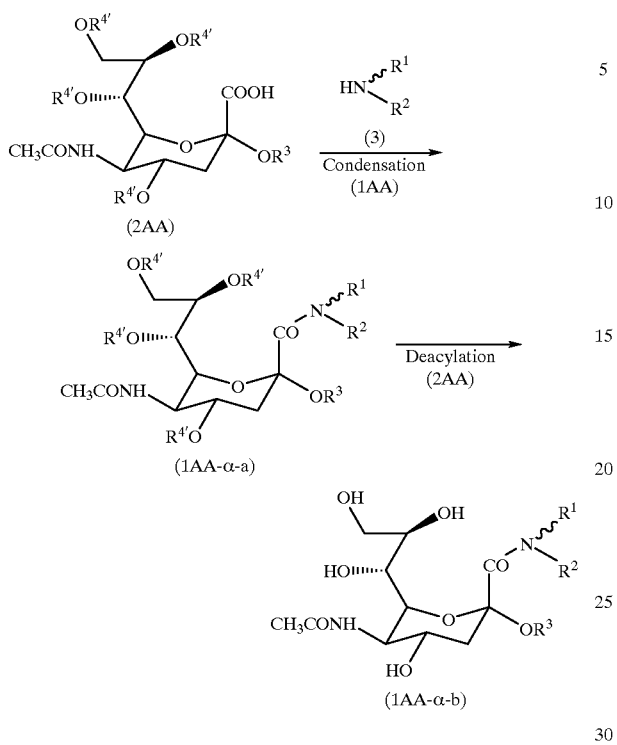

In the formulas, $R^1$, $R^2$, and $R^3$ have the same meanings as those defined in the general formula (1AA), and $R^{4'}$ represents a $C_2$–$C_7$ acyl group.

A compound of formula (2AA) is first reacted with a compound of formula (3AA) [step (1AA)] to obtain a compound of formula (1AA-α-a), and then the product is subsequently subjected to deacylation by reaction with an alkoxide such as sodium methoxide to prepare a compound of formula (1AA-α-b) [step (2AA)].

The step (1AA) may be performed by reacting 0.9–10 equivalents, preferably 1.0–5.0 equivalents of an ester of a chlorocarbonic acid such as isobutyl chlorocarbonate with 0.9–10 equivalents, preferably 1.0–5.0 equivalents of a tertiary amine such as N-methylmorpholine or triethylamine in a solvent such as tetrahydrofuran, dioxane, acetonitrile, dichloromethane, or dichloroethane at a temperature ranging from –50° C. to 50° C., preferably from –20° C. to room temperature to obtain a mixed acid anhydride corresponding to the compound of formula (2AA), and then treating the product with 0.9–10 equivalents, preferably 1.0–5.0 equivalents of a compound of formula (3AA) or a salt of the compound of formula (3AA) such as hydrochloride together with an equimolar tertiary amine at a temperature ranging from –50° C. to 50° C., preferably from –20° C. to room temperature.

Alternatively, the step (1AA) may be carried out by reacting 0.9–10 equivalents, preferably 1.0–5.0 equivalents of a chloride such as thionyl chloride, phosphorous pentachloride, or phosphorus oxychloride with 0.9–20 equivalents, preferably 1.0–10 equivalents of a base such as pyridine in a solvent such as tetrahydrofuran, dioxane, acetonitrile, dichloromethane, or dichloroethane at a temperature ranging from –50° C. to 50° C., preferably from –20° C. to room temperature to form an acid chloride corresponding to a compound of formula (2AA), and then treating the product with 0.9–10 equivalents, preferably 1.0–5.0 equivalents of a compound of formula (3AA) or a salt of the compound of formula (3AA) such as hydrochloride together with an equimolar tertiary amine at a temperature ranging from –50° C. to 50° C., preferably from –20° C. to room temperature. Operations for the reactions and reactions per se may preferably be carried out under anhydrous condition.

The step (2AA) may be performed by using 0.05–5.0 equivalents, preferably 0.1–2.0 equivalents of alkoxide in a solvent such as methanol at a temperature ranging from 0° C. to 50° C., preferably from 0° C. to room temperature. Operations for the reactions and reactions per se may preferably be carried out under anhydrous condition.

(ii) Where X is sulfur atom:

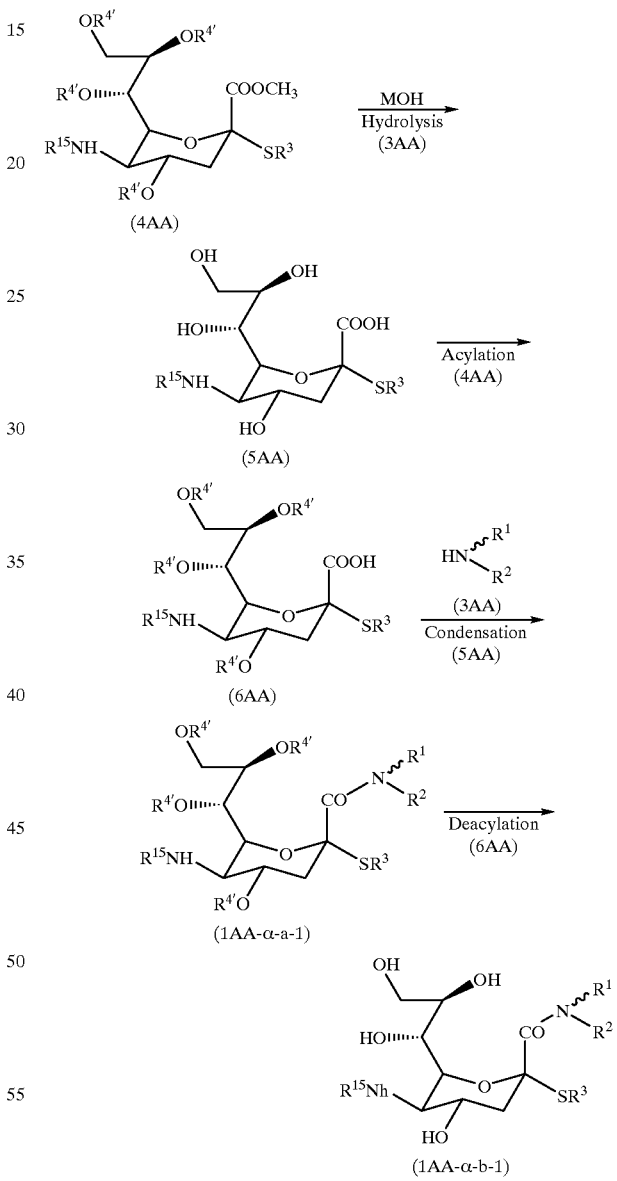

In the formulas, $R^1$, $R^2$ $R^3$, and $R^{4'}$ have the same meanings as those defined above, and M represents an alkali metal.

A compound of formula (4AA) is first reacted with an alkali such as sodium hydroxide, and then the product is subjected to hydrolysis to form a compound of formula (5AA) [step (3AA)]. The product is then acylated to form a compound of formula (6AA) [step (4AA)] and successively reacted with a compound of formula (3AA) to form a compound of formula (1AA-α-a-1) [step (5AA)], and then the product is subjected to deacylation by reaction with an alkoxide such as sodium methoxide to obtain a compound of formula (1AA-α-b- 1) [step (6AA)].

The step (3AA) may be carried out by using 0.9–10 equivalents, preferably 1.0–5.0 equivalents of a base such as sodium hydroxide or potassium hydroxide in a solvent such as water, methanol, or ethanol at a temperature ranging from 0° C. to 50° C., preferably from 0° C. to room temperature. The step (4AA) may be carried out by using 4.0–200 equivalents, preferably 4.4–100 equivalents of an acid anhydride such as acetic anhydride or an acid chloride such as acetyl chloride, propionyl chloride, butyryl chloride, valeryl chloride, or benzoyl chloride in a solvent such as pyridine at a temperature ranging from 0° C. to 50° C., preferably from 0° C. to room temperature. For the reaction, presence of 0.1–1 equivalent, preferably 0.1–0.5 equivalent of a base such as 4-dimethylaminopyridine in a reaction system is preferred to achieve a higher yield. Operations for the reactions and reactions per se may preferably be carried out under anhydrous condition. The step (5AA) may be carried out under the same condition as in the step (1AA). The step (6AA) may be carried out under the same condition as in the step (2AA).

(b) Method for preparation wherein the 2-position of sialic acid is β-configuration
(i) Where X is oxygen atom:

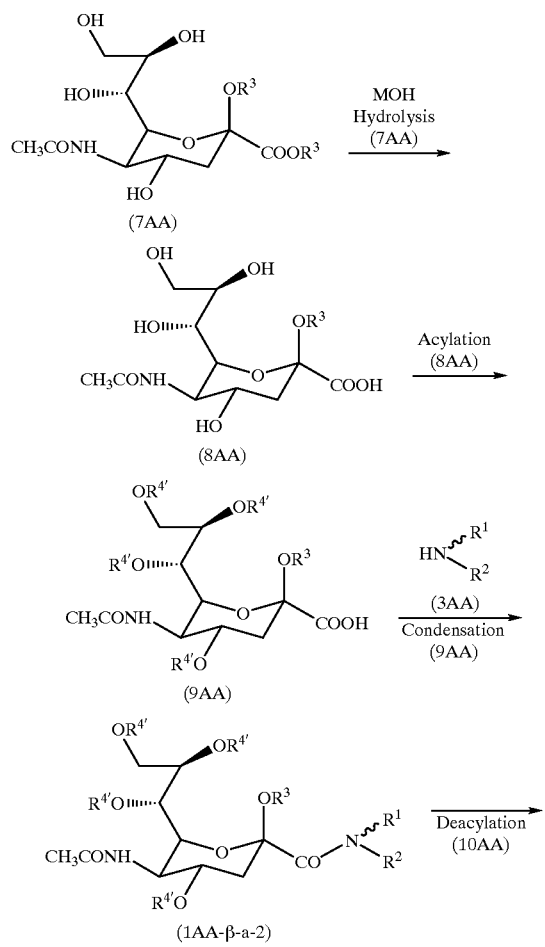

(1AA-β-a-2)

-continued

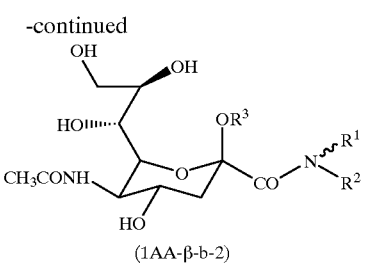

(1AA-β-b-2)

In the formulas, $R^1$, $R^2$, $R^3$, $R^{4'}$, and M have the same meanings as those defined above.

A compound of formula (7AA) is first subjected to hydrolysis by reaction with an alkali such as sodium hydroxide to form a compound of formula (8AA) [step (7AA)], and then the product is acylated to form a compound of formula (9AA) [step (8AA)]. The resulting compound is then reacted with a compound of formula (3AA) to form a compound of formula (1AA-β-a-2) [step (9AA)], and the product is subsequently deacylated by reaction with an alkoxide such as sodium methoxide to obtain a compound of formula (1AA-β-b-2) [step (10AA)]. The step (7AA) may be carried out under the same condition as in the step (3AA). The step (8AA) may be carried out under the same condition as in the step (4AA). The step (9AA) may be carried out under the same condition as in the step (1AA). The step (10AA) may be carried out under the same condition as in the step (2AA).

(ii) Where X is sulfur atom:

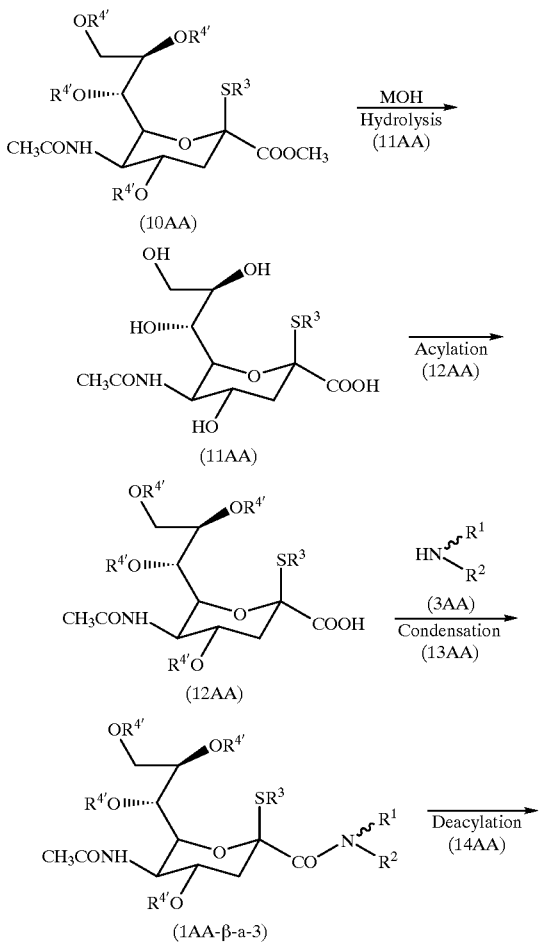

(1AA-β-a-3)

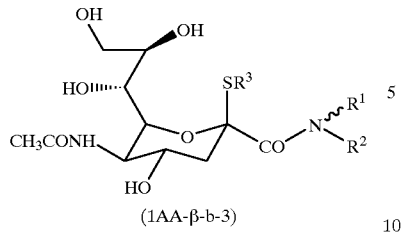

(1AA-β-b-3)

In the formulas, $R^1$, $R^2$, $R^3$, $R^{4'}$, and M have the same meanings as those defined above.

A compound of formula (10AA) is first hydrolyzed by reaction with an alkali such as sodium hydroxide to form a compound of formula (11AA) [step (11AA)], and then the product is acylated to form a compound of formula (12AA) [step (12AA)]. The resulting compound is reacted with a compound of formula (3AA) to form a compound of formula (1AA-β-a-3) [step (13AA)], and then the product is subjected to deacylation by reaction with an alkoxide such as sodium methoxide to obtain a compound of formula (1AA-β-b-3) [step (14AA)]. The step (11AA) may be carried out under the same condition as in the step (3AA). The step (12AA) may be carried out under the same condition as in the step (4AA). The step (13AA) may be carried out under the same condition as in the step (1AA). The step (14AA) may be carried out under the same condition as in the step (2AA).

2. Compound of the general formula (1AA) wherein $R^5$ is a group of $R^{15}NH$— (wherein $R^{15}$ has the same meaning as that defined for the general formula (1AA) except for $CH_3CO$— group)

(a) Where the 2-position of sialic acid is α-configuration
(i) Where X is oxygen atom:

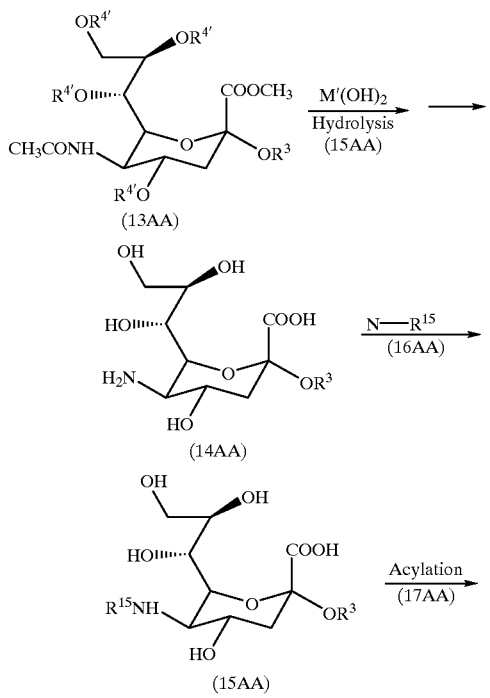

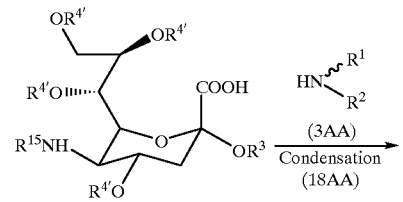

(16AA)

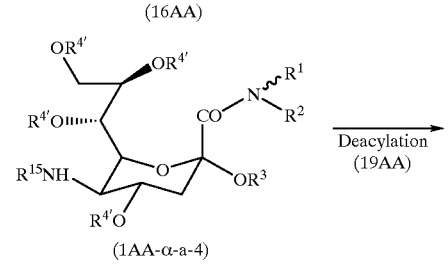

(1AA-α-a-4)

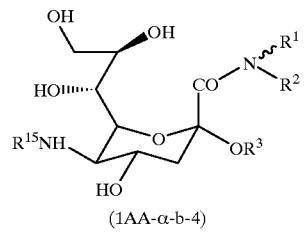

(1AA-α-b-4)

In the formulas, $R^1$, $R^2$, $R^3$, $R^{4'}$, and $R^{15}$ have the same meanings as those defined above, and M' represents an alkaline earth metal.

A compound of formula (13AA) is first hydrolyzed by reaction with an alkali such as barium hydroxide to form a compound of formula (14AA) [step (15AA)], and then the product is N-acylated or N-oxycarbonylated to form a compound of formula (15AA) [step (16AA)]. Then, the resulting compound is acylated to obtain a compound of formula (16AA) [step (17AA)] and the product is further reacted with a compound of formula (3AA) to form a compound of formula (1AA-α-a-4) [step (18AA)]. The resulting compound is then deacylated by reaction with an alkoxide such as sodium methoxide to obtain a compound of formula (1AA-α-b-4) [step (19AA)].

The step (15AA) may be carried out by using 0.9–10 equivalents, preferably 1.0–5.0 equivalents of a base such as barium hydroxide in a solvent such as water, methanol, ethanol at a temperature ranging from 0° C. to 100° C., preferably from 50° C. to 100° C. The step (16AA) may be carried out by N-acylation using 0.9–10 equivalents, preferably 1.0–3.0 equivalents of an acid anhydride such as acetic anhydride or propionic anhydride or an acid chloride such as acetyl chloride, propionyl chloride, or benzoyl chloride, together with 0.9–10 equivalents, preferably 1.0–3.0 equivalents of a tertiary amine such as triethylamine in a solvent such as water, methanol, ethanol, dioxane, or tetrahydrofuran, or alternatively, by N-oxycarbonylation using 0.9–10 equivalents, preferably 1.0–3.0 equivalents of di-t-butyl carbonate, carbobenzoxy chloride or the like and 0.9–10 equivalents, preferably 1.0–3.0 equivalents of a tertiary amine such as triethylamine. These reactions may be carried out at temperature ranging from 0° C. to 80° C., preferably from 0° C. to 50° C. The step (17AA) may be carried out under the same condition as in the step (4AA). The step (18AA) may be carried out under the same condition as in the step (1AA). The step (19AA) may be carried out under the same condition as in the step (2AA).

(ii) Where X is sulfur atom:

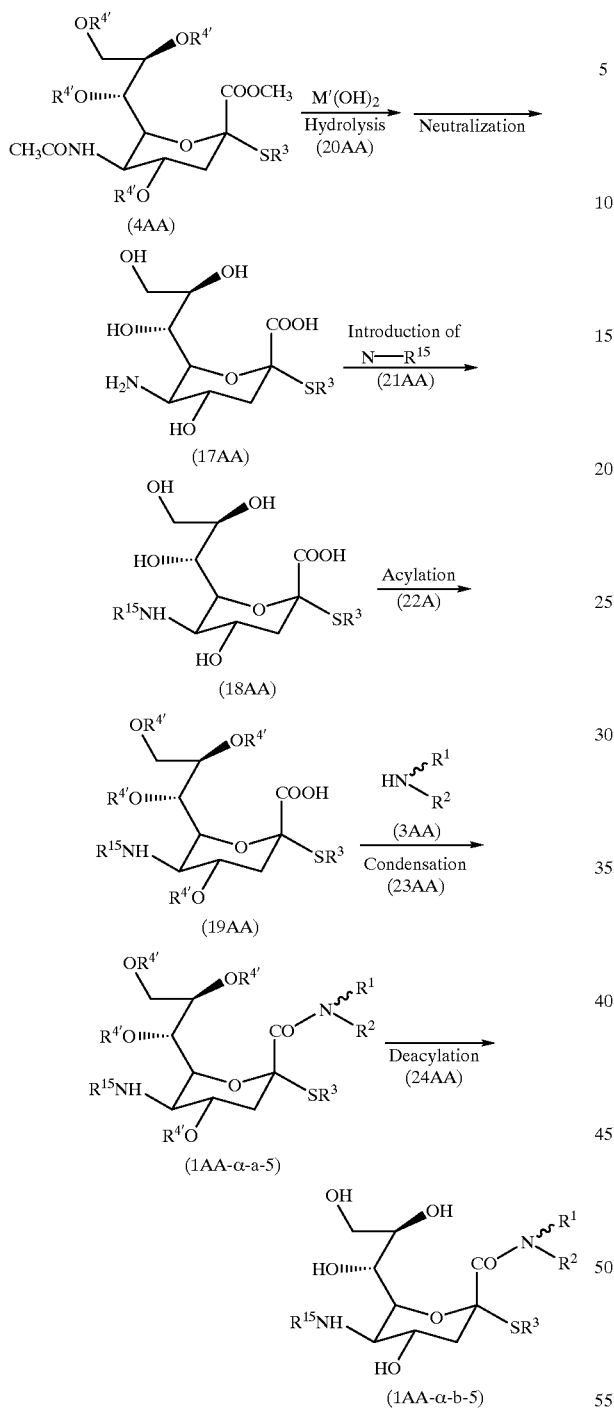

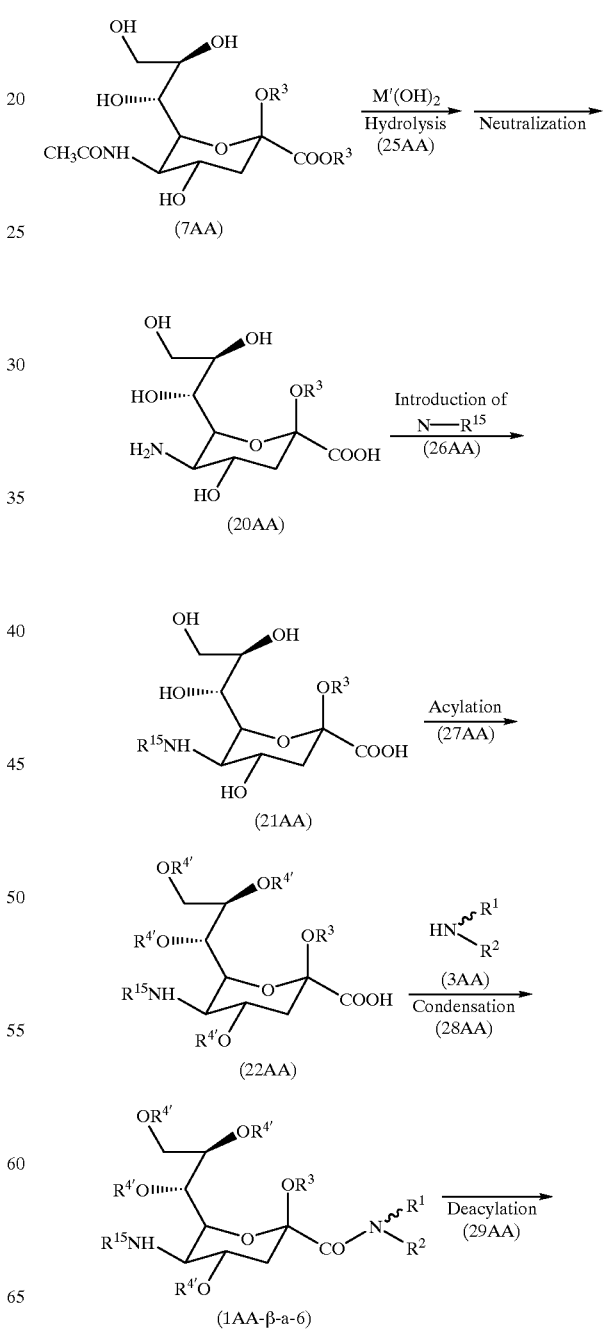

In the formulas, $R^1$, $R^2$, $R^3$, $R^{4'}$, $R^{15}$, and M' have the same meanings as those defined above.

A compound of formula (4AA) is first hydrolyzed by reaction with an alkali such as barium hydroxide to form a compound of formula (17AA) [step (20AA)], and then the product is N-acylated or N-oxycarbonylated to form a compound of formula (18AA) [step (21AA)]. The resulting compound is then acylated to obtain a compound of formula (19AA) [step (22AA)], and the product is reacted with a compound of formula (3AA) to obtain a compound of formula (1AA-α-a-5) [step (23AA)]. The resulting compound is subsequently deacylated by reaction with an alkoxide such as sodium methoxide to obtain a compound of formula (1AA-α-b-5) [step (24AA)]. The step (20AA) may be carried out under the same condition as in the step (15AA). The step (21AA) may be carried out under the same condition as in the step (16AA). The step (22AA) may be carried out under the same condition as in the step (4AA). The step (23AA) may be carried out under the same condition as in the step (1AA). The step (24AA) may be carried out under the same condition as in the step (2AA).

(b) Method for preparation of the compound wherein the 2-position of sialic acid is β-configuration (i) Where X is oxygen atom:

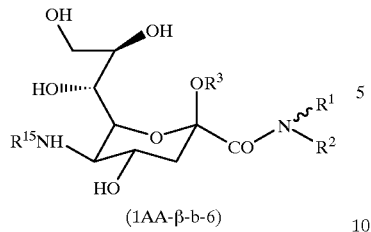

(1AA-β-b-6)

In the formulas, $R^1$, $R^2$, $R^3$, $R^{4'}$, $R^{15}$, and $M'$ have the same meanings as those defined above.

A compound of formula (7AA) is first hydrolyzed by reaction with an alkali such as barium hydroxide to form a compound of formula (20AA) [step (25AA)], and the product is then N-acylated or N-oxycarbonylated to form a compound of formula (21AA) [step (26AA)]. The resulting compound is acylated to obtain a compound of formula (22AA) [step (27AA)], and the product is then reacted with a compound of formula (3AA) to produce a compound of formula (1AA-β-a-6) [step (28AA)]. The resulting compound is subsequently deacylated by reaction with an alkoxide such as sodium methoxide to produce a compound of formula (1AA-β-b-6) [step (29AA)]. The step (25AA) may be carried out under the same condition as in the step (15AA). The (26AA) step is carried out under the same condition as in the step (16AA). The step (27AA) may be carried out under the same condition as in the step (4AA). The step (28AA) may be carried out under the same condition as in the step (1AA). The step (29AA) may be carried out under the same condition as in the step (2AA).

(ii) Where X is sulfur atom:

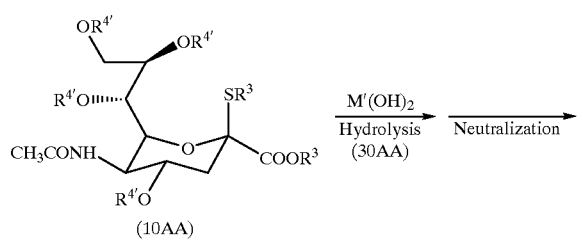

(10AA)

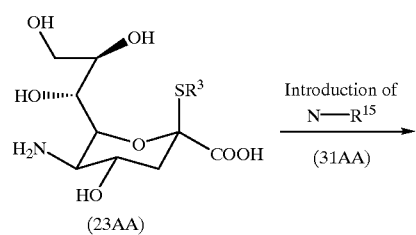

(23AA)

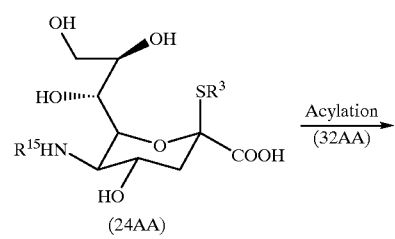

(24AA)

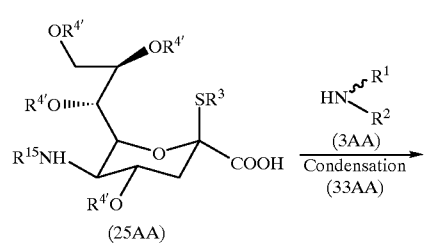

(25AA)

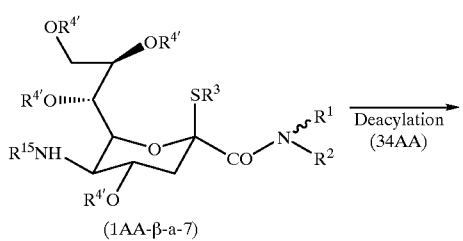

(1AA-β-a-7)

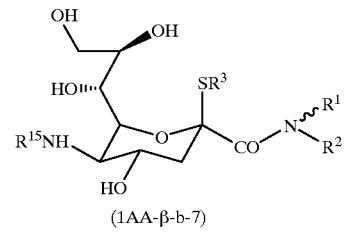

(1AA-β-b-7)

In the formulas, $R^1$, $R^2$, $R^3$, $R^{4'}$, $R^{15}$, and $M'$ have the same meanings as those defined above.

A compound of formula (10AA) is first hydrolyzed by reaction with an alkali such as barium hydroxide to form a compound of formula (23AA) [step (30AA)], and the product is then N-acylated or N-oxycarbonylated to form a compound of formula (24AA) [step (31AA)]. The resulting compound is acylated to form a compound of formula (25AA) [step (32AA)], and the product is then is reacted with a compound of formula (3AA) to produce a compound of formula (1AA-β-a-7) [step (33AA)]. The resulting compound is subsequently deacylated by reaction with an alkoxide such as sodium methoxide to obtain a compound of formula (1AA-β-b-7) [step (34AA)]. The step (30AA) may be carried out under the same condition as in the step (15AA). The (31AA) step is carried out under the same condition as in the step (16AA). The step (32AA) may be carried out under the same condition as in the step (4AA). The step (33AA) may be carried out under the same condition as in the step (1AA). The step (34AA) may be carried out under the same condition as in the step (2AA).

3. Compounds of the general formula (1AA) wherein $R^5$ is a group of $R^{14}O$— (wherein $R^{14}$ has the same meaning as that defined in the general formula (1AA))

(a) Method for preparation of the compound wherein the 2-position of sialic acid is α-configuration (i) Where X is oxygen atom:

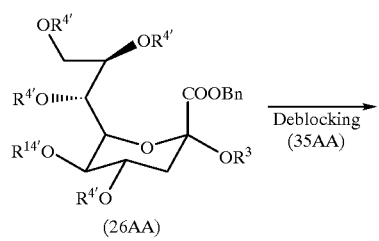
(26AA)

Deblocking (35AA) →

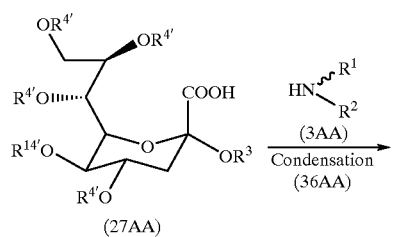
(27AA)

$HN\overset{R^1}{\underset{R^2}{\diagdown}}$ (3AA)
Condensation (36AA) →

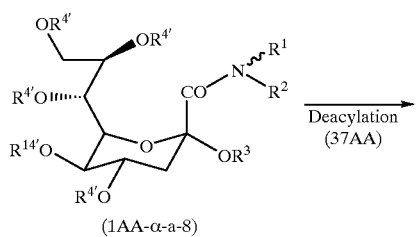
(1AA-α-a-8)

Deacylation (37AA) →

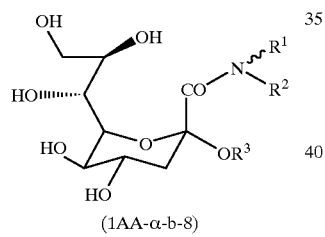
(1AA-α-b-8)

In the formulas, $R^1$, $R^2$, $R^3$, and $R^{4'}$ have the same meanings as those defined above, and $R^{14'}$ represents a $C_2$–$C_7$ acyl group.

A compound of formula (26AA) is first reduced to obtain a compound of formula (27AA) [step (35AA)], and the product is then reacted with a compound of formula (3AA) to form a compound of formula (1AA-α-a-8) [step (36AA)]. The resulting compound is subsequently deacylated by reaction with an alkoxide such as sodium methoxide to produce a compound of formula (1AA-α-b-8) [step (37AA)].

The step (35AA) may be carried out in a solvent such as methanol, ethanol, tetrahydrofuran, or dioxane at a temperature ranging from 0° C. to 50° C., preferably from 0° C. to room temperature in the presence of 0.1–200% by weight, preferably 1.0–100% by weight of a catalyst such as palladium black or palladium carbon under hydrogen atmosphere. The step (36AA) may be carried out under the same condition as in the step (1AA). The step (37AA) may be carried out under the same condition as in the step (2AA).

(ii) Where X is sulfur atom:

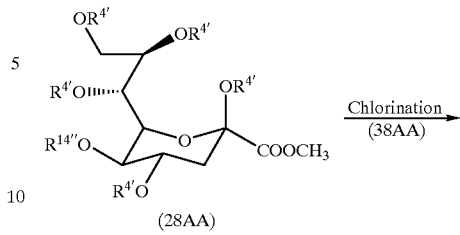
(28AA)

Chlorination (38AA) →

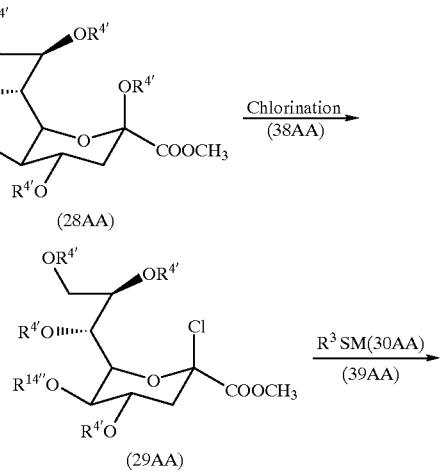
(29AA)

$R^3SM(30AA)$ (39AA) →

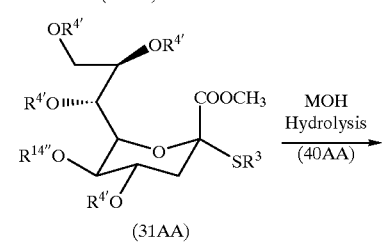
(31AA)

MOH Hydrolysis (40AA) →

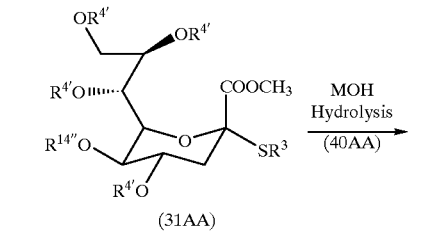
(32AA)

Acylation (41AA) →

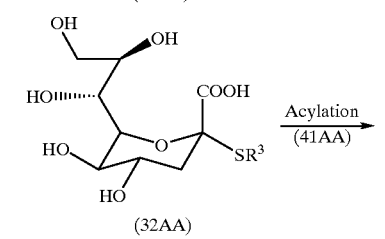
(33AA)

$HN\overset{R^1}{\underset{R^2}{\diagdown}}$ (3AA)
Condensation (42AA) →

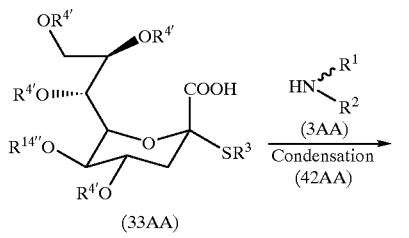
(1AA-α-a-9)

Deacylation (43AA) →

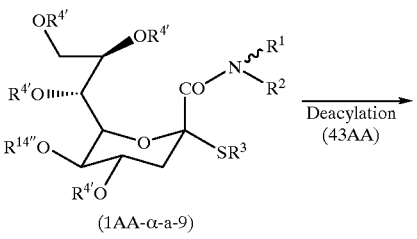

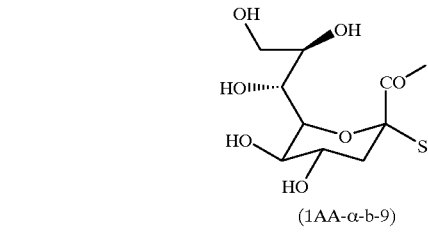
(1AA-α-b-9)

In the formulas, $R^1$, $R^2$, $R^3$, $R^{4'}$, and M have the same meanings as those defined above, and $R^{14''}$ has the same meaning as $R^{4'}$.

A compound of formula (28AA) is first chlorinated to obtain a compound of formula (29AA) [step (38AA)], and the product is then reacted with a compound of formula (30AA) to form a compound of formula (31AA) [step (39AA)]. The resulting compound is subsequently hydrolyzed to form a compound of formula (32AA) [step (40AA)], and then the product is acylated to form a compound of formula (33AA) [step (41AA)]. The resulting compound is subsequently reacted with a compound of formula (3AA) to obtain a compound of formula (1AA-α-a-9) [step (42AA)], and the product is then deacylated by reaction with an alkoxide such as sodium methoxide to produce a compound of formula (1AA-α-b-9) [step (43AA)].

The step (38AA) may be carried out in an acid chloride such as acetyl chloride, propionyl chloride, butyryl chloride, valeryl chloride, or benzoyl chloride at a temperature ranging from −20° C. to 50° C., preferably from 0° C. to room temperature. For the reaction, reaction mixture may preferably be saturated with hydrogen chloride gas to achieve a higher yield. Operations for the reaction and the reaction per se may preferably be carried out under anhydrous condition. The step (39AA) may be carried out by using 0.9–200 equivalents, preferably 1.0–100 equivalents of a compound of formula (30AA) in a solvent such as acetonitrile, tetrahydrofuran, dioxane, dimethylformamide, or dimethyl sulfoxide at a temperature ranging from 0° C. to 50° C., preferably from 0° C. to room temperature. The reaction may preferably be performed in the presence of 0.1–10 equivalents, preferably 0.9–50 equivalents of a silver catalyst such as silver trifluoromethanesulfonate, silver salicylate, silver carbonate, or silver oxide to achieve a higher yield. Operations for the reaction and the reaction per se may preferably be carried out under anhydrous condition. The step (40AA) may be carried out under the same condition as in the step (3AA). The step (41AA) may be carried out under the same condition as in the step (4AA). The step (42AA) may be carried out under the same condition as in the step (1AA). The step (43AA) may be carried out under the same condition as in the step (2AA).

(b) Method for preparation of compound wherein the 2-position of sialic acid is β-configuration
(i) Where X is oxygen atom:

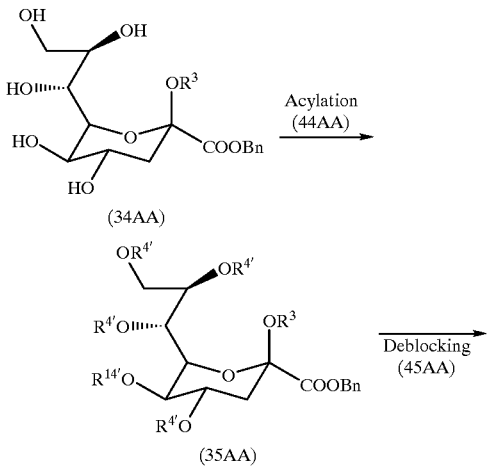

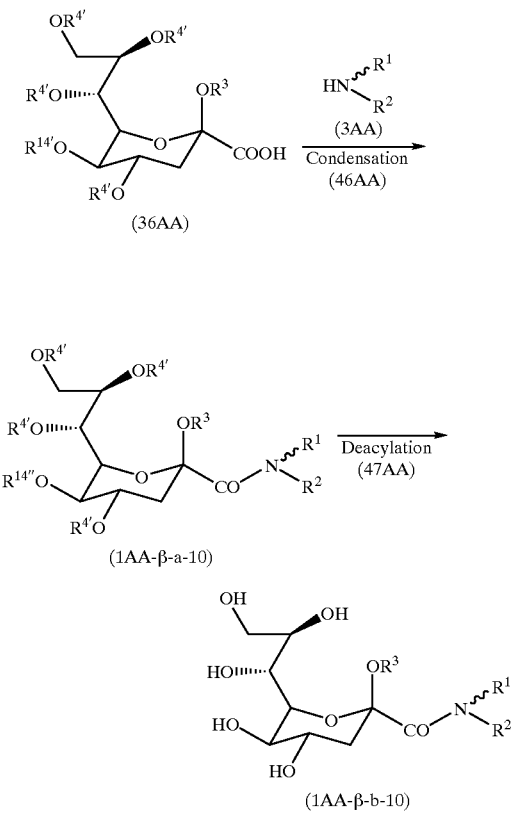

In the formulas, $R^1$, $R^2$, $R^3$, $R^{4'}$, and $R^{14''}$ have the same meanings as those defined above.

A compound of formula (34AA) is first acylated to obtain a compound of formula (35AA) [step (44AA)], and then the product is reduced to obtain a compound of formula (36AA) [step (45AA)]. The resulting compound is reacted with a compound of formula (3AA) to form a compound of formula (1AA-β-a-10) [step (46AA)], and the product is subsequently deacylated by reaction with an alkoxide such as sodium methoxide to produce a compound of formula (1AA-β-b10) [step (47AA)]. The step (44AA) may be carried out under the same condition as in the step (4AA). The step (45AA) may be carried out under the same condition as in the step (35AA). The step (46AA) may be carried out under the same condition as in the step (1AA). The step (47AA) may be carried out under the same condition as in the step (2AA).

(ii) Where X is sulfur atom:

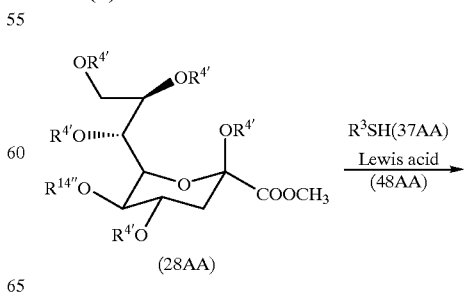

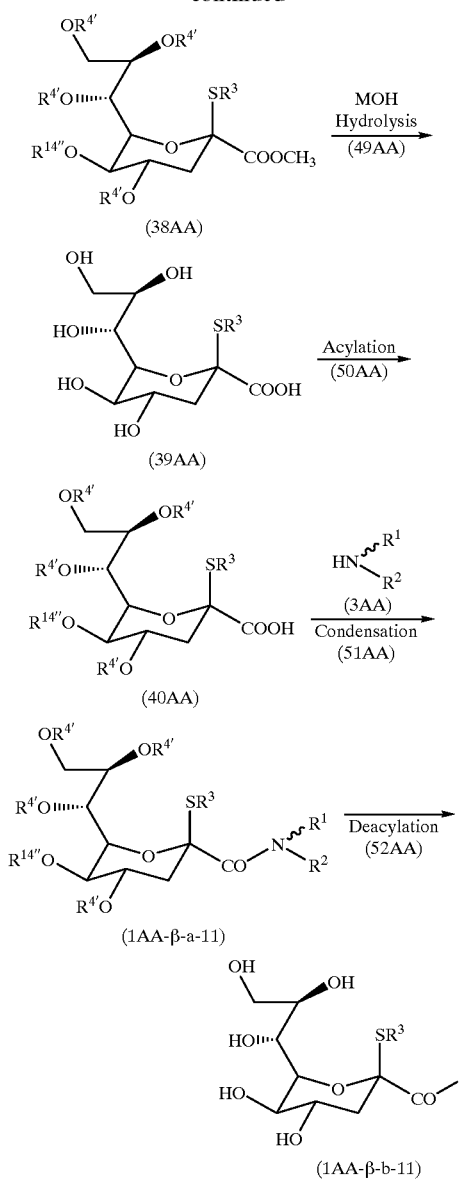

(38AA)

(39AA)

(40AA)

(1AA-β-a-11)

(1AA-β-b-11)

In the formulas, $R^1$, $R^2$, $R^3$, $R^{4'}$, $R^{14''}$, and M have the same meanings as those defined above.

A compound of formula (28AA) is first reacted with a compound of formula (37AA) in the presence of Lewis acid to form a compound of formula (38AA) [step (48AA)], and the product is then hydrolyzed to obtain a compound of formula (39AA) [step (49AA)]. The resulting compound is acylated to form a compound of formula (40AA) [step (50AA)], and the product is reacted with a compound of formula (3AA) to form a compound of formula (1AA-β-a-11) [step (51AA)]. The resulting compound is deacylated by reaction with an alkoxide such as sodium methoxide to produce a compound of formula (1AA-β-b-11) [step (52AA)].

The step (48AA) may be carried out by using 0.9–10 equivalents, preferably 1.0–5.0 equivalents of a compound of formula (37AA) in a solvent such as dichloromethane, dichloroethane, or ether in the presence of 0.9–10 equivalent, preferably 1.0–5.0 equivalents of a Lewis acid as a catalyst such as $BF_3$, $ZnCl_2$, or $AlCl_3$ at a temperature ranging from 0° C. to 50° C., preferably from 0° C. to room temperature. Operations for the reaction and the reaction per se may preferably be performed under anhydrous condition. The step (49AA) may be carried out under the same condition as in the step (3AA). The step (50AA) may be carried out under the same condition as in the step (4AA). The step (51AA) may be carried out under the same condition as in the step (1AA). The step (52AA) may be carried out under the same condition as in the step (2AA).

In the above reaction, when an ester group exists in the group $R^1$ or $R^3$, the ester may be hydrolyzed to obtain a carboxylic acid derivative, and when a 1,3-dioxolane group exists in the group $R^1$, the dioxolane may be subjected to deacetalization to convert into oxo group. When a benzyl ether group exists in the group $R^1$, $R^3$, or $R^5$, the group may be reduced to obtain a hydroxy derivative. When benzyloxycarbonylamino group exists in the group $R^3$, the group may be reduced to obtain an amino derivative, and the product may further be acylated to obtain an acylamino derivative.

The compounds of the formulae (2AA), (4AA), (7AA), (10AA), (13AA), (26AA), (28AA), and (34AA), which are used as starting materials of the preparation of the compounds of the present invention, can be readily prepared by the methods described in the literatures set out below or by similar methods: Carbohydr. Res. 78, pp.190–194 (1980) for compounds of formula (2AA); Chem. Ber. 99, pp.611–617 (1966) for those of formulas (7AA) and (13AA); Carbohydr. Res. 187, pp.35–42 (1989) for those of formulas (4AA) and (10AA); Chem. Pharm. Bull. 36 (12), pp.4807–4813 (1988) for those of formulas (26AA) and (34AA); and Chem. Pharm. Bull. 40 (4), pp.879–885 (1992) for those of formula (28AA).

The compounds of formula (3AA) can be prepared by the methods described in literatures such as J. Org. Chem. 27, pp.2925–2927 (1962); Steroids, 56, pp.395–398 (1991), and Tetrahedron Letters, 35 (4), pp.565–568 (1994) or by similar methods, or alternatively, by the method shown in the following section 4.

4. Method for preparation of the compound of the following general formula (3AA) (wherein $R^1$ and $R^2$ have the same meaning as those defined above)

(3AA)

(a) Method for preparation of the compound of the general formula (3'AA) wherein $R^2$ is hydrogen atom, and $R^1$ is a group of

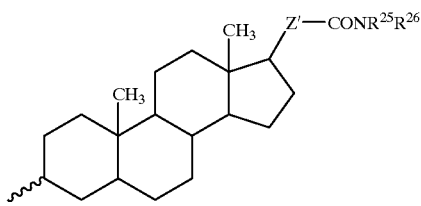

wherein $R^{25}$ and $R^{26}$ have the same meanings as those defined above, and Z' represents a $C_1$–$C_{10}$ alkylene group or a $C_2$–$C_{11}$ alkenylene group

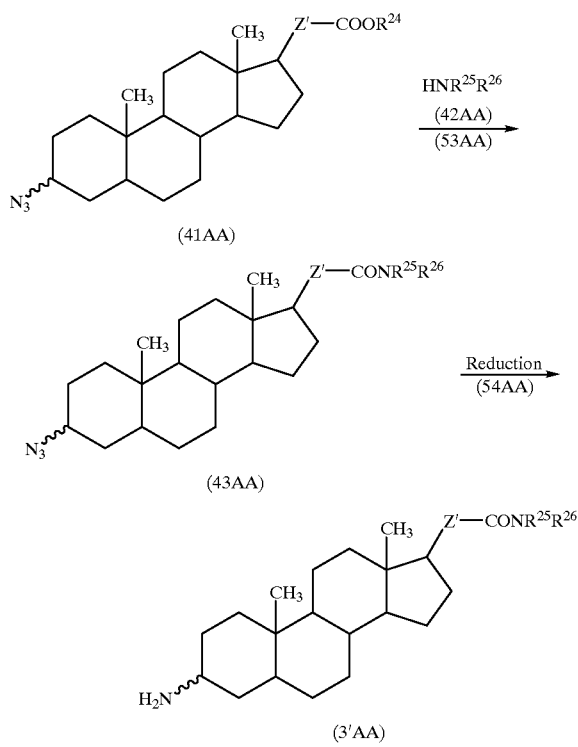

In the formulas, $R^{24}$, $R^{25}$, $R^{26}$, and Z' have the same meanings as those defined above.

A compound of formula (41AA) is first reacted with a compound of formula (42AA) to obtain a compound of formula (43AA) [step (53AA)], and then the product is reduced to produce a compound of formula (3'AA) [step (54AA)].

The step (53AA) may be carried out by using 0.9–100 equivalents, preferably 1.0–50 equivalents of a compound of formula (42AA) in a solvent such as methanol, ethanol, or tetrahydrofuran at a temperature ranging from 0° C. to 70° C., preferably from 0° C. to 50° C. Operations for the reaction and the reaction per se may preferably be carried out under anhydrous condition. The step (54AA) may be carried out under the same condition as in the step (35AA).

A compound of formula (43AA) can also be produced as follows.

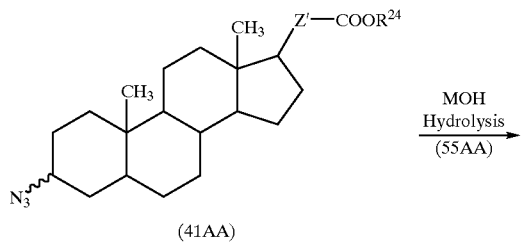

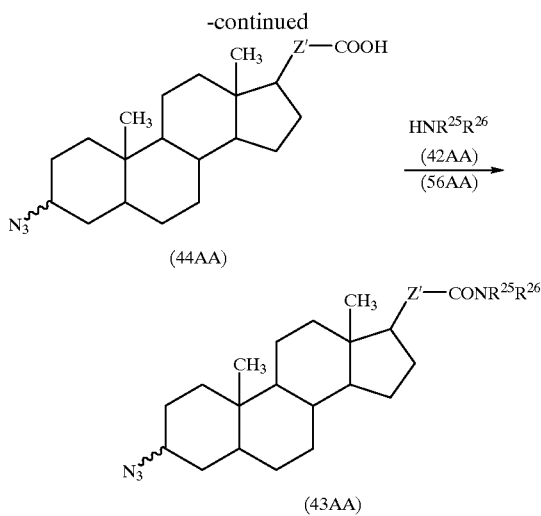

In the formulas, $R^{24}$, $R^{25}$, $R^{26}$, M, and Z' have the same meanings as defined above.

A compound of formula (41AA) is first hydrolyzed by reaction with an alkali such as sodium hydroxide to form a compound of formula (44AA) [step (55AA)], and then the product is reacted with a compound of formula (42AA) to obtain a compound of formula (43AA) [step (56AA)].

The step (55AA) may be carried out under the same condition as in the step (3AA). The step (56AA) may be carried out under the same condition as in the step (1AA).

(b) Method for preparation of the compound of the general formula (3'AA) wherein $R^2$ is hydrogen atom and $R^1$ is a group of:

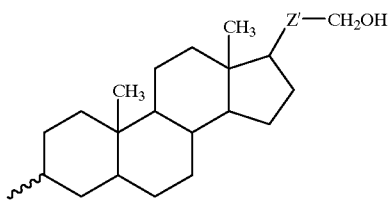

wherein Z' has the same meaning as that defined above

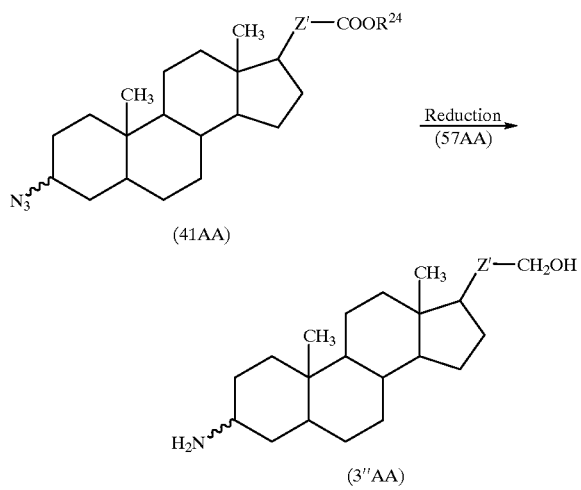

In the formulas, $R^{24}$ and Z' have the same meanings as those defined above.

A compound of formula (41AA) is reduced to produce a compound of formula (3"AA) [step (57AA)].

The step (57AA) may be carried out in a solvent such as tetrahydrofuran or diethyl ether by using 3.9–50 equivalents, preferably 4.0–20 equivalents of a reducing agent such as lithium aluminum hydride at a temperature ranging from 0° C. to 60° C., preferably from 0° C. to 40° C. Operations for the reaction and the reaction per se may preferably be carried out under anhydrous condition.

A compound of formula (3"AA) can also be prepared as follows.

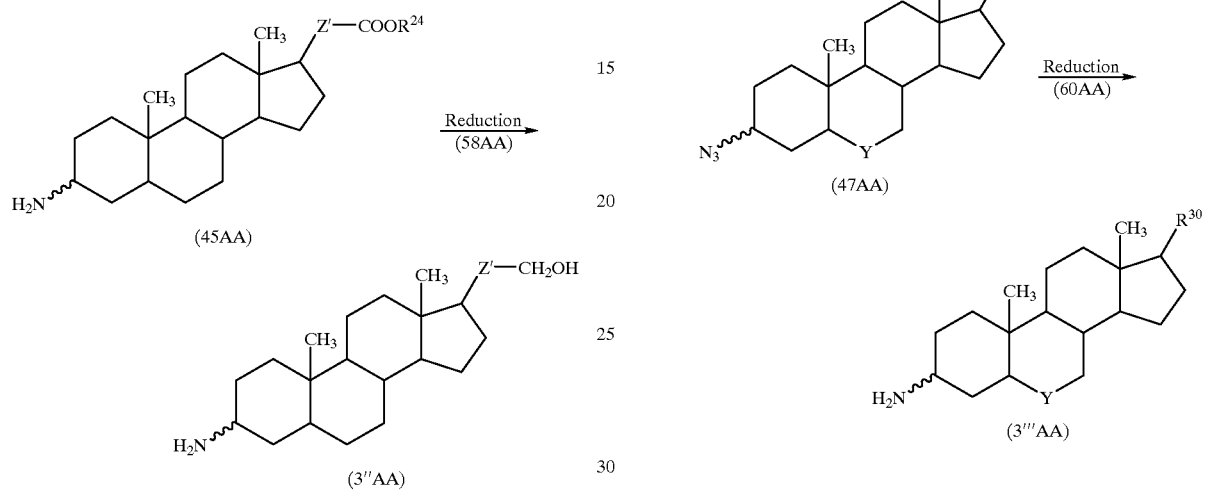

In the formulas, $R^{24}$ and Z' have the same meanings as those defined above.

A compound of formula (45AA) is reduced to obtain a compound of formula (3"AA) [step (58AA)].

The step (58AA) may be carried out in a solvent such as tetrahydrofuran or diethyl ether by using 1.9–50 equivalents, preferably 2.0–20 equivalents of a reducing agent such as lithium aluminum hydride or sodium borohydride at a temperature ranging from 0° C. to 60° C., preferably from 0° C. to 40° C. Operations for the reaction and the reaction per se may preferably be carried out under anhydrous condition.

(c) Method for preparation of the compound of the general formula (3'''AA) wherein $R^2$ is hydrogen atom, and $R^1$ is a group of

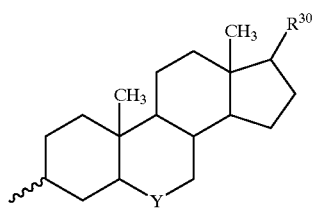

wherein Y represents a group of:

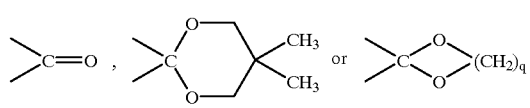

wherein q represents an integer of 1–4, and $R^{30}$ represents a $C_1$–$C_{10}$ alkyl group or a $C_2$–$C_{11}$ alkenyl group

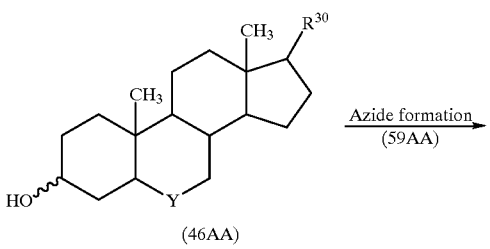

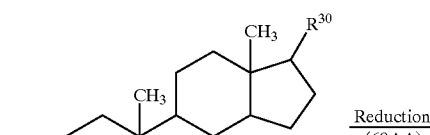

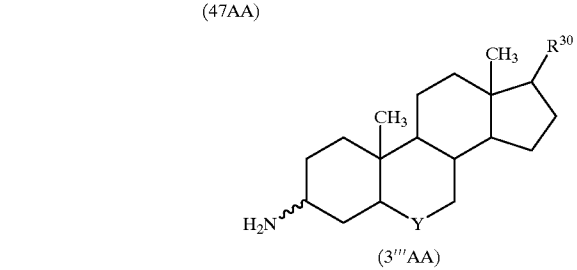

In the formulas, Y and $R^{30}$ have the same meanings as those defined above.

A compound of formula (46AA) is first subjected to a azide formation to form a compound of formula (47AA) [step (59AA)], and the product is reduced to obtain a compound of formula (3'''AA) [step (60AA)].

The step (59AA) may be carried out in a solvent such as tetrahydrofuran, dioxane, acetonitrile, benzene, toluene, or dichloromethane by using 0.9–10 equivalents, preferably 1.0–5.0 equivalents of a phosphine such as triphenylphosphine, and 0.9–10 equivalents, preferably 1.0–5.0 equivalents of an azodicarboxylic acid ester such as diethyl azodicarboxylate or diisopropyl azodicarboxylate, together with 0.9–10 equivalents, preferably 1.0–5.0 equivalents of an azidating agent such as diphenylphosphoryl azide at a temperature ranging from −20° C. to 50° C., preferably from 0° C. to 50° C. Operations for the reaction and the reaction per se may preferably be carried out under anhydrous condition. The step (60AA) may be carried out under the same condition as in the step (57AA) or the step (35AA).

The compounds of the formulae (41AA) and (45AA) used as the starting materials in the above (a) and (b) can be synthesized by methods described in literatures such as Tetrahedron Letters, 35 (4), pp.565–568 (1994), or similar methods.

The compounds represented by the above general formula (1BB) according to the second aspect of the present invention can be prepared by the method explained below.

1. Compounds of the general formula (1BB) wherein $R^{105}$ is a group of $CH_3$—CO—NH—

(a) Method for preparation of the compound wherein the 2-position of sialic acid is α-configuration (i) Where X is oxygen atom:

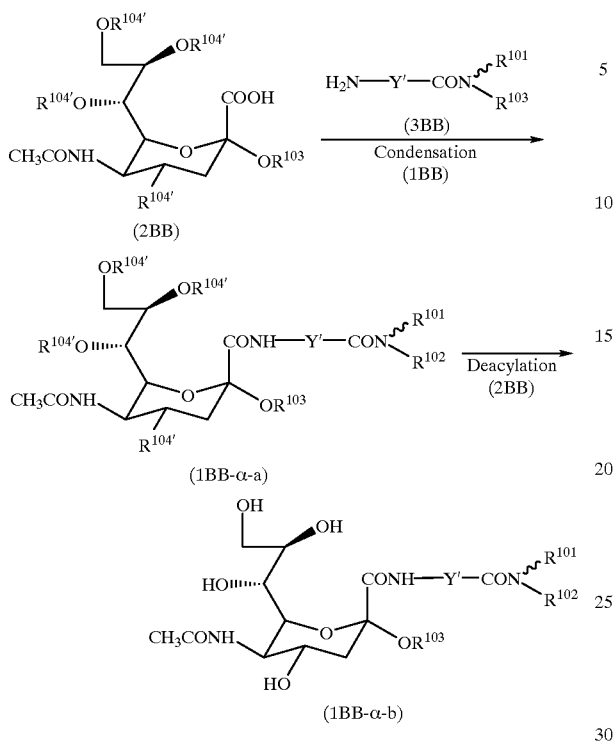

In the above formulas, $R^{101}$, $R^{102}$, $R^{103}$, and Y' have the same meanings as those defined for the general formula (1BB), and $R^{104'}$ represents a $C_2$–$C_7$ acyl group.

A compound of formula (2BB) is first reacted with a compound of formula (3BB) [step (1BB)] to obtain a compound of formula (1BB-α-a), and then the product is deacylated by reaction with an alkoxide such as sodium methoxide to prepare a compound of formula (1BB-α-b) [step (2BB)].

The step (1BB) may be carried out by reacting 0.9–10 equivalents, preferably 1.0–5.0 equivalents of an ester of chlorocarbonic acid such as isobutyl chlorocarbonate with 0.9–10 equivalents, preferably 1.0–5.0 equivalents of a tertiary amine such as N-methylmorpholine or triethylamine in a solvent such as tetrahydrofuran, dioxane, acetonitrile, dichloromethane, or dichloroethane at a temperature ranging from −50° C. to 50° C., preferably from −20° C. to room temperature to form a mixed acid anhydride corresponding to a compound of formula (2BB). The reaction is then carried out by using 0.9–10 equivalents, preferably 1.0–5.0 equivalents of a compound of formula (3BB) or a salt of the compound of formula (3BB) such as hydrochloride together with an equimolar tertiary amine at a temperature ranging from −50° C. to 50° C., preferably from −20° C. to room temperature. Alternatively, the step (1BB) may be carried out by reaction using 0.9–10 equivalents, preferably 1.0–5.0 equivalents of a chloride such as thionyl chloride, phosphorous pentachloride, or phosphorus oxychloride together with 0.9–20 equivalents, preferably 1.0–10 equivalents of a base such as pyridine in a solvent such as tetrahydrofuran, dioxane, acetonitrile, dichloromethane, or dichloroethane at a temperature ranging from −50° C. to 50° C., preferably from −20° C. to room temperature to obtain an acid chloride corresponding to a compound of formula (2BB), and then by treatment using 0.9–10 equivalents, preferably 1.0–5.0 equivalents of a compound of formula (3BB) or a salt of a compound of formula (3BB) such as hydrochloride together with an equimolar tertiary amine at a temperature ranging from −50° C. to 50° C., preferably from −20° C. to room temperature. Operations for these reactions and reactions per se may preferably be carried out under anhydrous condition. The step (2BB) may be carried out by using 0.05–5.0 equivalents, preferably 0.1–2.0 equivalents of alkoxide in a solvent such as methanol at a temperature ranging from 0° C. to −50° C., preferably from 0° C. to room temperature. Operations for the reaction and reaction per se may preferably be carried out under anhydrous condition.

(ii) Where X is sulfur atom:

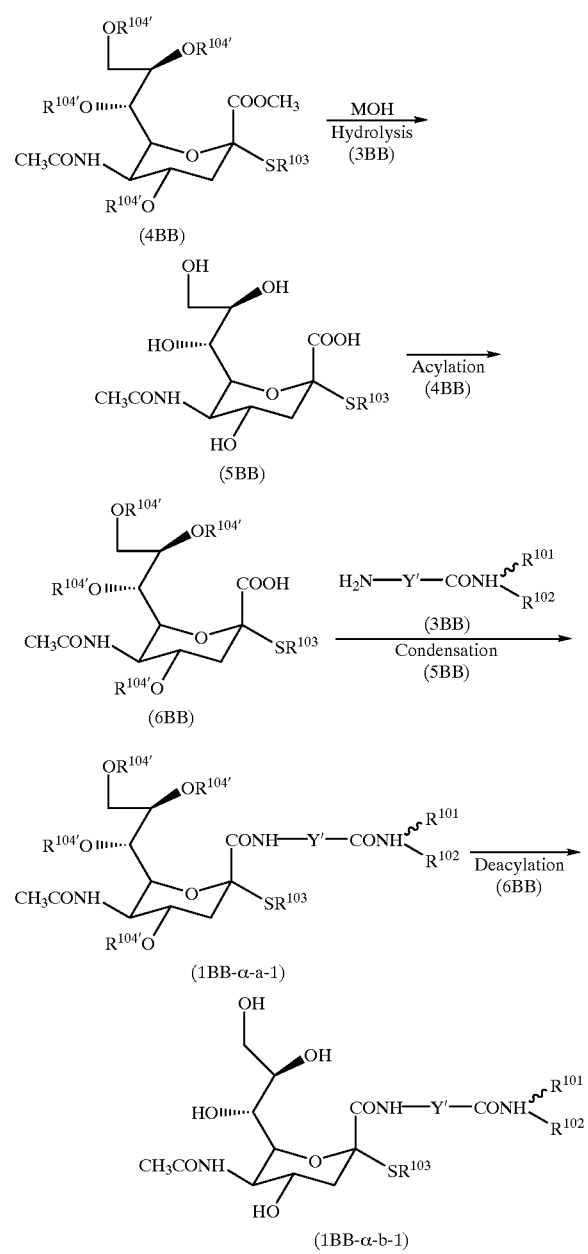

In the formulas, $R^{101}$, $R^{102}$ $R^{103}$, $R^{104'}$, and Y' have the same meanings as those defined above, and M represents an alkali metal.

A compound of formula (4BB) is first reacted with an alkali such as sodium hydroxide for hydrolysis to obtain a compound of formula (5BB) [step (3BB)], and then the product is acylated to form a compound of formula (6BB)

[step (4BB)]. The resulting compound is reacted with a compound of formula (3BB) to form a compound of formula (1BB-α-a-1) [step (5BB)], and the product is then subjected to deacylation by reaction with an alkoxide such as sodium methoxide to prepare a compound of formula (1BB-α-b-1) [step (6BB)].

The step (3BB) may be carried out by using 0.9–10 equivalents, preferably 1.0–5.0 equivalents of a base such as sodium hydroxide or potassium hydroxide in a solvent such as water, methanol, or ethanol at a temperature ranging from 0° C. to 50° C., preferably from 0° C. to room temperature. The step (4BB) may be carried out by using 4.0–200 equivalents, preferably 4.4–100 equivalents of an acid anhydride such as acetic anhydride or an acid chloride such as acetyl chloride, propionyl chloride, butyryl chloride, valeryl chloride, or benzoyl chloride in a solvent such as pyridine at a temperature ranging from 0° C. to 50° C., preferably from 0° C. to room temperature. For the reaction, presence of 0.1–1 equivalent, preferably 0.1–0.5 equivalent of a base such as 4-dimethylaminopyridine in a reaction system is preferred to achieve a higher yield. Operations for the reaction and reaction per se may preferably be carried out under anhydrous condition. The step (5BB) may be carried out under the same condition as in the step (1BB), and the step (6BB) may be carried out under the same condition as in the step (2BB).

(b) Method for preparation of the compound wherein the 2-position of sialic acid is β-configuration (i) Where X is oxygen atom:

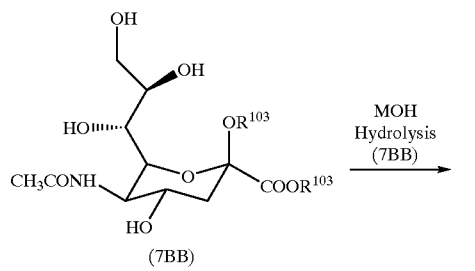

(7BB)

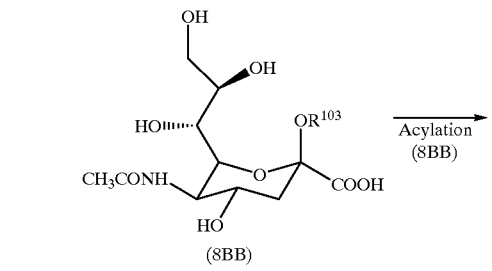

(8BB)

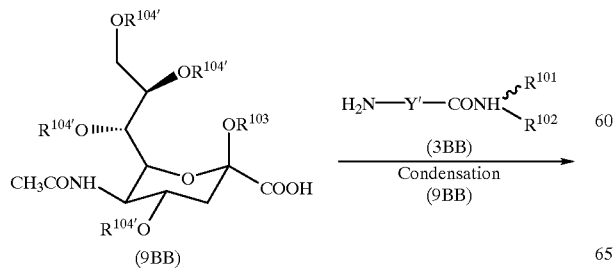

(9BB)

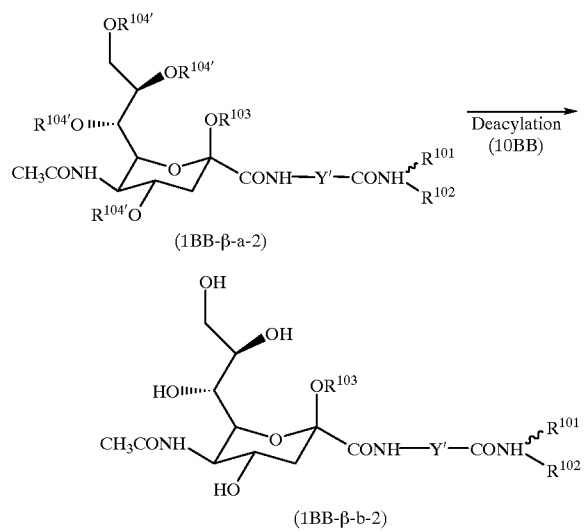

(1BB-β-a-2)

(1BB-β-b-2)

In the formulas, $R^{101}$, $R^{102}$, $R^{103}$, $R^{104'}$, Y', and M have the same meanings as those defined above.

A compound of formula (7BB) is first hydrolyzed by reaction with an alkali such as sodium hydroxide to form a compound of formula (8BB) [step (7BB)], and then the product is acylated to obtain a compound of formula (9BB) [step (8BB)]. The resulting compound is then reacted with a compound of formula (3BB) to form a compound of formula (1BB-β-a-2) [step (9BB)], and the product is deacylated by reaction with an alkoxide such as sodium methoxide to produce a compound of formula (1BB-β-b-2) [step (10BB)].

The step (7BB) may be carried out under the same condition as in the step (3BB). The step (8BB) may be carried out under the same condition as in the step (4BB). The step (9BB) may be carried out under the same condition as in the step (1BB). The step (10BB) may be carried out under the same condition as in the step (2BB).

(ii) Where X is sulfur atom:

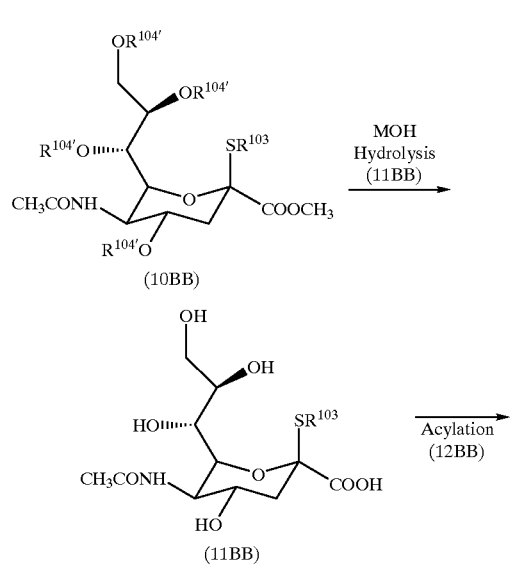

(10BB)

(11BB)

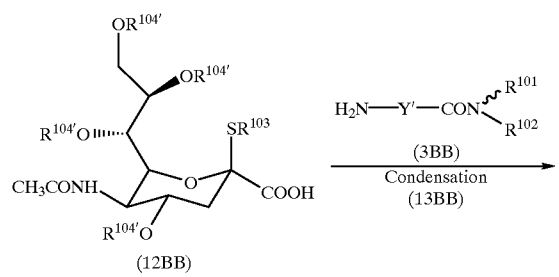
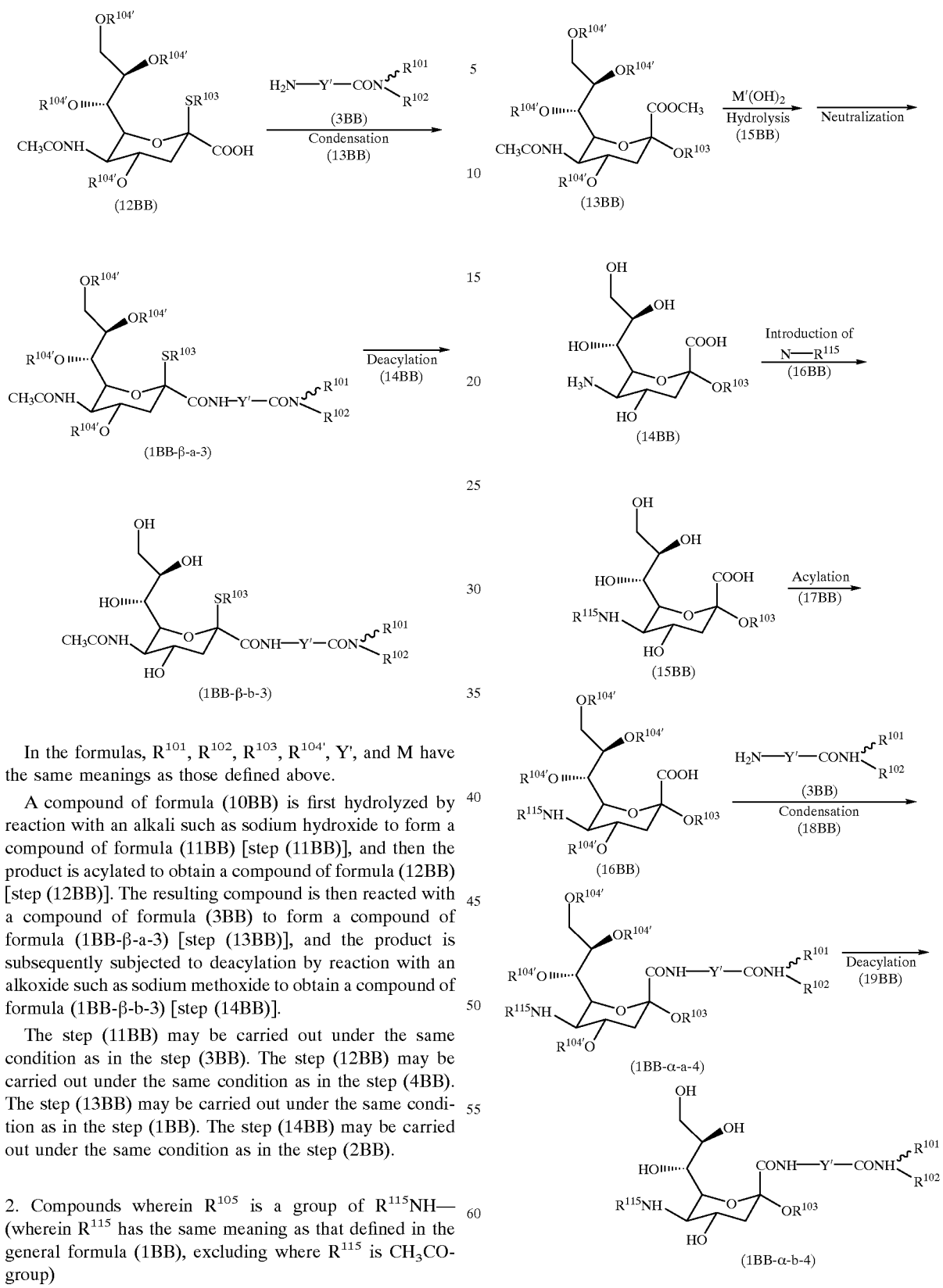

In the formulas, $R^{101}$, $R^{102}$, $R^{103}$, $R^{104'}$, Y', and M have the same meanings as those defined above.

A compound of formula (10BB) is first hydrolyzed by reaction with an alkali such as sodium hydroxide to form a compound of formula (11BB) [step (11BB)], and then the product is acylated to obtain a compound of formula (12BB) [step (12BB)]. The resulting compound is then reacted with a compound of formula (3BB) to form a compound of formula (1BB-β-a-3) [step (13BB)], and the product is subsequently subjected to deacylation by reaction with an alkoxide such as sodium methoxide to obtain a compound of formula (1BB-β-b-3) [step (14BB)].

The step (11BB) may be carried out under the same condition as in the step (3BB). The step (12BB) may be carried out under the same condition as in the step (4BB). The step (13BB) may be carried out under the same condition as in the step (1BB). The step (14BB) may be carried out under the same condition as in the step (2BB).

2. Compounds wherein $R^{105}$ is a group of $R^{115}NH-$ (wherein $R^{115}$ has the same meaning as that defined in the general formula (1BB), excluding where $R^{115}$ is $CH_3CO-$ group)

(a) Compounds wherein the 2-position of sialic acid is α-configuration (i) Where X is oxygen atom In the formulas, $R^{101}$, $R^{102}$, $R^{103}$, $R^{104'}$, $R^{115}$, and Y' have the same meanings as those defined above, and M represents an alkaline earth metal.

259

A compound of formula (13BB) is first hydrolyzed by reaction with an alkali such as barium hydroxide to form a compound of formula (14BB) [step (15BB)], and then the product is N-acylated or N-oxycarbonylated to form a compound of formula (15BB) [step (16BB)]. The resulting compound is then acylated to form a compound of formula (16BB) [step (17BB)], and the product is further reacted with a compound of formula (3BB) to form a compound of formula (1BB-α-a-4) [step (18BB)]. The resulting compound is then deacylated by reaction with an alkoxide such as sodium methoxide to obtain a compound of formula (1BB-α-b-4) [step (19BB)].

The step (15BB) may be carried out by using 0.9–10 equivalents, preferably 1.0–5.0 equivalents of a base such as barium hydroxide in a solvent such as water, methanol, ethanol at a temperature ranging from 0° C. to 100° C., preferably from 50° C. to 100° C. The step (16BB) may be carried out by N-acylation using 0.9–10 equivalents, preferably 1.0–3.0 equivalents of an acid anhydride such as acetic anhydride or propionic anhydride, or acid chloride such as acetyl chloride, propionyl chloride, or benzoyl chloride, together with 0.9–10 equivalents, preferably 1.0–3.0 equivalents of a tertiary amine such as triethylamine in a solvent such as water, methanol, ethanol, dioxane, or tetrahydrofuran, or alternatively, N-oxycarbonylation using 0.9–10 equivalents, preferably 1.0–3.0 equivalents of di-t-butyl carbonate, carbobenzoxy chloride or the like together with 0.9–10 equivalents, preferably 1.0–3.0 equivalents of a tertiary amine such as triethylamine. These reactions are performed at a temperature range of from 0° C. to 80° C., preferably from 0° C. to 50° C. The step (17BB) may be carried out under the same condition as in the step (4BB). The step (18BB) may be carried out under the same condition as in the step (1BB). The step (19BB) may be carried out under the same condition as in the step (2BB).

(ii) Where X is sulfur atom:

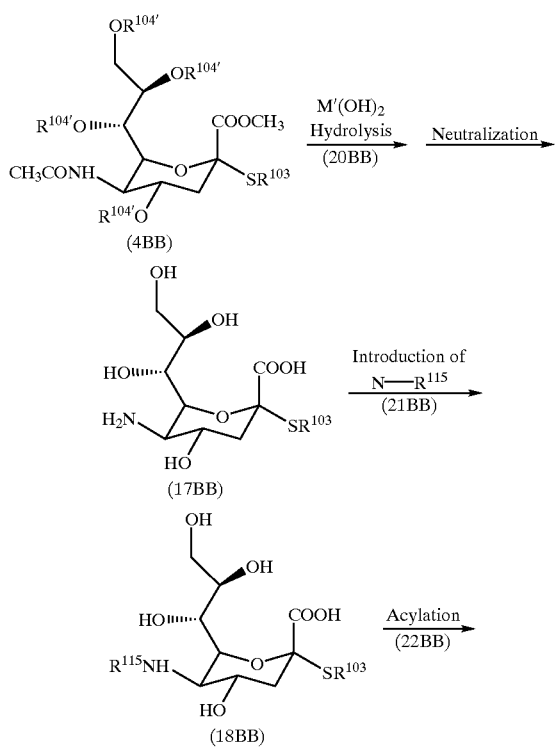

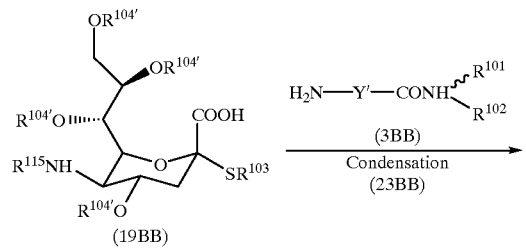

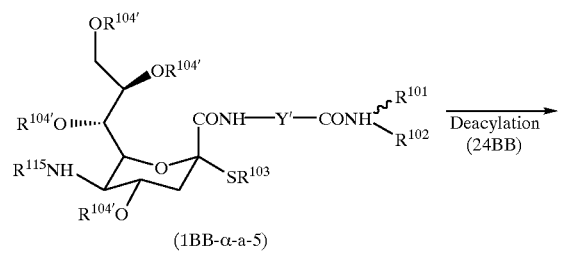

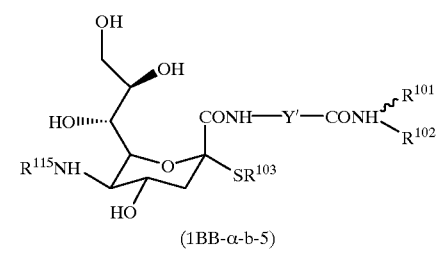

In the formulas, $R^{102}$, $R^{102'}$, $R^{103}$, $R^{104'}$, $R^{115}$, Y', and M' have the same meanings as those defined above.

A compound of formula (4BB) is first hydrolyzed by reaction with an alkali such as barium hydroxide to form a compound of formula (17BB) [step (20BB)], and then the product is N-acylated or N-oxycarbonylated to form a compound of formula (18BB) [step (21BB)]. The resulting compound of formula (18BB) is acylated to form a compound of formula (19BB) [step (22BB)], and then the product is reacted with a compound of formula (3BB) to obtain a compound of formula (1BB-α-a-5) [step (23BB)]. The resulting compound is subsequently subjected to deacylation by reaction with an alkoxide such as sodium methoxide to prepare a compound of formula (1BB-β-b-5) [step (24BB)].

The step (20BB) may be carried out under the same condition as in the step (15BB). The step (21BB) may be carried out under the same condition as in the step (16BB). The step (22BB) may be carried out under the same condition as in the step (4BB). The step (23BB) may be carried out under the same condition as in the step (1BB). The step (24BB) may be carried out under the same condition as in the step (2BB).

(b) Method for preparation of compounds wherein the 2-position of sialic acid is β-configuration

261

(i) Where X is oxygen atom:

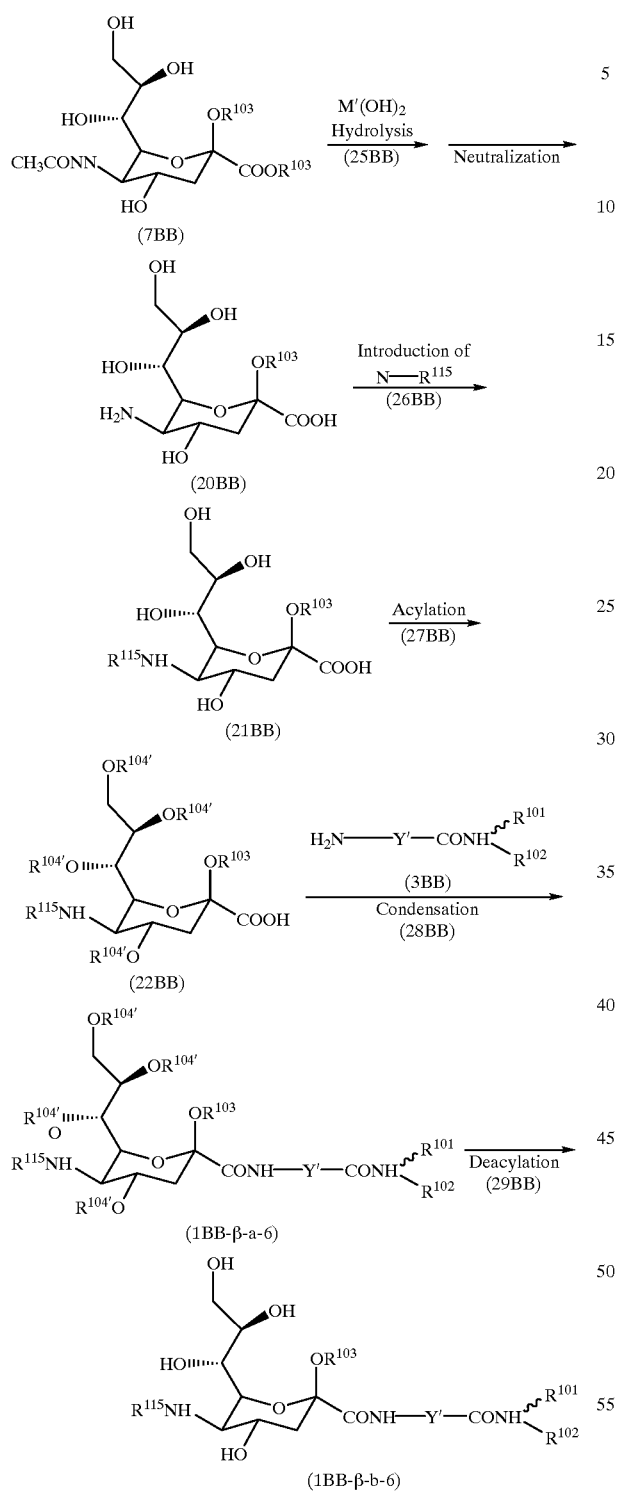

In the formulas, $R^{101}$, $R^{102}$, $R^{103}$, $R^{104'}$, $R^{115}$, Y', and M' have the same meanings as those defined above.

A compound of formula (7BB) is first hydrolyzed by reaction with an alkali such as barium hydroxide to form a compound of formula (20BB) [step (25BB)], and then the product is N-acylated or N-oxycarbonylated to form a compound of formula (21BB) [step (26BB)]. The resulting compound is acylated to form a compound of formula

262

(22BB) [step (27BB)], and the product is reacted with a compound of formula (3BB) to produce a compound of formula (1BB-β-a-6) [step (28BB)]. The resulting compound is subsequently subjected to deacylation by reaction with an alkoxide such as sodium methoxide to obtain a compound of formula (1BB-β-b-6) [step (29BB)].

The step (25BB) may be carried out under the same condition as in the step (15BB). The step (26BB) may be carried out under the same condition as in the step (16BB). The step (27BB) may be carried out under the same condition as in the step (4BB). The step (28BB) may be carried out under the same condition as in the step (1BB). The step (29BB) may be carried out under the same condition as in the step (2BB).

(ii) Where X is sulfur atom:

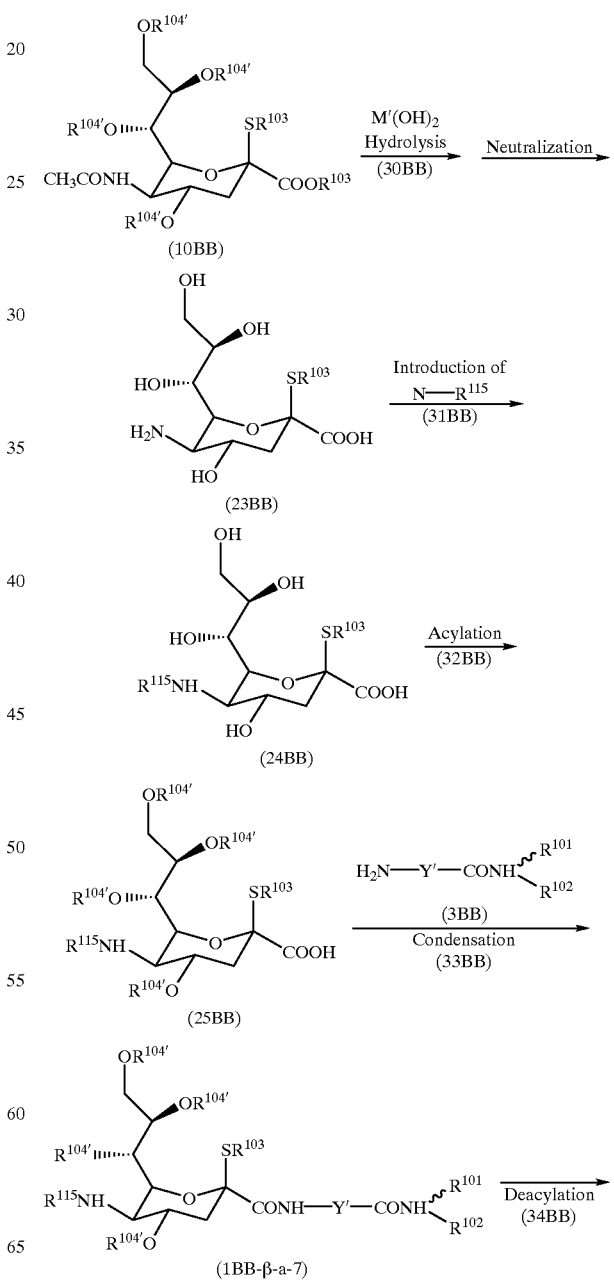

-continued

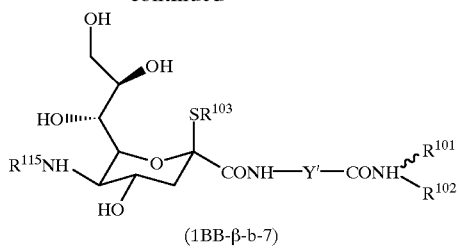

(1BB-β-b-7)

-continued

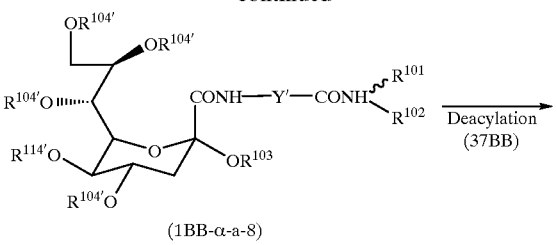

(1BB-α-a-8)

In the formulas, $R^{101}$, $R^{102}$, $R^{103}$, $R^{104'}$, $R^{115}$, Y', and M' have the same meanings as those defined above.

A compound of formula (10BB) is first hydrolyzed by reaction with an alkali such as barium hydroxide to form a compound of formula (23BB) [step (30BB)], and the product is N-acylated or N-oxycarbonylated to form a compound of formula (24BB) [step (31BB)]. The resulting compound is then acylated to form a compound of formula (25BB) [step (32BB)], and the product is reacted with a compound of formula (3BB) to produce a compound of formula (1BB-β-a-7) [step (33BB)]. The resulting compound is subsequently subjected to deacylation by reaction with an alkoxide such as sodium methoxide to obtain a compound of formula (1BB-β-b-7) [step (34BB)].

The step (30BB) may be carried out under the same condition as in the step (15BB). The step (31BB) may be carried out under the same condition as in the step (16BB). The step (32BB) may be carried out under the same condition as in the step (4BB). The step (33BB) may be carried out under the same condition as in the step (1BB). The step (34BB) may be carried out under the same condition as in the step (2BB).

3. Compounds wherein $R^{105}$ is a group of $R^{114}O$— (wherein $R^{114}$ has the same meaning as that defined in the general formula (1BB))

(a) Method for preparation of compounds wherein the 2-position of sialic acid is α-configuration
(i) Where X is oxygen atom

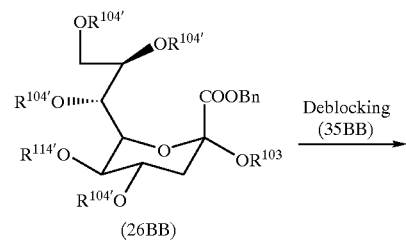

(26BB)

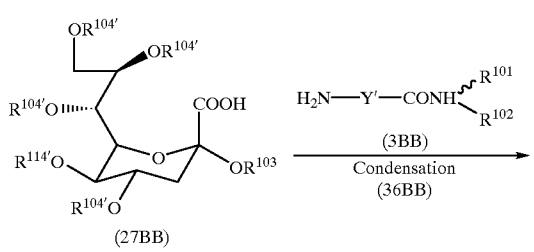

(27BB)

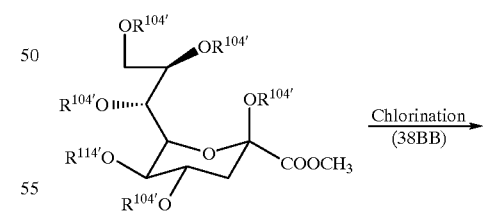

(1BB-α-b-8)

In the formulas, $R^{101}$, $R^{102}$, $R^{103}$, $R^{104'}$, and Y' have the same meanings as those defined above, and $R^{114'}$ represents a $C_2$–$C_7$ acyl group.

A compound of formula (26BB) is first reduced to obtain a compound of formula (27BB) [step (35BB)], and the product is then reacted with a compound of formula (3BB) to form a compound of formula (1BB-α-a-8) [step (36BB)]. The resulting compound is then subjected to deacylation by reaction with an alkoxide such as sodium methoxide to produce a compound of formula (1BB-α-b-8) [step (37BB)].

The step (35BB) may be carried out in a solvent such as methanol, ethanol, tetrahydrofuran, or dioxane at a temperature ranging from 0° C. to 50° C., preferably from 0° C. to room temperature in the presence of 0.1–200% by weight, preferably 1.0–100% by weight of a catalyst such as palladium black or palladium carbon under hydrogen atmosphere. The step (36BB) may be carried out under the same condition as in the step (1BB). The step (37BB) may be carried out under the same condition as in the step (2BB).

(ii) Where X is sulfur atom:

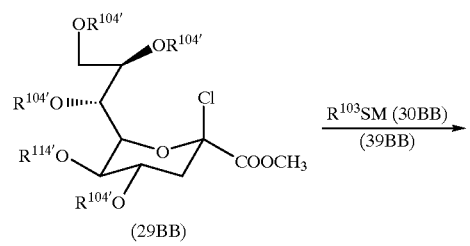

(28BB)

(29BB)

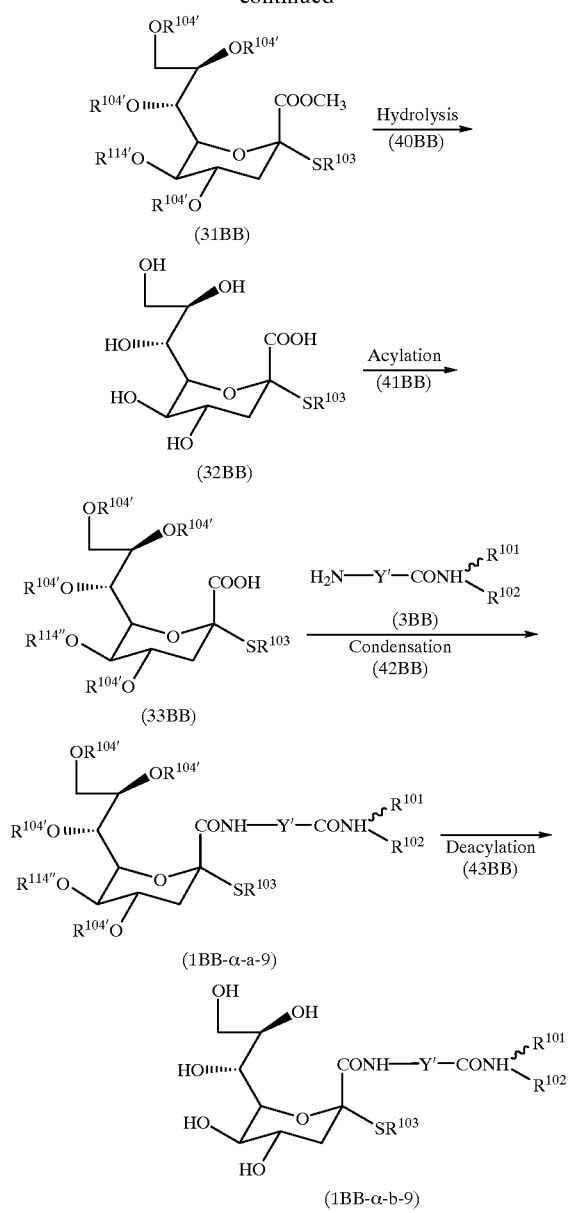

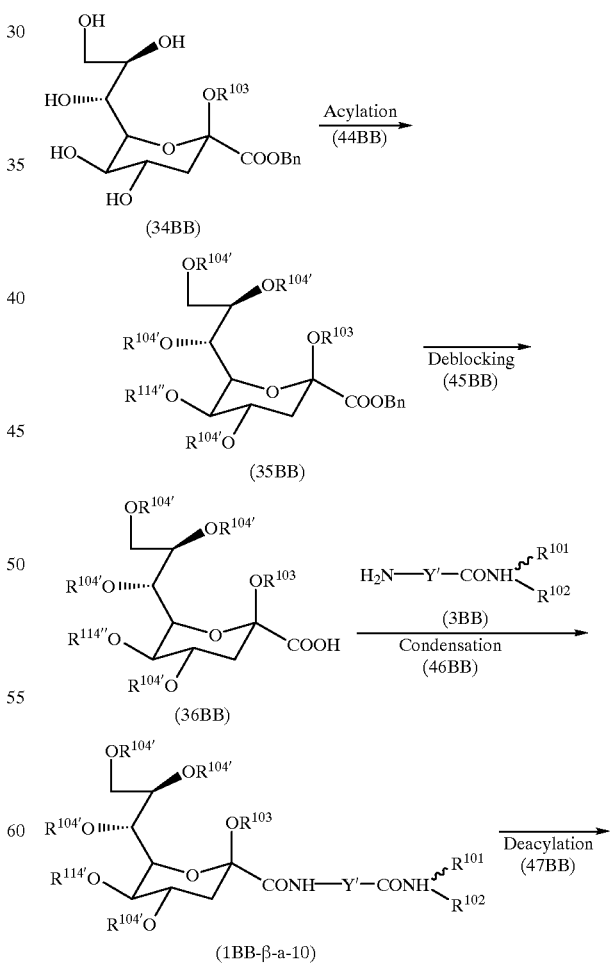

In the formulas, $R^{101}$, $R^{102}$, $R^{103}$, $R^{104'}$, Y', and M have the same meanings as defined above, and $R^{114''}$ has the same meaning as $R^{104'}$.

A compound of formula (28BB) is first chlorinated to form a compound of formula (29BB) [step (38BB)], and the product is then reacted with a compound of formula (30BB) to form a compound of formula (31BB) [step (39BB)]. The resulting compound is then hydrolyzed to form a compound of formula (32BB) [step (40BB)], and the product is acylated to obtain a compound of formula (33BB) [step (41BB)]. The resulting compound is then reacted with a compound of formula (3BB) to form a compound of formula (1BB-α-a-9) [step (42BB)], and the product is deacylated by reaction with an alkoxide such as sodium methoxide to produce a compound of formula (1BB-α-b-9) [step (43BB)].

The step (38BB) may be carried out in an acid chloride such as acetyl chloride, propionyl chloride, butyryl chloride, valeryl chloride, or benzoyl chloride at a temperature rang- ing from −20° C. to 50° C., preferably from 0° C. to room temperature. For the reaction, reaction mixture may prefer- ably be saturated with hydrogen chloride gas to achieve higher yield. Operations for the reaction and the reaction per se may preferably be performed under anhydrous condition. The step (39BB) may be carried out by using 0.9–200 equivalents, preferably 1.0–100 equivalents of a compound of formula (30BB) in a solvent such as acetonitrile, tetrahydrofuran, dioxane, dimethylformamide, or dimethyl sulfoxide at a temperature range of 0° C. to 50° C., prefer- ably 0° C. to room temperature. This reaction may prefer- ably be performed in the presence of 0.1–10 equivalents, preferably 0.9–50 equivalents of a silver catalyst such as silver trifluoromethanesulfonate, silver salicylate, silver carbonate, or silver oxide to achieve higher yield. The reaction operation and the reaction are preferably performed under anhydrous condition. The step (40BB) may be carried out under the same condition as in the step (3BB). The step (41BB) may be carried out under the same condition as in the step (4BB). The step (42BB) may be carried out under the same condition as in the step (1BB). The step (43BB) may be carried out under the same condition as in the step (2BB).

(b) Method for preparation of compounds wherein the 2-position of sialic acid is β-configuration
  (i) Where X is oxygen atom:

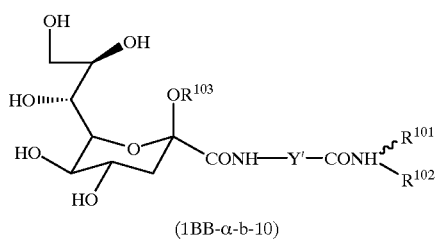

(1BB-α-b-10)

In the formulas, $R^{101}$, $R^{102}$, $R^{103}$, $R^{104'}$, $R^{114''}$, and Y' have the same meanings as defined above.

A compound of formula (34BB) is first acylated to form a compound of formula (35BB) [step (44BB)], and the product is then reduced to obtain a compound of formula (36BB) [step (45BB)]. The resulting compound is reacted with a compound of formula (3BB) to form a compound of formula (1BB-β-a-10) [step (46BB)], and then the product is deacylated by reaction with an alkoxide such as sodium methoxide to obtain a compound of formula (1BB-β-b-10) [step (47BB)].

The step (44BB) may be carried out under the same condition as in the step (4BB). The step (45BB) may be carried out under the same condition as in the step (35BB). The step (46BB) may be carried out under the same condition as in the step (1BB). The step (47BB) may be carried out under the same condition as in the step (2BB).

(ii) Where X is sulfur atom:

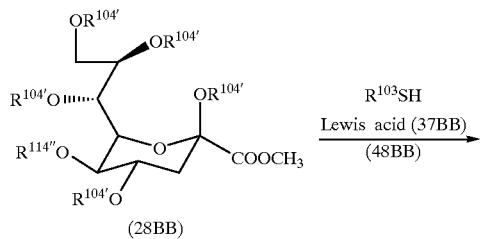

(28BB)

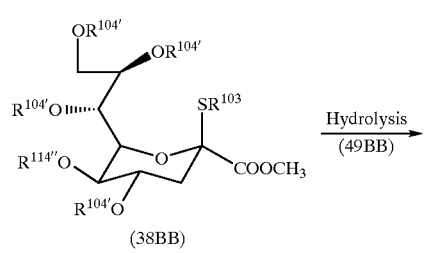

(38BB)

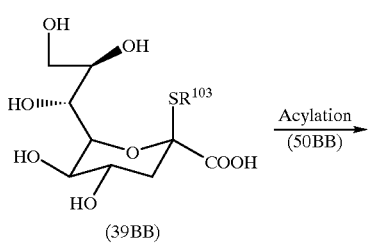

(39BB)

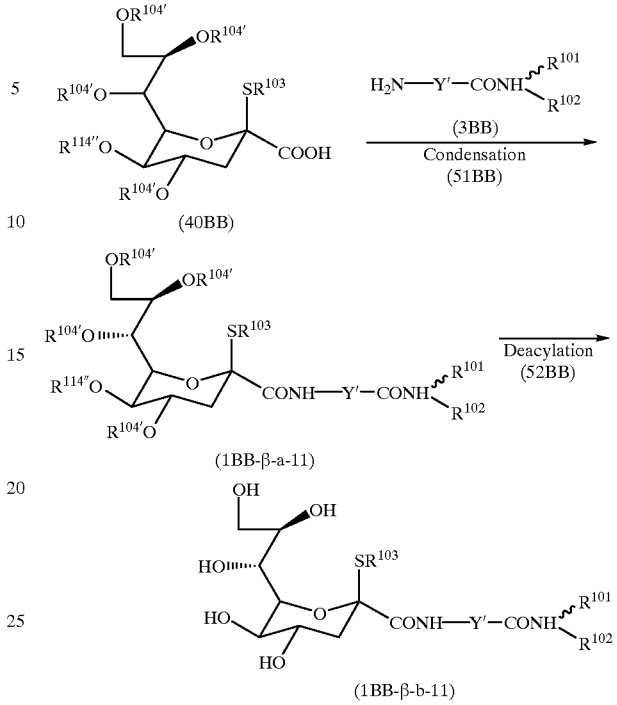

In the formulas, $R^{101}$, $R^{102}$, $R^{103}$, $R^{104'}$, $R^{114''}$, and Y' have the same meanings as defined above.

A compound of formula (28BB) is first reacted with a compound of formula (37BB) in the presence of Lewis acid to form a compound of formula (38BB) [step (48BB)], and the product is hydrolyzed to obtain a compound of formula (39BB) [step (49BB)]. The resulting compound is then acylated to form a compound of formula (40BB) [step (50BB)], and the product is then reacted with a compound of formula (3BB) to form a compound of formula (1BB-β-a-11) [step (51BB)]. The resulting compound is subjected to deacylation by reaction with an alkoxide such as sodium methoxide to produce a compound of formula (1BB-β-b-11) [step (52BB)].

The step (48BB) may be carried out by using 0.9–10 equivalents, preferably 1.0–5.0 equivalents of a compound of formula (37BB) in a solvent such as dichloromethane, dichloroethane, or ether in the presence of 0.9–10 equivalent, preferably 1.0–5.0 equivalents of a Lewis acid catalyst such as $BF_3$, $ZnCl_2$, or $AlCl_3$ at a temperature ranging from 0° C. to 50° C., preferably from 0° C. to room temperature. Operations for the reaction and the reaction per se may preferably be performed under anhydrous condition. The step (49BB) may be carried out under the same condition as in the step (3BB). The step (50BB) may be carried out under the same condition as in the step (4BB). The step (51BB) may be carried out under the same condition as in the step (1BB). The step (52BB) may be carried out under the same condition as in the step (2BB).

In the above reaction, when an ester group exists in $R^{101}$, $R^{103}$, or Y, the group may be hydrolyzed to obtain a carboxylic acid derivative, and when a 1,3-dioxolane group exists in $R^{101}$, the group may be subjected to deacetalization to convent into oxo group. When a benzyl ether group exists in $R^{101}$, $R^{103}$, $R^{105}$, or Y', the group may be reduced to obtain a hydroxy derivative. When benzyloxycarbonylamino group exists in $R^{103}$, the group may be reduced to obtain an amino derivative, and the product may further be acylated to to obtain an acylamino derivative.

The compounds of the formulas (2BB), (4BB), (7BB), (10BB), (13BB), (26BB), (28BB), and (34BB), which are used as starting materials of the preparation of the compounds of the present invention, can be readily prepared according to methods described in the literatures set out below and similar methods thereto; Carbohydr. Res. 78, pp.190–194 (1980) for compounds of formula (2BB); Chem. Ber. 99, pp.611–617 (1966) for those of the formulas (7BB) and (13BB); Carbohydr. Res. 187, pp.35–42 (1989) for those of the formulas (4BB) and (10BB); Chem. Pharm. Bull. 36 (12), pp.4807–4813 (1988) for those of the formulas (26BB) and (34BB); and Chem. Pharm. for those of formula (28BB).

The compounds of formula (3BB) can be produced by the method shown in the following section 4.

4. Method for preparation of compounds of the general formula (3BB):

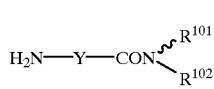

(3BB)

wherein $R^{101}$, $R^{102}$ and Y have the same meaning as defined above.

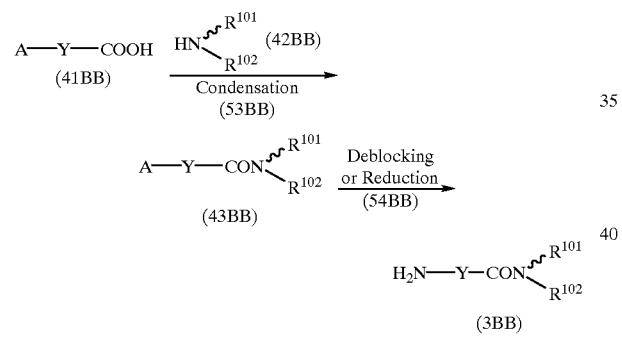

In the formulas, $R^{101}$, $R^{102}$, and Y have the same meaning as those defined above, and A represents a functional group which can be converted into an amino group by deblocking reaction or reduction reaction such as benzyloxycarbonylamino group, tert-butyloxycarbonylamino group, phthalimide group, or nitro group.

A compound of formula (41BB) is first reacted with a compound of formula (42BB) to form a compound of formula (43BB) [step (53BB)], and the product is then reduced to produce a compound of formula (3BB) [step (54BB)]. Where a functional group such as hydroxyl group, amino group, or carboxyl group exists in Y', the group may be protected with a suitable protective group before the step (53BB).

The step (53BB) may be carried out under the same condition as in the step (1BB), or by using 1–10 equivalents, preferably 1–5.0 equivalents of a condensing agent such as carbonylduimidazole or cyclohexylcarbodilimide and 0.9–10 equivalents, preferably 1.0–5.0 equivalents of a compound of formula (42BB) in a solvent such as tetrahydrofuran, dioxane, dichloromethane, or dichloroethane at a temperature ranging from −50° C. to 50° C., preferably from 0° C. to room temperature. The step (54BB) may be carried out under the same condition as in the step (35BB) when A is benzyloxycarbonylamino group or nitro group; carried out by using 1–10 equivalents, preferably 1–5 equivalents of hydrazine in a solvent such as ethanol or tetrahydrofuran at a temperature ranging from 0° C. to 100° C., preferably from 50° C. to 100° C. when A is phthalimide group; or performed by using 1–50 equivalents, preferably 1–10 equivalents of an acid such as hydrochloric acid, sulfuric acid, or trifluoroacetic acid in a solvent such as ethyl acetate or dioxane at a temperature ranging from 0° C. to 100° C., preferably from 0° C. to room temperature when A is tert-butyloxycarbonylamino group.

The compound of formula (41BB) as the starting material of the above step (53BB) can be synthesized from commercially available compounds according to the methods described in, for example, "Protective Groups in Organic Synthesis" (T. W. Greene and P. G. M. Wuts, John Wiley & Sons, Inc.), or similar methods thereto. The compound of formula (42BB) can be synthesized according to the methods described in, for example, J. Org. Chem., 27, pp.2925–2927, (1962); Steroids, 56, pp.395–398 (1991); and Tetrahedron Letters, 35(4), pp.565–568 (1994) or similar methods, or alternatively, according to the methods shown in the following (a) and (b) [the compounds of the formulas (44BB) and (47BB) as the starting materials of the processes of the following (a) and (b) can be synthesized according to the methods described in Tetrahedron Letters, 35(4), pp.565–568 (1994) or similar methods].

(a) Method for preparation of the compounds of formula (42'BB) wherein $R^{102}$ is hydrogen atom, and $R^{101}$ is a group of:

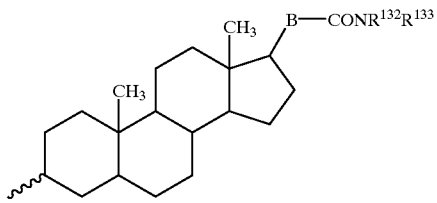

(wherein $R^{132}$ and $R^{133}$ have the same meanings as those defined above, and B represents a $C_1$–$C_{10}$ alkyl group or a $C_2$–$C_{11}$ alkenyl group)

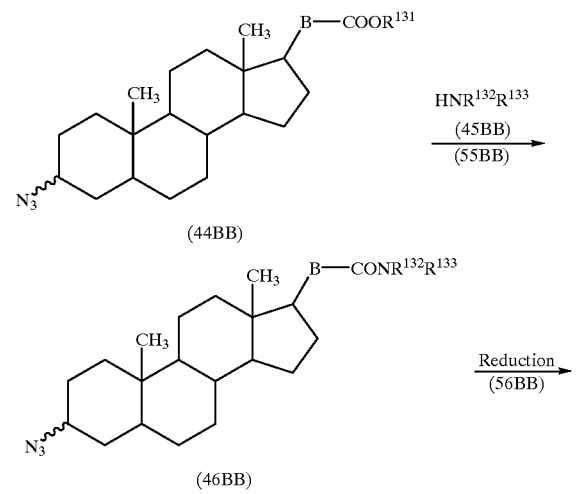

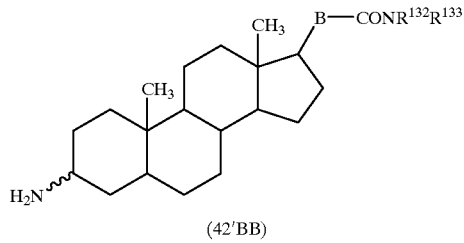

(42'BB)

In the formulas, $R^{131}$, $R^{132}$, $R^{133}$, and B have the same meanings as those defined above.

A compound of formula (44BB) is first reacted with a compound of formula (45BB) to obtain a compound of formula (46BB) [step (55BB)], and then the product is reduced to produce a compound of formula (42'BB) [step (56BB)].

The compounds of formula (46BB) may also be produced as follows.

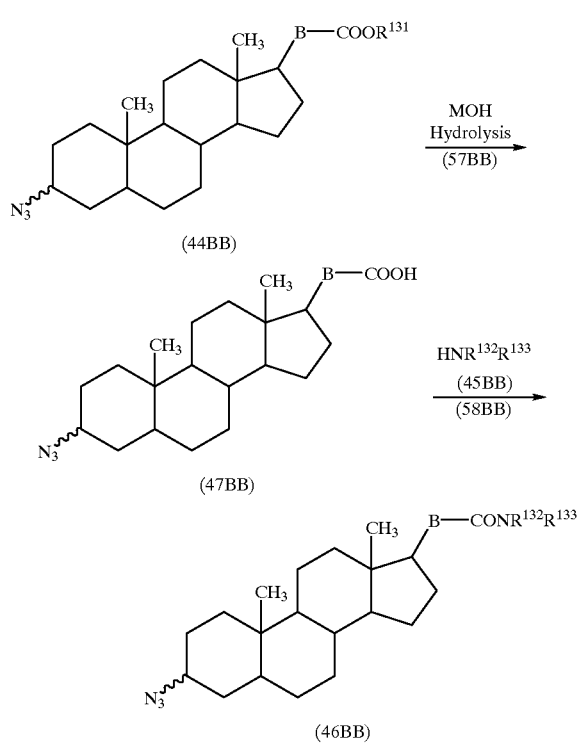

In the formulas, $R^{131}$, $R^{132}$, $R^{133}$, and B have the same meanings as defined above.

A compound of formula (44BB) is first hydrolyzed by reaction with an alkali such as sodium hydroxide to form a compound of formula (47BB) [step (57BB)], and the product is reacted with a compound of formula (45BB) to produce a compound of formula (46BB) [step (58BB)].

The step (55BB) may be carried out by using 0.9–100 equivalents, preferably 1.0–50 equivalents of a compound of formula (45BB) in a solvent such as methanol, ethanol, or tetrahydrofuran at a temperature ranging from 0° C. to 70° C., preferably 0° C. to 50° C. Operations for the reaction and the reaction per se may preferably be performed under anhydrous condition. The step (56BB) may be carried out under the same condition as in the step (35BB). The step (57BB) may be carried out under the same condition as in the step (3BB). The step (58BB) may be carried out under the same condition as in the step (1BB).

(b) Method for preparation of compounds of the general formula (42"BB) wherein $R^{102}$ is hydrogen atom, and $R^{101}$ is a group of:

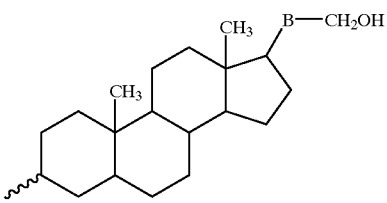

wherein Z represents a $C_1$–$C_{10}$ alkyl group or a $C_2$–$C_{11}$ alkenyl group

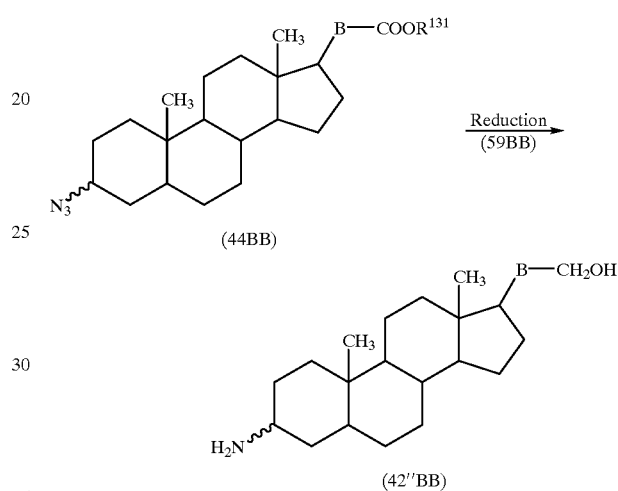

In the formulas, $R^{131}$ and B have the same meanings as those defined above.

A compound of formula (44BB) is reduced to produce a compound of formula (42"BB) [step (59BB)].

The compounds of formula (42"BB) may also be produced as follows.

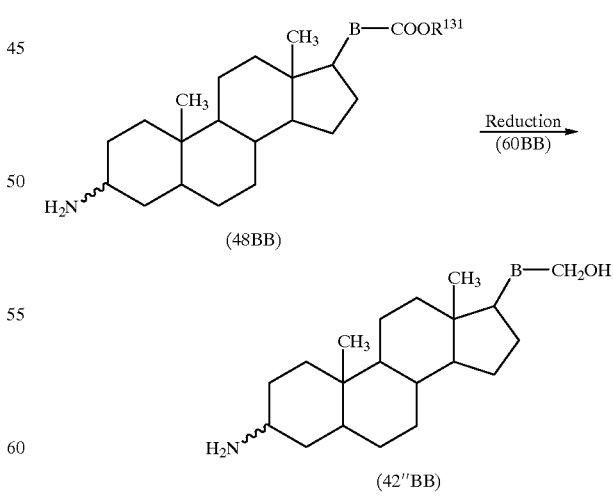

In the formulas, $R^{131}$ and B have the same meanings as those defined above.

A compound of formula (48BB) is reduced to produce a compound of formula (42"BB) [step (60BB)].

The step (59BB) may be carried out in a solvent such as tetrahydrofuran or diethyl ether by using 3.9–50 equivalents, preferably 4.0–20 equivalents of a reducing agent such as lithium aluminium hydride at a temperature ranging from 0° C. to 60° C., preferably from 0° C. to 40° C. Operations for the reaction and the reaction per se may preferably be performed under anhydrous condition. The step (60BB) may be carried out in a solvent such as tetrahydrofuran or diethyl ether by using 1.9–50 equivalents, preferably 2.0–20 equivalents of a reducing agent such as lithium aluminium hydride at a temperature ranging from 0° C. to 60° C., preferably from 0° C. to 40° C. The reaction operation and the reaction per se may preferably be performed under anhydrous condition.

Separation and purification of the compounds from reaction mixtures, which are produced by the methods 1, 2, 3, and 4 for the preparation of the compounds according to the first aspect of the present invention and the methods 1, 2, 3 and 4 for the preparation of the compounds according to the second aspect of the present invention, can be carried out by conventional methods such as extraction, recrystallization and chromatography.

The compounds of the present invention have activating effect on choline acetyltransferase (ChAT) in the cholinergic nerve cells. Therefore, a substance selected from the group consisting of the aforementioned compound of the present invention and its pharmaceutically acceptable salt, and a hydrate and a solvate thereof according to the present invention is expected to have preventive and therapeutic effect on dementia, memory disorder, and other symptoms accompanied with the diseases.

More specifically, they are expected as useful for preventive and therapeutic treatment of, for example, senile dementia including Alzheimer's disease; cerebrovascular dementia accompanying stroke, cerebral hemorrhage, brain infarction and the like; memory disorder, decreased attentiveness, speech disturbance, hypobulia, emotional disorder, hallucination, paranoid state, behavioral disorder and the like accompanying head injury, after-trouble of encephalitis, cerebral palsy, Huntington's disease, Pick's disease, Down's syndrome, Parkinson's disease and the like. They are also useful for preventive and therapeutic treatment of, for example, tardive dyskinesia; glaucoma; sleep disturbance; peripheral nervous disorders such as those of motor nerves, sensory nerves and autonomic nerves including traumatological and inflammatory neurological disorders; peripheral nervous disorders such as alcoholic neuropathy, drug neuropathy caused by anticancer agent and the like, metabolic neuropathy originating from diabetes and the like, cataplectic neuropathy caused by anticancer agent and the like; facial nerve palsy; ischiadic nerve palsy; myelopathic muscular atrophy; muscular dystrophy; myasthenia gravis; multiple sclerosis; amyotrophic lateral sclerosis; acute disseminated encephalomyelitis; Guillain-Barre syndrome; postvaccinal encephalitis; subacute myelo-optico-neuropathy and the like.

When the substance selected from the aforementioned group is used for therapeutic and preventive treatment of the aforementioned diseases, the substance per se may be administered, or alternatively, may be administered as a pharmaceutical composition prepared by combination with a pharmaceutically acceptable carrier. A type of the pharmaceutical composition may be decided depending on solubility and chemical properties of the substance, route of administration, dosage regimen and the like. For example, formulations such as granules, fine granules, powders, tablets, hard syrups, soft capsules, syrups, emulsions, suspensions, liposome suspensions, or solutions may be prepared and administered orally, or alternatively, injections may be prepared and administered intravenously, intramuscularly, or subcutaneously. Powders for injection may be manufactured and prepared as injections before use.

In addition, organic or inorganic solid or liquid carriers for pharmaceutical use, which are suitable for oral, enteral, parenteral, or topical administration, can be used for the preparation of the pharmaceutical compositions described above. Examples of excipients used for manufacturing solid pharmaceutical compositions include, for example, lactose, sucrose, starch, talc, cellulose, dextrin, kaolin, calcium carbonate and the like. Ordinarily used inert diluents such as vegetable oils may be added to liquid pharmaceutical compositions for oral administration, e.g., emulsions, syrups, suspensions, or solutions. These pharmaceutical composition may also contain auxiliaries such as, for example, wetting agents, suspending aids, sweeteners, aromatics, colorants, preservatives and the like in addition to the aforementioned inert diluents. Liquid pharmaceutical compositions may be encapsulated in capsules made of an absorbable material such as gelatin. Examples of a solvent or a suspending medium used for the preparation of pharmaceutical compositions for parenteral administration such as injections or drip infusions include, for example, water, propylene glycol, polyethylene glycol, benzyl alcohol, ethyl oleate, lecithin or the like. The pharmaceutical formulations may be prepared by ordinary processes.

Dose for a clinical application may generally be within the range of from 1 to 1,000 mg, preferably from 1 to 200 mg per day for an adult as a weight of the compounds of the present invention when the medicament is applied as an oral administration. However, it is preferable that the dose may be appropriately increased or decreased depending on the age, symptoms, and conditions of a patient, or presence or absence of a medicament administered in combination. The daily dose of the compound of the present invention may be administered once a day, or may be administered twice or three times a day with an appropriate interval as divided portions. The dose may be administered intermittently. When used as injection, daily dose may generally be within the range of from 0.1 to 100 mg, preferably from 0.1 to 50 mg for an adult as a weight of the compound of the present invention.

EXAMPLES

The present invention will be explained more specifically by referring to the following examples. The following examples are described solely for the purpose of specific explanations of the present invention, and they should not be construed as limiting the scope of the present invention. In the following examples, the indication "α" or "β" represents the configuration at 3-position of a residue of a steroid compound, and "L-isomer" or "D-isomer" represents the configuration of the group Y'. Expressions of "Example AA" and "Example BB" in titles of the following examples indicate that compounds obtained in examples correspond to the compounds or their synthetic intermediates falling within the scope of the general formulas (1AA) and (1BB), respectively.

Synthetic Example AA1: 3α-amino-24-hydroxy-5β-cholane Hydrochloride [hydrochloride of compound of the formula (3"AA) wherein Z is —CH(CH$_3$) CH$_2$CH$_2$-group].

Lithium aluminium hydride (104 mg, 2.74 mmol) was suspended in diethyl ether (30 ml), and the suspension was added with a solution of 3α-azide-5β-cholanate (388 mg, 0.93 mmol) in diethyl ether (15 ml) over 50 minutes under reflux by heating, and then the mixture was refluxed by heating for further three hours. After the reaction was completed, excess lithium aluminium hydride was quenched by adding saturated aqueous sodium sulfate to the reaction mixture with ice cooling, and the organic layer was separated from the mixture. Diethyl ether was further added to the reaction mixture and stirring was continued, and the resulting organic layers were then combined and concentrated. The resulting syrup was dissolved in ethyl acetate (100 ml), and the solution was added with 13% hydrochloric acid/ethyl acetate. The resulting precipitates were collected by filtration to obtain the title compound (307 mg, yield; 82.5%).

$^1$H-NMR (CD$_3$OD, ppm): 0.74 (3H, s, 18-CH$_3$), 0.98–1.05 (6H, m, 19-CH$_3$, 21-CH$_3$), 3.10–3.21 (1H, m, H-3), 3.55 (2H, t, J=6.0 Hz, 24-CH$_2$—OH).

Example AA1: Synthesis of 3α-[N-(5-acetamido-4,7,8,9-tetra-O-acetyl-3,5-dideoxy-2-O-methyl-α-D-glycero-D-galacto-2-nonulopyranosonyl)amino]-24-hydroxy-5β-cholane (α-isomer of Compound No. 1 in Table 1AA)

5-Acetamido-4,7,8,9-tetra-O-acetyl-3,5-dideoxy-2-O-methyl-α-D-glycero-D-galacto- 2-nonulopyranosonic acid (302 mg, 0.61 mmol) was dissolved in tetrahydrofuran (20 ml) and the solution was cooled to –10° C. and added with N-methylmorpholine (0.08 ml, 0.72 mmol) and isobutyl chlorocarbonate (0.09 ml, 0.70 mmol), and then stirring was continued for one hour. Then, the compound obtained in Synthetic Example AA1 (250 mg, 0.63 mmol) and N-methylmorpholine (0.08 ml, 0.72 mmol) were added to the reaction mixture over ten minutes, and the mixture was stirred for one hour and then warmed up to room temperature, and stirring was continued for 20 hours. Ethyl acetate (50 ml) was added to the reaction mixture, and the mixture was washed with 0.1 N hydrochloric acid, water, saturated aqueous sodium hydrogen carbonate, and saturated brine successively, and dried over anhydrous magnesium sulfate. After the solvent was evaporated, the residue was purified by column chromatography (Merck silica gel 60, developing solvent; chloroform/methanol) to obtain the title compound (489 mg, yield; 95.3%).

$^1$H-NMR (CDCl$_3$, ppm): 0.62 (3H, s, 18'-CH$_3$), 0.87–0.92 (6H, m, 19'-CH$_3$, 21'-CH$_3$), 1.85, 1.99, 2.03, 2.06, 2.12 (15H, s X5, Ac), 2.29 (1H, dd, J=5.6 Hz, 13.2 Hz, H-3$_{eq}$), 3.37 (3H, s, OCH$_3$), 3.58 (2H, t, J=6.2 Hz, 24'-CH$_2$OH), 3.60–3.71 (1H, m, H-3'), 3.88–4.20 (3H, m, H-5, 9, 9), 4.56–4.62 (1H, m, H-6), 5.21–5.34 (4H, m, H-4, 7, 8, AcNH), 6.76 (1H, d, J=8.4 Hz, NH).

Example AA2: Synthesis of 3α-[N-(5-acetamide-3,5-dideoxy-2-O-methyl-α-D-glycero-D-galacto-2-nonulopyranosonyl)amino]-24-hydroxy-5β-cholane (α-isomer of Compound No. 4 in Table 1AA)

The compound obtained in Example AA1 (452 mg, 0.54 mmol) was dissolved in methanol (20 ml), and the solution was added with 4.9N solution of sodium methoxide in methanol (0.06 ml, 0.29 mmol) under ice cooling. Then, the mixture was warmed up to room temperature, and stirred for eight hours. The reaction mixture was neutralized by adding Dowex (50WX8, H$^+$) resin and then filtered. The filtrate was purified by column chromatography (ODS MCIGEL, developing solvent; water/methanol) to obtain the title compound (266 mg, yield; 73.3%).

Melting point: 248–262° C. $^1$H-NMR (CD$_3$OD, ppm): 0.74 (3H, s, 18'-CH$_3$), 0.97–1.02 (6H, m, 19'-CH$_3$, 21'-CH$_3$), 2.05 (3H, s, Ac), 2.85 (1H, dd, J=4.4 Hz, 12.6 Hz, H-3$_{eq}$), 3.36 (3H, s, OCH$_3$).

Synthetic Example AA2: 3β-amino-24-hydroxy-5β-cholane hydrochloride [hydrochloride of compound of the formula (3"AA) wherein Z is —CH(CH$_3$)CH$_2$CH$_2$-group]

By using methyl 3β-azido-5β-cholanate (500 mg, 1.20 mmol), the title compound was obtained in the same manner as in Synthetic Example AA1 (356 mg, yield; 74.3%).

$^1$H-NMR (CD$_3$OD, ppm): 0.75 (3H, s, 18-CH$_3$), 0.98–1.09 (6H, m, 19-CH$_3$, 21-CH$_3$), 3.55 (2H, t, J=6.3 Hz, 24-CH$_2$—OH), 3.61 (1H, m, H-3).

Example AA3: Synthesis of 3β-[N-(5-acetamido-4,7,8,9-tetra-O-acetyl-3,5-dideoxy-2-O-methyl-α-D-glycero-D-galacto-2-nonulopyranosonyl)amino]-24-hydroxy-5β-cholane (β-isomer of Compound No. 1 in Table 1AA)

By using 5-acetamido-4,7,8,9-tetra-O-acetyl-3,5-dideoxy-2-O-methyl-α-D-glycero-D-galacto-2-nonulopyranosonic acid (282 mg, 0.57 mmol) and the compound obtained in Synthetic Example AA2 (230 mg, 0.58 mmol), the title compound was obtained in the same manner as in Example AA1 (268 mg, yield; 55.9%).

$^1$H-NMR (CDCl$_3$, ppm): 0.62 (3H, s, 18'-CH$_3$), 0.88–0.94 (6H, m, 19'-CH$_3$, 21'-CH$_3$), 1.86, 1.99, 2.00, 2.04, 2.11 (15H, s×5, Ac), 3.38 (3H, s, OCH$_3$), 3.58 (2H, t, J=5.8 Hz, 24'-CH$_2$OH), 3.97–4.17 (3H, m, H-3', 5, 9), 4.31–4.37 (1H, m, H-9), 4.43–4.48 (1H, m, H-6), 5.24–5.44 (4 H, m, H-4, 7, 8, AcNH), 6.79 (1H, d, J=7.6 Hz, NH).

Example AA4: Synthesis of 3β-[N-(5-acetamido-3,5-dideoxy-2-O-methyl-α-D-glycero-D-galacto-2-nonulopyranosonyl)amino]-24-hydroxy-5β-cholane (β-isomer of Compound No. 4 in Table 1AA)

By using the compound obtained in Example AA3 (251 mg, 0.30 mmol), the title compound was obtained in the same manner as in Example AA2 (144 mg, yield; 71.6%).

Melting point: 244–248° C. $^1$H-NMR (CD$_3$OD, ppm): 0.74 (3H, s, 18'-CH$_3$), 0.98–1.03 (6H, m, 19'-CH$_3$, 21'-CH$_3$), 2.04 (3H, s, Ac), 2.84 (1H, dd, J=4.3 Hz, 12.7 Hz, H-3$_{eq}$), 3.38 (3H, s, OCH$_3$), 3.55 (2H, t, J=6.4 Hz, 24'-CH$_2$OH), 4.11 (1H, m, H-3').

Example AA5: Synthesis of methyl 3α-[N-(5-acetamido-4,7,8,9-tetra-O-acetyl-3,5-dideoxy-2-O-methyl-α-D-glycero-D-galacto-2-nonulopyranosonyl)amino]-5β-cholanate (α-isomer of Compound No. 54 in Table 1AA)

By using 5-acetamido-4,7,8,9-tetra-O-acetyl-3,5-dideoxy-2-O-methyl-α-D-glycero-D-galacto-2-nonulopyranosonic acid (370 mg, 0.75 mmol) and methyl 3α-amino-5β-cholanate hydrochloride (320 mg, 0.75 mmol), the title compound was obtained in the same manner as in Example AA1 (317 mg, yield; 48.8%).

$^1$H-NMR (CDCl$_3$, ppm): 0.64 (3H, s, 18'-CH$_3$), 0.89–0.94 (6H, m, 19'-CH$_3$, 21'-CH$_3$), 1.88, 2.02, 2.06, 2.08, 2.14 (15H, s×5, Ac), 3.40 (3H, s, OCH$_3$), 3.66 (3H, s, COOCH$_3$), 3.96–4.20 (3H, m, H-5, 9, 9), 4.59–4.64 (1H, m, H-6), 5.27–5.40 (4 H, m, H-4, 7, 8, AcNH), 6.78 (1H, d, J=8.3 Hz, NH).

Example AA6: Synthesis of methyl 3α-[N-(5-acetamido-3,5-dideoxy-2-O-methyl-α-D-glycero-D-galacto-2-nonulopyranosonyl)amino]-5β-cholanate (α-isomer of Compound No. 55 in Table 1AA)

By using the compound obtained in Example AA5 (300 mg, 0.35 mmol), the title compound was obtained in the same manner as in Example AA2 (135 mg, yield; 55.8%).

Melting point: 268° C. (decomposition) $^1$H-NMR (CD$_3$OD, ppm): 0.73 (3H, s, 18'-CH$_3$), 0.96–1.02 (6H, m, 19'-CH$_3$, 21'-CH$_3$), 2.05 (3H, s, Ac), 2.85 (1H, dd, J=4.4 Hz, 12.6 Hz, H-3$_{eq}$), 3.36 (3H, s, OCH$_3$), 3.68 (3H, s, COOCH$_3$).

Example AA7: Synthesis of sodium 3α-[N-(5-acetamido-3,5-dideoxy-2-O-methyl-α-D-glycero-D-galacto-2-nonulopyranosonyl)amino]-5β-cholanate (sodium salt of α-isomer of Compound No. 57 in Table 1AA)

The compound obtained in Example AA6 (97.8 mg, 0.14 mmol) was dissolved in tetrahydrofuran (10 ml), and the solution was added with 0.1N aqueous solution of sodium hydroxide (2.0 ml, 0.2 mmol), and then the mixture was stirred at room temperature for three days. After the solvent was evaporated, the resulting syrup was purified by column chromatography (ODS MCIGEL, developing solvent; water/methanol) to obtain the title compound (76.2 mg, yield; 77.0%).

Melting point: 265–275"C (decomposition) $^1$H-NMR (CD$_3$OD, ppm): 0.73 (3H, s, 18'-CH$_3$), 0.97–1.02 (6H, m, 19'-CH$_3$, 21'-CH$_3$), 2.05 (3H, s, Ac), 2.85 (1H, dd, J=4.3 Hz, 12.6 Hz, H-3$_{eq}$), 3.36 (3H, s, OCH$_3$).

Example AA8: Synthesis of methyl 3β-[N-(5-acetamido-4,7,8,9-tetra-O-acetyl-3,5-dideoxy-2-O-methyl-α-D-glycero-D-galacto-2-nonulopyranosonyl)amino]-5β-cholanate (β-isomer of Compound No. 54 in Table 1AA)

By using 5-acetamido-4,7,8,9-tetra-O-acetyl-3,5-dideoxy-2-O-methyl-α-D-glycero-D-galacto-2-nonulopyranosonic acid (500 mg, 1.02 mmol) and methyl 3β-amino-5β-cholanate hydrochloride (434 mg, 1.02 mmol), the title compound was obtained in the same manner as in Example AA1 (482 mg, yield; 54.9%).

$^1$H-NMR (CDCl$_3$, ppm): 0.62 (3H, s, 18'-CH$_3$), 0.86–0.94 (6H, m, 19'-CH$_3$, 21'-CH$_3$), 1.86, 1.99, 2.01, 2.04, 2.11 (15H, s×5, Ac), 3.38 (3H, s, OCH$_3$), 3.64 (3H, s, COOCH$_3$), 3.97–4.17 (3H, m, H-3', 5, 9,), 4.31–4.37 (1H, m, H-9), 4.44–4.48 (1H, m, H-6), 5.24–5.44 (4 H, m, H-4, 7, 8, AcNH), 6.79 (1H, d, J=7.6 Hz, NH).

Example AA9: Synthesis of methyl 3β-[N-(5-acetamido-3,5-dideoxy-2-O-methyl-α-D-glycero-D-galacto-2-nonulopyranosonyl)amino]-5β-cholanate (β-isomer of Compound No. 55 in Table 1AA)

By using the compound obtained in Example AA8 (454 mg, 0.53 mmol), the title compound was obtained in the same manner as in Example AA2 (264 mg, yield; 72.1%).

Melting point: 228–243° C. $^1$H-NMR (CD$_3$OD, ppm): 0.73 (3H, s, 18'-CH$_3$), 0.96–1.03 (6H, m, 19'-CH$_3$, 21'-CH$_3$), 2.04 (3H, s, Ac), 2.84 (1H, dd, J=4.4 Hz, 12.7 Hz, H-3$_{eq}$), 3.38 (3H, s, OCH$_3$), 3.69 (3H, s, COOCH$_3$), 4.11 (1H, m, H-3').

Example AA10: Synthesis of sodium 3β-[N-(5-acetamido-3,5-dideoxy-2-O-methyl-α-D-glycero-D-galacto-2-nonulopyranosonyl)amino]-5β-cholanate (sodium salt of β-isomer of Compound No. 57 in Table 1AA)

By using the compound obtained in Example AA9 (171 mg, 0.25 mmol), the title compound was obtained in the same manner as in Example AA7 (61.7 mg, yield; 35.7%).

Melting point: 250° C. (decomposition) $^1$H-NMR (CD$_3$OD, ppm): 0.73 (3H, s, 18'-CH$_3$), 0.98–1.03 (6H, m, 19'-CH$_3$, 21'-CH$_3$), 2.05 (3H, s, Ac), 2.84 (1H, dd, J=4.0 Hz, 12.5 Hz, H-3$_{eq}$), 3.38 (3H, s, OCH$_3$), 4.11 (1H, m, H-3').

Synthetic Example AA3: Synthesis of 3α-azido-6-ketocholestane ethylene ketal [compound of the formula (47AA) where R$^{30}$ is —CH(CH$_3$)CH$_2$CH$_2$CH$_2$CH(CH$_3$)$_2$ group, and Y is a group of:

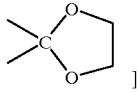 ]

3β-Hydroxy-6-ketocholestane ethylene ketal (1.10 g, 2.46 mmol) and triphenylphosphine (970 mg, 3.70 mmol) were dissolved in tetrahydrofuran (25 ml), and the solution was added with a solution of diethyl azodicarboxylate (650 mg, 3.73 mmol) in tetrahydrofuran (6 ml) under water cooling over 15 minutes. Then, a solution of diphenylphosphoryl azide (1.02 g, 3.70 mmol) in tetrahydrofuran (10 ml) was added to the mixture over ten minutes, and the mixture was stirred under ice cooling for two hours, and then warmed up to room temperature and stirred for 40 hours. After the reaction was completed, the solvent was evaporated, and the resulting syrup was purified by silica gel column chromatography (Merck silica gel 60, developing solvent; hexane/methanol) to obtain the title compound (590 mg, yield; 50.9%).

$^1$H-NMR (CDCl$_3$, ppm): 0.64 (3H, s, 18-CH$_3$), 0.77–0.89 (12H, m, 19-CH$_3$, 21-CH$_3$, 26-CH$_3$, 27-CH$_3$), 3.67–3.92 (5H, m, H-3, —OCH$_2$CH$_2$O—).

Synthetic Example AA4: Synthesis of 3α-amino-6-ketocholestane ethylene ketal hydrochloride [hydrochloride of compound of the formula (3'"AA) wherein R$^{30}$ is —CH(CH$_3$)CH.$_2$CH$_2$CH$_2$CH(CH$_3$)$_2$ group, and Y is a group of:

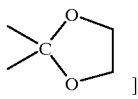 ]

By using the compound obtained in Synthetic Example AA3 (590 mg, 1.25 mmol), the title compound was obtained in the same manner as in Synthetic Example AA1 (393 mg, yield; 65.2%).

$^1$H-NMR (CD$_3$OD, ppm): 0.75 (3H, s, 18-CH$_3$), 0.90–1.02 (12H, m, 19-CH$_3$, 21-CH$_3$, 26-CH$_3$, 27-CH$_3$), 3.63 (1H, m, H-3), 3.74–4.02 (4 H, m, —OCH$_2$CH$_2$O—).

Example AA11: Synthesis of 3α-[N-(5-acetamido-4,7,8,9-tetra-O-acetyl-3,5-dideoxy-2-O-methyl-α-D-glycero-D-galacto-2-nonulopyranosonyl)amino]-6-ketocholestane ethylene ketal (α-isomer of Compound No. 58 in Table 1AA)

By using 5-acetamido-4,7,8,9-tetra-O-acetyl-3,5-dideoxy-2-O-methyl-α-D-glycero-D-galacto-2-nonulopyranosonic acid (350 mg, 0.71 mmol) and the compound obtained in Synthetic Example AA4 (343 mg, 0.71 mmol), the title compound was obtained in the same manner as in Example AA1 (415 mg, yield; 63.4%).

$^1$H-NMR (CDCl$_3$, ppm): 0.65 (3H, s, 18'-CH$_3$), 0.82–0.91 (12H, m, 19'-CH$_3$, 21'-CH$_3$, 26'-CH$_3$, 27'-CH$_3$), 1.86, 2.00, 2.01, 2.04, 2.12 (15H, s×5, Ac), 2.20 (1H, dd, J=5.2 Hz, 13.2 Hz, H-3$_{eq}$), 3.38 (3H, s, OCH$_3$), 4.32–4.46 (2H, m, H-6, 9), 5.24–5.41 (3H, m, H-4, 7, 8), 5.47 (1H, d, J=10.2 Hz, AcNH), 6.74 (1H, d, J=7.6 Hz, NH).

Example AA12: Synthesis of 3α-[N-(5-acetamido-3,5-dideoxy-2-O-methyl-α-D-glycero-D-galacto-2-nonulopyranosonyl)amino]-6-ketocholestane ethylene ketal (α-isomer of Compound No. 59 in Table 1AA)

By using the compound obtained in Example AA11 (360 mg, 0.39 mmol), the title compound was obtained in the same manner as in Example AA2 (211 mg, yield; 71.8%).

Melting point: 152–165° C. $^1$H-NMR (CD$_3$OD, ppm): 0.74 (3H, s, 18'-CH$_3$), 0.90–1.00 (12H, m, 19'-CH$_3$, 21'-CH$_3$, 26'-CH$_3$, 27'-CH$_3$), 2.05 (3H, s, Ac), 2.86 (1H, dd, J=4.4 Hz, 12.8 Hz, H-3$_{eq}$), 3.37 (3H, s, OCH$_3$), 4.09 (1H, m, H-3').

Synthetic Example AA5: Synthesis of 3α-azido-6-ketocholestane [compound of the formula (47AA) wherein R$^{30}$ is —CH(CH$_3$)CH$_2$CH$_2$CH$_2$CH(CH$_3$)$_2$ group, and Y is a group of —CO—]

By using 3β-hydroxy-6-ketocholestane (2.0 g, 4.97 mmol), the title compound was obtained in the same manner as in Synthetic Example AA3 (725 mg, yield; 33.9%).

$^1$H-NMR (CDCl$_3$, ppm): 0.63 (3H, s, 18-CH$_3$), 0.71–0.91 (12H, m, 19-CH$_3$, 21-CH$_3$, 26-CH$_3$, 27-CH$_3$), 2.51 (1H, dd, J=5.2 Hz, 10.3 Hz, H-5), 3.94–3.98 (1H, m, H-3).

Synthetic Example AA6: Synthesis of 3α-amino-6-ketocholestane hydrochloride [hydrochloride of compound the formula (3'''AA) wherein R$^{30}$ is —CH(CH$_3$)CH$_2$CH$_2$CH$_2$CH(CH$_3$)$_2$ group, and Y is a group of —CO—]

The compound obtained in Synthetic Example AA5 (399 mg, 0.93 mmol) was dissolved in a mixed solvent of tetrahydrofuran (5 ml) and ethanol (15 ml), and the solution was added with 5% palladium/carbon (120 mg) and the mixture was stirred for 7.5 hours under hydrogen flow. After the reaction was completed, the catalyst was removed by filtration, and the solvent was evaporated. The resulting syrup was dissolved in ethyl acetate, and the solution was added with 13% hydrochloric acid/ethyl acetate, and the resulting precipitates were collected by filtration to obtain the title compound (275 mg, yield; 67.2%).

$^1$H-NMR (CD$_3$OD, ppm): 0.76 (3H, s, 18-CH$_3$), 0.81–1.01 (12H, m, 19-CH$_3$, 21-CH$_3$, 26-CH$_3$, 27-CH$_3$), 3.66 (1H, m, H-3).

Example AA13: Synthesis of 3α-[N-(5-acetamido-4,7,8,9-tetra-O-acetyl-3,5-dideoxy-2-O-methyl-α-D-glycero-D-galacto-2-nonulopyranosonyl)amino]-6-ketocholestane (α-isomer of Compound No. 60 in Table 1AA)

By using 5-acetamido-4,7,8,9-tetra-O-acetyl-3,5-dideoxy-2-O-methyl-α-D-glycero-D-galacto-2-nonulopyranosonic acid (277 mg, 0.56 mmol) and the compound obtained in Synthetic Example AA6 (247 mg, 0.56 mmol), the title compound was obtained in the same manner as in Example AA1 (260 mg, yield; 52.7%).

$^1$H-NMR (CDCl$_3$, ppm): 0.64 (3H, s, 18'-CH$_3$), 0.73 (3H, s, 19'-CH$_3$), 0.82–0.91 (9H, m, 21'-CH$_3$, 26'-CH$_3$, 27'-CH$_3$), 1.87, 1.98, 2.00, 2.06, 2.12 (15H, s×5, Ac), 2.28 (1H, dd, J=4.1 Hz, 12.5 Hz, H-3$_{eq}$), 3.38 (3H, s, OCH$_3$), 5.21–5.34 (4 H, m, H-4, 7, 8, AcNH) 6.64 (1H, d, J=7.0 Hz, NH).

Example AA14: Synthesis of 3α-[N-(5-acetamido-3,5-dideoxy-2-O-methyl-α-D-glycero-D-galacto-2-nonulopyranosonyl)amino]-6-ketocholestane (α-isomer of Compound No. 61 in Table 1AA)

By using the compound obtained in Example AA13 (244 mg, 0.28 mmol), the title compound was obtained in the same manner as in Example AA2 (113 mg, yield; 57.4%).

Melting point: 281–285° C. (decomposition) $^1$H-NMR [CDCl$_3$-CD$_3$OD (1:1), ppm]: 0.90–1.00 (12H, m, 19'-CH$_3$, 21'-CH$_3$, 27'-CH$_3$), 2.05 (3H, s, Ac).

Synthetic Example AA7: Synthesis of 3β-azido-5β-cholanic Acid [compound of the formula (44AA) wherein Z is —CH(CH$_3$)CH$_2$CH$_2$-group]

Methyl 3β-azido-5β-cholanate (2.00 g, 4.81 mmol) was dissolved in tetrahydrofuran (20 ml), and the solution was added with 1N aqueous solution of sodium hydroxide (4.81 ml, 4.81 mmol), and the mixture was stirred at room temperature for three days. After the reaction was completed, the solvent was evaporated, and then water (20 ml) and 1N aqueous solution of hydrochloric acid (5 ml) were added to the residue, and the mixture was extracted twice with ethyl acetate (50 ml). The extract was washed with saturated brine, and dried over anhydrous sodium sulfate. The solvent was evaporated, and the resulting solid was washed by suspending it in methanol (20 ml) to obtain the title compound (1.74 g, yield; 90%).

IR (KBr, cm$^{-1}$): 2936, 2865, 2103, 1705. $^1$H-NMR (CDCl$_3$, ppm): 0.65 (3H, s, 18-CH$_3$), 0.92 (3H, d, J=6.3 Hz, 21-CH$_3$), 0.95 (3H, s, 19-CH$_3$), 2.20–2.44 (2H, m, H-23), 3.96 (1H, m, H-3).

Synthetic Example AA8: Synthesis of 3β-azido-5β-cholanic acid methylamide [compound of the formula (43AA) wherein Z is —CH(CH$_3$)CH$_2$CH$_2$-group, R$^{25}$ is methyl group, and R$^{26}$ is hydrogen atom]

The compound obtained in Synthetic Example AA7 (600 mg, 1.49 mmol) was dissolved in tetrahydrofuran (6 ml), cooled to −10° C., and the solution was added with triethylamine (0.208 ml, 1.49 mmol) and isobutyl chlorocarbonate (0.194 ml, 1.49 mmol). The mixture was stirred for 15 minutes, and then added with a 40% solution of methylamine (174 mg, 2.24 mmol) in methanol. After the mixture was stirred at 0° C. for two hours, water (10 ml) was added to the mixture, and then the mixture was extracted with ethyl acetate (25 ml). The extract was washed with 0.1N aqueous hydrochloric acid, saturated aqueous sodium hydrogen carbonate, and saturated brine successively and dried over anhydrous sodium sulfate, and then the solvent was evaporated. The resulting syrup was purified by silica gel column chromatography (Merck silica gel 60, developing solvent: methylene chloride/methanol) to obtain the title compound (576 mg, yield; 93%).

IR (KBr, cm$^{-1}$): 3434, 3285, 2934, 2865, 2105, 1644. $^1$H-NMR (CDCl$_3$, ppm): 0.63 (3H, s, 18-CH$_3$), 0.91 (3H, d, J=6.3 Hz, 21-CH$_3$), 0.95 (3H, s, 19-CH$_3$), 2.80 (3H, d, J=4.8 Hz, NH—CH$_3$), 3.95 (1H, m, H-3), 5.45 (1H, m, NH).

Synthetic Example AA9: Synthesis of 3β-amino-5β-cholanic Acid Methylamide [compound of the formula (3'AA) wherein Z is —CH(CH$_3$)CH$_2$CH$_2$-group, R$^{25}$ is methyl group, and R$^{26}$ is hydrogen atom]

The compound obtained in Synthetic Example AA8 (449 mg 1.08 mmol) was dissolved in tetrahydrofuran (8 ml), and the solution was added with 5% palladium/carbon (40 mg), and the mixture was stirred for eight hours under hydrogen flow. After the reaction was completed, the catalyst was removed by filtration, and then the solvent was evaporated. The resulting solid was washed by suspending it in ethyl acetate to obtain the title compound (260 mg, yield; 62%).

IR (KBr, cm$^{-1}$): 3426, 3297, 1657. $^1$H-NMR (CDCl$_3$, ppm): 0.64 (3H, s, 18-CH$_3$), 0.91 (3H, d, J=6.3 Hz, 21-CH$_3$), 0.95 (3H, s, 19-CH$_3$), 2.81 (3H, d, J=4.8 Hz, —NHCH$_3$), 3.23 (1H, m, H-3), 5.49 (1H, m, NH).

Example AA15: Synthesis of 3β-[N-(5-acetamido-4,7,8,9-tetra-O-acetyl-3,5-dideoxy-2-O-methyl-α-D-glycero-D-galacto-2-nonulopyranosonyl)amino]-5β-cholanic Acid methylamide (β-isomer of Compound No. 72 in Table 1AA)

By using 5-acetamido-4,7,8,9-tetra-O-acetyl-3,5-dideoxy-2-O-methyl-α-D-glycero-D-galacto-2-nonulopyranosonic acid (200 mg, 0.407 mmol) and the compound obtained in Synthetic Example AA9 (174 mg, 0.448 mmol), the title compound was obtained in the same manner as in Synthetic Example AA8 (280 mg, yield; 80%).

IR (KBr, cm-$^1$): 3380, 2938, 2866, 1750, 1680. $^1$H-NMR (CDCl$_3$, ppm): 0.64 (3H, s, 18'-CH$_3$), 0.91 (3H, d, J=6.2 Hz, 21'-CH$_3$), 0.96 (3H, s, 19'-CH$_3$), 1.89, 2.02, 2.04, 2.06, 2.14 (15H, sx5, Ac), 2.80 (3H, d, J=4.8 Hz, —NHCH$_3$), 3.41 (3H, s, OCH$_3$), 4.01–4.09 (2H, m, H-3', 9,), 4.14 (1H, q, J=10.5 Hz, H-5), 4.37(1H, d, J=12.0 Hz, H-9), 4.48 (1H, d, J=10.5 Hz, H-6), 5.27–5.46 (5H, m, H-4, 7, 8, AcNH, NH), 6.82 (1H, d, J=7.6 Hz, NH).

Example AA16: Synthesis of 3β-[N-(5-acetamido-3,5-dideoxy-2-O-methyl-α-D-glycero-D-galacto-2-nonulopyranosonyl)amino]-5β-cholanic Acid Methylamide (β-isomer of Compound No. 73 in Table 1AA)

By using the compound obtained in Example AA15 (229 mg, 0.266 mmol), the title compound was obtained in the same manner as in Example AA2 (80 mg, yield; 43%).

Melting point: 250–255° C. (decomposition)

IR (KBr, cm$^{-1}$): 3420, 2935, 2864, 1649, 1525. $^1$H-NMR (CD$_3$OD, ppm): 0.68(3H, s, 18'-CH$_3$), 0.95 (3H, d, J=6.4 Hz, 21'-CH$_3$), 0.98 (3H, s, 19'-CH$_3$), 2.00 (3H, s, Ac), 2.69 (3H, s, —NHCH$_3$), 2.79 (1H, dd, J=4.4 Hz, 12.5 Hz, H-3$_{eq}$), 3.33 (3H, s, OCH$_3$), 4.06 (1H, m, H-3').

Synthetic Example AA10: Synthesis of 3β-azido-5β-cholanic Acid Dimethylamide [compound of the formula (43AA) wherein Z is —CH(CH$_3$)CH$_2$CH$_2$-group, and R$^{25}$ and R$^{26}$ are methyl groups]

The compound obtained in Synthetic Example AA7 (600 mg 1.49 mmol) was dissolved in tetrahydrofuran (6 ml), cooled to −10° C., and the solution was added with triethylamine (0.208 ml, 1.49 mmol) and isobutyl chlorocarbonate (0.194 ml, 1.49 mmol). The mixture was stirred for one hour, and then added with dimethylamine hydrochloride (182 mg, 2.24 mmol) and triethylamine (0.132 ml, 2.24 mmol) suspended in tetrahydrofuran (6 ml) and methylene chloride (1.5 ml), and the resulting mixture was stirred for two hours. After water (20 ml) was added to the mixture, pH of the mixture was adjusted to around 1 with 1N aqueous hydrochloric acid, and the mixture was extracted with methylene chloride (80 ml). The extract was washed with saturated aqueous sodium hydrogencarbonate, and saturated brine successively and dried over anhydrous sodium sulfate, and then the solvent was evaporated. The resulting solid was washed by suspending it in hexane for purification to obtain the title compound (432 mg, yield; 67%).

IR (KBr, cm$^{-1}$): 3437, 2932, 2859, 2105, 1651. $^1$H-NMR (CDCl$_3$, ppm): 0.65 (3H, s, 18-CH$_3$), 0.93 (3H, d, J=6.6 Hz, 21-CH$_3$), 0.94 (3H, s, 19-CH$_3$), 2.15–2.45 (2H, m, H-23), 2.94, 3.01 (6H, sx2, —N(CH$_3$)$_2$), 3.95 (1H, m, H-3).

Synthetic Example AA11: Synthesis of 3β-amino-5β-cholanic Acid Dimethylamide [compound of the formula (3'AA) wherein Z is —CH(CH$_3$)CH$_2$CH$_2$-group, and R$^{25}$ and R$^{26}$ are methyl groups]

By using the compound obtained in Synthetic Example AA10 (400 mg, 0.933 mmol), the title compound was obtained in the same manner as in Synthetic Example AA9 (277 mg, yield; 74%).

IR (KBr, cm$^{-1}$): 3439, 2934, 2863, 1632. $^1$H-NMR (CDCl$_3$, ppm): 0.65 (3H, s, 18-CH$_3$), 0.93 (3H, d, J=6.5 Hz, 21-CH$_3$), 0.95 (3H, s, 19-CH$_3$), 2.15–2.45 (2H, m, H-23), 2.94, 3.01 (6H, sx2, —N(CH$_3$)$_2$), 3.23 (1H, m, H-3).

Example AA17: Synthesis of 3β-[N-(5-acetamido-4,7,8,9-tetra-O-acetyl-3,5-dideoxy-2-O-methyl-α-D-glycero-D-galacto-2-nonulopyranosonyl)amino]-5β-cholanic Acid Dimethylamide (β-isomer of Compound No. 74 in Table 1AA)

By using 5-acetamido-4,7,8,9-tetra-O-acetyl-3,5-dideoxy-2-O-methyl-α-D-glycero-D-galacto-2-nonulopyranosonic acid (250 mg, 0.509 mmol) and the compound obtained in Synthetic Example AA11 (205 mg, 0.509 mmol), the title compound was obtained in the same manner as in Synthetic Example AA8 (319 mg, yield; 72%).

IR (KBr, cm$^{-1}$): 3434, 2940, 2866, 1748, 1684, 1223. $^1$H-NMR (CDCl$_3$, ppm): 0.65 (3H, s, 18'-CH$_3$), 0.93 (3H, d, J=6.3 Hz, 21'-CH$_3$), 0.96 (3H, s, 19'-CH$_3$), 1.89, 2.02, 2.04, 2.07, 2.14 (15H, sx5, Ac), 2.94, 3.01 (6H, d, J=4.8 Hz, —N(CH$_3$)$_2$), 3.41 (3H, s, OCH$_3$), 4.00–4.12 (2H, m, H-3', 9,), 4.14 (1H, q, J=10.5 Hz, H-5), 4.36 (1H, d, J=12.3 Hz, H-9), 4.49 (1H, d, J=10.5 Hz, H-6), 5.27–5.36 (3H, m, H-7,8, AcNH), 5.41 (1H, m, H-4), 6.81 (1H, d, J=7.5 Hz, NH).

Example AA18: Synthesis of 3β-[N-(5-acetamido-3,5-dideoxy-2-O-methyl-α-D-glycero-D-galacto-2-nonulopyranosonyl)amino]-5β-cholanic Acid Dimethylamide (β-isomer of Compound No. 75 in Table 1AA)

By using the compound obtained in Example AA17 (286 mg, 0.326 mmol), the title compound was obtained in the same manner as in Example AA2 (182 mg, yield; 79%).

Melting point: 129–131° C. (decomposition)

IR (KBr, cm$^{-1}$): 3397, 2938, 2866, 1636. $^1$H-NMR (CD$_3$OD, ppm): 0.70 (3H, s, 18'-CH$_3$), 0.97(3H, d, J=5.8 Hz, 21'-CH$_3$), 0.98(3H, s, 19'-CH$_3$), 2.00 (3H, s, Ac), 2.79 (1H, dd, J=4.5 Hz, 12.5 Hz, H-3$_{eq}$), 2.91 3.06 (6H, sx2, —N(CH$_3$)$_2$), 3.33 (3H, s, OCH$_3$), 4.07(1H, m, H-3').

Synthetic Example AA12: 3β-azido-5β-cholanic Acid Amide [compound of the formula (43AA) wherein Z is —CH(CH$_3$)CH$_2$CH$_2$-group, and R$^{25}$ and R$^{26}$ are hydrogen atoms]

By using the compound obtained in Synthetic Example AA7 (600 mg, 1.49 mmol) and aqueous ammonia (28%, 184 mg, 2.99 mmol), the title compound was obtained in the same manner as in Synthetic Example AA8 (565 mg, yield; 94%).

IR (KBr, cm$^{-1}$): 3409, 2936, 2865, 2103, 1655. $^1$H-NMR (CDCl$_3$, ppm): 0.65 (3H, s, 18-CH$_3$), 0.93 (3H, d, J=6.3 Hz, 21-CH$_3$), 0.95 (3H, s, 19-CH$_3$), 2.05–2.35 (2H, m, H-23), 3, 95 (1H, m, H-3), 5.44, 5.55 (2H, mx2, NH$_2$).

Synthetic Example AA13: 3β-amino-5β-cholanic Acid Amide [compound of the formula (3'AA) wherein Z is —CH(CH$_3$)CH$_2$CH$_2$-group, and R$^{25}$ and R$^{26}$ are hydrogen atoms]

By using the compound obtained in Synthetic Example AA12 (400 mg, 0.998 mmol), the title compound was obtained in the same manner as in Synthetic Example AA9 (230 mg, yield; 62%).

IR (KBr, cm$^{-1}$): 3407, 2932, 2863, 1665. $^1$H-NMR (CDCl$_3$, ppm): 0.65 (3H, s, 18-CH$_3$), 0.93 (3H, d, J=6.4 Hz, 21-CH$_3$), 0.95 (3H, s, 19-CH3), 2.08–2.35 (2H, m, H-23), 3.23 (1H, m, H-3), 5.44 (2H, m, —CONH$_2$).

Example AA19: Synthesis of 3β-[N-(5-acetamido-4,7,8,9-tetra-O-acetyl-3,5-dideoxy-2-O-methyl-α-D-glycero-D-galacto-2-nonulopyranosonyl)amino]-5β-cholanic acid amide (β-isomer of Compound No. 70 in Table 1AA)

By using 5-acetamido-4,7,8,9-tetra-O-acetyl-3,5-dideoxy-2-O-methyl-α-D-glycero-D-galacto-2-nonulopyranosonic acid (250 mg, 0.509 mmol) and the compound obtained in Synthetic Example AA13 (190 mg, 0.509 mmol), the title compound was obtained in the same manner as in Synthetic Example AA8 (240 mg, yield; 56%).

IR (KBr, cm$^{-1}$): 3434, 2940, 2866, 1748, 1671. $^1$H-NMR (CD$_3$OD, ppm): 0.65 (3H, s, 18'-CH3), 0.93 (3H, d, J=6.3 Hz, 21'-CH$_3$), 0.97(3H, s, 19'-CH$_3$), 1.89, 2.02, 2.04, 2.07, 2.14 (15H, sx5, Ac), 3.41 (3H, s, OCH$_3$), 4.01–4.15 (2H, m, H-3',9,), 4.14 (1H, q, J=10.5 Hz, H-5), 4.37 (1H, d, J=11.8 Hz, H-9), 4.48(1H, d, J=10.5 Hz, H-6), 5.28–5.45 (6H, m, H-4, 7, 8, AcN$\underline{H}$, CONH$_2$), 6.82 (1H, d, J=7.8 Hz, NH).

Example AA20: Synthesis of 3β-[N-(5-acetamido-3,5-dideoxy-2-O-methyl-α-D-glycero-D-galacto-2-nonulopyranosonyl)aminol-58-cholanic acid amide (β-isomer of Compound No. 71 in Table 1AA)

By using the compound obtained in Example AA19 (203 mg, 0.239 mmol), the title compound was obtained in the same manner as in Example AA2 (125 mg, yield; 77%).

Melting point: 272–274° C. (decomposition) IR (KBr, cm$^{-1}$): 3418, 2936, 2865, 1659, 1526. $^1$H-NMR (CD$_3$OD, ppm): 0.69 (3H, s, 18'-CH$_3$), 0.97 (3H, d, J=8.1 Hz, 21'-CH$_3$), 0.98 (3H, s, 19'-CH$_3$), 2.00 (3H, s, Ac), 2.79 (1H, dd, J=4.4 Hz, 12.7 Hz, H-3$_{eq}$), 3.33 (3H, s, OCH$_3$), 4.07(1H, m, H-3').

Synthetic Example AA14: Synthesis of 5-acetamido-4,7,8,9-tetra-O-acetyl-3,5-dideoxy-2-O-methyl-β-D-glycero-D-galacto-2-nonulopyranosonic Acid [compound of the formula (9AA) Wherein R$^{4'}$ is acetyl group, and R$^3$ is methyl group]

5-Acetamido-3,5-dideoxy-2-O-methyl-β-D-glycero-D-galacto-2-nonulopyranosonic acid methyl ester (1.00 g, 2.96 mol) was dissolved in methanol (10 ml), and the solution was added with 1N aqueous sodium hydroxide (3 ml), and then the mixture was stirred for 4.5 hours. The reaction mixture was acidified (pH 2~3) by adding Dowex (50WX8, H$^+$) resin, and then the solvent was evaporated. The residue was dissolved in pyridine (5 ml), and the solution was added with acetic anhydride (1.68 ml, 17.8 mmol) with ice cooling and stirred for one hour, and then further stirred for two days at room temperature. Water (20 ml) was added to the reaction mixture, and the mixture was washed with methylene chloride (20 ml). The washing liquid (methylene chloride solution) was extracted with water (20 ml), and the combined aqueous layer was concentrated to about 20 ml under reduced pressure. The concentrate was acidified (pH ~1) by adding 1N aqueous hydrochloric acid and saturated by adding sodium chloride, and the the mixture was extracted with methylene chloride (150 ml). The extract was dried over anhydrous sodium sulfate, and the solvent was evaporated. The residue was purified by silica gel column chromatography (Merck silica gel 60, developing solvent; methylene chloride/methanol) to obtain the title compound (730 mg, yield; 50%).

IR (KBr, cm$^{-1}$): 3370, 3080, 2980, 2630, 1750, 1660. $^1$H-NMR (CD3OD, ppm): 1.82 (1H, dd, J=11.8 Hz, 12.8 Hz, H-3ax), 1,89, 2.01, 2.04, 2.08, 2.15 (15H, sx5, Ac), 2.46 (1H, dd, J=5,0 Hz, 12.9 Hz, H-3$_{eq}$), 3.33 (3H, s, OCH$_3$), 3.96–4.10 (2H, m, H-5, 6), 4.19 (1H, dd, J=6.7 Hz, 12.5 Hz, H-9), 4.73 (1H, dd, J=2.5 Hz, 12.4 Hz, H-9), 5.23 (1H, m, H-4), 5.35 (1H, m, H-8), 5.45 (1H, m, H-7).

Synthetic Example AA15: Synthesis of 3β-amino-24-hydroxy-5β-cholane [compound of the formula (3"AA) wherein Z is —CH(CH$_3$)CH$_2$CH$_2$-group]

Lithium aluminum hydride (365 mg, 9.62 mmol) was suspended in tetrahydrofuran (40 ml), and the suspension was added with a solution of methyl 3β-azido-5β-cholanate (2.00 g, 4.81 mmol) in tetrahydrofuran (20 ml) over 50 minutes under reflux by heating, and then the mixture was further refluxed by heating for 1.5 hours. After the reaction was completed, excess lithium aluminum hydride was quenched by adding saturated aqueous sodium sulfate to the mixture with ice cooling, and the organic layer was separated. Diethyl ether was added to the reaction mixture, and the mixture was stirred. The resulting organic layers were combined and concentrated. The resulting solid was suspended and washed in methanol (15 ml) to obtain the title compound (1.54 g, yield; 88%).

IR (KBr, cm$^{-1}$): 3358, 3277, 2934, 2863, 1451, 1375. $^1$H-NMR (CDCl$_3$, ppm): 0.65 (3H, s, 18-CH$_3$), 0.92 (6H, d, J=6.5 Hz, 21-CH$_3$), 0.95 (3H, s, 19-CH$_3$), 3.23 (1H, m, H-3), 3.60 (2H, t, J=5.5 Hz, H-24).

Example AA21: Synthesis of 3β-[N-(5-acetamido-4,7,8,9-tetra-O-acetyl-3,5-dideoxy-2-O-methyl-β-D-glycero-D-galacto-2-nonulopyranosonyl)amino]-24-hydroxy-5β-cholane (β-isomer of Compound No. 108 in Table 1AA)

By using the compounds obtained in Synthetic Example AA14 (300 mg, 0.610 mmol) and Synthetic Example AA15 (242 mg, 0.671 mmol), the title compound was obtained in the same manner as in Synthetic Example AA8 (406 mg, yield; 80%).

IR (KBr, cm$^{-1}$): 3432, 2940, 2866, 1750, 1686, 1225. $^1$H-NMR (CDCl$_3$, ppm): 0.66 (3H, s, 18'-CH$_3$), 0.93 (3H, d, J=6.4 Hz, 21'-CH$_3$), 0.99 (3H, s, 19'-CH$_3$), 1.89, 2.02, 2.03, 2.09, 2.17 (15H, sx5, Ac), 2.54 (1H, dd, J=4.9 Hz, 13.3 Hz, 3$_{eq}$) 3.19 (3H, s, OCH$_3$), 3.62 (2H, m, H-24'), 3.94 (1H, dd, J=1.7 Hz, 10.6 Hz, H-6), 4.00–4.09 (2H, m, H-5, 9), 4.20 (1H, m, H-3'), 4.44 (1H, dd, J=2.7 Hz, 12.3 Hz, H-9), 5.20–5.41 (4H, m, H-4, 7, 8, AcN$\underline{H}$), 7.07(1H, d, J=8.1 Hz, NH).

Example AA22: Synthesis of 3β-[N-(5-acetamido-3,5-dideoxy-2-O-methyl-β-D-glycero-D-galacto-2-nonulopyranosonyl)amino]-24-hydroxy-5β-cholane (β-isomer of Compound No. 109 in Table 1AA)

By using the compound obtained in Example AA21 (360 mg, 0.431 mmol), the title compound was obtained in the same manner as in Example AA2 (109 mg, yield; 38%).

Melting point: 300° C. or more IR (KBr, cm$^{-1}$): 3407, 2938, 2865, 1674, 1532, 1037. $^1$H-NMR (CD$_3$OD, ppm): 0.69 (3H, s, 18'-CH$_3$), 0.95 (3H, d, J=6.4 Hz, 21'-CH$_3$), 1.00 (3H, s, 19'-CH$_3$), 2.02 (3H, s, Ac), 2.38(1H, dd, J=4.9 Hz, 12.9 Hz, H-3$_{eq}$), 3.20 (3H, s, OCH$_3$), 3.50 (2H, t, J=6.3 Hz, H-24').

Synthetic Example BB1: Synthesis of 3α-N-(3-N-tert-butyloxycarbonylamino-propionyl) aminocholestane 3-tert-Butyloxycarbonylaminopropionic acid (378 mg, 2.04 mmol) was dissolved in tetrahydrofuran (20 ml), cooled to −10° C., and the solution was added with triethylamine (0.314 ml, 2.25 mmol) and isobutyl chlorocarbonate (0.292 ml, 2.25 mmol). The mixture was stirred for 20 minutes, and then added with 3α-aminocholestane (874 mg, 2.25 mmol). Temperature of the reaction mixture was raised to room temperature over three hours, and the mixture was further stirred for 16 hours. The deposited triethylamine hydrochloride was removed by filtration and the solvent was evaporated, and then the residue was dissolved in ethyl acetate (50 ml). The solution was washed with 0.1N aqueous hydrochloric acid, saturated aqueous sodium hydrogen carbonate, and saturated brine successively and dried over anhydrous sodium sulfate, and then the solvent was evaporated. The resulting syrup was purified by silica gel column chromatography (Merck silica gel 60, developing solvent; hexane/ethyl acetate) to obtain the title compound (1.11 g, yield; 97%).

IR (KBr, cm$^{-1}$): 3312, 2932, 1695, 1633. $^1$H-NMR (CDCl$_3$, ppm): 0.65 (3H, s, 18-CH$_3$), 0.80 (3H, s, 19-CH$_3$), 0.85–0.91 (9H, 21-CH$_3$, 26-CH$_3$, 27-CH$_3$), 1.44 (9 H, s, tert-Bu), 2.40 (2H, t, J=6.1 Hz, BocNHCH$_2$CH$_2$CO—), 3.40 (2H, t, J=6.1 Hz, BocNHCH$_2$CH$_2$CO—), 4.12 (1H, m, H-3), 5.20 (1H, m, BocNH—), 5.95 (1H, d, J=8.0 Hz, CONH—).

Synthetic Example BB2: Synthesis of 3α-N-(3-aminopropionyl)aminocholestane

The compound obtained in Synthetic Example BB 1 (1.024 g, 1.83 mmol) was dissolved in ethyl acetate (30 ml), and the solution was added with a solution of hydrochloric acid (4N) in ethyl acetate with ice cooling. Temperature of the mixture was raised to room temperature, and then the mixture was stirred for one hour. The resulting precipitates were collected by filtration and dried, and then suspended in chloroform (50 ml). Saturated aqueous sodium hydrogencarbonate (20 ml) was added to the mixture, and then the mixture was stirred for one hour. The chloroform layer was dried over anhydrous sodium sulfate, and the solvent was evaporated to obtain the title compound (665 mg, yield; 79%).

IR (KBr, cm$^{-1}$): 3295, 2932, 2868, 1638, 1545. $^1$H-NMR (CDCl$_3$, ppm): 0.65 (3H, s, 18-CH$_3$), 0.80 (3H, s, 19-CH$_3$), 0.85–0.91 (9H, 21-CH$_3$, 26-CH$_3$, 27-CH$_3$), 2.32 (2H, t, J=5.9 Hz, NH$_2$CH$_2$CH$_2$CO—), 3.02 (2H, t, J=5.9 Hz, NH$_2$CH$_2$CH$_2$CO—), 4.14 (1H, m, H-3), 7.47 (1H, d, J=6.5 Hz, —CONH—).

Example BB1: Synthesis of 3α-[N-[3-[N-(5-acetamido-4,7,8,9-tetra-O-acetyl-3,5-dideoxy-2-O-methyl-α-D-glycero-D -galacto-2-nonulopyranosonyl)amino]propionyl]-amino] cholestane (α-isomer of Compound No. 21 in Table 1BB)

5-Acetamido-4,7,8,9-tetra-O-acetyl-3,5-dideoxy-2-O-methyl-α-D-glycero-D-galacto-2-nonulopyranosonic acid (300 mg, 0.618 mmol) was dissolved in tetrahydrofuran (20 ml), and the solution was cooled to −10° C. The solution was added with triethylamine (0.094 ml, 0.67 mmol) and isobutyl chlorocarbonate (0.087 ml, 0.67 mmol) and stirred for one hour, and then the mixture was added with the compound obtained in Synthetic Example BB 2 (308 mg, 0.67 mmol). Temperature of the reaction mixture was raised to room temperature over three hours, and the mixture was further stirred for 20 hours. The deposited triethylamine hydrochloride was removed by filtration, and then the solvent was evaporated and the residue was dissolved in ethyl acetate (50 ml). The solution was washed with 0.1N aqueous hydrochloric acid, saturated aqueous sodium hydrogencarbonate, and saturated brine successively and dried over anhydrous magnesium sulfate, and then the solvent was evaporated. The resulting syrup was purified by silica gel column chromatography [Merck silica gel 60, developing solvent; chloroform/methanol (100:1)] to obtain the title compound (460 mg, yield; 80%).

IR (KBr, cm$^{-1}$): 3389, 2938, 2868, 1750, 1670. $^1$H-NMR (CDCl$_3$, ppm): 0.65 (3H, s, 18'-CH$_3$), 0.80 (3H, s, 19'-CH$_3$), 0.85–0.91 (1H, dd, CH$_3$, 26'-CH$_3$, 27'-CH$_3$), 1.88, 2.02, 2.05, 2.11, 2.13 (15H, s×5, Ac), 2.27 (1H, dd, J=5.4 Hz, 13.1 Hz, H-3$_{eq}$), 2.41 (2H, t, J=6.1 Hz, —NHCH$_2$CH$_2$CO—), 3.37 (3H, s, —OCH$_3$), 3.54 (2H, t, J=6.1 Hz, —NHCH$_2$CH$_2$CO—), 4.01–4.19 (3H, m, H-5, H-9, H-3'), 4.37–4.46 (2H, m, H-6, H-9), 5.27–5.37 (3H, m, H-4, H-7, H-8), 6.24 (1H, d, J=7.6 Hz, —NHCH$_2$CH$_2$CONH—).

Example BB2: Synthesis of 3α-[N-[3-[N-(5-acetamido-3,5-dideoxy-2-O-methyl-α-D-glycero-D-galacto-2-nonulopyranosonyl)amino]propionyl] amino]cholestane (α-isomer of Compound No. 22 of Table 1BB)

The compound obtained in Example BB 1 (384 mg, 0.411 mmol) was dissolved in methanol (10 ml), and the solution was added with 4.9N solution of sodium methoxide (0.49 mmol) in methanol (0.1 ml). The mixture was warmed up to room temperature and then stirred for five hours. The reaction mixture was neutralized by adding Dowex (50WX8, H$^+$) resin and filtered, and the filtrate was purified by column chromatography (ODS MCIGEL, developing solvent; water/methanol) to obtain the title compound (74 mg, yield; 24%).

Melting point: 156–164° C. (decomposition) IR (KBr, cm$^{-1}$): 3323, 2934, 2868, 1655, 1545. $^1$H-NMR (CD$_3$OD, ppm): 0.74 (3H, s, 18'-CH$_3$), 0.88 (3H, s, 19'-CH$_3$), 0.91–1.01 (9H, 21'-CH$_3$, 26'-CH$_3$, 27'-CH$_3$), 2.05 (3H, s, Ac), 2.53 (2H, ddd, J=6.6 Hz, 6.6 Hz, 1.9 Hz, —NHCH$_2$CH$_2$CO—), 2.82 (1H, dd, J=4.5 Hz, 12.9 Hz, H-3$_{eq}$), 3.34 (3H, s, —OCH$_3$), 4.01 (1H, m, H-3').

Synthetic Example BB3: Synthesis of 3α-N-(N-tert-butyloxycarbonyl-L-phenylalanyl)-aminocholestane By using tert-butyloxycarbonyl-L-phenylalanine (530 mg, 2.00 mmol) and 3α-aminocholestane (855 mg, 2.20 mmol), the title compound was obtained in the same manner as in Synthetic Example BB1 (1.22 g, yield; 96%).

IR (KBr, cm$^{-1}$): 3428, 3326, 2934, 2868, 1690, 1653. $^1$H-NMR (CDCl$_3$, ppm): 0.63 (3H, s, 18-CH$_3$), 0.72 (3H, s, 19-CH$_3$), 0.85–0.97 (9H, 21-CH$_3$, 26-CH$_3$, 27-CH$_3$), 1.45 (9 H, s, tert-Bu), 2.98 (1H, dd, J=8.6 Hz, 13.6 Hz, —CH$_2$C$_6$H$_5$), 3.16 (1H, dd, J=5.8 Hz, 13.6 Hz, —CH$_2$C$_6$H$_5$), 4.00 (1H, m, H-3), 4.27 (1H, m, —NHCHCONH—), 5.22 (1H, m, BocNH—), 5.81 (1H, d, J=7.8 Hz, —NHCHCONH—), 7.20–7.34 (5H, m, —C$_6$H$_5$).

Synthetic Example BB4: Synthesis of 3α-L-phenylalanylaminocholestane hydrochloride The compound obtained in Synthetic Example BB3 (1.048 g, 1.648 mmol) was dissolved in ethyl acetate (10 ml), and the solution was added with a solution of hydrochloric acid (4N) in ethyl acetate (10 ml) with ice cooling. Temperature of the reaction mixture was raised to room temperature, and the mixture was stirred for one hour. The resulting precipitates were collected by filtration, and dried to obtain the title compound (829 mg, yield; 79%).

IR (KBr, cm$^{-1}$): 3412, 3254, 2934, 2866, 1672. $^{1}$H-NMR (CDCl$_3$, ppm): 0.72 (3H, s, 18-CH$_3$), 0.82 (3H, s, 19-CH$_3$), 0.92–1.00 (9 H, 21-CH$_3$, 26-CH$_3$, 27-CH$_3$), 3.12 (2H, m, —CH$_2$C$_6$H$_5$), 3.97 (1H, m, H-3), 4.24 (1H, t, —NHCHCONH—), 7.31–7.43 (5H, m, —C$_6$H$_5$).

Example BB3: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]-L-phenylalanylamino]-Cholestane (Compound No. 17 in Table 1BB wherein the configuration of Y' is L and the configuration at the 3-position of the Steroid is α)

5-Acetamido-4,7,8,9-tetra-O-acetyl-3,5-dideoxy-2-O-methyl-α-D-glycero-D-galacto-2-nonulopyranosonic acid (300 mg, 0.618 mmol) was dissolved in tetrahydrofuran (20 ml). The solution was cooled to −10° C. and added with triethylamine (0.094 ml, 0.67 mmol) and isobutyl chlorocarbonate (0.087 ml, 0.67 mmol), and then the mixture was stirred for one hour. Then, the compound obtained in Synthetic Example BB4 (427 mg, 0.671 mmol) and triethylamine (0.094 ml, 0.67 mmol) were added to the mixture, and the resulting mixture was warmed to room temperature over 2 hours, and stirring was continued for 20 hours. Ethyl acetate (50 ml) was added to the reaction mixture, and the mixture was washed with 0.1N hydrochloric acid, saturated aqueous sodium hydrogencarbonate, and saturated brine successively, and dried over anhydrous magnesium sulfate. After the solvent was evaporated, the residue was purified by silica gel column chromatography (Merck silica gel 60, developing solvent; chloroform/methanol) to obtain the title compound (570 mg, yield; 91%).

IR (KBr, cm$^{-1}$): 3383, 2936, 2868, 1748, 1670. $^{1}$H-NMR (CDCl$_3$, ppm): 0.64 (3H, s, 18'-CH$_3$), 0.72 (3H, s, 19'-CH$_3$), 0.85–0.93 (9H, 21'-CH$_3$, 26'-CH$_3$, 27'-CH$_3$), 1.88, 2.02, 2.06, 2.11, 2.14 (15H, s×5, Ac), 3.04 (1H, dd, J=9.0 Hz, 13.7 Hz, —CH$_2$C$_6$H$_5$), 3.25 (1H, dd, J=6.8 Hz, 13.7 Hz, —CH$_2$C$_6$H$_5$), 3.31 (3H, s, —OCH$_3$) , 3.97 (1H, dd, J=7.7 Hz, 12.2 Hz, H-9), 3.98 (1H, m, H-3), 4.09–4.18 (2H, m, H-5, H-6), 4.53 (1H, t, —NHCHCONH—), 4.62 (1H, dd, J=2.4 Hz, 12.2 Hz, H-9), 5.07 (1H, m, H-4), 5.24 (1H, d, J=5.6 Hz, H-7), 5.37 (1H, m, H-8), 5.53 (1H, m, AcNH—), 5.79 (1H, d, J=7.4 Hz, —NHCHCONH—), 7.21–7.36 (5H, m, —C$_6$H$_5$), 7.48 (1H, d, J=7.5 Hz, —NHCHCONH—).

Example BB 4: Synthesis of 3α-[N-[N-(5-acetamido-3,5-dideoxy-2-O-methyl-α-D-glycero-D-galacto-2-nonulopyranosonyl)]-L-phenylalanylamino]cholestane (Compound No. 18 in Table 1BB wherein the configuration of Y is L and the configuration at the 3-position of the steroid is α)

By using the compound obtained in Example BB3 (522 mg, 0.517 mg), the title compound was obtained in the same manner as in Example BB2 (244 mg, yield; 57%).

Melting point: 145–149° C. (decomposition) IR (KBr, cm$^{-1}$): 3409, 2934, 2866, 1653. $^{1}$H-NMR (CD$_3$OD, ppm): 0.73 (3H, s, 18'-CH$_3$), 0.85 (3H, s, 19'-CH$_3$), 0.91–0.97 (9H, 21-CH$_3$, 26'-Ch$_3$, 27'-CH$_3$), 2.07 (3H, s, Ac), 2.76 (1H, dd, J=4.6 Hz, 12.6 Hz, H-3$_{eq}$), 2.94 (3H, s, —OCH$_3$), 3.04 (2H, m, —CH$_2$C$_6$H$_5$), 3.54 (1H, m, H-4), 3.98 (1H, m, H-3'), 4.73 (1H, dd, J=7.0 Hz, 9.3 Hz, —NHCHCONH—), 7.21–7.44 (5H, m, —C$_6$H$_5$).

Synthetic Example BB5: Synthesis of 3α-N-(N-tert-butyloxycarbonyl-O-benzyl-L-tyrosyl)aminocholestane By using N-tert-butyloxycarbonyl-O-benzyl-L-tyrosine (500 mg, 2.03 mmol) and 3α-aminocholestane (866 mg, 2.23 mmol), the title compound was obtained in the same manner as in Synthetic Example BB1 (1.13 g, yield; 83.5%).

IR (KBr, cm$^{-1}$): 3425, 3329, 2932, 2866, 1653. $^{1}$H-NMR (CDCl$_3$, ppm): 0.61 (3H, s, 18-CH$_3$), 0.72 (3H, s, 19-CH$_3$), 0.85–0.88 (9H, 21-CH$_3$, 26-CH$_3$, 27-CH$_3$), 1.45 (9 H, s, t-Bu), 2.85 (1H, dd, J=8.8 Hz, 13.7 Hz, —CH$_2$—C$_6$H$_4$—O—), 3.11 (1H, dd, J=5.5 Hz, 13.7 Hz, —CH$_2$—C$_6$H$_4$—O—), 4.01 (1H, m, H-3), 4.21 (1H, m, Boc-NHCHCO—), 5.02 (2H, s, —O—CH$_2$—C$_6$H$_5$), 5.22 (1H, m, BocNHCHCONH), 5.81 (1H, d,J=7.9 Hz, BocNH—), 6.92 (2H, d, J=8.5 Hz,

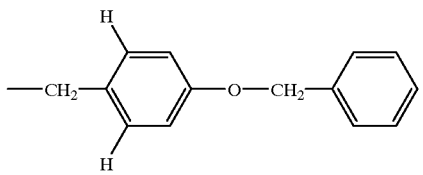

), 7.16 (2H, d, J=8.5 Hz,

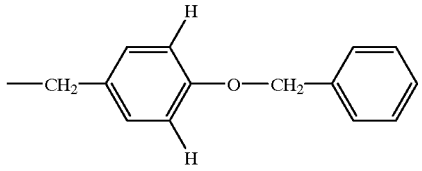

), 7.31–7.44 (5H, m, —O—CH$_2$C$_6$H$_5$).

Synthetic Example BB6: Synthesis of 3α-N-(O-benzyl-L-tyrosyl)aminocholestane Hydrochloride By using the compound obtained in Synthetic Example BB5 (1.04 g, 1.56 mmol), the title compound was obtained in the same manner as in Synthetic Example BB4 (837 mg, yield; 89%).

IR (KBr, cm$^{-1}$): 3424, 2932, 2864, 1653. $^{1}$H-NMR (CDCl$_3$, ppm): 0.58 (3H, s, 18-CH$_3$), 0.68 (3H, s, 19-CH$_3$), 0.79–0.85 (9H , 21-CH$_3$, 26-CH$_3$, 27-CH$_3$), 2.85 (1H, dd, J=8.6 Hz, 13.5 Hz, —CH$_2$—C$_6$H$_4$—O—), 3.00 (1H, dd, J=6.0 Hz, 13.5 Hz, —CH$_2$—C$_6$H$_4$—O—), 3.82 (1H, m, H-3), 4.08 (1H, m, NH$_2$CHCO—), 5.03 (2H, s, —O—CH$_2$—C$_6$H$_5$), 6.93 (2H, d, J=8.5 Hz,

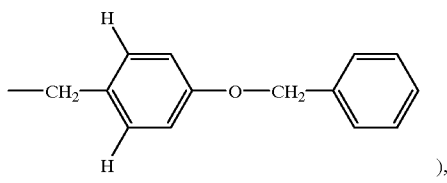

), 7.13 (2H, d, J=8.5 Hz,

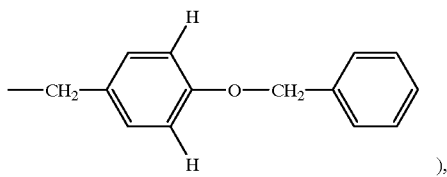

), 7.15–7.44 (5H, m, —O—CH$_2$—C$_6$H$_5$), 8.02 (1H, m, NH$_2$CHCONH), 8.31 (2H, s, —NH$_2$).

Example BB5: Synthesis of 3α-[N-[N-(5-acetamido-4,7,8,9-tetra-O-acetyl-3,5-dideoxy-2-O-methyl-α-Dglycero-Dgalacto-2nonulopyranosonyl)]-O-benzyl-L-tyrosylamino]-cholestane (Compound No. 25 in Table 1BB wherein the configuration of Y is L and the configuration at the 3-position of the steroid is α)

By using 5-acetamido-4,7,8,9-tetra-O-acetyl-3,5-dideoxy-2-O-methyl-α-D-glycero-D-galacto-2-nonulopyranosonic acid (500 mg, 1.02 mmol) and the compound obtained in Synthetic Example BB6 (675 mg, 1.12 mmol), the title compound was obtained in the same manner as in Example BB3 (1.103 g, quantitative).

IR (KBr, cm$^{-1}$): 3372, 2936, 2866, 1748, 1670. $^1$H-NMR (CDCl$_3$, ppm): 0.62 (3H, s, 18'-CH$_3$), 0.73 (3H, s, 19'-CH$_3$), 0.85–0.88 (9H, 21-CH$_3$, 26'-CH$_3$, 27—-CH$_3$), 1.81, 2.04, 2.06, 2.11, 2.13 (15H, s×5, Ac), 2.37 (1H, dd, J=5.1 Hz, 12.9 Hz, H-3$_{eq}$), 3.03 (1H, dd, J=8.7 Hz, 13.7 Hz, —CH$_2$—C$_6$H$_4$—O—), 3.23 (1H, dd, J=7.2 Hz, 13.7 Hz, —CH$_2$—C$_6$H$_4$—O—), 3.33 (3H, s, —OCH$_3$), 3.82 (1H, d, J=10.5 Hz, H-6), 3.95 (1H, dd, J=7.9 Hz, 12.4 Hz, H-9), 4.03 (1H, m, H-3'), 4.09 (1H, q, J=10.5 Hz, H-5), 4.45 (1H, q, J=8.0 Hz, —NHCHCO—), 4.65 (1H, dd, J=2.3 Hz, 12.4 Hz, H-9), 5.04 (2H, s, —O—CH$_2$—C$_6$H$_5$) ), 5.06 (1H, m, H-4), 5.21 (1H, m, H-7), 5.29–5.34 (2H, m, H-8, AcNH—), 5.95 (1H, d, J=7.6 Hz, —NHCHCONH—), 6.96 (2H, d, J=8.6 Hz,

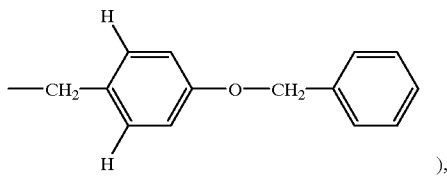

), 7.22 (2H, d, J=8.6 Hz,

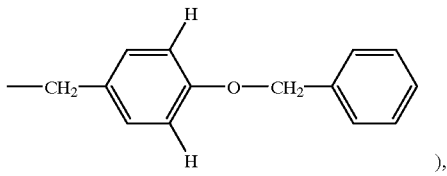

), 7.27–7.45 (5H, m, —O—CH$_2$—C$_6$H$_5$), 7.50 (1H, d, J=7.6 Hz, —CONHCHCO—).

Example BB6: Synthesis of 3α-[N-[N-(5-acetamido-3,5-dideoxy-2-O-methyl-α-D-glycero-D-galacto-2-nonulopyranosonyl)]-O-benzyl-L-tyrosylamino]cholestane (Compound No. 26 in Table 1BB wherein the configuration of Y is L and the configuration at the 3-position of the steroid is α)

The compound obtained in Example BB5 (307 mg, 0.299 mmol) was dissolved in methanol (10 ml), and the solution was added with 4.9N solution of sodium methoxide (0.49 mmol) in methanol (0.1 ml) with ice cooling, and the mixture was stirred for three hours. The reaction mixture was neutralized by adding Dowex (50WX8, H$^+$) resin, and filtered. The solvent of the filtrate was evaporated under reduced pressure, and then the residue was solidified by adding methanol to obtain the title compound (241 mg, yield; 94%).

Melting point: 220–223° C. (decomposition) IR (KBr, cm$^{-1}$): 3428, 2934, 2866, 1659, 1512. $^1$H-NMR (CD$_3$OD, ppm): 0.69 (3H, s, 18'-CH$_3$), 0.82 (3H, s, 19'-CH$_3$), 0.88–0.94 (9H, 21'-CH$_3$, 26'-CH$_3$, 27'-CH$_3$), 2.07 (3H, s, Ac), 2.77 (1H, dd, J=4.5 Hz, 12.5 Hz, H-3$_{eq}$), 3.00 (2H, m, —CH$_2$—C$_6$H$_4$—O—), 3.03 (3H, s, —OCH$_3$), 3.55 (1H, m, H-3'), 4.65 (1H, m, —NHCHCO—), 5.09 (2H, s, —O—CH$_2$—C$_6$H$_5$), 6.97 (2H, d, J=8.6 Hz,

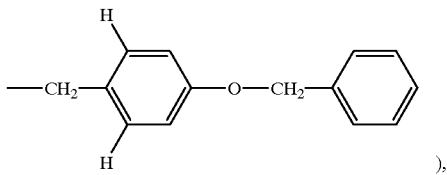

), 7.30 (2H, d, J=8.6 Hz,

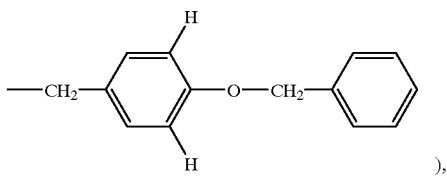

), 7.30–7.48 (5H, m, —O—CH$_2$—C$_6$H$_5$).

Example BB7: Synthesis of 3 α[N-[N-(5-acetamido-4,7,8,9-tetra-O-acetyl-3,5-dideoxy-2-O-methyl-α-D-glycero-D-galacto-2-nonulopyranosonyl)]-L-tyrosylamino]Choestane (Compound No. 27 in Table 1BB wherein the configuration of Y is L and the configuration at the 3-position of the steroid is α)

The compound obtained in Example BB5 (643 mg, 0.627 mmol) was dissolved in ethanol (12 ml), and the solution was added with 5% palladium carbon (60 mg), and the mixture was stirred for three hours under hydrogen flow. After the catalyst was filtered off, the solvent was evaporated, and the residue was purified by silica gel column chromatography (Merck silica gel 60, developing solvent; chloroform/methanol) to obtain the title compound (564 mg, yield; 95%).

IR (KBr, cm$^{-1}$): 3378, 2936, 2868, 1750, 1667. $^1$H-NMR (CDCl$_3$, ppm): 0.64 (3H, s, 18'-CH$_3$), 0.76 (3H, s, 19'-CH$_3$), 0.85–0.91 (9H, 21'-CH$_3$, 26'-CH$_3$, 27'-CH$_3$), 1.90, 2.03, 2.07, 2.10, 2.12 (15H, s×5, Ac), 2.37 (1H, dd, J=5.4 Hz, 13.1 Hz, H-3$_{eq}$), 3.23 (2H, m, —CH$_2$—C$_6$H$_4$—OH), 3.31 (3H, s, —OCH$_3$), 3.90 (1H, dd, J=8.2 Hz, 12.5 Hz, H-9), 4.00–4.13 (3H, m, H-3', H-5, H-9), 4.48 (1H, q, J=8.0 Hz, NHCHCO—), 4.61 (1H, d, J=12.5 HZ, H-9), 4.92 (1H, m, H-4), 5.18–5.20 (2H, m, H-7, H-8), 5.52 (1H, d, J=10.4 Hz, AcNH—), 6.41 (1H, s, —C$_6$H$_4$OH), 6.45 (1H, d, J=7.4Hz, —NHCHCONH—), 6.83 (2H, d, J=8.5 Hz,

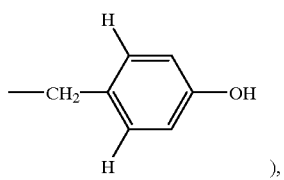

7.15 (2H, d, J=8.5 Hz,

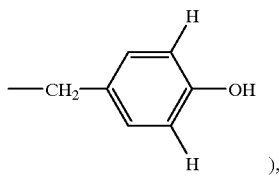

7.50 (1H, d, J=7.7 Hz, —CONHCHCO—).

Example BB8: Synthesis 3α-[N-[N-(5-acetamido-3,5-dideoxy-2-O-methyl-α-D-glycero-D-galacto-2-nonulopyranosonyl)]-L-tyrosylamino]cholestane (Compound No. 28 in Table 1BB wherein the configuration of Y is L and the configuration at the 3-position of the steroid is α)

By using the compound obtained in Example BB7 (255 mg, 0.252 mmol), the title compound was obtained in the same manner as in Example BB6 (159 mg, yield; 74%).

Melting point: 272–275° C. (decomposition) IR (KBr, cm$^{-1}$): 3420, 2934, 1651. $^1$H-NMR (CD$_3$OD, ppm): 0.73 (3H, s, 18'-CH$_3$), 0.84 (3H, s, 19'-CH$_3$), 0.91–0.99 (9H, 21'-CH$_3$, 26'-CH$_3$, 27'-CH$_3$), 2.07 (3H, s, Ac), 2.76 (1H, dd, J=4.7 Hz, 12.7 Hz, H-3$_{eq}$), 2.97 (2H, m, —CH$_2$—C$_6$H$_4$—OH), 3.02 (3H, s, —OCH$_3$), 3.54 (1H, m, H-4), 3.98 (1H, m, H-3'), 4.65 (1H, t, J=5.5 Hz, —NHCHCO—), 6.74 (2H, d, J=8.5 Hz,

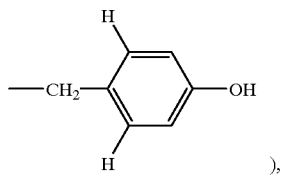

7.15 (2H, d, J=8.5 Hz,

Synthetic Example BB7: Synthesis of 3α-N-(N-tert-butyloxycarbonyl-O-benzyl-D-seryl) aminocholestane By using N-tert-butyloxycarbonyl-O-benzyl-D-serine (600 mg, 2.03 mmol) and 3α-aminocholestane (866 mg, 2.23 mmol), the title compound was obtained in the same manner as in Synthetic Example BB1 (1.13 g, yield; 83%).

IR (KBr, cm$^{-1}$): 3337, 2934, 2866, 1716, 1653. $^1$H-NMR (CDCl$_3$, ppm): 0.63 (3H, s, 18-CH$_3$), 0.77 (3H, s, 19-CH3), 0.85–0.90 (9H, 21-CH$_3$, 26-CH$_3$, 27-CH$_3$), 1.46 (9H, s, tert-Bu), 3.57 (1H, dd, J=7.4 Hz, 9.2 Hz, —CH$_2$OCH$_2$C$_6$H$_5$), 3.90 (1H, dd, J=4.0 Hz, 9.2 Hz, —CH$_2$OCH$_2$C$_6$H$_5$), 4.11 (1H, m, H-3), 4.23 (1H, m, —NHCHCO—), 4.54, 4.61 (2H, d×2, J=11.6 Hz, —OCH$_2$C$_6$H$_5$), 5.46 (1H, m, —NHCHCONH—), 7.28–7.38 (5H, m, —C$_6$H$_5$).

Synthetic Example BB8: Synthesis of 3α-N-(O-benzyl-D-seryl)aminocholestane Hydrochloride By using the compound obtained in Synthetic Example BB7 (1.04 g, 1.56 mmol), the title compound was obtained in the same manner as in Synthetic Example BB4 (837 mg, yield; 89%).

IR (KBr, cm$^{-1}$): 3264, 2934, 2866, 1670. $^1$H-NMR (CDCl$_3$, ppm): 0.61 (3H, s, 18-CH$_3$), 0.70 (3H, s, 19-CH$_3$), 0.85–0.90 (9H, 21-CH$_3$, 26-CH$_3$, 27-CH$_3$), 3.99 (1H, m, H-3), 4.08 (2H, d, J=4.7 Hz, —CH$_2$OCH$_2$C$_6$H$_5$), 4.55 (1H, m, —NHCHCO—), 4.59 (2H, s, —OCH$_2$C$_6$H$_5$), 7.24–7.32 (5H, m, —C$_6$H$_5$), 7.81 (1H, m, NH$_2$CHCONH—), 8.40 (2H, s, —NH$_2$).

Example BB9: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]-O-benzyl-D-serylamino]-cholestane (D-isomer for the steric configuration of Y and α-isomer for the steric configuration of the 3-position of steroid structure of Compound No. 11 in Table 1BB)

By using 5-acetamido-4,7,8,9-tetra-O-acetyl-3,5-dideoxy-2-O-methyl-α-D-glycero-D-galacto-2-nonulopyranosonic acid (500 mg, 1.02 mmol) and the compound obtained in Synthetic Example BB8 (675 mg, 1.02 mmol), the title compound was obtained in the same manner as in Example BB3 (1.10 g, quantitative).

IR (KBr, cm$^{-1}$): 3383, 2935, 2868, 1750, 1670. $^1$H-NMR (CDCl$_3$, ppm): 0.63 (3H, s, 18'-CH$_3$), 0.77 (3H, s, 19'-CH$_3$), 0.88–0.95 (9H, 21'-CH$_3$, 26'-CH$_3$, 27'-CH$_3$), 1.82, 1.99, 2.01, 2.05, 2.12 (15H, s×5, Ac), 2.43 (1H, dd, J=5.3 Hz, 12.8 Hz, H-3$_{eq}$), 3.42 (3H, s, —OCH$_3$), 3.82 (2H, d, J=7.2 Hz, —CH$_2$OCH$_2$C$_6$H$_5$), 3.90 (1H, dd, J=10.6 Hz, 12.3 Hz, H-9), 4.03–4.14 (3H, m, H-5, H-6, H-3'), 4.55, 4.61 (2H, d×2, J=11.7 Hz, —CH$_2$OCH$_2$C$_6$H$_5$), 4.65–4.76 (2H, m, H-9, —NHCHCO—), 4.90 (1H, m, AcNH—), 5.12 (1H, d, J=4.5

Hz, H-7), 5.18 (1H, m, H-4), 5.27 (1H, m, H-8), 6.80 (1H, m, —NHCHCONH—), 7.26–7.42 (5H, m, —C$_6$H$_5$), 7.65 (1H, d, J=8.3 Hz, —CONHCHCO—).

Example BB10: Synthesis of 3α-[N-[N-(5-acetamido-3,5-dideoxy-2-O-methyl-α-D-glycero-D-galacto-2-nonulopyranosonyl)]-O-benzyl-D-serylamino]cholestane (Compound No. 12 in Table 1BB wherein the configuration of Y is D and the configuration at the 3-position of the steroid is α)

The compound obtained in Example BB9 (307 mg, 0.299 mmol) was dissolved in methanol, and the solution was added with 4.9N solution of sodium methoxide (0.29 mmol) in methanol (0.06 ml) with ice cooling, and the mixture was stirred for three hours. The deposited solid was collected by filtration to obtain the title compound (241 mg, yield; 94%).

Melting point: 184–189° C. (decomposition) IR (KBr, cm$^{-1}$): 3410, 3265, 2934, 2866, 1672, 1653. $^1$H-NMR [CDCl$_3$-CD$_3$OD (1:1), ppm]: 0.66 (3H, s, 18'-CH$_3$), 0.80 (3H, s, 19'-CH$_3$), 0.86–0.91 (9H, 21'-CH$_3$, 26'-CH$_3$, 27'-CH$_3$), 2.01 (3H, s, Ac), 2.79 (1H, dd, J=4.6 Hz, 12.9 Hz, H-3$_{eq}$), 3.38 (3H, s, —OCH$_3$), 3.53 (2H, m, —CH$_2$OCH$_2$C$_6$H$_5$), 4.02 (3H, m, H-3'), 4.59 (2H, s, —CH$_2$OCH$_2$C$_6$H$_5$), 4.64 (1H, t, J=6.2 Hz, —NHCHCO—), 7.30–7.37 (5H, m, —C$_6$H$_5$). (5H, m, —C$_6$H$_5$).

Example BB11: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]-D-serylamino]-cholestane (Compound No. 1 in Table 1BB wherein the configuration of Y is D and the configuration at the 3-position of the steroid is α)

By using the compound obtained in Example BB9 (643 mg, 0.627 mmol), the title compound was obtained in the same manner as in Example BB7 (564 mg, yield; 95%).

IR (KBr, cm$^{-1}$): 3368, 2938, 2868, 1750, 1669. $^1$H-NMR (CD$_3$OD, ppm): 0.74 (3H, s, 18'-CH$_3$), 0.89–0.99 (12H, 19'-CH$_3$, 21'-CH$_3$, 26'-CH$_3$, 27'-CH$_3$), 1.88, 2.02, 2.06, 2.13, 2.15 (15H, s×5, Ac), 2.48 (1H, dd, J=6.0 Hz, 13.6 Hz, H-3$_{eq}$), 3.49 (3H, s, —OCH$_3$), 3.87 (2H, d, J=5.6 Hz, —CH$_2$OH), 4.07 (1H, m, H-3'), 4.08 (1H, dd, J=6.8 Hz, 12.3 Hz, H-9), 4.21 (1H, t, J=10.5 Hz, H-5), 4.3 (1H, dd, J=1.9 Hz, 10.5 Hz, H-6), 4.49 (1H, t, J=5.6 Hz, —NHCHCO—), 4.58 (1H, dd, J=2.3 Hz, 12.3 Hz, H-9), 5.21 (1H, m, H-4), 5.35 (1H, dd, J=1.9 Hz, 6.7 Hz, H-7), 5.44 (1H, m, H-8).

Example BB12: Synthesis of 3α-[N-[N-(5-acetamido-3,5-dideoxy-2-O-methyl-α-D-glycero-D-galacto-2-nonulopyranosonyl)]-D-serylamino]cholestane (Compound No. 4 in Table 1BB wherein the configuration of Y is D and the configuration at the 3-position of the steroid is α)

By using the compound obtained in Example BB11 (527 mg, 0.556 mmol), the title compound was obtained in the same manner as in Example BB10 (121 mg, yield; 28%).

Melting point: 161–164° C. (decomposition) IR (KBr, cm$^{-1}$): 3381, 2932, 1653. $^1$H-NMR [CD$_3$OD-CDCl$_3$ (1:1), ppm]: 0.68 (3H, s, 18'-CH$_3$), 0.83 (3H, s, 19'-CH$_3$), 0.86–0.93 (9H, 21'-CH$_3$, 26'-CH$_3$, 27'-CH$_3$), 2.04 (3H, s, Ac), 2.74 (1H, dd, J=4.3 Hz, 12.8 Hz, H-3$_{eq}$), 3.41 (3H, s, —OCH$_3$), 3.55 (2H, m, —CH$_2$OH), 4.03 (1H, m, H-3'), 4.48 (1H, t, J=5.8 Hz, —NHCHCO—).

Synthetic Example BB9: Synthesis of 3α-N-(N-tert-butyloxycarbonyl-O-benzyl-L-seryl)aminocholestane By using N-tert-butyloxycarbonyl-O-benzyl-L-serine (2.28 g, 7.72 mmol) and 3α-aminocholestane (3.00 g, 7.74 mmol), the title compound was obtained in the same manner as in Synthetic Example BB1 (4.64 g, yield; 90.4%).

Melting point: 55–67° C. $^1$H-NMR (CDCl$_3$, ppm): 0.61 (3H, s, 18-CH$_3$), 0.73–0.90 (12H, 19-CH$_3$, 21-CH$_3$, 26-CH$_3$, 27-CH$_3$), 1.44 (9H, s, tert-Bu), 3.54 (1H, dd, J=7.7 Hz, 9.2 Hz, —CH$_2$OCH$_2$C$_6$H$_5$), 3.89 (1H, dd, J=4.0 Hz, 9.2 Hz, —CH$_2$OCH$_2$C$_6$H$_5$), 4.09 (1H, m, H-3), 4.21 (1H, m, —NHCHCO—), 4.50, 4.58 (2H, dX2, J=11.6 Hz, —OCH$_2$C$_6$H$_5$), 5.40 (1H, m, —NHCHCONH—), 6.81 (1H, d, J=5.3 Hz, —NHCHCONH—), 7.28–7.38 (5H, m, —C$_6$H$_5$).

Synthetic Example BB10: Synthesis of 3α-N-(O-benzyl-L-seryl)aminocholestane Hydrochloride By using the compound obtained in Synthetic Example BB9 (4.39 g, 6.60 mmol), the title compound was obtained in the same manner as in Synthetic Example BB4 (3.64 g, yield; 91.7%).

Melting point: 220–228° C. $^1$H-NMR (CD$_3$OD, ppm): 0.74 (3H, s, 18-CH$_3$), 0.85–1.00 (12H, 19-CH$_3$, 21-CH$_3$, 26-CH$_3$, 27-CH$_3$), 3.78–3.86 (2H, m, —CH$_2$OCH$_2$C$_6$H$_5$), 4.06 (1H, m, H-3), 4.18 (1H, m, —NHCHCO—), 4.60, 4.70 (2H, d×2, —OCH$_2$C$_6$H$_5$), 7.33–7.42 (5H, m, —CH$_6$H$_5$).

Example BB13: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]-O-benzyl-L-serylamino]cholestane (Compound No. 11 in Table 1BB wherein the configuration of Y is L and the configuration at the 3-position of the steroid is α)

By using 5-acetamido-4,7,8,9-tetra-O-acetyl-3,5-dideoxy-2-O-methyl-α-D-glycero-D-galacto-2-nonulopyranosonic acid (774 mg, 1.57 mmol) and the compound obtained in Synthetic Example BB10 (950 mg, 1.58 mmol), the title compound was obtained in the same manner as in Example BB3 (1.22 g, yield; 74.4%). $^1$H-NMR (CDCl$_3$, ppm): 0.61 (3H, s, 18'-CH$_3$), 0.71–0.95 (12H, 19'-CH$_3$, 21'-CH$_3$, 26'-CH$_3$, 27'-CH$_3$), 1.85, 1.99, 1.99, 2.05, 2.12 (15H, sX5, Ac), 2.40 (1H, dd, J=5.0 Hz, 12.9 Hz, H-3$_{eq}$), 3.38 (3H, s, —OCH$_3$), 3.67 (1H, t, J=9.4 Hz, —CH$_2$OCH$_2$C$_6$H$_5$), 3.81 (1H, dd, J=4.5 Hz, 9.4 Hz, —CH$_2$OCH$_2$C$_6$H$_5$), 3.92–4.18 (3H, m, H-5, H-9, H-3'), 4.45 (1H, dd, J=2.0 Hz, 10.7 Hz, H-6), 4.51–4.66 (4H, m, H-9, —NHCHCO—, —CH$_2$OCH$_2$C$_6$H$_5$), 5.08 (1H, m, H-4), 6.93 (1H, d, J=7.8 Hz, —NH—), 7.28–7.36 (5H, m, —C$_6$H$_5$), 7.38 (1H, d, J=7.4 Hz, —NH—).

Example BB14: Synthesis of 3α-[N-[N-(5-acetamido-3,5-dideoxy-2-O-methyl-α-D-glycero-D-galacto-2-nonulopyranosonyl)]-O-benzyl-L-serylamino]cholestane (Compound No. 12 in Table 1BB wherein the configuration of Y is L and the configuration at the 3-position of the steroid is α)

By using the compound obtained in Example BB13 (447 mg, 0.43 mmol), the title compound was obtained in the same manner as in Example BB2 (100 mg, yield; 26.7%).

Melting point: 188–192° C. IR (KBr, cm$^{-1}$): 3420, 2930, 2870, 1660. $^1$H-NMR (CD$_3$OD, ppm): 0.73 (3H, s, 18'-CH$_3$), 0.85 (3H, s, 19'-CH$_3$), 0.91–1.01 (9H, 21'-Ch$_3$, 26'-CH$_3$, 27'-CH$_3$), 2.06 (3H, s, Ac), 2.80 (1H, dd, J=4.5 Hz, 12.6 Hz, H-3$_{eq}$), 3.36 (3H, s, —OCH$_3$), 4.03 (3H, m, H-3'), 4.62 (2H, s, —CH$_2$OCH$_2$C$_6$H$_5$), 4.73 (1H, t, J=6.6 Hz, —NHCHCO—), 7.31–7.40 (5H, m, —C$_6$H$_5$).

Example BB15: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]-L-serylamino]cholestane (Compound No. 1 in Table 1BB wherein the configuration of Y is L and the configuration at the 3-position of the steroid is α)

By using the compound obtained in Example BB13 (500 mg, 0.48 mmol), the title compound was obtained in the same manner as in Example BB7 (402 mg, yield; 88.0%).

¹H-NMR (CDCl₃, ppm): 0.62 (3H, s, 18'-CH₃), 0.77 (3H, s, 19'-CH₃), 0.82–0.89 (9H, 21'-CH₃, 26'-CH₃, 27'-CH₃), 1.85, 1.99, 2.02, 2.06, 2.13 (15H, s×5, Ac), 2.43 (1H, dd, J=5.3 Hz, 13.2 Hz, H-3$_{eq}$), 3.40 (3H, s, —OCH₃), 3.75–4.02 (3H, m, H-9, —CH₂OH), 4.05–4.22 (2H, m, H-5, H-3'), 4.30–4.39 (2H, m, H-6, —NHCH₂CO—), 4.65 (1H, dd, J=2.2 Hz, 12.2 Hz, H-9), 5.11 (1H, m, H-4), 5.91 (1H, d, J=10.1 Hz, —NH—), 6.83 (1H, d, J=7.5 Hz, —NH—), 7.53 (1H, d, J=7.1 Hz, —NH—).

Example BB16: Synthesis of 3α-[N-[N-(5-acetamido-3,5-dideoxy-2-O-methyl-α-D-glycero-D-galacto-2-nonulopyranosonyl)]-L-serylamino] cholestane (Compound No. 4 in Table 1BB wherein the configuration of Y is L and the configuration at the 3-position of the steroid is α)

By using the compound obtained in Example BB15 (370 mg, 0.39 mmol), the title compound was obtained in the same manner as in Example BB2 (66 mg, yield; 21.7%).

Melting point: ~196° C. IR (KBr, cm⁻¹): 3420, 2930, 2870, 1660. ¹H-NMR (CD3OD, ppm): 0.74 (3H, s, 18'-CH₃), 0.89–1.00 (12H, 19'-CH₃, 21'-CH₃, 26'-CH₃, 27'-CH₃), 2.06 (3H, s, Ac), 2.80 (1H, dd, J=4.5 Hz, 12.6 Hz, H-3$_{eq}$), 3.40 (3H, s, OCH₃), 4.05 (1H, m, H-3'), 4.53 (1H, t, J=6.6 Hz, —NHCHCO—).

Synthetic Example BB11: Synthesis of 3α-N-(N$^α$-tert-butyloxycarbonyl-N$^ε$-benzyloxycarbonyl-L-lysyl)aminocholestane By using N$^α$-tert-butyloxycarbonyl-N$^ε$-benzyloxycarbonyl-L-lysine (760 mg, 2.00 mmol) and 3α-aminocholestane (853 mg, 2.20 mmol), the title compound was obtained in the same manner as in Synthetic Example BB 1 (1.57 g, quantitative).

IR (KBr, cm⁻¹): 3325, 2934, 2866, 1705, 1657. ¹H-NMR (CDCl₃, ppm): 0.64 (3H, s, 18-CH₃), 0.79 (3H, s, 19-CH₃), 0.91–0.95 (9H, 21-CH₃, 26-CH₃, 27-CH₃), 1.45 (9H, s, tert-Bu), 3.20 (2H, q, J=6.4 Hz, —CH₂NHCOOCH₂C₆H₅), 3.97 (1H, m, BocNHCHCO—), 4.10 (1H, m, H-3), 4.89 (1H, m, —CH₂NHCOOCH₂C₆H₅), 5.10 (2H, s, —NHCOOCH₂C₆H₅), 5.15 (1H, m, —NHBoc), 6.55 (1H, d, J=8.0 Hz, BocNHCHCONH—), 7.26–7.40 (5H, m, —NHCOOCH₂C₆H₅).

Synthetic Example BB12: Synthesis of 3α-N-(N$^ε$-benzyloxycarbonyl-L-lysyl)aminocholestane Hydrochloride By using the compound obtained in Synthetic Example BB11 (829 mg, 1.11 mmol), the title compound was obtained in the same manner as in Synthetic Example BB4 (691 mg, yield; 96%).

IR (KBr, cm⁻¹): 3347, 2932, 2866, 1705, 1651. ¹H-NMR (CDCl₃, ppm): 0.64 (3H, s, 18-CH₃), 0.80 (3H, s, 19-CH₃), 0.85–0.91 (9H, 21-CH₃, 26-CH₃, 27-CH₃), 3.20 (2H, q, J=6.3 Hz, —CH₂NHCOOCH₂C₆H₅), 3.32 (1H, dd, J=4.1 Hz, 9.6 Hz, NH₂CHCO—), 4.09 (1H, m, H-3), 4.88 (1H, m, —CH₂NHCOOCH₂C₆H₅), 5.09 (2H, s, —NHCOOCH₂C₆H₅), 7.30–7.37 (5H, m, —NHCOOCH₂C₆H₅), 7.62 (1H, d, J=8.1 Hz, NH₂CHCONH—).

Example BB17: Synthesis of 3α-[N-[N -(5-acetamido-4,7,8,9-tetra-O-acetyl-3,5-dideoxy-2-O-methyl-α-D-glycero-D-galacto-2-nonulopyranosonyl)]-N$^ε$-benzyloxy-carbonyl-L-lysylamino]cholestane (Compound No. 15 in Table 1BB wherein the configuration of Y is L and the configuration at the 3-position of the steroid is α)

By using 5-acetamido-4,7,8,9-tetra-O-acetyl-3,5-dideoxy-2-O-methyl-α-D-glycero-D-galacto-2-nonulopyranosonic acid (364 mg, 0.742 mmol) and the compound obtained in Synthetic Example BB12 (531 mg, 0.817 mmol), the title compound was obtained in the same manner as in Example BB3 (490 mg, yield; 59%).

IR (KBr, cm⁻¹): 3350, 2930, 2868, 1748, 1669. ¹H-NMR (CD₃OD, ppm): 0.73 (3H, s, 18'-CH₃), 0.87–0.98 (12H, 19'-CH₃, 21'-CH₃, 26'-CH₃, 27'-CH₃), 1.86, 1.95, 2.03, 2.13, 2.14 (15H, s×5, Ac), 2.54 (1H, dd, J=5.3 Hz, 13.3 Hz, H-3$_{eq}$), 3.18 (2H, m, —CH₂NHCOOCH₂C₆H₅), 3.38 (3H, s, —OCH₃), 4.03 (1H, m, H-3'), 4.09 (1H, dd, J=6.5 Hz, 12.5 Hz, H-9), 4.18 (1H, t, J=10.0 Hz, H-5), 4.44 (1H, dd, J=2.5 Hz, 12.5 Hz, H-9), 4.50 (1H, m, —CONHCHCO—), 4.56 (1H, dd, J=1.9 Hz, 10.0 Hz, H-6), 5.00 (1H, ddd, J=5.4 Hz, 10.0 Hz, 10.0 Hz, H-4), 5.11 (2H, s, —CH₂C₆H₅), 5.34 (1H, dd, J=1.9 Hz, 7.9 Hz, H-7), 5.48 (1H, m, H-8), 7.30–7.45 (5H, m, —NHCOOCH₂C₆H₅).

Example BB18: Synthesis of 3α-[N-[N$^α$-(5-acetamido-3,5-dideoxy-2-O-methyl-α-D-glycero-D-galacto-2-nonulopyranosonyl)]-N-$^ε$ benzyloxycarbonyl-L-lysylamino]-cholestane (Compound No. 16 in Table 1BB wherein the configuration of Y is L and the configuration at the 3-position of the steroid is α)

By using the compound obtained in Example BB 17 (220 mg, 0.19 6 mmol), the title compound was obtained in the same manner as in Example BB6 (140 mg, yield; 75%).

Melting point: 124–127° C. (decomposition) IR (KBr, cm⁻¹): 3337, 2936, 2868, 1696, 1644. ¹H-NMR (CD₃OD, ppm): 0.73 (3H, s, 18'-CH₃), 0.88–0.98 (12H, 19'-CH₃, 21'-CH₃, 26'-CH₃, 27'-CH₃), 2.06 (3H, s, Ac), 2.80 (1H, dd, J=5.3 Hz, 13.3 Hz, H-3$_{eq}$), 3.18 (2H, m, CH₂NHCOOCH₂C₆H₅), 3.35 (3H, s, —OCH₃), 4.02 (1H, m, H-3'), 4.38 (1H, t, J=7.1 Hz, —CONHCHCO—), 5.11 (2H, s, —CH₂C₆H₅), 7.30–7.40 (5H, m, —NHCOOCH₂C₆H₅).

Example BB19: Synthesis of 3α-[N-[N$^α$-(5-acetamido-4,7,8,9-tetra-O-acetyl-3,5-dideoxy-2-O-methyl-α-D-glycero-D-galacto-2-nonulopyranosonyl)]-L-lysylamino]-cholestane (Compound No. 13 in Table 1BB wherein the configuration of Y is L and the configuration at the 3-position of the steroid is α)

By using the compound obtained in Example BB17 (268 mg, 0.238 mmol), the title compound was obtained in the same manner as in Example BB7 (90 mg, yield; 47%).

IR (KBr, cm⁻¹): 3400, 2936, 2868, 1750, 1657. ¹H-NMR (CD₃OD, ppm): 0.74 (3H, s, 18'-CH₃), 0.83–0.99 (12H, 19'-CH₃, 21'-CH₃, 26'-CH₃, 27'-CH₃), 1.89, 2.03, 2.05, 2.14, 2.15 (15H, s×5, Ac), 2.52 (1H, dd, J=5.4 Hz, 13.4 Hz, H-3$_{eq}$), 2.84 (2H, dd, —CH₂NH₂), 3.40 (3H, s, —OCH₃), 4.04 (1H, m, H-3'), 4.09 (1H, dd, J=6.7 Hz, 12.5 Hz, H-9), 4.15 (1H, t, J=10.5 Hz, H-5), 4.44 (1H, dd, J=2.6 Hz, 12.5 Hz, H-9), 4.51 (1H, m, —CONHCHCO—), 4.62 (1H, dd, J=1.8 Hz, 10.5 Hz, H-6), 5.00 (1H, m, H-4), 5.33 (1H, dd, J=1.8 Hz, 8.0 Hz, H-7), 5.47 (1H, m, H-8).

Example BB20: Synthesis of 3α-[N-[N$^α$-(5-acetamido-3,5dideoxy-2-O-methyl-α-D-glycero-D-galacto-2-nonulopyranosonyl) -L-lysylaminoicholestane Hydrochloride (Compound No. 14 in Table 1BB wherein the configuration of Y is L and the configuration at the 3-position of the steroid is α)

The compound obtained in Example BB 19 (75 mg, 0.091 mmol) was dissolved in methanol (1 ml), and the solution was added with 4.9N solution of sodium methoxide (0.098 mmol) in methanol (0.02 ml) with ice cooling, and then the mixture was warmed up to room temperature and stirring was continued for five hours. The reaction mixture was neutralized by adding Dowex (50WX8, H$^+$) resin and filtered. A solution of hydrochloric acid (4N, 0.05 ml, 0.2 mmol) in ethyl acetate was added to the filtrate, and the mixture was stirred for 1 hour. The residue was solidified with ethyl acetate to obtain the title compound (50 mg, yield; 65%).

Melting point: 177–185° C. (decomposition) IR (KBr, cm$^{-1}$): 3391, 2934, 2868, 1649, 1543. $^1$H-NMR (CD$_3$OD, ppm): 0.74 (3H, s, 18'-CH$_3$), 0.89–0.98 (12H, 19'-CH$_3$, 21'-CH$_3$, 26'-CH$_3$, 27'-CH$_3$), 2.07 (3H, s, Ac), 2.79 (1H, dd, J=4.7 Hz, 12.6 Hz, H-3$_{eq}$), 2.99 (2H, dd, CH$_2$NH$_2$), 3.38 (3H, s, —OCH$_3$), 4.04 (1H, m, H-3'), 4.40 (1H, m, —CONHCHCO—).

Synthetic Example BB13: Synthesis of 3α-N-(N-tert-butyloxycarbonyl-L-asparagyl)aminocholestane By using N-tert-butyloxycarbonyl-L-asparagine (464 mg, 2.00 mmol) and 3α-aminocholestane (777 mg, 2.00 mmol), the title compound was obtained in the same manner as in Synthetic Example BB1 (670 mg, yield; 56%).

IR (KBr, cm$^{-1}$): 3381, 2934, 2866, 1678. $^1$H-NMR (CDCl$_3$, ppm): 0.64 (3H, s, 18-CH$_3$), 0.79 (3H, s, 19-CH$_3$), 0.85–0.91 (9H, 21-CH$_3$, 26-CH$_3$, 27-CH$_3$), 1.48 (9H, s, tert-Bu), 2.53 (1H, dd, J=6.7 Hz, 15.2 Hz, —CH$_2$CONH$_2$), 2.88 (1H, dd, J=3.9 Hz, 15.2 Hz, —CH$_2$CONH$_2$), 4.06 (1H, m, H-3), 4.40 (1H, m, BocNHCHCONH—), 5.48 (1H, s, —CONH$_2$), 6.15–6.21 (2H, m, —CONH$_2$, BocNH—), 7.33 (1H, d, J=6.4 Hz, BocNHCHCONH—).

Synthetic Example BB14: Synthesis of 3α-L-asparagylaminocholestane Hydrochloride By using the compound obtained in Synthetic Example BB13 (633 mg, 1.05 mmol), the title compound was obtained in the same manner as in Synthetic Example BB4 (465 mg, yield; 82%).

IR (KBr, cm$^{-1}$): 3196, 3065, 2934, 2868, 1672, 1556. $^1$H-NMR (DMSO-d$_6$, ppm): 0.62 (3H, s, 18-CH$_3$), 0.74 (3H, s, 19-CH$_3$), 0.82–0.88 (9H, 21-CH$_3$, 26-CH$_3$, 27-CH$_3$), 2.63 (2H, m, —CH$_2$CONH$_2$), 3.92 (1H, m, H-3), 4.09 (1H, m, NH$_2$CHCONH—), 7.26, 7.75 (2H, s×2, —CONH$_2$), 8.16 (2H, d, J=3.0 Hz, NH$_2$CHCONH—), 8.37 (1H, d, J=7.3 Hz, NH$_2$CHCONH—).

Example BB21: Synthesis of 3α-[N-[N-(5-acetamido-4,7,8,9-tetra-O-acetyl-3,5-dideoxy-2-O-methyl-α-D-glycero-D-galacto-2nonulopyranosonyl)]-L-asparagylamino]cholestane (Compound No. 23 in Table 1BB wherein the configuration of Y is L and the configuration at the 3-position of the steroid is α)

By using 5-acetamido-4,7,8,9-tetra-O-acetyl-3,5-dideoxy-2-O-methyl-α-D-glycero-D-galacto-2-nonulopyranosonic acid (300 mg, 0.618 mmol) and the compound obtained in Synthetic Example BB14 (360 mg, 0.618 mmol), the title compound was obtained in the same manner as in Example BB3 (287 mg, yield; 48%).

IR (KBr, cm$^{-1}$): 3368, 2936, 2868, 1750, 1670. $^1$H-NMR (CDCl$_3$, ppm): 0.64 (3H, s, 18'-CH$_3$), 0.79 (3H, s, 19'-CH$_3$), 0.85–0.94 (9H, 21'-CH$_3$, 26'-CH$_3$, 27'-CH$_3$), 1.88, 2.01, 2.07, 2.09, 2.14 (15H, s×5, Ac), 2.45 (1H, dd, J=5.3 Hz, 13.1 Hz, H-3$_{eq}$), 2.73 (1H, dd, J=6.1 Hz, 15.5 Hz, —CH$_2$CONH$_2$), 2.85 (1H, dd, J=7.3 Hz, 15.5 Hz, —CH$_2$CONH$_2$), 3.41 (3H, s, —OCH$_3$), 3.97 (1H, dd, J=7.0 Hz, 12.5 Hz, H-9), 4.04 (1H, m, H-3'), 4.16 (1H, q, J=10.0 Hz, H-5), 4.40 (1H, d, J=10.0 Hz, H-6), 4.58 (1H, m, —NHCHCONH—), 4.71 (1H, d, J=12.5 Hz, H-9), 5.10 (1H, m, H-4), 5.30–5.35 (2H, m, H-7, H-8), 6.06, 6.59 (2H, s×2, —CONH$_2$) ), 6.20 (1H, d, J=10.0 Hz, AcNH—), 7.13 (1H, d, J=7.7 Hz, —NHCHCONH—), 7.87 (1H, d, J=7.1 Hz, —NHCHCONH—).

Example BB22: Synthesis of 3α-[N-[N-(5-acetamido-3,5-dideoxy-2-O-methyl-α-D-glycero-D-galacto-2-nonulopyranosonyl)]-L-asparagylamino] cholestane (Compound No. 24 in Table 1BB wherein the configuration of Y is L and the configuration at the 3-position of the steroid is α)

By using the compound obtained in Example BB21 (225 mg, 0.234 mmol), the title compound was obtained in the same manner as in Example BB6 (160 mg, yield; 86%).

Melting point: 172–174° C. (decomposition) IR (KBr, cm$^{-1}$): 3422, 2936, 2868, 1667, 1543. $^1$H-NMR (CD$_3$OD, ppm): 0.74 (3H, s, 18'-CH$_3$), 0.89–0.99 (12H, 19'-CH$_3$, 21'-CH$_3$, 26'-CH$_3$, 27'-CH$_3$), 2.07 (3H, s, Ac), 2.69 (2H, d, J=7.4 Hz, —CH$_2$CONH$_2$), 2.80 (1H, dd, J=4.5 Hz, 12.6 Hz, H-3$_{eq}$), 3.36 (3H, s, —OCH$_3$), 4.03 (1H, m, H-3'), 4.78 (1H, m, —NHCHCONH—).

Synthetic Example BB15: Synthesis of 3α-N-(N-tert-butyloxycarbonylglycyl)amino-cholestane By using tert-butyloxycarbonylglycine (522 mg, 2.98 mmol) and 3α-aminocholestane (1.16 g, 2.99 mmol), the title compound was obtained in the same manner as in Synthetic Example BB1 (1.65 g, quantitative).

$^1$H-NMR (CDCl$_3$, ppm): 0.62 (3H, s, 18-CH$_3$), 0.77 (3H, s, 19-CH$_3$), 0.82–0.89 (9H, 21-CH$_3$, 26-CH$_3$, 27-CH$_3$), 1.45 (9H, s, tert-Bu), 3.72 (2H, t, J=6.1 Hz, BocNHCH$_2$CO—), 4.09 (1H, m, H-3), 5.19 (1H, m, BocNH—), 6.54 (1H, m, —CONH—).

Synthetic Example BB 16: Synthesis of 3α-N-glycylaminocholestane Hydrochloride

By using the compound obtained in Synthetic Example BB15 (1.60 g, 2.94 mmol), the title compound was obtained in the same manner as in Synthetic Example BB4 with (1.20 g, yield; 85.1%).

$^1$H-NMR (DMSO-$_6$, ppm): 0.62 (3H, s, 18-CH$_3$), 0.75 (3H, s, 19-CH$_3$), 0.81–0.89 (9H, 21-CH$_3$, 26-CH$_3$, 27-CH$_3$), 3.54 (2H, m, NH$_2$CH$_2$CO—), 3.95 (1H, m, H-3), 8.32 (1H, d, J=7.4 Hz, —CONH—).

Example BB23: Synthesis of 3α-[N-[N-(5-acetamido-4,7,8,9-tetra-O-acetyl-3,5-dideoxy-2-O-methyl-α-D-glycero-D-galacto-2-nonulopyranosonyl)]glycylamino]cholestane (α-isomer of Compound No. 19 in Table 1BB)

By using 5-acetamido-4,7,8,9-tetra-O-acetyl-3,5-dideoxy-2-O-methyl-α-D-glycero-D-galacto-2-nonulopyranosonic acid (356 mg, 0.72 mmol) and the compound obtained in Synthetic Example BB16 (352 mg, 0.73 mmol), the title compound was obtained in the same manner as in Example BB3 (588 mg, yield; 88.4%).

$^1$H-NMR (CDCl$_3$, ppm): 0.62 (3H, s, 18'-CH$_3$), 0.77 (31H, s, 19'-CH$_3$), 0.82–0.89 (9H, 21'-CH$_3$, 26'-CH$_3$, 27'-CH$_3$), 1.85, 1.99, 2.01, 2.04, 2.13 (15H, s×5, Ac), 2.45 (1H, dd, J=5.4 Hz, 12.9 Hz, H-3$_{eq}$), 3.42 (3H, s, —OCH$_3$), 4.62

(1H, dd, J=1.9 Hz, 12.2 Hz, H-9), 5.20 (1H, m, H-4), 5.28–5.37 (2H, m, H-7, H-8), 5.81 (1H, m, —NH—), 6.25 (1H, m, —NH—), 7.54 (1H, t, J=5.8 Hz, —CONHCH$_2$CO—).

Example BB24: Synthesis of 3α-[N-[N-(5-acetamido-3,5-dideoxy-2-O-methyl-α-D-glycero-D-galacto-2-nonulopyranosonyl)]glycylamino]cholestane (α-isomer of Compound No. 20 in Table 1BB)

By using the compound obtained in Example BB23 (552 mg, 0.60 mmol), the title compound was obtained in the same manner as in Example BB2 (82 mg, yield; 18.2%).

Melting point: ~195° C. IR (KBr, cm$^{-1}$): 3410, 2930, 2870, 1660. $^1$H-NMR (CD$_3$OD, ppm): 0.74 (3H, s, 18'-CH$_3$), 0.83–0.99 (12H, 19'-CH$_3$, 21'-CH$_3$, 26'-CH$_3$, 27'-CH$_3$), 2.06 (3H, s, Ac), 2.80 (1H, dd, J=4.2 Hz, 13.0 Hz, H-3$_{eq}$), 3.41 (3H, s, —OCH$_3$).

Synthetic Example BB17: Synthesis of 3α-N-(4-N-benzyloxycarbonylaminobenzoyl)-aminocholestane By using 4-N-benzyloxycarbonylaminobenzoic acid (675 mg, 2.49 mmol) and 3α-aminocholestane (970 mg, 2.50 mmol), the title compound was obtained in the same manner as in Synthetic Example BB1 (699 mg, yield; 44.0%).

$^1$H-NMR (DMSO-$_6$, ppm): 0.62 (3H, s, 18-CH$_3$), 0.76 (3H, s, 19-CH$_3$), 0.81–0.89 (9H, 21-CH$_3$, 26-CH$_3$, 27-CH$_3$), 4.07 (1H, m, H-3), 5.16 (2H, s, —CH$_2$C$_6$H$_5$), 7.33–7.45 (5H, m, —C$_6$H$_5$), 10.00 (1H, s, —NHC$_6$H$_4$—).

Synthetic Example BB 18: Synthesis of 3α-N-(4-aminobenzoyl)aminocholestane Hydrochloride By using the compound obtained in Synthetic Example BB17 (855 mg, 1.33 mmol), the title compound was obtained in the same manner as in Synthetic Example BB4 (580 mg, yield; 80.0%).

$^1$H-NMR (CD$_3$OD, ppm): 0.75 (3H, s, 18-CH$_3$), 0.81–0.89 (12H, 19-CH$_3$, 21-CH3, 26-CH$_3$, 27-CH$_3$), 4.22 (1H, m, H-3), 7.52 (2H, d, J=8.6 Hz,

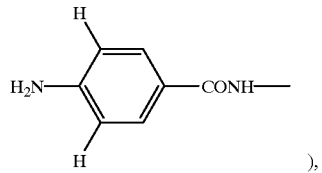

), 7.98 (2H, d, J=8.6 Hz,

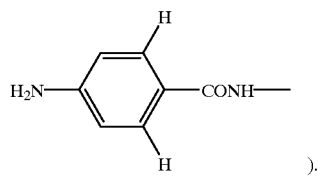

).

Example BB25: Synthesis of 3α-[N-[4-[N-(5-acetamido-4,7,8,9-tetra-O-acetyl-3,5-dideoxy-2-O-methyl-α-D-glycero-D-galacto-2-nonulopyranosonyl)amino]benzoyl]-amino]cholestane (α-isomer of Compound No. 59 in Table 1BB)

By using 5-acetamido-4,7,8,9-tetra-O-acetyl-3,5-dideoxy-2-O-methyl-α-d-glycero-D-galacto-2-nonulopyranosonic acid (399 mg, 0.81 mmol) and the compound obtained in Synthetic Example BB18 (530 mg, 0.98 mmol), the title compound was obtained in the same manner as in Example BB3 (667 mg, yield; 83.8%).

Melting point: 140–160° C. $^1$H-NMR (CDCl$_3$, ppm): 0.63 (3H, s, 18'-CH$_3$), 0.81–0.89 (12H, 19'-CH$_3$, 21'-CH$_3$, 26'-CH$_3$, 27'-CH$_3$), 1.78, 1.84, 2.01, 2.02, 2.13 (15H, s×5, Ac), 2.38 (1H, dd, J=5.5 Hz, 13.0 Hz, H-3$_{eq}$), 3.48 (3H, s, —OCH$_3$), 3.94 (1H, dd, J=5.8 Hz, 13.4 Hz, H-9), 4.09–4.28 (3H, m, H-5, H-6, H-3'), 6.37 (1H, d, —NH—), 7.67–7.78 (4H, m, —C$_6$H$_4$—), 8.67 (1H, s, —NH—).

Example BB26: Synthesis of 3α-[N-[4-[N-(5-acetamido-3,5-dideoxy-2-O-methyl-α-D-glycero-D-galacto-2-nonulopyranosonyl)amino]benzoyl]amino]cholestane (α-isomer of Compound No. 60 in Table 1BB)

By using the compound obtained in Example BB25 (471 mg, 0.48 mmol), the title compound was obtained in the same manner as in Example BB10 (261 mg, yield; 66.9%).

Melting point: 243–251° C. $^1$H-NMR (CDCl$_3$, ppm): 0.70 (3H, s, 18'-CH$_3$), 0.86–0.95 (12H, 19'-CH$_3$, 21'-CH$_3$, 26'-CH$_3$, 27'-CH$_3$), 2.03 (3H, s, Ac), 2.95 (1H, dd, J=4.6 Hz, 12.7 Hz, H-3$_{eq}$), 3.44 (3H, s, —OCH$_3$), 4.22 (1H, m, H-3'), 7.74–7.84 (4H, m, —C$_6$H$_4$—).

Synthetic Example BB19: Synthesis of 3α-N-14-(N-benzyloxycarbonylaminomethyl)-benzoyl]aminocholestane By using 4-N-benzyloxycarbonylaminomethylbenzoic acid (512 mg, 1.79 mmol) and 3α-aminocholestane (700 mg, 1.81 mmol), the title compound was obtained in the same manner as in Synthetic Example BB1 (500 mg, yield; 42.4%). $^1$H-NMR (CDCl$_3$, ppm): 0.62 (3H, s, 18-CH$_3$), 0.81–0.89 (12H, 19-CH$_3$, 21-CH$_3$, 26-CH$_3$, 27-CH$_3$), 4.29 (1H, m, H-3), 4.41 (2H, d, J=6.1 Hz, —NHCH$_2$C$_6$H$_4$CO—), 5.12 (2H, s, CH$_2$C$_6$H$_5$), 6.32 (1H, d, J=7.3 Hz, —NH—), 7.31–7.35 (7 H, m, —C$_6$H$_5$,

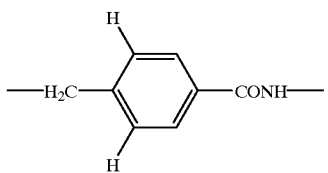

), 7.70 (H, d, J=8.2 Hz,

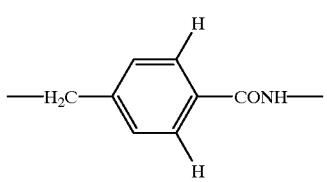

).

Synthetic Example BB20: Synthesis of 3α-N-(4-aminomethylbenzoyl)aminocholestane hydrochloride The compound obtained in Synthetic Example BB19 (477 mg, 0.73 mmol) was dissolved in a mixed solvent of tetrahydrofuran (25 ml) and ethanol (15 ml), and the solution was added with 5% palladium/carbon (140 mg), and then the mixture was stirred for four hours under hydrogen flow. After the reaction was completed, the catalyst was removed by filtration, and the solvent was evaporated under reduced pressure. The resulting syrup was dissolved in ethyl acetate, and then 13% hydrochloric acid/ethyl acetate was added to the solution and the resulting precipitates were collected by filtration to obtain the title compound (292 mg, yield; 71.9%).

$^1$H-NMR (CD$_3$OD, ppm): 0.74 (3H, s, 18-CH$_3$), 0.90–0.99 (12H, 19-CH$_3$, 21-CH$_3$, 26-CH$_3$, 27-CH$_3$), 4.23 (2H, s, —NHC$\underline{H}_2$C$_6$H$_4$CO—), 7.60 (2H, d, J=8.3 Hz,

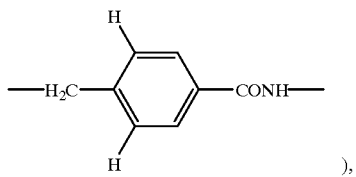

7.91 (2H, d, J=8.3 Hz,

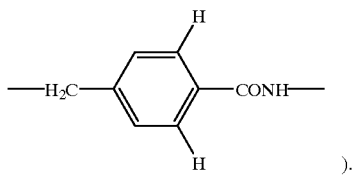

Example BB27: Synthesis of 3α-[N-[4-[N-(5-acetamido-4,7,8,9-tetra-O-acetyl-3,5-dideoxy-2-O-methyl-α-D-glycero-D-galacto-2-nonulopyranosonyl)aminomethyl]-benzoyl]amino]cholestane (α-isomer of Compound No. 63 in Table 1BB)

By using 5-acetamido-4,7,8,9-tetra-O-acetyl-3,5-dideoxy-2-O-methyl-α-D-glycero-D-galacto-2-nonulopyranosonic acid (243 mg, 0.49 mmol) and the compound obtained in Synthetic Example BB20 (276 mg, 0.50 mmol), the title compound was obtained in the same manner as in Example BB3 (220 mg, yield; 44.7%).

Melting point: 130–145° C. $^1$H-NMR (CDCl$_3$, ppm): 0.63 (3H, s, 18'-CH$_3$), 0.82–0.89 (12H, 19'-CH$_3$, 21'-CH$_3$, 27'-CH$_3$), 1.86, 1.98, 2.00, 2.03, 2.12 (15H, s×5, Ac), 2.35 (1H, dd, J=5.6 Hz, 13.1 Hz, H-3$_{eq}$), 3.37 (3H, s, —OCH$_3$), 3.92 (1H, dd, J=7.0 Hz, 12.2 Hz, H-9), 4.07–4.18 (2H, m, H-5, H-6), 4.29 (1H, m, H-3'), 4.42–4.47 (2H, m, —C$\underline{H}_2$C$_6$H$_4$—), 5.18–5.36 (4H, m, H-4, H-7, H-8, —NH—), 7.33–7.44 (3H, m, —NH—,

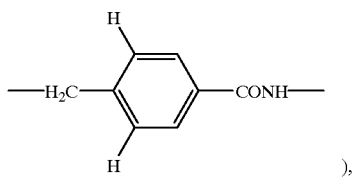

7.72 (2H, d, J=8.2 Hz,

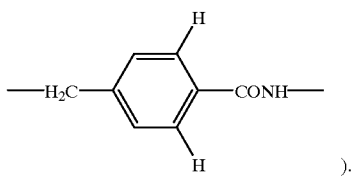

Example BB28: Synthesis of 3α-[N-[4-[N-(5-acetamido-3,5-dideoxy-2-O-methyl-α-D-glycero-D-galacto-2-nonulopyranosonyl)aminomethyl]benzoyl]amino]cholestane (α-isomer of Compound No. 64 in Table 1BB)

By using the compound obtained in Example BB27 (180 mg, 0.18 mmol), the title compound was obtained in the same manner as in Example BB2 (43.2 mg, yield; 28.8%).

Melting point: 170–185° C. $^1$H-NMR (CD$_3$OD, ppm): 0.74 (3H, s, 18'-CH$_3$), 0.90–0.99 (12H, 19'-CH$_3$, 21'-CH$_3$, 26'-CH$_3$, 27'-CH$_3$), 2.05 (3H, s, Ac), 2.83 (1H, dd, J=4.5 Hz, 12.8 Hz, H-3$_{eq}$), 3.33 (3H, s, —OCH$_3$) 4.02 (1H, m, H-3'), 4.45, 4.57 (2H, d×2, J=15.0 Hz, —C$\underline{H}_2$C$_6$H$_4$—), 7,47 (2H, d, J=8.2 Hz), 7.79 (2H, d, J=8.2 Hz,

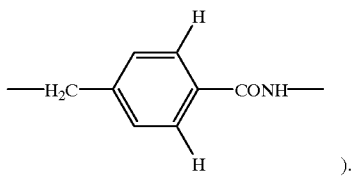

Synthetic Example BB21: Synthesis of 4-tert-butyloxycarbonylaminosalicylic acid 4-Aminosalicylic acid (5.00 g, 32.6 mmol) was suspended in dioxane (35 ml) and water (35 ml), and the suspension was added with aqueous sodium hydroxide (2N) and a solution of di-tert-butyl carbonate dicarbonate (8.5 g, 39.0 mmol) in dioxane (35 ml), and then the mixture was stirred at room temperature for seven days. After the dioxane of the reaction mixture was evaporated, the residue was made weakly acidic (pH~4) with 1N hydrochloric acid, and then extracted with ether. The extract was dried over anhydrous sodium sulfate, and the solvent was evaporated. The resulting syrup was solidified with hexane and ethyl acetate to obtain the title compound (4.58 g, yield; 55%).

IR (KBr, cm$^{-1}$): 3366, 2986, 1709, 1641. $^1$H-NMR (DMSO-d$_6$, ppm): 1.46 (9H, s, t-Bu), 6.97 (1H, dd, J=1.8 Hz, 8.7 Hz,

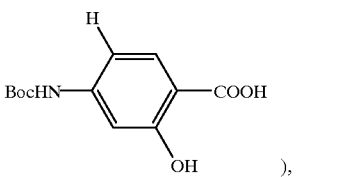

7.12 (1H, d, J=1.8 Hz,

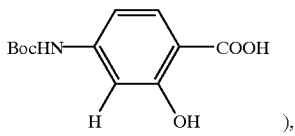), 7.64 (1H, d, J=8.7 Hz,

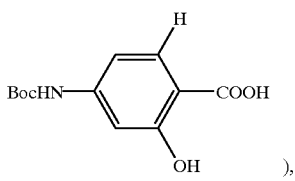), 9.7 (1H, s,

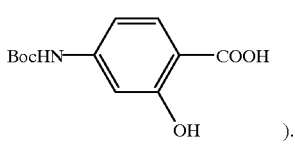).

Synthetic Example BB22: Synthesis of 3α-[N-[4-(tert-butyloxycarbonylamino)-2-hydroxybenzoyl]amino]cholestane The compound synthesized in Synthetic Example BB21 (253 mg, 1.00 mmol) was dissolved in tetrahydrofuran (10 ml), and the solution was added with carbonyldiimidazole (178 mg, 1.10 mmol) with ice cooling, and then the mixture was stirred for two hours. Then, 3α-aminocholestane (428 mg, 1.10 mmol) was added to the mixture, and the mixture was then warmed up to room temperature and stirred for 12 hours. The resulting solid was removed by filtration, and the filtrate was diluted with ethyl acetate (50 ml), washed with saturated aqueous sodium hydrogen carbonate and saturated brine successively, and then dried over anhydrous magnesium sulfate. After the solvent was evaporated, the residue was purified by silica gel column chromatography (Merck silica gel 60, developing solvent; hexane/ethyl acetate) to obtain the title compound (227 mg, yield; 36%).

IR (KBr, cm$^{-1}$): 3422, 2936, 2868, 1667, 1543. $^1$H-NMR (CDCl$_3$, ppm): 0.66 (3H, s, 18-CH$_3$), 0.84–0.92 (12H, 19-CH$_3$, 21-CH$_3$, 26-CH$_3$, 27-CH$_3$), 1.52 (9H, s, tert-Bu), 4.29 (1H, m, H-3), 6.39 (1H, d, J=7.0 Hz.

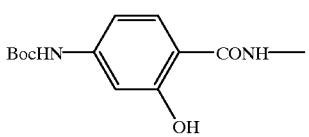), 6.58 (1H, s, BocNH—), 6.87 (1H, d, J=2.3 Hz,

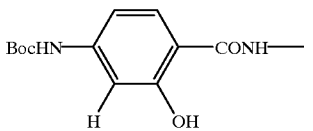), 7.00 (1H, m,

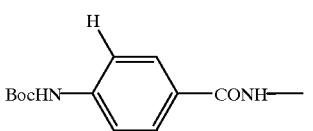), 7.27 (1H, d, J=8.8 Hz,

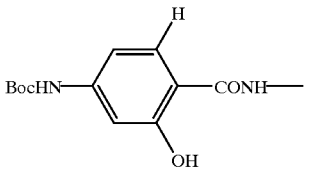), 12.59 (1H, s, —OH).

Synthetic Example BB23: Synthesis of 3α-(4-amino-2-hydroxybenzoyl)aminocholestane hydrochloride By using the compound obtained in Synthetic Example BB22 (196 mg, 0.314 mmol), the title compound was obtained in the same manner as in Synthetic Example BB4 (151 mg, yield; 86%).

IR (KBr, cm$^{-1}$): 3393, 2932, 2866, 1645, 1599. $^1$H-NMR (DMSO-$_6$, ppm): 0.62 (3H, s, 18-CH$_3$), 078 (3H, s, 19-CH$_3$), 0.81–0.89 (9H, 21-CH$_3$, 26-CH$_3$, 27-CH$_3$), 4.10 (1H, m, H-3), 6.4–6.45 (2H, m,

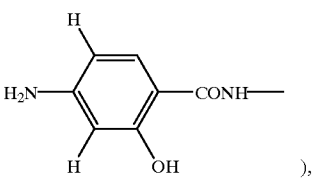), 7.80 (1H, d, J=9.1 Hz,

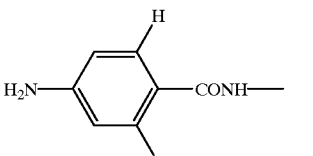), 8.15 (1H, d, J=8.0 Hz, —CONH—).

Example BB29: Synthesis of 3α-[N-[4-[N-(5-acetamido-4,7,8,9-tetra-O-acetyl-3,5-dideoxy-2-O-methyl-α-D-glycero-D-galacto-2-nonulopyranosonyl)amino]-2-hydroxy-benzoyl]amino]cholestane (α-isomer of Compound No. 65 in Table 1BB)

By using 5-acetamido-4,7,8,9-tetra-O-acetyl-3,5-dideoxy-2-O-methyl-α-D-glycero-D-galacto-2-nonulopyranosonic acid (114 mg, 0.232 mmol) and the compound obtained in Synthetic Example BB23 (130 mg, 0.232 mmol), the title compound was obtained in the same manner as in Example BB3 (159 mg, yield; 69%).

IR (KBr, cm$^{-1}$): 3393, 2936, 2866, 1750. $^1$H-NMR (CDCl$_3$, ppm): 0.66 (3H, s, 18'-CH$_3$), 0.74–0.92 (12H, 19'-CH$_3$, 21'-CH$_3$, 26'-CH$_3$, 27'-CH$_3$), 1.86, 1.88, 2.04, 2.05, 2.16 (15H, s×5, Ac), 2.40 (1H, dd, J=5.5 Hz, 13.0 Hz, H-3$_{eq}$), 3.50 (3H, s, —OCH$_3$), 3.95 (1H, m, H-9), 4.13–4.30 (3H, m, H-5, H-6, H-3'), 4.49 (1H, d, J=13.3 Hz, H-9), 5.25–5.32 (2H, m, H-7, H-8), 5.49–5.59 (2H, m, H-4, AcN<u>H</u>—), 6.56 (1H, m,

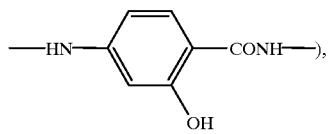

7.20 (1H, m,

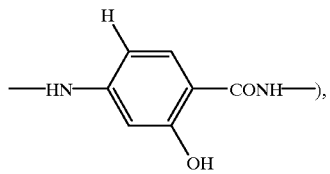

7.26 (1H, s,

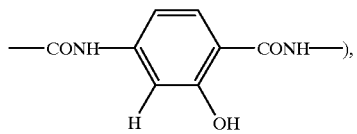

7.39 (1H, d, J=8.8 Hz,

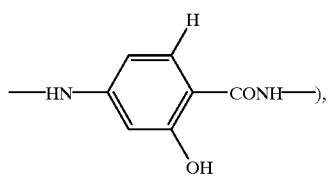

8.64 (1H, s,

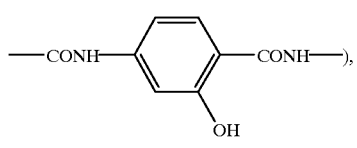

12.55 (1H, s, —OH).

Example BB30: Synthesis of 3α-[N-[4-[N-(5-acetamido-3,5-dideoxy-2-O-methyl-α-D-glycero-D-galacto-2-nonulopyranosonyl)amino] -2-hydroxybenzoyl] amino]cholestane (α-isomer of Compound No. 66 in Table 1BB)

By using the compound obtained in Example BB29 (136 mg, 0.137 mmol), the title compound was obtained in the same manner as in Example BB6 (89 mg, yield; 78%).

Melting point: 275–280° C. (decomposition) IR (KBr, cm$^{-1}$): 3383, 3285, 2934, 2868, 1694, 1618, 1532. $^1$H-NMR [CDCl$_3$-CD$_3$OD (1:1), ppm]: 0.69 (3H, s, 18'-CH$_3$), 0.86–0.91 (12H, 19'-CH$_3$, 21'-CH$_3$, 26'-CH$_3$, 27'-CH$_3$), 2.03 (3H, s, Ac), 2.93 (1H, dd, J=5.5 Hz, 13.0 Hz, H-3$_{eq}$), 3.42 (3H, s, —OCH$_3$), 4.27 (1H, m, H-3'), 7.18 (1H, d, J=8.7 Hz,

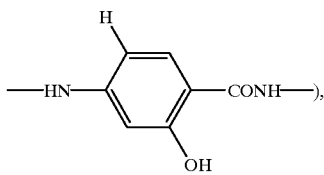

7.47 (1H, s,

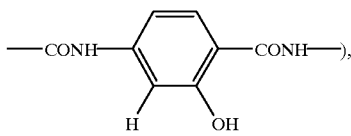

7.84 (1H, d, J=8.7 Hz,

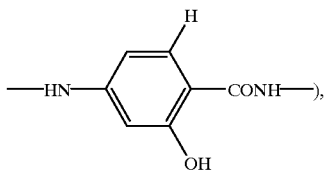

Synthetic Example BB24: Synthesis of 3α-N-(2-acetamido-4-nitrobenzoyl)amino-cholestane By using 2-acetamido-4-nitrobenzoic acid (800 mg, 3.57 mmol) and 3α-aminocholestane (1.4 g, 3.61 mmol), the title compound was obtained in the same manner as in Synthetic Example BB1 (784 mg, yield; 37.0%).

$^1$H-NMR (CDCl$_3$, ppm): 0.64 (3H, s, 18-CH$_3$), 0.82–0.90 (12H, 19-CH$_3$, 21-CH$_3$, 26-CH$_3$, 27-CH$_3$), 2.21 (3H, s, Ac), 4.29 (1H, m, H-3), 6.48 (1H, d, J=6.8 Hz, —NH—), 7.57 (1H, d, J=8.5 Hz,

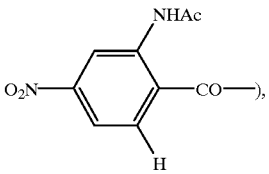

7.89 (1H, dd, J=2.2 Hz, 8.5 Hz,

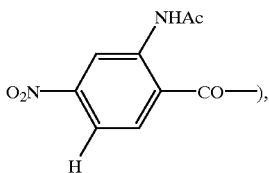

9.44 (1H, d, J=2.2 Hz,

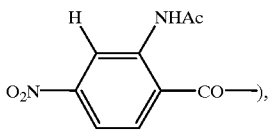

11.0 (1H, s, —NHAc).

Synthetic Example BB25: Synthesis of 3α-N-(2-acetamido-4-aminobenzoyl)amino-cholestane The compound obtained in Synthetic Example BB24 (765 mg, 1.29 mmol) was dissolved in a mixed solvent of tetrahydrofuran (20 ml) and ethanol (20 ml), added with 5% palladium/carbon (110 mg), and stirred for seven hours under hydrogen flow. After the reaction was completed, the catalyst was removed by filtration, and the solvent was evaporated under reduced pressure. The resulting syrup was solidified with methanol to obtain the title compound (505 mg, yield; 69.6%).

$^1$H-NMR (CDCl$_3$, ppm): 0.63 (3H, s, 18-CH$_3$), 0.81–0.89 (12H, 19-CH$_3$, 21-CH$_3$, 26-CH$_3$, 27-CH$_3$), 2.15 (3H, s, Ac), 4.21 (1H, m, H-3), 6.25–6.34 (3H, m, —NH$_2$, —NH—), 11.6 (1H, s, —NH—).

Example BB31: Synthesis of 3α-[N-[2-acetamido-4-[N-(5-acetamido-4,7,8,9-tetra-O-acetyl-3,5-dideoxy-2-O-methyl-α-D-glycero-D-galacto-2-nonulopyranosonyl)amino]-benzoyl]amino]cholestane (α-isomer of Compound No. 69 in Table 1BB)

By using 5-acetamido-4,7,8,9-tetra-O-acetyl-3,5-dideoxy-2-O-methyl-α-D-glycero-D-galacto-2-nonulopyranosonic acid (580 mg, 1.18 mmol) and the compound obtained in Synthetic Example BB25 (670 mg, 1.19 mmol), the title compound was obtained in the same manner as in Example BB1 (704 mg, yield; 57.7%).

Melting point: 253–255° C. $^1$H-NMR (CDCl$_3$, ppm): 0.64 (3H, s, 18'-CH$_3$), 0.82–0.90 (12H, 19'-CH$_3$, 21'-CH$_3$, 27'-CH$_3$), 1.84, 1.99, 2.02, 2.03, 2.15, 2.20 (18 H, s×6, Ac), 2.42 (1H, dd, J=5.0 Hz, 13.0 Hz, H-3$_{eq}$), 3.41 (3H, s, —OCH$_3$), 4.00 (1H, dd, J=6.3 Hz, 12.2 Hz, H-9), 5.28–5.35 (2H, m, H-7, H-8), 5.25–5.32 (2H, m, H-7, H-8), 5.50 (1H, m, H-4), 5.97 (1H, d, J=9.8 Hz, —NH—), 6.42 (1H, d, J=7.0 Hz, —NH—), 7.35 (1H, d, J=8.7 Hz,

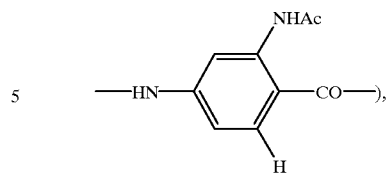

7.79 (1H, dd, J=1.9 Hz, 8.7 Hz,

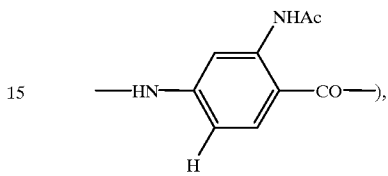

8.45 (1H, d, J=1.9 Hz,

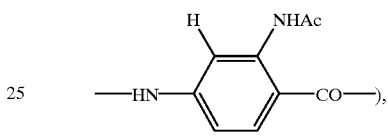

9.00 (1H, s, —NH—), 11.3 (1H, s, —NH—).

Example BB32: Synthesis of 3α-[N-[2-acetamido-4-[N-(5-acetamido-3,5-dideoxy-2-O-methyl-α-D-glycero-D-galacto-2-nonulopyranosonyl)amino]benzoyl]amino]cholestane (α-isomer of Compound No. 70 in Table 1BB)

By using the compound obtained in Example BB29 (503 mg, 0.48 mmol), the title compound was obtained in the same manner as in Example BB2 (128 mg, yield; 30.4%).

Melting point: 197–203° C. $^1$H-NMR [CDCl$_3$—CD$_3$OD (1:1), ppm]: 0.73 (3H, s, 18'-CH$_3$), 0.90–0.98 (12H, 19'-CH$_3$, 21'-CH$_{3,\,26}$'-CH$_3$, 27'-CH$_3$), 2.04 (3H, s, Ac), 2.20 (3H, s, Ac), 2.94 (1H, dd, J=4.3 Hz, 12.6 Hz, H-3$_{eq}$), 3.44 (3H, s, —OCH$_3$), 4.21 (1H, m, H-3'), 7.63–7.87 (2H, m,

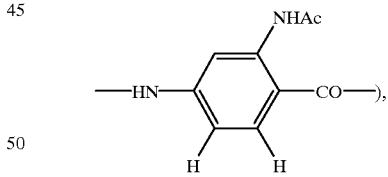

8.50 (1H, d, J=1.7 Hz,

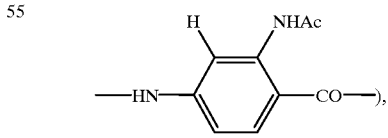

Synthetic Example BB26: Synthesis of 3β-amino-24-hydroxy-5β-cholane [compound the formula (42"BB) wherein B is —CH(CH$_3$)CH$_2$CH$_2$-group]

Lithium aluminum hydride (365 mg, 9.62 mmol) was suspended in tetrahydrofuran (40 ml), and the suspension was added with a solution of methyl 3β-azido-5β-cholanate (2.00 g, 4.81 mmol) in tetrahydrofuran (20 ml) over 50 minutes under reflux by heating, and then the mixture was further refluxed by heating for 1.5 hours. After the reaction was completed, excess lithium aluminum hydride was quenched by adding saturated aqueous sodium sulfate to the mixture with ice cooling. The organic layer was separated, and the remaining layer was added with diethyl ether and stirred. The resulting organic layers were combined and concentrated. The resulting solid was suspended and washed in methanol (15 ml) to obtain the title compound (1.54 g, yield; 88%).

IR (KBr, cm$^{-1}$): 3358, 3277, 2934, 2863, 1451, 1375. $^1$H-NMR (CDCl$_3$, ppm): 0.65 (3H, s, 18-CH$_3$), 0.92 (6H, d, J=6.5 Hz, 21-CH$_3$), 0.95 (3H, s, 19-CH$_3$), 3.23 (1H, m, H-3), 3.60 (2H, t, J=5.5 Hz, H-24).

Synthetic Example BB27: Synthesis of 3β-N-(N-tert-butyloxycarbonyl-O-benzyl-D-seryl)amino-24-hydroxy-5β-cholane By using N-tert-butyloxycarbonyl-O-benzyl-D-serine (300 mg, 1.02 mmol) and the compound obtained in Synthetic Example BB26 (367 mg, 1.02 mmol), the title compound was obtained in the same manner as in Synthetic Example BB1 (623 mg, yield; 96%).

IR (KBr, cm$^{-1}$): 3430, 2934, 2865, 1716, 1665. $^1$H-NMR (CDCl$_3$, ppm): 0.63 (3H, s, 18-CH$_3$), 0.82 (3H, s, 19-CH$_3$), 0.92 (3H, d, J=6.5 Hz, 21-CH$_3$), 1.45 (9H, s, tert-Bu), 3.50–3.63 (3H, m, H-24, —CH$_2$OCH$_2$C$_6$H$_5$), 3.91 (1H, m, CH$_2$OCH$_2$C$_6$H$_5$), 4.14–4.28 (2H, m, H-3, —NHCHCO—), 4.52, 4.59 (2H, dX2, J=11.4 Hz, —CH$_2$C$_6$H$_5$), 6.46 (1H, m, —NHCHCONH—), 6.85 (1H, m, BocNH—), 7.26–7.35 (5H, m, —C$_6$H$_5$).

Synthetic Example BB28: Synthesis of 3β-N-(O-benzyl-D-seryl)amino-24-acetoxy-5β-cholane Hydrochloride By using the compound obtained in Synthetic Example BB27 (553 mg, 0.865 mmol), the title compound was obtained in the same manner as in Synthetic Example BB4 (493 mg, yield; 92%).

IR (KBr, cm$^{-1}$): 3430, 3219, 2938, 2866, 1742, 1688. $^1$H-NMR (CD$_3$OD, ppm): 0.69 (3H, s, 18-CH$_3$), 0.95 (3H, d, J=6.7 Hz, 21-CH$_3$), 0.96 (3H, s, 19-CH$_3$), 2.01 (3H, s, Ac), 3.77 (2H, m, —CH$_2$OCH$_2$C$_6$H$_5$), 4.02 (2H, t, J=6.5 Hz, H-24), 4.07–4.12 (2H, m, H-3, —NHCHCO—), 4.55, 4.64 (2H, dx2, J=12.0 Hz, —CH$_2$C$_6$H$_5$), 7.28–7.37 (5H, m, —C$_6$H$_5$).

Example BB33: Synthesis of 3β-[N-[N-(5-acetamido-4,7,8,9-tetra-O-acetyl-3,5-dideoxy-2-O-methyl-α-D-glycero-D-galacto-2-nonulopyranosonyl)]-O-benzyl-D-serylamino]-24-acetoxy-5β-cholane (Compound No. 92 in Table 1BB wherein the configuration of Y' is D and the configuration at the 3-position of the steroid is β)

By using 5-acetamido-4,7,8,9-tetra-O-acetyl-3,5-dideoxy-2-O-methyl-α-D-glycero-D-galacto-2-nonulopyranosonic acid (200 mg, 0.407 mmol) and the compound obtained in Synthetic Example BB28 (234 mg, 0.379 mmol), the title compound was obtained in the same manner as in Example BB3 (269 mg, yield; 62%).

IR (KBr, cm$^{-1}$): 3397, 2940, 2866, 1746, 1686. $^1$H-NMR (CDCl$_3$, ppm): 0.63 (3H, s, 18'-CH$_3$), 0.84 (3H, s, 19'-CH$_3$), 0.91 (3H, d, J=6.4 Hz, 21'-CH$_3$), 1.82, 1.99, 2.01, 2.05, 2.05, 2.11 (18H, sx6, Ac), 2.41 (1H, dd, J=5.3 Hz, 12.9 Hz, H-3$_{eq}$), 3.41 (3H, s, —OCH$_3$), 3.83 (2H, m, —CH$_2$OCH$_2$C$_6$H$_5$), 3.89 (1H, dd, J=8.1 Hz, 12.4 Hz, H-9), 3.98–4.09 (3H, m, H-24', 5), 4.18(1H, m, H-3'), 4.57(2H, s, —CH$_2$C$_6$H$_5$). 4.67–4.76 (2H, m, H-6,9), 4.88 (1H, m, AcNH—), 5.11 (1H, m, H-7), 5.17–5.31 (2H, m, H-4, 8), 6.83 (1H, d, J=7.9 Hz, NH), 7.26–7.42 (5H, m, —C$_6$H$_5$), 7.65 (1H, d, J=8.3 Hz, NH).

Example BB34: Synthesis of 3β-[N-[N-(5-acetamido-4,7,8,9-tetra-O-acetyl-3,5-dideoxy-2-O-methyl-α-D-glycero-D-galacto-2-nonulopyranosonyl)]-D-serylamino]- 24-acetoxy-5β-cholane (Compound No. 91 in Table 1BB wherein the configuration of is D and the configuration at the 3-position of the steroid is β)

By using the compound obtained in Example BB33 (246 mg, 0.233 mmol), the title compound was obtained in the same manner as in Example BB7 (228 mg, yield; 97%).

IR (KBr, cm$^{-1}$): 3387, 2939, 2866, 1748, 1231. $^1$H-NMR (CD$_3$OD, ppm): 0.69 (3H, s, 18'-CH$_3$), 0.95 (3H, d, J=6.4 Hz, 21'-CH$_3$), 0.99 (3H, s, 19'-CH$_3$), 1.97, 2.00, 2.01, 2.02, 2.10 (18H, sx6, Ac), 2.41 (1H, dd, J=5.7 Hz, 13.6 Hz, H-3$_{eq}$), 3.50 (3H, s, —OCH$_3$), 3.81 (2H, d, J=4.3 Hz, —CH$_2$OH), 3.95–4.16 (4H, m, H-24', 3', 5), 4.35 (1H, dd, J=1.9 Hz, 10.9 Hz, H-6), 4.45 (1H, t, J=5.6 Hz, —NHCHCO—), 4.54 (1H, dd, J=2.2 Hz, 12.3 Hz, H-9), 5.15 (1H, m, H-4), 5.29 (1H, dd, J=1.9 Hz, 6.7 Hz, H-7), 5.37(1H, m, H-8).

Example BB35: Synthesis of 3β-[N-[N-(5-acetamido-3,5-dideoxy-2-O-methyl-α-D-glycero-D-galacto -2-nonulopyranosonyl)]-D-serylamino]-24-hydroxy-5β-cholane (Compound No. 88 in Table 1BB wherein the configuration of Y is D and the configuration at the 3-position of the steroid is β)

By using the compound obtained in Example BB34 (214 mg, 0.222 mmol), the title compound was obtained in the same manner as in Example BB10 (135 mg, yield; 81%).

Melting point: 242–246° C. (decomposition) IR (KBr, cm$^{-1}$): 3399, 2938, 2866, 1653, 1534. $^1$H-NMR (CD$_3$OD, ppm): 0.69 (3H, s, 18'-CH$_3$), 0.95 (3H, d, J=6.3 Hz, 21'-CH$_3$), 1.00 (3H, s, 19'-CH$_3$), 2.00 (3H, s, Ac), 2.74 (1H, dd, J=4.0 Hz, 13.0 Hz, H-3$_{eq}$), 3.37 (3H, s, —OCH$_3$), 4.07 (1H, m, H-3'), 4.50 (1H, t, J=6.1 Hz, —NHCHCO—).

Synthetic Example BB29: Synthesis of 3β-N-(N-tert-butyloxycarbonyl-O-benzyl-L-seryl)amino-24-hydroxy-5β-cholane By using N-tert-butyloxycarbonyl-O-benzyl-L-serine (600 mg, 2.03 mmol) and the compound obtained in Synthetic Example BB26 (808 mg, 2.24 mmol), the title compound was obtained in the same manner as in Synthetic Example BB1 (1.30 g, quantitative).

IR (KBr, cm$^{-1}$): 3420, 2940, 2865, 1665. $^1$H-NMR (CDCl$_3$, ppm): 0.63 (3H, s, 18-CH$_3$), 0.83 (3H, s, 19-CH$_3$), 0.92 (3H, d, J=6.3 Hz, 21-CH$_3$), 1.45 (9H, s, tert-Bu), 3.50–3.65 (3H, m, H-24, —CH$_2$OCH$_2$C$_6$H$_5$), 3.91 (1H, dd, J=6.5 Hz, 9.1 Hz, —CH$_2$OCH$_2$C$_6$H$_5$), 4.10–4.30 (2H, m, H-3, —NHCHCO—), 4.51, 4.60 (2H, dx2, J=11.6 Hz, —CH$_2$C$_6$H$_5$), 5.47 (1H, m, —NHCHCONH—), 6.84 (1H, m,BocNH—), 7.25–7.36 (5H, m, —C$_6$H$_5$).

Synthetic Example BB30: Synthesis of 3β-N-(O-benzyl-L-seryl)amino-24-hydroxy-5β-cholane hydrochloride By using the compound obtained in Synthetic Example BB29 (1.20 g, 1.88 mmol), the title compound was obtained in the same manner as in Synthetic Example BB4 (850 mg, yield; 79%).

IR (KBr, cm$^{-1}$): 3401, 3270, 2940, 2865, 1672. $^1$H-NMR (CD$_3$OD, ppm): 0.69 (3H, s, 18-CH$_3$), 0.95 (3H, d, J=8.4 Hz, 21-CH$_3$), 0.97 (3H, s, 19-CH$_3$), 3.50 (2H, t, J=6.4 Hz, H-24), 3.80 (2H, m, —CH$_2$OCH$_2$C$_6$lH$_5$), 4.11 (1H, m, H-3), 4.13 (1H, m, —NHCHCO—), 4.55, 4.64 (2H, d×2, J=12.0 Hz, —CH$_2$C$_6$H$_5$), 7.25–7.36 (5H, m, —C$_6$H$_5$).

Example BB36: Synthesis of 3β-[N-[N-(5-acetamido-4,7,8,9-tetra-O-acetyl-3,5-dideoxy-2-O-methyl-α-D-glycero-D-galacto-2-nonulopyranosonyl)]-O-benzyl-L-seryl amino]-24-hydroxy-5β-cholane (Compound No. 89 in Table 1BB wherein the configuration is D and the configuration at the 3-position of the steroid is β)

By using 5-acetamido-4,7,8,9-tetra-O-acetyl-3,5-dideoxy-2-O-methyl-α-D-glycero-D-galacto-2-nonulopyranosonic acid (500 mg, 1.02 mmol) and the compound obtained in Synthetic Example BB30 (585 mg, 1.02 mmol), the title compound was obtained in the same manner as in Example BB3 (618 mg, yield; 60%).

IR (KBr, cm$^{-1}$): 3389, 2940, 2866, 1748, 1670. $^1$H-NMR (CDCl$_3$, ppm): 0.63 (3H, s, 18'-CH$_3$), 0.78 (3H, s, 19'-CH$_3$), 0.91 (3H, d, J=6.4 Hz, 21'-CH$_3$), 1.88, 2.01, 2.02, 2.07, 2.14 (15H, sx5, Ac), 2.41 (1H, dd, J=5.1 Hz, 13.0 Hz, H-3$_{eq}$), 3.40 (3H, s, —OCH$_3$), 3.61 (2H, m, H-24'), 3.69 (1H, t, J=9.5 Hz, —CH$_2$OCH$_2$C$_6$H$_5$), 3.82 (1H, q, J=4.7 Hz, 9.5 Hz, —CH$_2$OCH$_2$C$_6$H$_5$), 3.98 (1H, dd, J=7.5 Hz, 12.4 Hz, H-9), 4.14 (1H, q, J=10.5 Hz, H-5), 4.16 (1H, m, H-3'), 4.45 (1H, dd, J=2.0 Hz, 10.5 Hz, H-6), 4.50–4.56 (2H, m, H-9, —NHCHCO—), 4.55, 4.64 (2H, dx2, J=11.5 Hz, —CH$_2$C$_6$H$_5$), 5.11 (1H, m, H-4), 5.28 (1H, m, H-7), 5.30–5.49 (2H, m, H-8, AcNH), 6.96 (1H, d, J=7.8 Hz, NH), 7.26–7.40 (5H, m, —C$_6$H$_5$).

Example BB37: Synthesis of 3β-[N-[N-(5-acetamido-3,5-dideoxy-2-O-methyl-α-D-glycero-D-galacto-2-nonulopyranosonyl)]-O-benzyl-L-serylamino]-24-hydroxy-5β-cholane (Compound No. 90 in Table 1BB wherein the configuration is D and the configuration at the 3-position of the steroid is β)

By using the compound obtained in Example BB36 (214 mg, 0.211 mmol), the title compound was obtained in the same manner as in Example BB10 (108 mg, yield; 62%).

Melting point: 139–144° C. (decomposition) IR (KBr, cm$^{-1}$): 3412, 2938, 2865, 1659. $^1$H-NMR (CD$_3$OD, ppm): 0.69 (3H, s, 18'-CH$_3$), 0.93 (3H, s, 19'-CH$_3$), 0.94 (3H, d, J=8.2 Hz, 21'-CH$_3$), 2.02 (3H, s, Ac), 2.76 (1H, dd, J=4.5 Hz, 11.0 Hz, H-3$_{eq}$), 3.29 (3H, s, —OCH$_3$), 3.50 (2H, t, J=6.3 Hz, H-24'), 4.05 (1H, m, H-3'), 4.55 (2H, s, —CH$_2$C$_6$H$_5$), 4.68 (1H, t, J=6.6 Hz, —NHCHCO—), 7.26–7.34 (5H, m, —C$_6$H$_5$).

Example BB38: Synthesis of 3β-[N-[N-(5-acetamido-4,7,8,9-tetra-O-acetyl-3,5-dideoxy-2-O-methyl-α-D-glycero-D-galacto-2-nonulopyranosonyl)]-L-serylamino]-24-hydroxy-5β-cholane (Compound No. 87 in Table 1BB wherein the configuration of Y is L and the configuration at the 3-position of the steroid is β)

By using the compound obtained in Example BB36 (350 mg, 0.346 mmol), the title compound was obtained in the same manner as in Example BB7 (300 mg, yield; 94%).

IR (KBr, cm$^{-1}$): 3383, 2940, 2866, 1750, 1667. $^1$H-NMR (CD$_3$OD, ppm): 0.69 (3H, s, 18'-CH$_3$), 0.95 (3H, d, J=6.5 Hz, 21'-CH$_3$), 1.04 (3H, s, 19'-CH$_3$), 1.84, 2.00, 2.07, 2.10, 2.12 (15H, sx5, Ac), 2.45 (1H, dd, J=5.6 Hz, 13.5 Hz, H-3$_{eq}$), 3.38(3H, s, —OCH$_3$), 3.50 (2H, t, J=6.3 Hz, H-24'), 3.77 (2H, d, J=6.0 Hz, —CH$_2$OH), 4.04 (1H,dd, J=6.4 Hz, 12.3 Hz, H-9), 4.07(1H, m, H-3'), 4.11 (1H, t, J=10.6 Hz, H-5), 4.42 (1H, dd, J=2.5 Hz, 12.3 Hz, H-9), 4.50 (1H, t, J=5.6 Hz, —NHCHCO—), 4.53 (1H, dd, J=2.0 Hz, 10.6 Hz, H-6), 5.02 (1H, m, H-4), 5.29 (1H, dd, J=2.0 Hz, 7.5Hz, H-7), 5.42 (1H, m, H-8).

Example BB39: Synthesis of 3β-[N-[N-(5-acetamido-3,5-dideoxy-2-O-methyl-α-D-glycero-D-galacto-2-nonulopyranosonyl)]-L-serylamino]-24-hydroxy-5β-cholane (Compound No. 88 in Table 1BB wherein the configuration of Y is L and the configuration at the 3-position of the steroid is β)

By using the compound obtained in Example BB38 (242 mg, 0.262 mmol), the title compound was obtained in the same manner as in Example BB10 (144 mg, yield; 73%).

Melting point: 168–178° C. IR (KBr, cm$^{-1}$): 3407, 2938, 2866, 1657. $^1$H-NMR (CD$_3$OD, ppm): 0.70 (3H, s, 18'-CH$_3$), 0.95 (3H, d, J=6.4 Hz, 21'-CH$_3$), 1.01 (3H, s, 19'-CH$_3$), 2.02 (3H, s, Ac), 2.76 (1H, dd, J=4.5 Hz, 12.6 Hz, H-3$_{eq}$), 3.46 (3H, s, —OCH$_3$), 4.07 (1H, m, H-3'), 4.48 (1H, t, J=6.6 Hz, —NHCHCO—).

Synthetic Example BB31: Synthesis of 5-acetamido-4,7,8,9-tetra-O-acetyl-3,5-dideoxy-2-O-methyl-β-D-glycero-D-galacto-2-nonulopyranosonic Acid [compound of the formula (9BB) wherein R$^{4'}$ is acetyl group, and R$^3$ is methyl group]

5-Acetamido-3,5-dideoxy-2-O-methyl-β-D-glycero-D-galacto-2-nonulopyranosonic acid methyl ester (1.00 g, 2.96 mmol) was dissolved in methanol (10 ml), and the solution was added with 1N aqueous sodium hydroxide (3 ml), and then the mixture was stirred for 4.5 hours. The reaction mixture was acidified (pH 2–3) by adding Dowex (50WX8, H$^+$) resin, and then the solvent was evaporated. The residue was dissolved in pyridine (5 ml), and the solution was added with acetic anhydride (1.68 ml, 17.8 mmol) with ice cooling, and the mixture was stirred for one hour, and then stirring was further continued for two days at room temperature. Water (20 ml) was added to the reaction mixture, and the mixture was washed with methylene chloride (20 ml). The washing liquor (methylene chloride solution) was extracted with water (20 ml), and the aqueous layers were combined and concentrated to about 20 ml under reduced pressure. The concentrate was acidified (pH ~1) by adding 1N aqueous hydrochloric acid and saturated with sodium chloride, and then extracted with methylene chloride (150 ml). The extract was dried over anhydrous sodium sulfate, and the solvent was evaporated. The residue was purified by silica gel column chromatography (Merck silica gel 60, developing solvent: methylene chloride/methanol) to obtain the title compound (730 mg, yield; 50%).

IR (KBr, cm$^{-1}$): 3370, 3080, 2980, 2630, 1750, 1660. $^1$H-NMR (CD3OD, ppm): 1.82 (1H, dd, J=11.8 Hz, 12.8 Hz, H-3ax), 1.89, 2.01, 2.04, 2.08, 2.15 (15H, sx5, Ac), 2.46 (1H, dd, J=5.0 Hz, 12.9 Hz, H-3$_{eq}$), 3.33 (3H, s, OCH$_3$), 3.96–4.10 (2H, m, H-5,9), 4.19 (1H, dd, J=6.7 Hz, 12.5 Hz, H-9), 4.73 (1H, dd, J=2.5 Hz, 12.4 Hz, H-9), 5.23 (1H, m, H-4), 5.35 (1H, m, H-8), 5.45 (1H, m, H-7).

Example BB40: Synthesis of 3β-[N-[N-(5-acetamido-4,7,8,9-tetra-O-acetyl-3,5-dideoxy-2-O-methyl-β-D-glycero-D-galacto-2-nonulopyranosonyl)]-O-benzyl-D-serylamino]-24-acetoxy-5β-cholane (Compound No. 324 in Table 3BB wherein the configuration of Y' is D and the configuration at the 3-position of the steroid is β)

By using the compounds obtained in Synthetic Example BB31 (200 mg, 0.407 mmol) and Synthetic Example BB28

(234 mg, 0.379 mmol), the title compound was obtained in the same manner as in Example BB3 (259 mg, yield; 60%).

IR (KBr, cm$^{-1}$): 3400, 2940, 2866, 1748, 1674. $^1$H-NMR (CDCl$_3$, ppm): 0.63 (3H, s, 18'-CH$_3$), 0.80 (3H, s, 19'-CH$_3$), 0.91 (3H, d, J=6.4 Hz, 21'-CH$_3$), 1.90, 2.00, 2.01, 2.05, 2.08, 2.15 (18H, s×6, Ac), 2.52 (1H, dd, J=5.1 Hz, 13.2 Hz, H-3$_{eq}$) 3.21 (3H, s, —OCH$_3$), 3.64 (1H, t, J=9.0 Hz, —CH$_2$OCH$_2$C$_6$H$_5$), 3.90 (1H, dd, J=4.3 Hz, 9.0 Hz, —CH$_2$OCH$_2$C$_6$H$_5$), 3.97–4.11 (5H, m, H-24', 5, 6, 9), 4.17 (1H, m, H-3'), 4.50–4.68 (4H, m, H-9, —CH$_2$C$_6$H$_5$, —NHCHCO—), 5.24–5.38 (4H, m, H-4, 7, 8, AcNH—), 6.86 (1H, d, J=7.9 Hz, NH), 7.26–7.35 (5H, m, —C$_6$H$_5$), 7.63 (1H, d, J=7.0 Hz, NH).

Example BB41: Synthesis of 3β-[N-[N-(5-acetamido-4,7,8,9-tetra-O-acetyl-3,5-dideoxy-2-O-methyl-β-D-glycero-D-galacto-2-nonulopyranosonyl)]-D-serylamino]-24-acetoxy-5β-cholane (Compound No. 323 in Table 3BB wherein the configuration of Y' is D and the configuration at the 3-position of the steroid is β)

By using the compound obtained in Example BB40 (230 mg, 0.218 mmol), the title compound was obtained in the same manner as in Example BB7 (200 mg, yield; 95%).

IR (KBr, cm$^{-1}$): 3401, 2940, 2866, 1746, 1669. $^1$H-NMR (CD$_3$OD, ppm): 0.69 (3H, s, 18'-CH$_3$), 0.95 (3H, d, J=6.4 Hz, 21'-CH$_3$), 1.00 (3H, s, 19'-CH$_3$), 1.86, 1.96, 2.00, 2.01, 2.07, 2.13 (18H, s×6, Ac), 2.45 (1H, dd, J=4.9 Hz, 13.0 Hz, H-3$_{eq}$), 3.24 (3H, s, —OCH$_3$), 3.80 (2H, m, —CH$_2$OH), 3.97–4.15 (5H, m, H-24', 5, 6, 9), 4.49 (1H, t, J=5.5 Hz, —NHCHCO—), 4.56 (1H, dd, J=2.5 Hz, 12.6 Hz, H-9), 5.20 (1H, m, H-4), 5.33–5.44 (2H, m, H-7, 8).

Example BB42: Synthesis of 3β-[N-[N-(5-acetamido-3,5-dideoxy-2-O-methyl-β-D-glycero-D-galacto-2-nonulopyranosonyl)]-D-serylamino]-24-hydroxy-5β-cholane (Compound No. 320 in Table 3BB wherein the configuration of Y is D and the configuration at the 3-position of the steroid is β)

By using the compound obtained in Example BB41 (185 mg, 0.192 mmol), the title compound was obtained in the same manner as in Example BB10 (83 mg, yield; 55%).

Melting point: 180–190° C. (decomposition) IR (KBr, cm$^{-1}$): 3422, 2936, 2866, 1653. $^1$H-NMR (CD$_3$OD, ppm): 0.69 (3H, s, 18'-CH$_3$), 0.95 (3H, d, J=6.4 Hz, 21'-CH$_3$), 1.01 (3H, s, 19'-CH$_3$), 2.02 (3H, s, Ac), 2.38(1H, dd, J=5.0 Hz, 13.0 Hz, H-3$_{eq}$), 3.23 (3H, s, —OCH$_3$), 3.50 (2H, t, J=7.0 Hz, H-24'), 4.50 (1H, t, J=6.1 Hz, —NHCHCO—).

Test Example 1: Effect on activity of acetylcholine Synthetase (choline acetyltransferase; ChAT) of Septal Area Cholinergic Neurons from Rat Neonates Cultivation of septal area neurons from rat neonates was carried out according to the method of Hatanaka (Hatanaka et al., Dev. Brain. Res., 39, 85–95, 1988). Septal areas were removed from 14-day rat brains and minced, and then the cells were dispersed enzymatically (papain treatment in the presence of DNase I) or mechanically (pipetting). The resulting separated cells were inoculated on a 48-well plate, on which astroglia cells had been grown in a form of a sheet, at a density of about $5 \times 10^5$ cell/cm$^2$, and then the cells were cultivated with DF medium (1:1 mixture of Dulbecco's modified Eagle's medium and Ham's F12 medium) containing 5% semi-fetal bovine serum and 5% immobilized bovine serum. The astroglia cells were prepared from cerebral cortex of rat embryo E20, and used after growth of several generations. On the next day of the start of the cultivation, the medium was replaced with the same medium supplemented with a test compound at a prescribed concentration. After cultivation for 1 week, the cells were sonicated in 5 mM Tris-HCl buffer containing 0.1% Triton X-100. The resulting preparation, as a crude enzyme sample, was mixed with [$^{14}$C]-acetyl coenzyme A (0.3 KBq), and then the mixture was incubated at 37° C. for one hour. After the reaction was stopped, [$^{14}$C]-acetylcholine formed was extracted into a toluene scintillator, and measured using a liquid scintillation counter. The ChAT activity of a control group was usually about 1.5 pmol/min/culture per well, and ChAT activity of the test compound was calculated as a ratio (%) based on the ChAT activity of a control group which was assumed as 0. The results of the experiments are shown in Table 2 set out below. The symbols AA and BB indicated before the serial numbers of compounds mean that compounds are listed in Table 1AA and Table 1BB, respectively.

TABLE 2

| | Concentration (μM) | | |
|---|---|---|---|
| Compound number | 3 | 10 | 30 |
| β-isomer of AA No. 4 | 83* | 136** | 92** |
| α-isomer of AA No. 55 | 31* | 35* | 47** |
| α-isomer of AA No. 61 | 24 | 51** | 80** |
| L, α-isomer of BB No. 4 | 102** | 166** | −18* |
| L, α-isomer of BB No. 12 | 84* | 47* | 58* |
| D, α-isomer of BB No. 4 | 6 | 79* | 126** |
| D, α-isomer of BB No. 12 | 28* | 57** | 31* |
| L, α-isomer of BB No. 14 | 50** | 97** | 110** |
| L, α-isomer of BB No. 16 | 30 | 50** | 52** |
| L, α-isomer of BB No. 24 | 51* | 80 | 127* |
| L, α-isomer of BB No. 30 | 29** | 41** | −53* |
| L, α-isomer of BB No. 59 | 46 | 57** | 90** |
| L, α-isomer of BB No. 60 | 49* | 67** | 93** |
| L, α-isomer of BB No. 69 | 28* | 55** | 20 |

*p < .05; **p < 0.01

Industrial Applicability

The compounds of the present invention activate ChAT activity in cholinergic nerve cells. Therefore, they are useful as an active ingredient of medicaments for preventive and therapeutic treatment of dementia, memory disturbance, and other symptoms accompanied by these disease.

What is claimed is:

1. A sialic acid derivative represented by the following general formula (1AA) or its salt, or a hydrate or a solvate thereof:

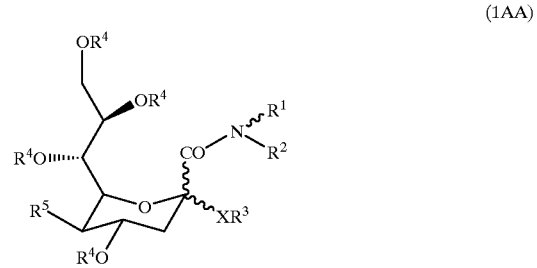

(1AA)

wherein:
R$^1$ represent a residue of a steroid compound excluding cholestane residue and cholestene residue,
R$^2$ represents hydrogen atom or methyl group,

315

$R^3$ represents a $C_1$-$C_6$ alkyl group, a group of formula:

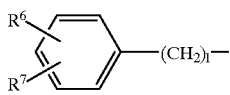

wherein $R^6$ and $R^7$ independently represent hydrogen atom, a halogen atom, a $C_1$-$C_4$ alkyl group, hydroxyl group, a group of formula $R^8O$— (wherein $R^8$ represents a $C_1$-$C_4$ alkyl group, phenyl group, or a phenyl-($C_1$-$C_3$ alkyl) group), nitro group, amino group, a $C_1$-$C_4$ alkylamino group, a $C_2$-$C_8$ dialkylamino group, or a group of formula $R^9O$—CO— (wherein $R^9$ represents hydrogen atom, a $C_1$-$C_4$ alkyl group, phenyl group, or a phenyl-($C_1$-$C_3$ alkyl) group), and l represents an integer of 0–6; a group of $R^{10}O(CH_2)_m$— (wherein $R^{10}$ represents hydrogen atom; a $C_1$-$C_4$ alkyl group; phenyl group which may optionally have one or more substituents selected from the group consisting of a $C_1$-$C_4$ alkyl group, a halogen atom, hydroxyl group, nitro group, amino group, and carboxyl group; or a phenyl-($C_1$-$C_3$ alkyl) group which may optionally have one or more substituents selected from the group consisting of a $C_1$-$C_4$ alkyl group, a halogen atom, hydroxyl group, nitro group, amino group, and carboxyl group, and m represents an integer of 2–6); or a group of $(R^{11})(R^{12})N(CH_2)_n$— wherein $R^{11}$ represents hydrogen atom or a $C_1$-$C_4$ alkyl group, and $R^{12}$ represents hydrogen atom; a $C_1$-$C_4$ alkyl group; a $C_2$-$C_7$ acyl group; a $C_1$-$C_4$ alkylsulfonyl group; phenylsulfonyl group which may optionally have one or more substituents selected from the group consisting of a $C_1$-$C_4$ alkyl group, a halogen atom, hydroxyl group, nitro group, amino group, and carboxyl group; or a group of $R^{13}O$—CO— (wherein $R^{13}$ represents a $C_1$-$C_4$ alkyl group, phenyl group, or a phenyl-($C_1$-$C_3$ alkyl) group), and n represents an integer of 2–6, $R^4$ represents hydrogen atom or a $C_2$-$C_7$ acyl group, $R^5$ represents a group of $R^{14}O$— (wherein $R^{14}$ represents hydrogen atom or a $C_2$-$C_7$ acyl group) or a group of $R^{15}NH$— wherein $R^{15}$ represents a $C_2$-$C_7$ acyl group, a group of $R^{16}O(CH_2)_p$—CO— (wherein $R^{16}$ represents hydrogen atom, a $C_1$-$C_6$ alkyl group, phenyl group, or a phenyl-($C_1$-$C_3$ alkyl) group, and p represents an integer of 0–4); a $C_7$-$C_{11}$ aroyl group which may optionally have one or more substituents selected from the group consisting of a $C_1$-$C_4$ alkyl group, a halogen atom, hydroxyl group, nitro group, amino group, and carboxyl group; or a phenyl-($C_1$-$C_3$ alkyl) carbonyl group which may optionally have one or more substituents selected from the group consisting of a $C_1$-$C_4$ alkyl group, a halogen atom, hydroxyl group, nitro group, amino group, and carboxyl group, and X represents oxygen atom or sulfur atom.

2. The compound or its salt, or the hydrate or the solvate thereof according to claim 1, wherein $R^1$ is a residue of a steroid compound, excluding cholestane residue and cholestene residue, which is represented by the group of:

316

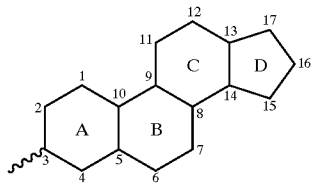

wherein rings A, B, C, and D independently represent a saturated ring, a partially saturated ring, or an unsaturated ring, and the rings A, B, C, and D may independently have one or more substituents selected from the group consisting of a $C_1$-$C_{10}$ alkoxy group; hydroxyl group; a $C_1$-$C_{10}$ alkyl group which may have one or more substituents selected from the group consisting of a $C_1$-$C_4$ alkyl group, a halogen atom, a $C_1$-$C_4$ alkoxy group, hydroxyl group, oxo group, 1,3-dioxolane residue, a group of —COOR$^{17}$ (wherein $R^{17}$ represents hydrogen atom, a $C_1$-$C_6$ alkyl group, or a phenyl-($C_1$-$C_3$ alkyl) group), and a group of —CONR$^{18}$R$^{19}$ (wherein $R^{18}$ and $R^{19}$ independently represent hydrogen atom, a $C_1$-$C_6$ alkyl group, or a phenyl-($C_1$-$C_3$ alkyl) group); a $C_2$-$C_{11}$ alkenyl group which may optionally have one or more substituents selected from the group consisting of a $C_1$-$C_4$ alkyl group, a halogen atom, a $C_1$-$C_4$ alkoxy group, hydroxyl group, oxo group, 1,3-dioxolane residue, a group of —COOR$^{17}$ (wherein $R^{17}$ has the same meaning as defined above), and a group of —CONR$^{18}$R$^{19}$ (wherein $R^{18}$ and $R^{19}$ have the same meanings as defined above); a halogen atom; oxo group; 1,3-dioxolane residue; a group of —COOR$^{20}$ (wherein $R^{20}$ represents hydrogen atom, a $C_1$-$C_6$ alkyl group, or a phenyl-($C_1$-$C_3$ alkyl) group); and a group of —CONR$^{21}$R$^{22}$ (wherein $R^{21}$ and $R^{22}$ independently represent hydrogen atom, a $C_1$-$C_6$ alkyl group or a phenyl-($C_1$-$C_3$ alkyl) group).

3. The compound or its salt, or the hydrate or the solvate thereof according to claim 1, wherein $R^1$ is a residue of a steroid compound, excluding cholestane residue, represented by a group of:

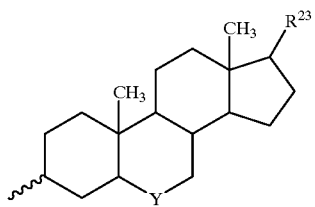

wherein $R^{23}$ represents hydrogen atom; a $C_1$-$C_{10}$ alkyl group which may optionally have one or more substituents selected from the group consisting of a $C_1$-$C_4$ alkyl group, a $C_1$-$C_4$ alkoxy group, hydroxyl group, oxo group, 1,3-dioxolane residue, a group of —COOR$^{24}$ (wherein $R^{24}$ represents hydrogen atom, a $C_1$-$C_6$ alkyl group or a phenyl-($C_1$-$C_3$ alkyl) group), and a group of —CONR$^{25}$R$^{26}$ (wherein $R^{25}$ and $R^{26}$ independently represent hydrogen atom, a $C_1$-$C_6$ alkyl group or a phenyl-($C_1$-$C_3$ alkyl) group); a $C_2$-$C_{11}$ alkenyl group which may optionally have one or more substituents selected from the group consisting of a $C_1$-$C_4$ alkyl group, a $C_1$-$C_4$ alkoxy group, hydroxyl group, oxo group, 1,3-dioxolane residue, a group of —COOR$^{24}$ (wherein $R^{24}$ has the same meaning as defined above), and a group of —CONR$^{25}$R$^{26}$ (wherein $R^{25}$ and $R^{26}$ have the same meanings as defined above); a $C_1$-$C_4$ alkoxy group; hydroxyl group; oxo group; 1,3-dioxolane residue; a group of —COOR$^{27}$ (wherein R$^{27}$ represents hydrogen atom, a C$_1$–C$_6$ alkyl group, or a phenyl-(C$_1$–C$_3$ alkyl) group); or a group of —CONR$^{28}$R$^{29}$ (wherein R$^{28}$ and R$^{29}$ independently represent hydrogen atom, a C$_1$–C$_6$ alkyl group or a phenyl-(C$_1$–C$_3$ alkyl) group); and Y represents a group of

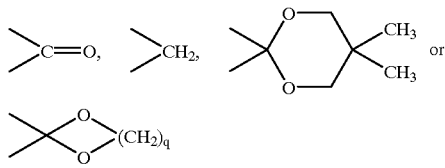

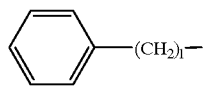

(wherein q represents an integer of 1–4),

R$^2$ represents hydrogen atom or methyl group,

R$^3$ represents a C$_1$–C$_6$ alkyl group or a group of

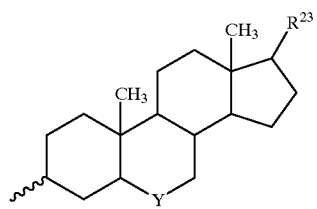

(wherein l represents an integer of 0–3),

R$^4$ represents hydrogen atom or a C$_2$–C$_4$ acyl group,

R$^5$ represents a group of R$^{14}$O— (wherein R$^{14}$ represents hydrogen atom or acetyl group); or a group of R$^{15}$NH— wherein R$^{15}$ represents a C$_2$–C$_7$ acyl group, a group of R$^{16}$O(CH$_2$)$_p$—CO— (wherein R$^{16}$ represents hydrogen atom, a C$_1$–C$_4$ alkyl group, a phenyl-(C$_1$–C$_3$ alkyl) group, or a C$_7$–C$_{11}$ aroyl group, and p represents an integer of 0–4), and X represents oxygen atom.

4. The compound or its salt, or the hydrate or the solvate thereof according to claim 3, wherein R$^1$ is a residue of a steroid compound, excluding cholestane residue, represented by a group of:

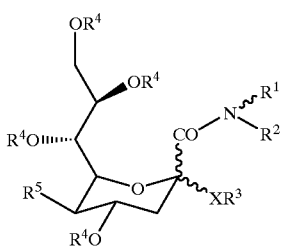

wherein R$^{23}$ and Y have the same meanings as defined in claim 3,

R$^2$ represents hydrogen atom,

R$^3$ represents a C$_1$–C$_3$ alkyl group,

R$^4$ represents hydrogen atom or acetyl group,

R$^5$ represents a group of R$^{14}$O— (wherein R$^{14}$ represents hydrogen atom or acetyl group); or a group of R$^{15}$NH— (wherein R$^{15}$ represents a C$_2$–C$_4$ acyl group), and X represents oxygen atom.

5. The compound or its salt, or the hydrate or the solvate thereof according to claim 3, wherein R$^1$ is a residue of a steroid compound, excluding cholestane residue, represented by a group of:

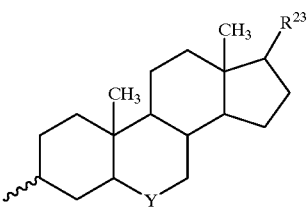

wherein R$^{23}$ represents a C$_1$–C$_{10}$ alkyl group which may optionally have one or more substituents selected from the group consisting of a C$_1$–C$_4$ alkyl group, a C$_1$–C$_4$ alkoxy group, hydroxyl group, oxo group, 1,3-dioxolane residue, a group of —COOR$^{24}$ (wherein R$^{24}$ has the same meaning as defined in claim 3), and a group of —CONR$^{25}$R$^{26}$ (wherein R$^{25}$ and R$^{26}$ have the same meanings as defined in claim 3); or a C$_2$–C$_{11}$ alkenyl group which may optionally have one or more substituents selected from the group consisting of a C$_1$–C$_4$ alkyl group, a C$_1$–C$_4$ alkoxy group, hydroxyl group, oxo group 1,3-dioxolane residue, a group of —COOR$^{24}$ (wherein R$^{24}$ has the same meaning as defined in claim 3), and a group of—CONR$^{25}$R$^{25}$ (wherein R$^{25}$ and R$^{26}$ have the same meanings as defined in claim 3), and Y has the same meaning as defined in claim 3, R$^2$ represents hydrogen atom, R$^3$ represents a C$_1$–C$_3$ alkyl group, R$^4$ represents hydrogen atom or acetyl group, R$^5$ represents a group of R$^{15}$NH (wherein R$^{15}$ represents acetyl group), and X represents oxygen atom.

6. A sialic acid derivative represented by the following general formula (1AA) or its salt, or a hydrate or a solvate thereof:

(1AA)

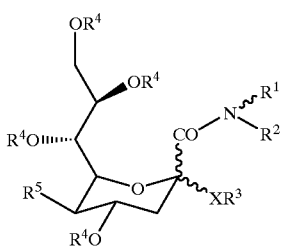

wherein:

R$^1$ represents a steroid residue of the formula:

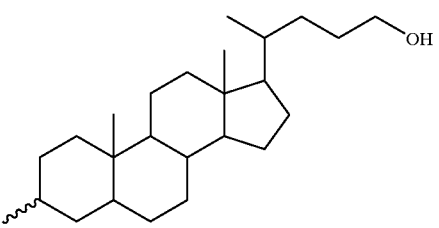

,

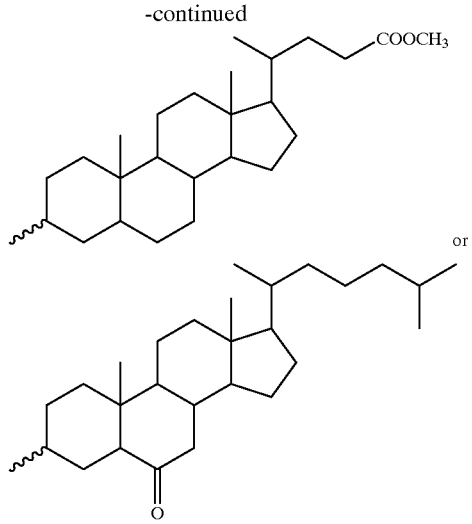

R² represents hydrogen atom or methyl group,

R³ represents a $C_1$–$C_6$ alkyl group, a group of formula:

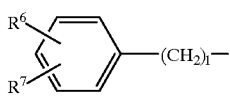

wherein $R^6$ and $R^7$ independently represent hydrogen atom, a halogen atom, a $C_1$–$C_4$ alkyl group, hydroxyl group, a group of formula $R^8O$— (wherein $R^8$ represents a $C_1$–$C_4$ alkyl group, phenyl group, or a phenyl-($C_1$–$C_3$ alkyl) group), nitro group, amino group, a $C_1$–$C_4$ alkylamino group, a $C_2$–$C_8$ dialkylamino group, or a group of formula $R^9O$—CO— (wherein $R^9$ represents hydrogen atom, a $C_1$–$C_4$ alkyl group, phenyl group, or a phenyl-($C_1$–$C_3$ alkyl) group), and l represents an integer of 0–6; a group of $R^{10}O(CH_2)_m$— (wherein $R^{10}$ represents hydrogen atom; a $C_1$–$C_4$ alkyl group; phenyl group which may optionally have one or more substituents selected from the group consisting of a $C_1$–$C_4$ alkyl group, a halogen atom, hydroxyl group, nitro group, amino group, and carboxyl group; or a phenyl-($C_1$–$C_3$ alkyl) group which may optionally have one or more substituents selected from the group consisting of a $C_1$–$C_4$ alkyl group, a halogen atom, hydroxyl group, nitro group, amino group, and carboxyl group, and m represents an integer of 2–6); or a group of $(R^{11})(R^{12})N(CH_2)_n$— wherein $R^{11}$ represents hydrogen atom or a $C_1$–$C_4$ alkyl group, and $R^{12}$ represents hydrogen atom; a $C_1$–$C_4$ alkyl group; a $C_2$–$C_7$ acyl group; a $C_1$–$C_4$ alyilsulfonyl group; phenylsulfonyl group which may optionally have one or more substituents selected from the group consisting of a $C_1$–$C_4$ alkyl group, a halogen atom, hydroxyl group, nitro group, amino group, and carboxyl group; or a group of $R^{13}O$—CO— (wherein $R^{13}$ represents a $C_1$–$C_4$ alkly group, phenyl group, or a phenyl-($C_1$–$C_3$ alkyl) group), and n represents an integer of 2–6, $R^4$ represents hydrogen atom or a $C_2$–$C_7$ acyl group, $R^5$ represents a group of $R^{14}O$— (wherein $R^{14}$ represents hydrogen atom or a $C_2$–$C_7$ acyl group) or a group of $R^{15}NH$— wherein $R^{15}$ represents a $C_2$–$C_7$ acyl group, a group of $R^{16}O(CH_2)_p$—CO— (wherein $R^{16}$ represents hydrogen atom, a $C_1$–$C_6$ alkyl group, phenyl group, or a phenyl-($C_1$–$C_3$ alkyl) group), and p represents an integer of 0–41); a $C_7$–$C_{11}$ aroyl group which may optionally have one or miore substituents selected from the group consisting of a $C_1$–$C_4$ alkyl group, a halogen atom, hydroxyl group, nitro group, amino group, and carboxyl group or a phenyl-($C_1$–$C_3$ alkyl) carbonyl group which may optionally have one or miore substituents selected from the group consisting of a $C_1$–$C_4$ alkyl group, a halogen atom, hydroxyl group, nitro group, amino group, and carboxyl group, and X represents oxygen atom or sulfur atom.

7. The compound or its salt, or the hydrate or the solvate thereof according, to claim 6, wherein $R^1$ is a steroid residue of the formula:

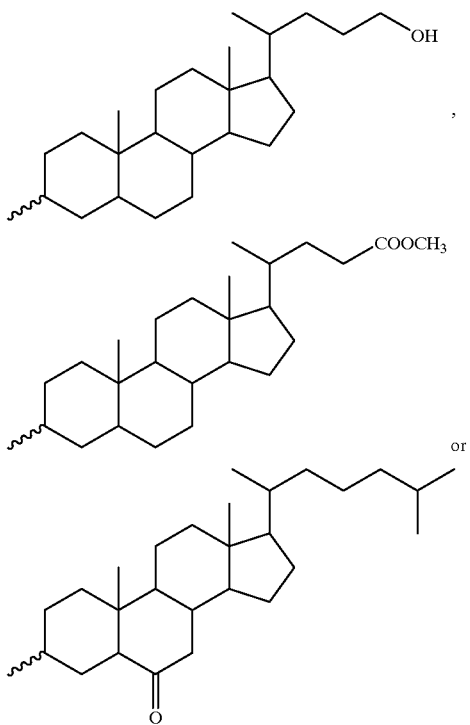

$R^2$ represents hydrogen atom or methyl group, $R^3$ represents a $C_1$–$C_6$ alkyl group or a group of:

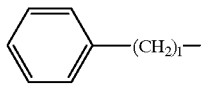

(wherein l represents an integer of 0–3), $R^4$ represents hydrogen atom or a $C_2$–$C_4$ acyl group, $R^5$ represents a group of $R^{14}O$— (wherein $R^{14}$ represents hydrogen atom or acetyl group); or a group of $R^{15}NH$— wherein $R^{15}$ represents a $C_2$–$C_7$ acyl group, a group of $R^{16}O(CH_2)_p$—CO— (wherein $R^{16}$ represents hydrogen atom, a $C_1$–$C_4$ alkyl group, a phenyl-($C_1$–$C_3$ alkyl) group, or a $C_7$–$C_{11}$ aroyl group, and p represents an integer of 0–4), and X represents oxygen atom.

8. The compound or its salt, or the hydrate or the solvate thereof according to claim 7, wherein $R^1$ is a steroid residue of the formula:

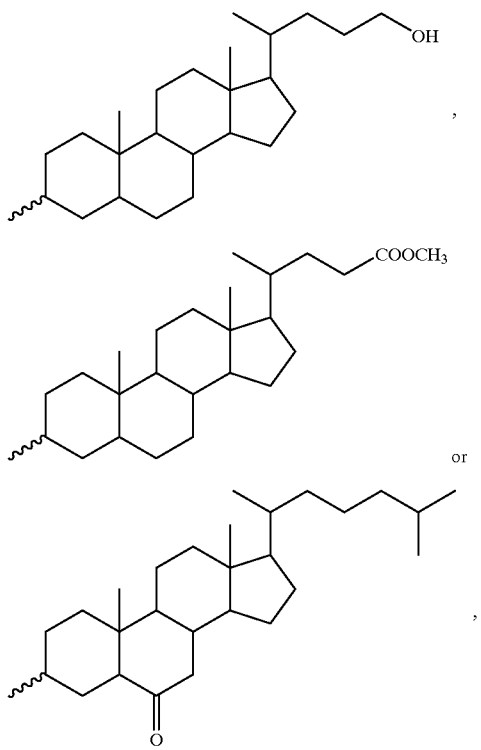

$R^2$ represents hydrogen atom, $R^3$ represents a $C_1$–$C_3$ alkyl group, $R^4$ represents hydrogen atom or acetyl group, $R^5$ represents a group of $R^{14}O$— (wherein $R^{14}$ represents hydrogen atom or acetyl group); or a group of $R^{15}NH$— (wherein $R^{15}$ represents a $C_2$–$C_4$ acyl group), and X represents oxygen atom.

9. The compound or its salt, or the hydrate or the solvate thereof according to claim 7, wherein $R^1$ is a steroid residue of the formula:

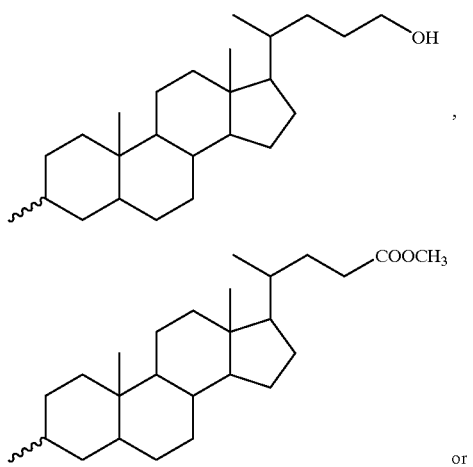

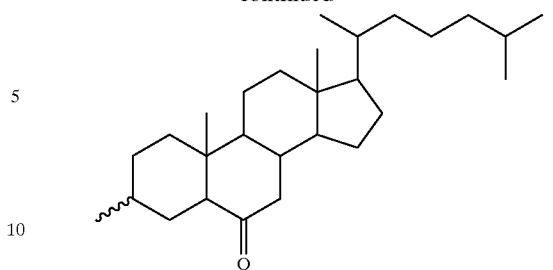

$R^2$ represents hydrogen atom, $R^3$ represents a $C_1$–$C_3$ alkyl group, $R^4$ represents hydrogen atom or acetyl group, $R^5$ represents a group of $R^{15}NH$— (wherein $R^{15}$ represents acetyl group), and X represents oxygen atom.

10. 3β-[N-(5-acetamido-3,5-dideoxy-2-O-methyl-α-D-glycero-D-galacto-2-nonulopyranosonyl)amino]-24-hydroxy-5β-cholane, or a hydrate or a solvate thereof.

11. 3α-[N-(5-acetamido-3,5-dideoxy-2-O-methyl-α-D-glycero-D-galacto-2-nonulopyranosonyl)amino]-6-ketocholestane, or a hydrate or a solvate thereof.

12. Methyl 3α-[N-(5-acetamido-3,5-dideoxy-2-O-methyl-α-D-glycero-D-galacto-2-nonulopyranosonyl)amino]-5β-cholanate, or a hydrate or a solvate thereof.

13. A medicament comprising a substance selected from the group of a sialic acid derivative and its salt, and a hydrate and a solvate thereof according to any one of claims 1 to 5.

14. A pharmaceutical composition comprising a substance selected from the group of a sialic acid derivative and its salt, and a hydrate and a solvate thereof according to any one of claims 1 to 5 together with a pharmaceutically acceptable carrier.

15. The pharmaceutical composition according to claim 14 which is used for preventive and/or therapeutic treatment of senile dementia; cerebrovascular dementia accompanying stroke, cerebral hemorrhage, or brain infarction; memory disorder, decreased attentiveness, speech disturbance, hypobulia, emotional disorder, hallucination, paranoid state, or behavioral disorder accompanying head injury, aftertrouble of encephalitis, cerebral palsy, Huntington's disease, Pick's disease, Down's syndrome, or Parkinson's disease; tardive dyskinesia; glaucoma; sleep disturbance; peripheral nervous disorders; facial nerve palsy; ischiadic nerve palsy; myelopathic muscular atrophy; muscular dystrophy; myasthenia gravis; multiple sclerosis; amyotrophic lateral sclerosis; acute disseminated encephalomyelitis; Guillain-Barre syndrome; postvaccinal encephalitis; or subacute myelo-optico-neuropathy.

16. The pharmaceutical composition according to claim 14 which is used for preventive and/or therapeutic treatment of peripheral nervous disorder.

17. The pharmaceutical composition according to claim 15 which is used for preventive and/or therapeutic treatment of senile dementia.

18. The pharmaceutical composition according to claim 15 which is used for preventive and/or therapeutic treatment of Alzheimer's disease.

19. The pharmaceutical composition according to claim 15 which is used for preventive and/or therapeutic treatment of cerebrovascular dementia accompanied with stroke, cerebral hemorrhage, or brain infarction.

20. The pharmaceutical composition according to claim 15 which is used for preventive and/or therapeutic treatment of memory disorder, decreases attentiveness, speech disturbance, hypobulia, emotional disorder, hallucination, paranoid state, or behavioral disorder accompanied with head injury, after-trouble of encephalitis, cerebral palsy, Huntington's disease, Pick's disease, Down's syndrome, or Parkinson's disease.

21. The pharmaceutical composition according to claim 15 which is used for preventive and/or therapeutic treatment of metabolic neuropathy caused by diabetes.

22. A medicament in a single dose form comprising a substance selected from the group of a sialic acid derivative and its salt, and a hydrate and a solvate thereof according to any one of claims 6–12.

23. A pharmaceutical composition comprising a substance selected from the group of a sialic acid derivative and its salt, and a hydrate and a solvate thereof according to any one of claims 6–12 together with a pharmaceutically acceptable carrier.

24. The pharmaceutical composition according to claim 23 which is used for preventive and/or therapeutic treatment of dementia, memory disorder, or a symptom accompanied with said disease.

25. The pharmaceutical composition according to claim 23 which is used for preventive and/or therapeutic treatment of peripheral nervous disorder.

26. The pharmaceutical composition according to claim 24 which is used for preventive and/or therapeutic treatment of senile dementia.

27. The pharmaceutical composition according to claim 24 which is used for preventive and/or therapeutic treatment of Alzheimer's disease.

28. The pharmaceutical composition according to claim 24 which is used for preventive and/or therapeutic treatment of cerebrovascular dementia accompanied with stroke, cerebral hemorrhage, brain infarction and the like.

29. The pharmaceutical composition according to claim 24 which is used for preventive and/or therapeutic treatment of memory disorder, decreased attentiveness, speech disturbance, hypobulia, emotional disorder, hallucination, paranoid state, behavioral disorder and the like accompanied with head injury, after-trouble of encephalitis, cerebral palsy, Huntington's disease, Pick's disease, Down's syndrome, Parkinson's disease and the like.

30. The pharmaceutical composition according to claim 24 which is used for preventive and/or therapeutic treatment of metabolic neuropathy caused by diabetes and the like.

31. A method for therapeutic treatment of dementia, memory disorder, or a symptom accompanied with said disease which comprises the step of administering a therapeutically effective amount of a substance selected from the group of a sialic acid derivative and its salt, and a hydrate and a solvate thereof according to any one of claims 6–8 to a patient.

32. A method for therapeutic treatment of senile dementia; cerebrovascular dementia accompanying stroke, cerebral hemorrhage, or brain infarction; memory disorder, decreased attentiveness, speech disturbance, hypobulia, emotional disorder, hallucination, paranoid state, or behavioral disorder accompanying head injury, after-trouble of encephalitis, cerebral palsy, Huntington's disease, Pick's disease, Down's syndrome, or Parkinson's disease; tardive dyskinesia; glaucoma; sleep disturbance; peripheral nervous disorders; facial nerve palsy; ischiadic nerve palsy; myelopathic muscular atrophy; muscular dystrophy; myasthenia gravis; multiple sclerosis; amyotrophic lateral sclerosis; acute disseminated encephalomyelitis; Guillain-Barre syndrome; postvaccinal encephalitis; or subacute myelo-optico-neuropathy, which comprises the step of administering a therapeutically effective amount of a substance selected from the group of a sialic acid derivative and its salt, and a hydrate and solvate thereof according to any one of claims 1 to 5 to a patient.

33. A method of manufacturing a pharmaceutical composition, which comprises mixing a substance selected from the group consisting of a sialic acid derivative, a salt thereof, a hydrate thereof and a solvate thereof according to any one of claims 1 to 5 with a pharmaceutically acceptable carrier.

34. A method of manufacturing a pharmaceutical composition, which comprises mixing a substance selected from the group consisting of a sialic acid derivative, a salt thereof, a hydrate thereof and a solvate thereof according to any one of claims 6–12 with a pharmaceutically acceptable carrier.

* * * * *